US010208056B2

(12) United States Patent
Pastor Fernández et al.

(10) Patent No.: US 10,208,056 B2
(45) Date of Patent: Feb. 19, 2019

(54) CONDENSED TRICYCLIC COMPOUNDS AS PROTEIN KINASE INHIBITORS

(71) Applicant: FUNDACIÓN DEL SECTOR PÚBLICO ESTATAL CENTRO NACIONAL DE INVESTIGACIONES ONCOLÓGICAS CARLOS III (F.S.P. CNIO), Madrid (ES)

(72) Inventors: Joaquín Pastor Fernández, Madrid (ES); Sonia Martínez González, Madrid (ES); Carmen Blanco-Aparicio, Madrid (ES); Ana Isabel Hernández Higueras, Madrid (ES); Cristina Ana Gómez De La Oliva, Madrid (ES); Virginia Rivero Buceta, Madrid (ES); Rosario Concepción Riesco Fagundo, Madrid (ES)

(73) Assignee: FUNDACIÓN DEL SECTOR PÚBLICO ESTATAL CENTRO NACIONAL DE INVESTIGACIONES ONCOLÓGICAS CARLOS III (F.S.P. CNIO), Madrid (ES)

( * ) Notice: Subject to any disclaimer, the term of this patent is extended or adjusted under 35 U.S.C. 154(b) by 0 days.

(21) Appl. No.: 15/755,019

(22) PCT Filed: Aug. 25, 2016

(86) PCT No.: PCT/GB2016/052641
§ 371 (c)(1),
(2) Date: Feb. 23, 2018

(87) PCT Pub. No.: WO2017/033019
PCT Pub. Date: Mar. 2, 2017

(65) Prior Publication Data
US 2018/0244687 A1 Aug. 30, 2018

(30) Foreign Application Priority Data
Aug. 26, 2015 (EP) .................................. 15382431

(51) Int. Cl.
C07D 491/147 (2006.01)
C07D 491/16 (2006.01)
C07D 491/22 (2006.01)
A61K 45/06 (2006.01)
A61K 31/5377 (2006.01)
A61K 31/437 (2006.01)
A61P 35/00 (2006.01)
A61K 31/4545 (2006.01)

(52) U.S. Cl.
CPC ........ C07D 491/147 (2013.01); A61K 31/437 (2013.01); A61K 31/4545 (2013.01); A61K 31/5377 (2013.01); A61K 45/06 (2013.01); A61P 35/00 (2018.01); C07D 491/16 (2013.01); C07D 491/22 (2013.01)

(58) Field of Classification Search
CPC .............. A61K 31/437; A61K 31/4545; A61K 31/5377; A61K 45/06; A61P 35/00; C07D 491/147; C07D 491/16; C07D 491/22
See application file for complete search history.

(56) References Cited

FOREIGN PATENT DOCUMENTS

WO 2012/101029 A1 8/2012
WO 2014/154723 A1 10/2014

OTHER PUBLICATIONS

International Search Report for PCT/GB2016/052641, dated Nov. 16, 2016.
Ikemoto et al., "A Practical Synthesis of the Chronic Renal Disease Agent, 4,5-Dihydro-3H-1,4,8b-triazaacenaphthylen-3-one Derivatives, Using Regioselective Chlorination of Ethyl 5-methylimidazo[1,2-α]pyridine-3-carboxylate with N-Chlorosuccinimide", Tetrahedron 56:7915-7921 (2000).
Han et al., "Recent development of peptide coupling reagents in organic synthesis", Tetrahedron 60:2447-2467 (2004).
Lainton et al., "Design and Synthesis of a Diverse Morpholine Template Library", J. Comb. Chem. 5:400-407 (2003).
Wiggins "A Convenient Procedure for the Reduction of Diarylmethanols with Dichlorodimethylsilane/Sodium Iodide", Synthetic Communications, 18(7):741-749 (1988).
Lens et al., "Shared and separate functions of polo-like kinases and aurora kinases in cancer", Nature Reviews, Cancer 10:825-841 (2010).

(Continued)

Primary Examiner — Valerie Rodriguez-Garcia
(74) Attorney, Agent, or Firm — Merchant & Gould P.C.

(57) ABSTRACT

There is provided compounds of formula I,

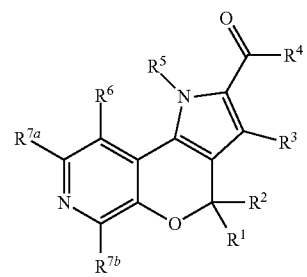

wherein $R^1$, $R^2$, $R^3$, $R^4$, $R^5$, $R^6$, $R^{7a}$ and $R^{7b}$ have meanings given in the description, and pharmaceutically-acceptable esters, amides, solvates or salts thereof, which compounds are useful in the treatment of diseases in which inhibition of a protein or lipid kinase (e.g. CDK8 and/or Haspin kinase) is desired and/or required, and particularly in the treatment of cancer or a proliferative disease.

13 Claims, 4 Drawing Sheets

(56) References Cited

OTHER PUBLICATIONS

Nicolaou et al., "Calicheamicin θII: A Rationally Designed Molecule with Extremely Potent and Selective DNA Cleaving Properties and Apoptosis Inducing Activity", Angew. Chem. Int. Ed. Engl. 33(2):183-186 (1994).
Stragliotto et al., "Multiple Infusions of Anti-epidermal Growth Factor Receptor (EGFR) Monoclonal Antibody (EMD 55 900) in Patients with Recurrent Malignant Gliomas", European Journal of Cancer 32A(4):636-640 (1996).
Johns et al., "Identification of the Epitope for the Epidermal Growth Factor Receptor-specific Monoclonal Antibody 806 Reveals That It Preferentially Recognizes an Untethered Form of the Receptor", The Journal of Biological Chemistry 279(29):30375-30384 (2004).
Crouch et al., "The use of ATP bioluminescence as a measure of cell proliferation and cytotoxicity", Journal of Immunological Methods, 160:81-88 (1993).
Cree et al., "Methotrexate chemosensitivity by ATP luminescence in human leukemia cell lines and in breast cancer primary cultures: comparison of the TCA-100 assay with a clonogenic assay", Anti-Cancer Drugs 6:398-404 (1995).
Blanco-Aparicio et al., "Pim 1 kinase inhibitor ETP-45299 suppresses cellular proliferation and synergizes with PI3K inhibition", Cancer Letters 300:145-153 (2011).
Cohen "The development and therapeutic potential of protein kinase inhibitors", Current Opinion in Chemical Biology 3:459-464 (1999).
Rzymski, T et al., "CDK8 kinase—An emerging target in targeted cancer therapy", Biochim. Biophys. Acta (2015).
Knuesel M.T. et al., "The Human CDK8 Subcomplex Is a Histone Kinase That Requires Med12 for Activity and Can Function Independently of Mediator", Molecular and Cellular Biology 29(3):650-661 (2009).
Meyer K.D. et al., "Cooperative activity of cdk8 and GCN5L within Mediator directs tandem phosphoacetylation of histone H3", The EMBO Journal 27(10):1447-1457 (2008).
Firestein et al., "CDK8 is a colorectal cancer oncogene that regulates β-catenin activity", Nature (2008) Sep. 25;455(7212):547-551.
Firestein et al., "Revving the Throttle on an Oncogene: CDK8 Takes the Driver Seat" Cancer Res 69(20):7899-7901 (2009).
Firestein et al., "CDK8 Expression in 470 Colorectal Cancers in Relation to β-Catenin Activation, Other Molecular Alterations and Patient Survival", Int J Cancer 126(12):2863-2873 (2010).
Seo et al., "Role of CDK8 and β-catenin in colorectal adenocarcinoma", Oncology Reports 24:285-291 (2010).
Xiao-Yu Li et al., "siRNA-mediated silencing of CDK8 inhibits proliferation and growth in breast cancer cells [Retraction]", Journal of Clinical and Experimental Pathology 7(1):92-100 (2014).
Xu D. et al., "Skp2—MacroH2A1—CDK8 axis orchestrates G2/M transition and tumorigenesis", Nature Communications, 6:6641 (2015).
Kapoor et al., "The histone variant macroH2A suppresses melanoma progression through regulation of CDK8", Nature 468(7327):1105-1109 (2010).
Kim et al., "Roles of cyclin-dependent kinase 8 and β-catenin in the oncogenesis and progression of gastric adenocarcinom", International Journal of Oncology 38: 1375-1383 (2011).
Song et al., "MicroRNA-107 promotes proliferation of gastric cancer cells by targeting cyclin dependent kinase 8", Diagnostic Pathology 9:164 (2014).
Xu et al., "Mutated K-ras activates CDK8 to stimulate the epithelial-tomesenchymal transition in pancreatic cancer in part via the Wnt/β-catenin signaling pathway", Cancer Letters 356:613-627 (2015).
Porter et al., "Cyclin-dependent kinase 8 mediates chemotherapyinduced tumor-promoting paracrine activities", Proc. Natl. ACAD. SCI. 109(34):13799-13804 (2012).
Bancerek et al., "CDK8 Kinase Phosphorylates Transcription Factor STAT1 to Selectively Regulate the Interferon Response", Immunity 38:250-262 (2013).

Putz et al., "CDK8-Mediated STAT1-S727 Phosphorylation Restrains NK Cell Cytotoxicity and Tumor Surveillance", Cell Reports 4:437-444 (2013).
Adler et al., "CDK8 Maintains Tumor Dedifferentiation and Embryonic Stem Cell Pluripotency", Cancer Research, Tumor and Stem Cell Biology 72(8):2129-2139 (2012).
Tanaka et al., "Isolation and characterization of cDNA clones specifically expressed in testicular germ cells", FEBS Letters 355:4-10 (1994).
Tanaka et al., "Identification and Characterization of a Haploid Germ Cell-specific Nuclear Protein Kinase (Haspin) in Spermatid Nuclei and Its Effects on Somatic Cells", The Journal of Biological Chemistry 274(24):17049-17057 (1999).
Higgins "The Haspin gene: location in an intron of the Integrin αE gene, associated transcription of an Integrin αE-derived RNA and expression in diploid as well as haploid cells", Gene 267:55-69 (2001).
Dai et al., "The kinase haspin is required for mitotic histone H3 Thr 3 phosphorylation and normal metaphase chromosome alignment", Genes & Development 19(4):472-488 (2005).
Huertas et al., "Antitumor activity of a small-molecule inhibitor of the histone kinase Haspin", Oncogene 31 (11):1408-1408 (2012).
Kelly et al., "Survivin reads phosphorylated histone H3 threonine 3 to activate the mitotic kinase Aurora B", Science 330(6001):235-239 (2010).
Wang et al., "Histone H3 Thr-3 phosphorylation by Haspin positions Aurora B at centromeres in mitosis", Science 330 (6001):231-235 (2010).
Wang et al., "A Positive Feedback Loop Involving Haspin and Aurora B Promotes CPC Accumulation at Centromeres in Mitosis", Curr Biol 21(12):1061-1069 (2011).
Revesz et al., "In vivo and in vitro SAR of tetracyclic MAPKAP-K2 (MK2) inhibitors. Part II", Bioorganic & Medical Chemistry Letters 20:4719-4723 (2010).
TJ Wang et al., "Applications of 3D-QSAR and structure-based pharmacophore modeling, virtual screening, ADMET, and molecular docking of putative MAPKAP-K2 (MK2) inhibitors", Med Chem Res 22:4818-4829 (2013).
Weber et al., "The Synthesis and Reactivity of some 2-Amino-5-bromo-1,3,4-thiadiazoles and the Corresponding Δ2-1,3,4-Thiadiazolines", J. Heterocyclic Chem. 14:823 (1977).
A. Gadad et al., "Synthesis and anti-tubercular activity of a series of 2-sulfonamido/trifluoromethyl-6-substituted imidazo-[2,1-b]-1,3,4-thiadiazole derivatives", Bioorganic & Medicinal Chemistry 12:5651-5659 (2004).
H. Paul et al., "Über einige Umsetzungen von 2,5-Diamino- sowie 2-Amino-1,3,4-thiadiazolen mit α-Halogenketonen zu Imidazo [2,1-b ]-1,3,4-thiadiazolen", Monatshefte für Chemie 108:665-680 (1977).
M.A. El-Sherbeny et al., Synthesis and cardiotonic activity of certain imidazo[2,1-b ]-1,3,4-thiadiazole derivatives, Boll. Chim. Fannaceutico - Anno 136(3):253-256 (1997).
Nicolaou et al., "Palladium-Catalyzed Cross-Coupling Reactions in Total Synthesis", Angew. Chem. Int. Ed. 44:4442-4489 (2005).
Bretonnet et al., "NMR Screening Applied to the Fragment-Based Generation of Inhibitors of Creatine Kinase Exploiting a New Interaction Proximate to the ATP Binding Site", J. Med. Chem. 50:1865-1875 (2007).
Marin et al., Synthesis and Anthelmintic Activity of Carbamates Derived from Imidazo[2,1-b][1,3,4]Thiadiazole and Imidazo[2,1-b]Thiazole, II Farmaco 47(1):63-75 (1992).
Severinsen et al., "Versatile strategies for the solid phase synthesis of small heterocyclic scaffolds: [1,3,4]-thiadiazoles and [1,3,4]-oxadiazoles", Tetrahedron 61:5565-5575 (2005).
Kuwahara et al., "Synthetic Studies on Condensed-Azole Derivatives. IV. Synthesis and Anti-asthmatic Activities of ω-Sulfamoylalkyloxyimidazo[1,2-b]pyridazines", Chem. Pharm. Bull 44(1):122-131 (1996).
Wipf et al., "Formal Total Synthesis of (+)-Diepoxin σ", J. Org. Chem.65:6319-6337 (2000).

(56) References Cited

OTHER PUBLICATIONS

Shintani et al., "Carbon-Carbon Bond-Forming Enantioselective Synthesis of Chiral Organosilicon Compounds by Rhodium/Chiral Diene-Catalyzed Asymmetric 1,4-Addition Reaction", Organic letters 7(21):4757-4759 (2005).
Kobe et al., "Synthesis of Pyridazine Derivatives—XV Some Electrophilic Substitutions on Imidazo[1,2-b]-Pyridazines", Tetrahedron 24:239-245 (1968).
Fabio et al., "Synthesis of Carbon-14 and Deuterium Labeled 3-Nitro-6-Propdxvimidazo [1,2-B] Pyridazine—An Antiparasitic Agent", Journal of Labelled Compounds and Radiopharmaceuticals 15:407 (1978).
Bellamy et al., "Selective Reduction of Aromatic Nitro Compounds with Stannous Chloride in Non Acidic and Non Aqueous Medium", Tetrahedron Letters 25(8):839-842 (1984).
Abdel-Magid et al., "Reductive Amination of Aldehydes and Ketones with Weakly Basic Anilines Using Sodium Triacetoxyborohydride", Synthesis, Letters:537-539 (1990).
Wenwei et al., "Preparation of highly functionalized arylmagnesium reagents by the addition of magnesium phenylselenide to aryne", Tetrahedron Letters 47:1941-1944 (2006).
Plotkin et al., "A practical approach to highly functionalized benzodihydrofurans", Tetrahedron Letters 41:2269-2273 (2000).
Dermer "Metallic Salts of Alcohols and Alcohol Analogs", Chem. Rev. 14:385-430 (1934).
Defacqz et al., "Synthesis of C5-substituted imidazolines", Tetrahedron Letters 44:9111-9114 (2003).
Gregson et al., "Linker Length Modulates DNA Cross-Linking Reactivity and Cytotoxic Potency of C8/C8' Ether-Linked C2-exo-Unsaturated Pyrrolo[2,1-c][1,4]benzodiazepine (PBD) Dimers", J. Med. Chem. 47:1161-1174 (2004).
Abdel-Magid et al., "Reductive Amination of Aldehydes and Ketones with Sodium Triacetoxyborohydride. Studies on Direct and Indirect Reductive Amination Procedures", J. Org. Chem. 61:3849-3862 (1996).
Ikemoto et al., "Reactions With N-Chlorosuccinimide of Various 5-Methylimidazo[1,2-α]Pyridine Derivatives With an Electron-Withdrawing Group Substituted At the 3-Position", Heterocycles, 55(9):99-108 (2000).
Abignente et al., "Research on Heterocyclic Compounds. XXVII. Synthesis and Antiinflammatory Activity of 2-Phenylimidazo[1,2-b]Pyridazine-3-carboxylic Acids", IL Farmaco 45(10):1075-1087 (1990).

CONDENSED TRICYCLIC COMPOUNDS AS PROTEIN KINASE INHIBITORS

This application is a National Stage Application of PCT/GB2016/052641 filed 25 Aug. 2016, which claims benefit of European Patent Application No. 15382431.3, filed 26 Aug. 2015, which applications are incorporated herein by reference. To the extent appropriate, a claim of priority is made to each of the above disclosed applications.

FIELD OF THE INVENTION

This invention relates to novel pharmaceutically-useful compounds, which compounds are useful as kinase inhibitors (such as inhibitors of the CDK8 and/or Haspin kinases). The compounds are of potential utility in the treatment of diseases such as cancer (particularly colorectal/colon cancer, breast cancer, pancreatic cancer and cervical cancer). The invention also relates to the use of such compounds as medicaments, to the use of such compounds for in vitro, in situ and in vivo diagnosis or treatment of mammalian cells (or associated pathological conditions), to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465. In general, protein kinases are enzymes that mediate intracellular signalling by affecting a phosphoryl transfer from a nucleoside triphosphate to a protein acceptor that is involved in a signalling pathway. These phosphorylation events act as molecular on/off switches that can modulate or regulate the target protein biological function. These phosphorylation events are triggered in response to a variety of extracellular and other stimuli. Many diseases, such as those mentioned above (or hereinafter), are associated with abnormal cellular responses triggered by these types of protein kinase mediated events.

Initiation, progression and completion of the mammalian cell cycle are regulated by various cyclin-dependent kinase (CDK) complexes, which are critical for cell growth. CDK8 is a kinase that is involved in cell cycle control and also implicated in the regulation of transcription. CDK8 along with its closely related isoform or paralog CDK19 and together with its partner Cyclin C, MED12 and MED13 are components of multi-protein Mediator complex which couples action of transcription factors with the molecular machinery that carries out transcription, e.g. Cdk8 couple basal transcriptional machinery to sequence-specific transcription factors such as Notch, p53, β-catenin, and also repress the transcription of other genes (Rzymski, T. et al., *Biochim. Biophys. Acta, Proteins and Proteomics* (2015), e-publication ahead of print (doi:10.1016/j.bbapap.2015.05.011)). As Mediator independent roles CDK8 has been shown to act as part of a separate complex as a histone kinase (Knuesel M. T., et al., *Mol Cell Biol.* 2009, 29(3):650-61) phosphorylating H3 at S10, a mark associated with transcriptional activation of IER genes. CDk8 also interacts with acetyltransferase 2A (also known as GCN5L) and both proteins as a complex cooperatively phosphoacetylated histone H3 to generate the dual H3S10p/K14Acmark (Meyer, K. D., et al., *EMBO Journal* (2008), 27(10), 1447-1457).

Tumour development is associated with genetic alteration and deregulation of CDKs and their regulators, suggesting that inhibitors of CDKs may be useful as anti-cancer therapeutics.

Specifically, CDK8 is a serine-threonine protein kinase that is encoded by the CDK8 gene. It has been found that CDK8 is an oncogene that regulates β-catenin activity (see e.g. *Nature* (2008) vol. 455 (25) p 547-553 by Firestein et al and *Cancer Research* (2009); 69(20): p 7899-7901 by Firestein et al). CDK8 has been identified as a gene that both modulates β-catenin activity and is essential for colon cancer cell proliferation. The gene, which encodes a member of the mediator complex, is located at 13q12.13, which has been found to be a region of recurrent copy number gain in a substantial fraction (~60%) of colon cancers. The expression of this gene is therefore implicated in the proliferation of colon cancer cells, and hence its suppression may inhibit such proliferation (Firestein et al. *Nature* (2008) vol. 455 (25) p 547-553; Firestein et al. *Int. J. Cancer:* 126, 2863-2873 (2010); Seo, J.-O., et al., *Oncology Reports* (2010), 24(1), 285-291. The expression of this gene has also been implicated in the proliferation of breast cancer (Xiao-Yu Li et al., *Int. J. Clin. Exp. Pathol.* 2014, 7(1):92-100; Xu D. et al., *Nat. Commun.* 2015, 6:6641), malignant melanoma (Kapoor A. et al. *Nature* 2010, 468, 1105), gastric cancer (Kim et al. *Int. J. Oncol.* 2011; 38(5):1375-83 2011; Song, Y.-Q., et al., *Diagnostic Pathology* (2014), 9, 64/1-164/6), ovarian cancer (Roninson et al. *Proc. Natl. Acad. Sci. USA,* 2012; 109(34):13799-804), and pancreatic cancer (Xu W. et al. Cancer Lett. 2015; 356(2 Pt B): 613-27). Porter D. C. et al. *Proc. Natl. Acad. Sci. USA,* 2012; 109(34):13799-804 have also reported that CDK8 expression correlates with poor survival in breast and ovary cancer. Given that CDK8 over-expression is characterised by high levels of CDK8 and β-catenin hyperactivity, CDK8 may activate β-catenin and other genes to drive colon cancer progression. Hence, inhibitors of CDK8 may be useful in the treatment of such cancers (by which we include reducing the progression thereof) given that they may inhibit the expression of genes important for oncogenic progression and controlled by CDK8 and/or they may regulate β-catenin activity.

CDK8 has been identified as a major kinase in the response to IFN signalling mediated STAT1-S727 phosphorylation (Bancerek J., et al., *Immunity* 2013 38(2):250-62). Moreover, it has been shown an inhibitory role of STAT1-S727 phosphorylation for NK cell cytotoxicity (Putz E. M., et al., *Cell Rep.* 2013 4(3):437-44), and knockdown of CDK8 verified its essential role for basal STAT1-S727 phosphorylation in NK cells and significantly enhanced cytotoxicity. This could be a novel immune cell-based strategy that in combination with other therapies could enhance clinical efficacy and outcome.

CDK8 is also implicated in the control of cell fate determination. Silencing of CDK8 using an inducible short hairpin strategy showed CDK8 expression is required for tumor growth in vivo, maintains tumors in an undifferentiated state, and regulates the expression of a subset of genes normally expressed in pluripotent embryonic stem cells in xenografts derived from cell lines that harbor copy number gain and overexpression of CDK8. CDK8 expression also plays a key role in regulating the pluripotent state in embryonic stem cells and MYC is an essential downstream target (Adler A. S., et al., *Cancer Res.* 2012 72(8):2129-39). Moreover, CDK8 expression is required to maintain embryonic stem cells in an undifferentiated state.

The pivotal role of CDKs in co-ordinating and driving the cell cycle in proliferating cells is proven, as are the biochemical pathways they are involved in. Specifically, as discussed above, it has been shown that CDK8 is linked to certain cancers. Given that there is a significant medical need for a targeted treatment of certain cancers, it is clearly of benefit to develop CDK8 inhibitors specifically.

Antimitotic treatments are also used to target cancer. Unfortunately, resistance to mitotic poisons is a recurrent problem in the clinic and new antimitotic therapies have demonstrated limited clinical responses probably due to the need for sustained exposures through a number of cell cycles or time in mitosis to elicit the maximum therapeutic response.

Haspin inhibitors could behave as strong mitotic cell death enhancers. Haspin inhibition of phosphorylation of histone H3 inhibits Survivin promoted chromosomal passenger complex (CPC) formation producing defects in chromosome segregation and cytokinesis. It is known that Survivin represses mitotic cell death (MCD). Therefore Haspin inhibition could be an indirect way to inhibit Survivin in mitosis.

Haspin (also known as germ cell-specific gene 2 protein/ GSG2 or haploid germ cell-specific nuclear protein kinase) is a serine/threonine kinase (Tanaka H, et al., *FEBS Lett.* 1994, 355(1):4-10; Tanaka H et al., *J Biol Chem.* 1999, 274(24):17049-57; and Higgins J M, *Gene* 2001, 267(1): 55-69). Haspin activity is restricted to mitosis. Haspin is most strongly expressed in testes, but also appears ubiquitously present in proliferating somatic cells (Higgins J M, *Gene* 2001, 267(1):55-69). Unlike mitotic kinases such as Aurora B and PLK1 that are degraded at the end of mitosis, human haspin is expressed at near-constant levels throughout the cell cycle (Dai J, et al., *Genes Dev.* 2005, 19(4):472-88).

In Huertas D, et al., *Oncogene* 2012, 31(11):1408-18, Haspin inhibitor CHR-6494 was shown to reduce H3T3ph in tumoral cells from colon, breast and cervix in a dose dependent manner and cause a mitotic catastrophe with a characteristic spindle and centrosome phenotype. The phosphorylation of H3T3 is crucial for the recruitment of Aurora-B to centromeres and its upstream activation (Kelly A. E., et al. *Science* (2010) 330(6001):235-9; Wang F., et al. *Science* (2010) 330(6001):231-5). H3T3ph is directly recognized by Survivin which is a member of the chromosomal passenger complex (CPC). This binding mediates recruitment of the CPC to chromosomes and activation of its kinase subunit Aurora B to ensure accurate cell division regulating kinetochore-microtubule attachments. It also establishes a positive feedback loop in which Aurora B further increases the kinase activity of Haspin (Wang F, et al. *Curr. Biol.* (2011) 21(12):1061-9). Modulation of phosphorylated H3T3 after synchronization or in normal growth conditions can be used to evaluate cellular Haspin kinase inhibition.

The identification of compounds that inhibit the activity of CDK8 and/or haspin represents a desirable drug design approach for the needed development of pharmacological agents for the treatment of diseases associated with CDK8 and/or Haspin.

For the treatment of cancer, targeted therapies are becoming more important. That is, therapy that has the effect of interfering with specific target molecules that are linked to tumour growth and/or carcinogenesis. Such therapy may be more effective than current treatments (e.g. chemotherapy) and less harmful to normal cells (e.g. because chemotherapy has the potential to kill normal cells as well as cancerous cells). This, and also the fact that targeted therapies may be selective (i.e. it may inhibit a certain targeted molecule more selectively as compared to other molecular targets, e.g. as described hereinafter), may have the benefit of reducing side effects and may also have the benefit that certain specific cancers can be treated (also selectively). The latter may in turn also reduce side effects.

Hence, it is a clear goal of current oncologists to develop targeted therapies (e.g. ones that are selective). In this respect, it should be pointed out that several different molecular targets may exist that are linked to certain diseases (e.g. cancer). However, one simply cannot predict if a therapy (e.g. a small molecule as a therapeutic) that interferes with or inhibits one target molecule could inhibit a different molecular target (be it one that will ultimately have the effect of treating the same disease or a different one).

Targeted therapies (such as CDK8 and/or haspin targeted therapy) could potentially have other advantages over current anti-cancer treatments, for instance because it may not directly interact with DNA (compared to certain known anti-tumour therapies) and should therefore reduce the risk of secondary tumour development.

Polycyclic compounds that are potentially useful as MAP-KAP-K2 inhibitors are disclosed in Revesz L. et al. *Bioorg. Med. Chem. Lett.* 20 (2010) 4719-4723, and T.-J. Wang et al. *Med. Chem. Res.* (2013) 22:4818-4829. The compounds disclosed therein generally contain a tetracyclic core.

Compounds that are purportedly useful as CDK8 inhibitors are disclosed in WO 2014/154723. In the polycyclic compounds disclosed therein, the rings are not fused together but are coupled together via single bonds.

Pyrrolo-[2,3-f]-isoquinoline and dihydropyrroloisoquinoline compounds which are potentially useful as Cdc7 and AKT inhibitors are disclosed in WO 2008/065054. Tricyclic compounds which may be negative allosteric modulators of metabotropic receptors-subtype 5 are disclosed in WO 2010/049366. Polycyclic compounds which are potentially useful as PI3K inhibitors are disclosed in WO 2011/058149. None of these compounds are disclosed as being useful as CDK8 or haspin inhibitors, and the structures of these compounds differ in a number of ways from the compounds disclosed herein.

The listing or discussion of an apparently prior-published document in this specification should not necessarily be taken as an acknowledgement that the document is part of the state of the art or is common general knowledge.

DISCLOSURE OF THE INVENTION

According to the invention, there is provided a compound of formula I,

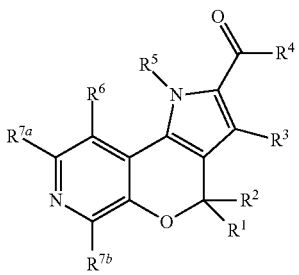

wherein:

$R^1$ and $R^2$ each independently represents hydrogen, $C_{1-12}$ alkyl, $C_{3-12}$ cycloalkyl or heterocycloalkyl (which latter three groups are optionally substituted by one or more substituents selected from =O and $Q^1$), provided that at least one of $R^1$ and $R^2$ is not hydrogen; or $R^1$ and $R^2$ may be linked together to form (e.g. along with the carbon atom to which they are both attached) a 3- to 12- (e.g. 3- to 8-) membered ring, optionally containing one or more heteroatoms (for example, one or more heteroatoms selected from oxygen, nitrogen and sulfur), optionally containing one or more unsaturations (e.g. double bonds), and which ring is optionally substituted by one or more substituents selected from =O, =S, =N($R^{20}$) and $E^1$;

$R^3$ represents hydrogen, halo, —CN, $C_{1-12}$ alkyl (optionally substituted by one or more $Q^2$ groups), $C_{3-12}$ cycloalkyl, heterocycloalkyl (which latter two groups are optionally substituted by one or more substituents selected from =O and $Q^3$), aryl or heteroaryl (which latter two groups are optionally substituted by one or more $Q^4$ groups);

$R^4$ represents —N($R^{40}$)$R^{41}$ or —O$R^{42}$;

$R^5$ represents hydrogen, $C_{1-12}$ alkyl, —C(O)—$C_{1-12}$ alkyl or —C(O)O—$C_{1-12}$ alkyl, which latter three groups are optionally substituted by one or more $Q^5$ groups;

$R^6$ represents hydrogen, halo, —CN, —N($R^{60}$)$R^{61}$, $C_{1-12}$ alkyl, $C_{3-12}$ cycloalkyl, heterocycloalkyl (which latter three groups are optionally substituted by one or more substituents selected from =O and $Q^6$), aryl or heteroaryl (which latter two groups are optionally substituted by one or more $Q^7$ groups);

$R^{7a}$ and $R^{7b}$ each independently represents hydrogen, halo, —N($R^{70}$)$R^{71}$ or —C(O)N($R^{72}$)$R^{73}$;

each $R^{20}$, $R^{40}$, $R^{41}$, $R^{42}$, $R^{60}$ and $R^{61}$ independently represents, on each occasion when used herein, hydrogen, $C_{1-6}$ alkyl, $C_{3-6}$ cycloalkyl, heterocycloalkyl (which latter three groups are optionally substituted by one or more substituents selected from $E^2$ and =O), aryl or heteroaryl (which latter two groups are optionally substituted by one or more substituents selected from $E^3$); or any relevant pair of $R^{40}$, $R^{41}$, $R^{60}$ and $R^{61}$ may (for example, when attached to the same atom) be linked together to form (e.g. along with the requisite nitrogen atom to which they may be attached) a 4- to 12- (e.g. 4- to 8-) membered ring, optionally containing one or more heteroatoms (for example, in addition to those that may already be present, e.g. (a) heteroatom(s) selected from oxygen, nitrogen and sulfur), optionally containing one or more unsaturations (e.g. triple or, preferably, double bonds), and which ring is optionally substituted by one or more substituents selected from $E^4$;

each $R^{70}$, $R^{71}$, $R^{72}$ and $R^{73}$ independently represents, on each occasion when used herein, hydrogen or $C_{1-3}$ alkyl optionally substituted by one or more halo atoms;

each $Q^1$, $Q^2$, $Q^3$, $Q^4$, $Q^5$, $Q^6$ and $Q^7$ independently represents, on each occasion when used herein:

halo, —CN, —N($R^{80}$)$R^{81}$, —O$R^{80}$, —C(=Y)—$R^{80}$, —C(=Y)—O$R^{80}$, —C(=Y)N($R^{80}$)$R^{81}$, —OC(=Y)—$R^{80}$, —OC(=Y)—O$R^{80}$, —OC(=Y)N($R^{80}$)$R^{81}$, —OS(O)$_2$O$R^{80}$, —OP(=Y)(O$R^{80}$)(O$R^{81}$), —OP(O$R^{80}$)(O$R^{81}$), —N($R^{82}$)C(=Y)$R^{81}$, —N($R^{82}$)C(=Y)O$R^{81}$, —N($R^{82}$)C(=Y)N($R^{80}$)$R^{81}$, —NR$^{82}$S(O)$_2$R$^{80}$, —NR$^{82}$S(O)$_2$N($R^{80}$)$R^{81}$, —S(O)$_2$N($R^{80}$)$R^{81}$, —SC(=Y)$R^{80}$, —SC(=Y)O$R^{80}$, —SC(=Y)N($R^{80}$)$R^{81}$, —S(O)$_2$$R^{80}$, —S$R^{80}$, —S(O)$R^{80}$, —S(O)$_2$O$R^{80}$, $C_{1-12}$ alkyl, $C_{3-12}$ cycloalkyl, heterocycloalkyl (which latter three groups are optionally substituted by one or more substituents selected from =O and $E^5$), aryl or heteroaryl (which latter two groups are optionally substituted by one or more substituents selected from $E^6$);

each $E^1$, $E^2$, $E^3$, $E^4$, $E^5$ and $E^6$ independently represents, on each occasion when used herein:

(i) $Q^8$;

(ii) $C_{1-6}$ alkyl, $C_{3-6}$ cycloalkyl or heterocycloalkyl, each of which is optionally substituted by one or more substituents selected from =O and $Q^9$; or (iii) aryl or heteroaryl, both of which are optionally substituted by one or more $Q^{10}$ groups;

each $Q^8$, $Q^9$ and $Q^{10}$ independently represents, on each occasion when used herein:

halo, —CN, —N($R^{83}$)$R^{84}$, —O$R^{83}$, —C(=$Y^a$)—$R^{83}$, —C(=$Y^a$)—O$R^{83}$, —C(=$Y^a$)N($R^{83}$)$R^{84}$, —N($R^{85}$)C(=$Y^a$)$R^{84}$, —NR$^{85}$S(O)$_2$R$^{83}$, —S(O)$_2$R$^{83}$, —S$R^{83}$, —S(O)$R^{83}$, $C_{1-6}$ alkyl or aryl, wherein the latter two groups are optionally substituted by one or more fluoro atoms;

each Y and $Y^a$ independently represents, on each occasion when used herein, =O or =S;

each $R^{80}$, $R^{81}$, $R^{82}$, $R^{83}$, $R^{84}$ and $R^{85}$ independently represents, on each occasion when used herein, hydrogen or $C_{1-6}$ alkyl optionally substituted by one or more substituents selected from fluoro, —O$R^{90}$ and —N($R^{91}$)$R^{92}$; and $R^{90}$, $R^{91}$ and $R^{92}$ independently represent hydrogen or $C_{1-6}$ alkyl optionally substituted by one or more fluoro atoms;

or a pharmaceutically acceptable ester, amide, solvate or salt thereof, which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of such an ester or amide, and solvates of such an ester, amide or salt. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of formula I may have an appropriate group, for example an acid group, converted to the appropriate ester or amide. For example, pharmaceutically acceptable esters (of carboxylic acids) that may be mentioned include optionally substituted $C_{1-6}$ alkyl, $C_{5-10}$ aryl and/or $C_{5-10}$ aryl-$C_{1-6}$ alkyl-esters. Optional substituents in this context include, but are not limited to, halogen atoms. Pharmaceutically acceptable amides (of carboxylic acids) that may be mentioned include those of the formula —C(O) N($R^{z1}$)$R^{z2}$, in which $R^{z1}$ and $R^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched. Optional substituents in this context include, but are not limited to, halogen atoms.

Preferably, specific esters and amides of compounds of the invention that may be mentioned include esters and amides of compounds of the invention.

Further compounds of the invention that may be mentioned include carbamate, carboxamido or ureido derivatives, e.g. such derivatives of existing amino functional groups.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention. For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise stated, the terms $C_{1-q}$ alkyl and $C_{1-q}$ alkylene (where q is the upper limit of the range) defined herein may be straight-chain or, when there is a sufficient number of carbon atoms, be branched-chain, saturated or unsaturated (so forming, for example, an alkenyl or alkynyl group).

$C_{3-q}$ cycloalkyl groups (where q is the upper limit of the range) that may be mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double or triple bonds (forming for example a cycloalkenyl or cycloalkynyl group). Substituents may be attached at any point on the cycloalkyl group. Further, where there is a sufficient number (i.e. a minimum of four) such cycloalkyl groups may also be part cyclic. For the avoidance of doubt, optional substituents may also be other cyclic groups, which may be attached via a single carbon atom common to both rings, so forming a spiro-cycle.

The term "halo", when used herein, includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between five and ten. Such heterocycloalkyl groups may also be bridged. Further, such heterocycloalkyl groups may be saturated or unsaturated containing one or more double and/or triple bonds, forming for example a $C_{2-q}$-heterocycloalkenyl (where q is the upper limit of the range) or a $C_{7-q}$-heterocycloalkynyl group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form (i.e. those heteroatoms may be substituted with one or two =O substituents, as appropriate). As stated herein other carbon atoms of the heterocycloalkyl groups mentioned herein may also be substituted by one or more =O substituents. For the avoidance of doubt, optional substituents may also be other cyclic groups, which may be attached via a single carbon atom common to both rings (so forming a spiro cycle).

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-10}$ aryl groups. Such groups may be monocyclic, bicyclic or tricyclic and have between 6 and 10 ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. However, when aryl groups are bicyclic or tricyclic, they are linked to the rest of the molecule via an aromatic ring. For the avoidance of doubt, optional substituents include those defined herein and also include =O substituents that may be attached to any non-aromatic rings of a polycyclic (e.g. bicyclic) aryl group (however, in an embodiment, =O substituents are not included). For the avoidance of doubt, optional substituents may also be other cyclic groups, which may be, when attached to a non-aromatic ring of an aryl group, attached via a single carbon atom common to both rings (so forming a spiro-cycle).

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 10 members and may be monocyclic or bicyclic, provided that at least one of the rings is aromatic (so forming, for example, a mono-, bi-, or tricyclic heteroaromatic group). However, when heteroaryl groups are bicyclic or tricyclic, they are linked to the rest of the molecule via an aromatic ring. Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazi-olyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. For the avoidance of doubt, optional substituents include those defined herein and also include =O substituents that may be attached to any non-aromatic rings of a polycyclic (e.g. bicyclic) heteroaryl group (but, in an embodiment, =O substituents are not included). For the avoidance of doubt, optional substituents may also be other cyclic groups, which may be, when attached to a non-aromatic ring of a heteroaryl group, attached via a single carbon atom common to both rings (so forming a spiro-cycle). The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form.

It may be specifically stated that the heteroaryl group is monocyclic or bicyclic. In the case where it is specified that the heteroaryl is bicyclic, then it may be consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulphur.

For the avoidance of doubt, in cases in which the identity of two or more substituents in a compound of the invention may be the same, the actual identities of the respective substituents are not in any way interdependent. For example, in the situation in which there is more than one $Q^1$ substituent present, then those $Q^1$ substituents may be the same or different. Further, in the case where there are two $Q^1$ substituents present, in which one represents —$OR^{70}$ and the other represents —$C(O)$—$R^{70}$, then those $R^{70}$ groups are not to be regarded as being interdependent.

For the avoidance of doubt, in the instance where cyclic substituents (e.g. cycloalkyl or heterocycloalkyl groups) are present on groups (such as alkyl groups), then those cyclic substituents may be attached to the same carbon atom, so forming for example a spiro-cyclic group.

All individual features (e.g. preferred features) mentioned herein may be taken in isolation or in combination with any other feature (including a preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

For the avoidance of doubt, when a term such as "$R^{80}$ to $R^{85}$" is employed herein, this will be understood by the skilled person to mean $R^{80}$, $R^{81}$, $R^{82}$, $R^{83}$, $R^{84}$ and $R^{85}$, inclusively.

In the compounds of the invention, at least one of $R^1$ and $R^2$ represents a group other than hydrogen. In a preferred embodiment, neither $R^1$ nor $R^2$ represents hydrogen.

In a further embodiment, $R^1$ and $R^2$ may independently represent $C_{1-12}$ alkyl, $C_{3-12}$ cycloalkyl or heterocycloalkyl (each of which is optionally substituted as defined above); or $R^1$ and $R^2$ may be linked together to form a 3- to 12- (e.g. 3- to 8-) membered ring, optionally containing one or more heteroatoms, optionally containing one or more unsaturations, and which ring is optionally substituted as defined above.

In a particular embodiment, $R^1$ and $R^2$ independently represent hydrogen, $C_{1-6}$ alkyl, $C_{3-6}$ cycloalkyl or a 3- to 6-membered heterocycloalkyl group (each of which is optionally substituted as defined above), provided that at least one of $R^1$ and $R^2$ is not hydrogen; or $R^1$ and $R^2$ may be linked together to form a 3- to 6-membered ring, optionally containing one or two heteroatoms (wherein the heteroatoms are selected from oxygen, nitrogen and sulphur), optionally containing one or two double bonds, and which ring is optionally substituted as defined above.

In another particular embodiment, $R^1$ and $R^2$ independently represent $C_{1-6}$ alkyl, $C_{3-6}$ cycloalkyl or a 3- to 6-membered heterocycloalkyl group (each of which is optionally substituted as defined above); or $R^1$ and $R^2$ may be linked together to form a 3- to 6-membered ring, optionally containing one or two heteroatoms (wherein the heteroatoms are selected from oxygen, nitrogen and sulphur), optionally containing one or two double bonds, and which ring is optionally substituted as defined above.

In a further embodiment, $R^1$ and $R^2$ independently represent $C_{1-6}$ alkyl, $C_{3-6}$ cycloalkyl or a 3- to 6-membered heterocycloalkyl group (each of which is optionally substituted as defined above).

In an alternative embodiment, $R^1$ and $R^2$ are linked together to form a 3- to 6-membered ring, optionally containing one or two heteroatoms selected from oxygen, nitrogen and sulphur, optionally containing one or two double bonds, and which ring is optionally substituted as defined above.

In embodiments in which $R^1$ and $R^2$ are linked to form a 3- to 12-membered ring, particular substituents on that ring that may be mentioned include substituents selected from $E^{1a}$, wherein $E^{1a}$ represents (i) halo; (ii) $C_{1-6}$ alkyl, $C_{3-6}$ cycloalkyl or heterocycloalkyl, each of which is optionally substituted by one or more substituents selected from $Q^9$; or (iii) aryl or heteroaryl, both of which are optionally substituted by one or more $Q^{10}$ groups. In particular such embodiments, $E^{1a}$ represents halo, $C_{1-4}$ alkyl (optionally substituted by one or more halo and phenyl groups) or $C_{3-6}$ cycloalkyl.

In embodiments in which $R^1$ and $R^2$ are linked to form a 3- to 12-membered ring, particular substituents on that ring that may be mentioned include substituents selected from $E^{1a}$, wherein $E^{1a}$ represents (i) halo; (ii) $C_{1-6}$ alkyl, $C_{3-6}$ cycloalkyl or heterocycloalkyl, each of which is optionally substituted by one or more substituents selected from =O and $Q^9$; or (iii) aryl or heteroaryl, both of which are optionally substituted by one or more $Q^{10}$ groups. In particular such embodiments, $E^{1a}$ represents halo, $C_{1-4}$ alkyl (optionally substituted by one or more substituents selected from =O, halo and phenyl) or $C_{3-6}$ cycloalkyl.

In a more particular embodiment, $R^1$ and $R^2$ independently represent $C_{1-3}$ alkyl, a $C_{4-6}$ cycloalkyl, or a 4- to 6-membered heterocycloalkyl group (which latter group is optionally substituted by one or more methyl groups), wherein the heterocycloalkyl group contains one or two heteroatoms selected from nitrogen and oxygen; or $R^1$ and $R^2$ are linked together to form a 4- to 6-membered cycloalkyl or heterocycloalkyl ring, which ring is optionally substituted by one or more $E^{1a}$ groups, wherein the heterocycloalkyl ring contains a heteroatom selected from oxygen and nitrogen, and wherein $E^{1a}$ represents halo, $C_{1-4}$ alkyl (optionally substituted by one or more halo and phenyl groups) or $C_{3-6}$ cycloalkyl.

In a more particular embodiment, $R^1$ and $R^2$ independently represent hydrogen, $C_{1-3}$ alkyl, a $C_{4-6}$ cycloalkyl optionally substituted by one or more halo groups, or a 4- to 6-membered heterocycloalkyl group (which latter group is optionally substituted by one or more methyl groups), wherein the heterocycloalkyl group contains one or two heteroatoms selected from nitrogen and oxygen; or $R^1$ and $R^2$ are linked together to form a 4- to 6-membered cycloalkyl or heterocycloalkyl ring, which ring is optionally substituted by one or more $E^{1a}$ groups, wherein the heterocycloalkyl ring contains a heteroatom selected from oxygen and nitrogen, and wherein $E^{1a}$ represents halo, $C_{1-4}$ alkyl (optionally substituted by one or more substituents selected from =O, halo and phenyl) or $C_{3-6}$ cycloalkyl.

It is preferred that, when $R^1$ and $R^2$ are linked together to form a 4- to 6-membered heterocycloalkyl ring which contains a nitrogen atom, then that nitrogen atom is substituted by $E^1$ (e.g. $E^{1a}$).

In an alternative embodiment, $R^1$ and $R^2$ are linked together to form a 4- to 6-membered heterocycloalkyl ring which contains an unsubstituted nitrogen atom.

In a further embodiment, $R^1$ and $R^2$ independently represent:

hydrogen, cyclopentyl, tetrahydropyranyl, 4,4-difluorocyclohexyl or, particularly, methyl, propyl, cyclohexyl or

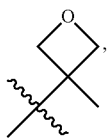 [SMILES: *C1(C)COC1]

provided that at least one of $R^1$ and $R^2$ does not represent hydrogen; or $R^1$ and $R^2$ are linked together to form a ring according to one of the following structures:

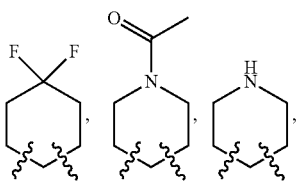

or, particularly,

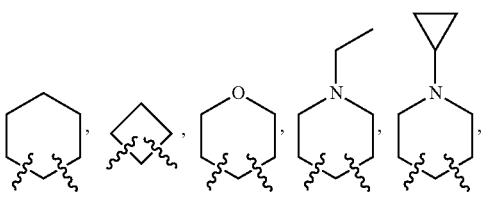

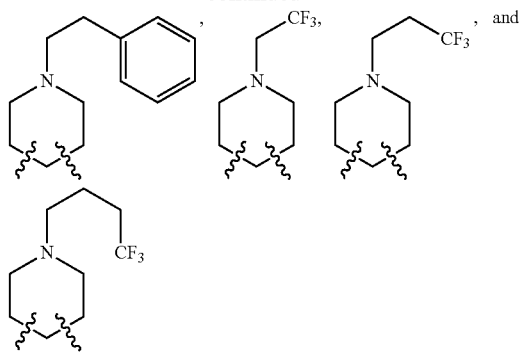

wherein the wavy lines shows the point of attachment of the $R^1$ and $R^2$ groups to the pyran ring, and the vertex enclosed between the wavy lines represents the carbon atom to which $R^1$ and $R^2$ are directly attached.

In a yet further embodiment, $R^1$ and $R^2$ are both methyl.

Particular $R^3$ groups that may be mentioned include hydrogen, halo, $C_{1-6}$ alkyl (optionally substituted by one or more $Q^2$ groups), $C_{3-6}$ cycloalkyl, heterocycloalkyl (which latter two groups are optionally substituted by one or more substituents selected from =O and $Q^3$), and aryl (optionally substituted by one or more $Q^4$ groups).

Particular $R^3$ groups that may be mentioned include hydrogen, halo, $C_{1-6}$ alkyl (optionally substituted by one or more $Q^2$ groups), $C_{3-6}$ cycloalkyl, heterocycloalkyl (which latter two groups are optionally substituted by one or more substituents selected from =O and $Q^3$), aryl (optionally substituted by one or more $Q^4$ groups), and heteroaryl (optionally substituted by one or more $Q^4$ groups).

Further particular $R^3$ groups that may be mentioned include hydrogen, halo, $C_{1-4}$ alkyl, heterocycloalkyl and aryl (optionally substituted by one or more groups selected from halo, $OR^{80}$, $-S(O)_2N(R^{80})R^{81}$, $-S(O)_2R^{80}$, and $C_{1-4}$ alkyl).

Further particular $R^3$ groups that may be mentioned include hydrogen, halo, $C_{1-4}$ alkyl, $C_{3-6}$ cycloalkyl, heterocycloalkyl, heteroaryl and aryl (optionally substituted by one or more groups selected from halo, $OR^{80}$, $-S(O)_2N(R^{80})R^{81}$, $-S(O)_2R^{80}$, and $C_{1-4}$ alkyl optionally substituted by one or more halo groups).

In one embodiment, $R^3$ represents hydrogen, halo, $C_{1-2}$ alkyl, cyclopropyl, a 6-membered heterocycloalkyl, indazolyl, or phenyl (which latter group is optionally substituted by one or more halo, $OCH_3$, OH, $CF_3$ or $-S(O)_2NH_2$ groups). For example, $R^3$ may represent H.

Particular groups that may be mentioned in respect of $R^{40}$, $R^{41}$ and $R^{42}$ include hydrogen, $C_{1-6}$ alkyl, $C_{3-6}$ cycloalkyl, heterocycloalkyl (which latter three groups are optionally substituted by one or more substituents selected from $E^2$) or aryl (optionally substituted by one or more substituents selected from $E^3$); or $R^{40}$ and $R^{41}$ may be linked together to form a 4- to 8-membered ring, optionally containing one or more further heteroatoms and/or one or more unsaturations, and which ring is optionally substituted by one or more substituents selected from $E^4$.

Further particular groups that may be mentioned in respect of $R^{40}$, $R^{41}$ and $R^{42}$ include hydrogen, $C_{1-4}$ alkyl, heterocycloalkyl (which latter two groups are optionally substituted by one or more substituents selected from $E^2$) or aryl (optionally substituted by one or more substituents selected from $E^3$); or $R^{40}$ and $R^{41}$ may be linked together to form a 4- to 6-membered ring, optionally containing a further heteroatom selected from oxygen, nitrogen and sulfur, and which ring is optionally substituted by one or more substituents selected from $E^4$.

In one embodiment, $R^{40}$, $R^{41}$ and $R^{42}$ independently represent hydrogen, $C_{1-4}$ alkyl, heterocycloalkyl (which latter two groups are optionally substituted by one or more substituents selected from halo, —O—$C_{1-4}$ alkyl, —C(O)O—$C_{1-4}$ alkyl, and phenyl) or aryl (optionally substituted by one or more halo groups); or $R^{40}$ and $R^{41}$ are linked together to form a 4- to 6-membered ring, optionally containing a further heteroatom selected from oxygen and nitrogen, and which ring is optionally substituted by one or more halo groups.

In a particular embodiment, $R^{40}$, $R^{41}$ and $R^{42}$ independently represent hydrogen, $C_{1-3}$ alkyl, a 6-membered heterocycloalkyl group (which latter two groups are optionally substituted by one or more substituents selected from halo, —O—$C_{1-4}$ alkyl, —C(O)O—$C_{1-4}$ alkyl, and phenyl) or aryl; or $R^{40}$ and $R^{41}$ are linked together to form a 6-membered ring, optionally containing a further heteroatom selected from oxygen and nitrogen.

In a further preferred embodiment, $R^{40}$, $R^{41}$ and $R^{42}$ independently represent hydrogen or $C_{1-2}$ alkyl, or $R^{40}$ and $R^{41}$ are linked together to form a morpholinyl ring.

Particularly preferred compounds of the invention include those in which $R^{40}$, $R^{41}$ and $R^{42}$ independently represent hydrogen or methyl. Thus particular $R^4$ groups that may be mentioned include —NH$_2$, —N(H)Me, —OH and —OMe.

Particular $R^5$ groups that may be mentioned include hydrogen, $C_{1-6}$ alkyl, —C(O)—$C_{1-6}$ alkyl and —C(O)O—$C_{1-6}$ alkyl, which latter three groups are optionally substituted as defined above.

In one embodiment, $R^5$ represents hydrogen, $C_{1-4}$ alkyl (optionally substituted by one or more groups selected from halo, —O—$C_{1-4}$ alkyl or phenyl), carbobenzyloxy (Cbz), p-methoxybenzyl carbonyl (Moz or MeOZ), tert-butyloxycarbonyl (BOC), acetyl (Ac), benzyl (Bn), p-methoxybenzyl (PMB) or 3,4-dimethoxybenzyl (DMPM).

In a particular embodiment, $R^5$ represents hydrogen or $C_{1-2}$ alkyl optionally substituted by one or more halo atoms or —OMe groups.

In a more particular embodiment, $R^5$ represents hydrogen or methyl.

Particular $R^6$ groups that may be mentioned include hydrogen, halo, —CN, —N($R^{60}$)$R^{61}$, $C_{1-6}$ alkyl, $C_{3-6}$ cycloalkyl, heterocycloalkyl (which latter three groups are optionally substituted as defined above), aryl or heteroaryl (which latter two groups are optionally substituted as defined above).

Further particular $R^6$ groups that may be mentioned include hydrogen, halo, $C_{1-4}$ alkyl (optionally substituted by one or more halo atoms) or aryl (optionally substituted by one or more halo atoms).

In one embodiment, $R^6$ represents hydrogen, halo (e.g. chloro) or aryl. In a further embodiment, $R^6$ represents hydrogen or halo.

Particular $R^{7a}$ and $R^{7b}$ groups that may be mentioned include hydrogen, halo, —NH($R^{70a}$) and —C(O)NHR$^{73a}$, wherein $R^{70a}$ and $R^{73a}$ represent hydrogen or $C_{1-3}$ alkyl (optionally substituted by one or more halo atoms).

In one embodiment, $R^{7a}$ and $R^{7b}$ independently represent hydrogen, halo, —NH$_2$, —C(O)NH$_2$, —NH($R^{70b}$), or —C(O)NHR$^{73b}$, wherein $R^{70b}$ and $R^{73b}$ represent $C_{1-3}$ alkyl.

In particular embodiments, $R^{7a}$ and $R^{7b}$ represent hydrogen or halo. For example, $R^6$, $R^{7a}$ and $R^{7b}$ may each independently represents hydrogen or halo.

In another embodiment of the invention, there is provided compounds of the invention as hereinbefore defined but in which:

$R^1$ and $R^2$ each independently represent a $C_{1-3}$ alkyl group, a $C_{4-6}$ cycloalkyl group or a heterocycloalkyl group optionally substituted by a $Q^1$ group; or $R^1$ and $R^2$ may be linked together to form a 4- to 6-membered ring, optionally containing one or more heteroatoms (for example, one or more heteroatoms selected from oxygen and nitrogen), which ring is optionally substituted by one or more substituents selected from $E^1$;

$R^3$ represents hydrogen, halo, $C_{1-2}$ alkyl, a 6-membered heterocycloalkyl group or aryl (which latter group is optionally substituted by one or more $Q^4$ groups);

$R^4$ represents —N($R^{40}$)$R^{41}$ or —OR$^{42}$;

$R^5$ represents hydrogen or $C_{1-3}$ alkyl optionally substituted by one or more $Q^5$ groups;

$R^6$ represents hydrogen, halo or aryl;

$R^{7a}$ and $R^{7b}$ each independently represents hydrogen or halo;

each $R^{40}$, $R^{41}$ and $R^{42}$ independently represents hydrogen, $C_{1-3}$ alkyl, heterocycloalkyl (which latter two groups are optionally substituted by one or more $E^2$ groups), or aryl optionally substituted by one or more $E^3$ groups; or $R^{40}$ and $R^{41}$ may be linked together to form a 6-membered ring optionally containing one or more heteroatoms (e.g. heteroatoms selected from oxygen and nitrogen);

each $Q^1$, $Q^4$ and $Q^5$ independently represents, on each occasion when used herein, halo, —OR$^{80}$, —S(O)$_2$N($R^{80}$)$R^{81}$, $C_{1-2}$ alkyl, or aryl;

each $E^1$, $E^2$ and $E^3$ independently represents, on each occasion when used herein:

(i) $Q^8$;

(ii) $C_{1-4}$ alkyl or $C_3$ cycloalkyl, each of which is optionally substituted by one or more $Q^9$ groups; or (iii) aryl;

each $Q^8$ and $Q^9$ independently represents, on each occasion when used herein:

halo, —OR$^{83}$, —C(O)—OR$^{83}$ or aryl; and each $R^{80}$, $R^{81}$ and $R^{83}$ independently represents, on each occasion when used herein:

hydrogen or $C_{1-4}$ alkyl.

In another embodiment of the invention, there is provided compounds of the invention as hereinbefore defined but in which:

$R^1$ and $R^2$ each independently represent a hydrogen, $C_{1-3}$ alkyl group, a $C_{4-6}$ cycloalkyl group optionally substituted by a $Q^1$ group or a heterocycloalkyl group optionally substituted by a $Q^1$ group, provided that at least one of $R^1$ and $R^2$ is not hydrogen; or $R^1$ and $R^2$ may be linked together to form a 4- to 6-membered ring, optionally containing one or more heteroatoms (for example, one or more heteroatoms selected from oxygen and nitrogen), which ring is optionally substituted by one or more substituents selected from $E^1$;

$R^3$ represents hydrogen, halo, $C_{1-2}$ alkyl, $C_3$ cycloalkyl, a 6-membered heterocycloalkyl group, heteroaryl or aryl (which latter group is optionally substituted by one or more $Q^4$ groups);

$R^4$ represents —N($R^{40}$)$R^{41}$ or —OR$^{42}$;

$R^5$ represents hydrogen or $C_{1-3}$ alkyl optionally substituted by one or more $Q^5$ groups;

$R^6$ represents hydrogen, halo or aryl;

$R^{7a}$ and $R^{7b}$ each independently represents hydrogen or halo;

each $R^{40}$, $R^{41}$ and $R^{42}$ independently represents hydrogen, $C_{1-3}$ alkyl, heterocycloalkyl (which latter two groups are optionally substituted by one or more $E^2$ groups), or aryl optionally substituted by one or more $E^3$ groups; or $R^{40}$ and $R^{41}$ may be linked together to form a 6-membered ring optionally containing one or more heteroatoms (e.g. heteroatoms selected from oxygen and nitrogen);

each $Q^1$, $Q^4$ and $Q^5$ independently represents, on each occasion when used herein, halo, —$OR^{80}$, —$S(O)_2N(R^{80})R^{81}$, $C_{1-2}$ alkyl optionally substituted by one or more halo atoms, or aryl;

each $E^1$, $E^2$ and $E^3$ independently represents, on each occasion when used herein:
(i) $Q^8$;
(ii) $C_{1-4}$ alkyl or $C_3$ cycloalkyl, each of which is optionally substituted by one or more substituents selected from =O and $Q^9$; or
(iii) aryl;

each $Q^8$ and $Q^9$ independently represents, on each occasion when used herein:
halo, —$OR^{83}$, —C(O)—$OR^{83}$ or aryl; and each $R^{80}$, $R^{81}$ and $R^{83}$ independently represents, on each occasion when used herein:
hydrogen or $C_{1-4}$ alkyl.

In a further embodiment of the invention, there is provided compounds of the invention as hereinbefore defined but in which:

$R^1$ and $R^2$ each independently represents hydrogen, a $C_{1-3}$ alkyl group, a $C_{4-6}$ cycloalkyl group, or a 4- to 6-membered heterocycloalkyl group (which latter group is optionally substituted by a methyl group), provided that at least one of $R^1$ and $R^2$ is not hydrogen; or $R^1$ and $R^2$ are linked together to form a 4- to 6-membered ring, optionally containing one or more heteroatoms (for example, one or more heteroatoms selected from oxygen and nitrogen), which ring is optionally substituted by one or more $E^1$ groups;

$R^3$ represents hydrogen, halo, $C_{1-2}$ alkyl, cyclopropyl, 6-membered heterocycloalkyl or aryl (which latter group is optionally substituted by one or more halo, OH, $CF_3$, $OCH_3$ or —$S(O)_2NH_2$ groups);

$R^4$ represents —$N(R^{40})R^{41}$ or —$OR^{42}$;

$R^5$ represents hydrogen, methyl or ethyl (which latter two groups are optionally substituted by one or more halo or $OCH_3$ groups);

$R^6$ represents hydrogen, halo or aryl;

$R^{7a}$ and $R^{7b}$ each independently represents hydrogen or halo;

each $R^{40}$, $R^{41}$ and $R^{42}$ independently represents, on each occasion when used herein, hydrogen or $C_{1-2}$ alkyl (which latter group is optionally substituted by one or more $E^2$ groups); or $R^{40}$ and $R^{41}$ may be linked together to form a morpholine ring; and each $E^1$ and $E^2$ independently represents, on each occasion when used herein:
(i) halo;
(ii) $C_{1-4}$ alkyl optionally substituted by one or more groups selected from halo, =O and phenyl; or
(iii) aryl.

In a further embodiment of the invention, there is provided compounds of the invention as hereinbefore defined but in which:

$R^1$ and $R^2$ independently represent hydrogen, a $C_{1-3}$ alkyl group, a 6-membered heterocycloalkyl group or a $C_{4-6}$ cycloalkyl group, provided that at least one of $R^1$ and $R^2$ is not hydrogen; or $R^1$ and $R^2$ are linked together to form a 4- to 6-membered ring, optionally containing one or more heteroatoms (for example, one or more heteroatoms selected from oxygen and nitrogen), which ring is optionally substituted by one or more $E^1$ groups;

$R^3$ represents hydrogen, halo, $C_{1-2}$ alkyl, cyclopropyl, a 6-membered heterocycloalkyl group (e.g. dihydropyranyl) or aryl (which latter group is optionally substituted by one or more $OCH_3$, $CF_3$ or —$S(O)_2NH_2$ groups);

$R^4$ represents —$N(R^{40})R^{41}$ or —$OR^{42}$;

$R^5$ represents hydrogen, methyl or ethyl (which latter two groups are optionally substituted by one or more halo or —$OCH_3$ groups);

$R^6$ represents hydrogen or halo;

$R^{7a}$ and $R^{7b}$ represent hydrogen;

$R^{40}$, $R^{41}$ and $R^{42}$ each independently represents hydrogen or methyl; and $E^1$ represents $C_{1-2}$ alkyl optionally substituted by one or more groups selected from halo and =O.

In a further embodiment of the invention, there is provided compounds of the invention as hereinbefore defined but in which:

$R^1$ and $R^2$ independently represent hydrogen, a $C_{1-3}$ alkyl group, a 6-membered heterocycloalkyl group or a cyclohexyl group, provided that at least one of $R^1$ and $R^2$ is not hydrogen; or $R^1$ and $R^2$ are linked together to form a 4- to 6-membered ring, optionally containing one or more heteroatoms (for example, one or more nitrogen or oxygen atoms), which ring is optionally substituted by one or more $E^1$ groups;

$R^3$ represents hydrogen, halo, $C_{1-2}$ alkyl, cyclopropyl, a 6-membered heterocycloalkyl group (e.g. dihydropyranyl) or aryl (which latter group is optionally substituted by one or more $OCH_3$, $CF_3$ or —$S(O)_2NH_2$ groups);

$R^4$ represents —$NH_2$, —OH or —OMe;

$R^5$ represents hydrogen, methyl or ethyl (which latter two groups are optionally substituted by one or more halo or —$OCH_3$ groups);

$R^6$ represents hydrogen or halo; and $R^{7a}$ and $R^{7b}$ represent hydrogen;

$E^1$ represents $C_{1-2}$ alkyl optionally substituted by one or more groups selected from halo and =O.

In a further embodiment of the invention, there is provided compounds of the invention as hereinbefore defined but in which:

$R^1$ and $R^2$ independently represent hydrogen, a $C_{1-3}$ alkyl group, a tetrahydropyranyl group or a cyclohexyl group, provided that at least one of $R^1$ and $R^2$ is not hydrogen; or $R^1$ and $R^2$ are linked together to form a 4- to 6-membered carbocyclic ring or a 6-membered heterocycloalkyl ring, which heterocycloalkyl ring is optionally substituted by one or more $E^1$ groups;

$R^3$ represents hydrogen, halo, cyclopropyl or aryl substituted by one or more —OMe or —$S(O)_2NH_2$ groups;

$R^4$ represents —$NH_2$, —OH or OMe;

$R^5$ represents hydrogen, methyl or ethyl (which latter two groups are optionally substituted by one or more halo or —$OCH_3$ groups);

$R^6$ represents hydrogen or halo;

$R^{7a}$ and $R^{7b}$ represent hydrogen; and $E^1$ represents $C_{1-2}$ alkyl optionally substituted by one or more groups selected from halo and =O.

In another embodiment of the invention, there is provided compounds of the invention as hereinbefore defined but in which:

$R^1$ and $R^2$ each independently represent hydrogen, methyl, ethyl, propyl, cyclohexyl or tetrahydropyranyl, provided that at least one of $R^1$ and $R^2$ is not hydrogen; or $R^1$ and $R^2$ may be linked together to form a 4- to 6-membered ring, optionally containing one or more heteroatoms (for example, one or more heteroatoms selected from oxygen and nitrogen), which ring is optionally substituted by one or more substituents selected from $E^1$;

$R^3$ represents hydrogen, halo, $C_{1-2}$ alkyl, cyclopropyl, a 6-membered heterocycloalkyl group, heteroaryl or aryl (which latter group is optionally substituted by one or more $Q^4$ groups);

$R^4$ represents $—NH_2$, $—N(H)Me$ or $—OH$;

$R^5$ represents hydrogen or $C_{1-2}$ alkyl optionally substituted by one or more $Q^5$ groups;

$R^6$ represents hydrogen or halo;

$R^{7a}$ and $R^{7b}$ represent hydrogen;

each $Q^4$ and $Q^5$ independently represents, on each occasion when used herein, halo, $—CF_3$, $—OR^{80}$ or $—S(O)_2N(R^{80})R^{81}$;

each $E^1$ represents $C_{1-2}$ alkyl optionally substituted by one or more $Q^9$ groups;

$Q^9$ represents halo or aryl; and $R^{80}$ and $R^{81}$ independently represent hydrogen or methyl.

In a further embodiment of the invention, there is provided compounds of the invention as hereinbefore defined but in which:

$R^1$ and $R^2$ each independently represent hydrogen, $C_{1-3}$ alkyl or cyclohexyl, provided that at least one of $R^1$ and $R^2$ is not hydrogen; or $R^1$ and $R^2$ are linked together to form a 4- to 6-membered ring optionally containing one or two heteroatoms selected from oxygen and nitrogen, which ring is optionally substituted by one or more substituents selected from $E^1$;

$R^3$ represents hydrogen, halo, $C_{1-2}$ alkyl, cyclopropyl or aryl;

$R^4$ represents $—NH_2$ or $—OH$;

$R^5$ represents hydrogen, methyl or ethyl (which latter two groups are optionally substituted by one or more halo groups);

$R^6$ represents hydrogen or halo;

$R^{7a}$ and $R^{7b}$ each represent hydrogen; and $E^1$ represents $C_{1-2}$ alkyl optionally substituted by one or more halo groups.

Particularly preferred compounds are those which are selective for CDK8 inhibition and/or haspin inhibition (preferably CDK8 inhibition). Selectivity for inhibition of a certain kinase may be determined via the relative inhibitory concentrations of a given compound against different kinases. A compound may be considered to be selective for a first kinase over a second kinase if the $IC_{50}$ value for the second kinase is at least 30 times larger (or preferably at least 100 times larger) than the $IC_{50}$ value for the first kinase. Preferred compounds are those which are capable of inhibiting CDK8 and/or CDK8 and haspin to a greater extent than any other kinase (e.g. wherein the $IC_{50}$ value for the other kinase is at least 30 times larger (or preferably at least 100 times larger) than the $IC_{50}$ value for CDK8 and/or haspin.

In another embodiment of the invention, there is provided compounds of the invention as hereinbefore defined but in which:

$R^1$ and $R^2$ each independently represent hydrogen, methyl, cyclohexyl or tetrahydropyranyl, provided that at least one of $R^1$ and $R^2$ is not hydrogen; or $R^1$ and $R^2$ may be linked together to form a cyclohexyl, tetrahydropyranyl or piperidinyl ring, optionally wherein said piperidinyl ring is substituted by a $C_{1-2}$ alkyl group or a fluorinated $C_{1-2}$ alkyl group;

$R^3$ represents hydrogen or aryl (which latter group is optionally substituted by one or more $Q^4$ groups);

$R^4$ represents $—NH_2$, $N(H)R^{40}$ or $—OH$;

$R^5$ represents hydrogen or $C_{1-2}$ alkyl optionally substituted by one or more $Q^5$ groups;

$R^6$, $R^{7a}$ and $R^{7b}$ represent hydrogen;

$R^{40}$ represents a $C_{1-2}$ alkyl group or a fluorinated $C_{1-2}$ alkyl group;

each $Q^4$ and $Q^5$ independently represents halo, $—OR^{80}$ or $—S(O)_2N(R^{80})R^{81}$; and each $R^{80}$ and $R^{81}$ independently represents, on each occasion when used herein, hydrogen or methyl.

The compound of Example 30, as defined below, is particularly preferred in view of the high CDK8 selectivity associated with that compound.

Certain compounds, such as the compound of Example 12 as defined below, show selectivity for Haspin over CDK8, and are also of interest.

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I which process comprises:

(i) for compounds of formula I in which $R^6$ represents an aryl or heteroaryl group (optionally substituted as hereinbefore defined), reaction of a corresponding compound of formula II,

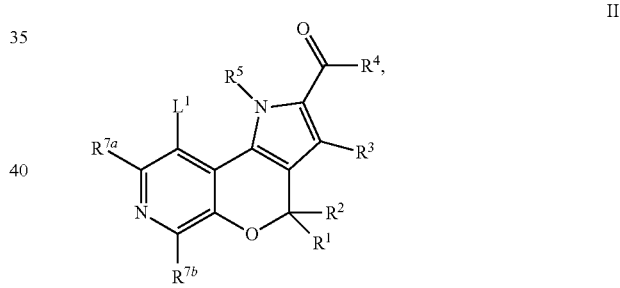

II wherein $L^1$ represents a suitable leaving group such as iodo, bromo, chloro or a sulfonate group (e.g. $—OS(O)_2CF_3$, $—OS(O)_2CH_3$ or $—OS(O)_2PhMe$) (most preferably $L^1$ represents iodo), and $R^1$, $R^2$, $R^3$, $R^4$, $R^5$, $R^{7a}$ and $R^{7b}$ are as hereinbefore defined, with a compound of formula III, $L^2-R^6$     III wherein $L^2$ represents a suitable group such as $—B(OH)_2$, $—B(OR^{wx})_2$ or $—Sn(R^{wx})_3$, in which each $R^{wx}$ independently represents a $C_{1-6}$ alkyl group, or, in the case of $—B(OR^{wx})_2$, the respective $R^{wx}$ groups may be linked together to form a 4- to 6-membered cyclic group (such as a 4,4,5,5-tetramethyl-1,3,2-dioxaborolan-2-yl group), and $R^6$ is an aryl or heteroaryl group (optionally substituted as hereinbefore defined; most preferably $L^2$ represents $—B(OR^{wx})_2$). This reaction may be performed, for example in the presence of a suitable catalyst system, e.g. a metal (or a salt or complex thereof) such as CuI, Pd/C, $PdCl_2$, $Pd(OAc)_2$, $Pd(Ph_3P)_2Cl_2$, $Pd(Ph_3P)_4$ (i.e. palladium tetrakistriphenylphosphine), $Pd_2(dba)_3$ or $NiCl_2$ and a ligand such as $t-Bu_3P$, $(C_6H_{11})_3P$, $Ph_3P$, $AsPh_3$, $P(o-Tol)_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenyl-phosphino)propane, xantphos, or a mixture thereof, together with a suitable base such as, $Na_2CO_3$, $K_3PO_4$, $Cs_2CO_3$, NaOH, KOH, $K_2CO_3$, CsF, $Et_3N$, $(i-Pr)_2NEt$, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran, dimethoxyethane (DME) or mixtures thereof (preferably a polar aprotic solvent is employed, e.g. dioxane or DME). The reaction may also be carried out for example at room temperature or above (e.g. at a high temperature such as the reflux temperature of the solvent system). The reaction may also be carried out under microwave irradiation reaction conditions, for example at elevated temperature (e.g. at above 100° C., such as at about 135 to 140° C.). Alternative $L^1$ groups that may be mentioned include alkali metal groups (e.g. lithium) and halo groups, which may be converted to a magnesium halide (i.e. a Grignard reagent), in which the magnesium may undergo a 'trans-metallation' reaction, thereby being exchanged with, for example, zinc;

(ii) for compounds of formula I in which wherein $R^3$ and $R^5$ are both hydrogen and $R^4$ represents $OR^{42}$, cyclisation of a corresponding compound of formula IV,

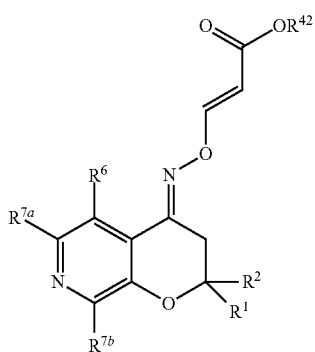

wherein $R^1$, $R^2$, $R^{42}$, $R^6$, $R^{7a}$ and $R^{7b}$ are as hereinbefore defined, under reaction conditions known to those skilled in the art, for example the reaction may be performed at around room temperature or above (e.g. up to 40-180° C.). The reaction may also be carried out under microwave irradiation reaction conditions, for example at elevated temperature (e.g. at above 100° C., such as at about 135 to 140° C.);

(iii) for compounds of formula I in which $R^4$ represents $NH_2$, (a) reaction of a compound of formula I in which $R^4$ represents $—OR^{42}$, wherein $R^{42}$ is as hereinbefore defined provided that $R^{42}$ does not represent hydrogen, with a source of ammonia (e.g. ammonia, ammonium acetate, ammonium bicarbonate or ammonium hydroxide) in the presence of a suitable solvent such as a lower alcohol, dimethylformamide or a mixture thereof; preferably the reaction is carried out with ammonium hydroxide in a methanol/dimethylformamide mixture, at a temperature ranging from about 50° C. to about 100° C.;

(b) reaction of a compound of formula I in which $R^4$ represents $—N(H)CH_2$-aryl (wherein said aryl is optionally substituted as hereinbefore defined), with a suitable deprotecting agent, such as via reaction with trifluoroacetic acid or via reduction in the presence of appropriate reduction reaction conditions (e.g. in the presence of a chemoselective reducing agent such as $LiAlH_4$);

(iv) for compounds of formula I in which $R^4$ represents $—N(R^{40})R^{41}$, wherein $R^{40}$ and $R^{41}$ are as hereinbefore defined, reaction of a corresponding compound of formula I in which $R^4$ represents $OR^{42}$, wherein $R^{42}$ is as hereinbefore defined, with a compound of formula V, $$HN(R^{40})R^{41} \qquad V$$

wherein $R^{40}$ and $R^{41}$ are as hereinbefore defined, under conditions known to those skilled in the art, for example by an amide coupling reaction, i.e. the formation of an amide from a carboxylic acid or ester thereof (i.e. the $—C(O)—OR^{42}$ group), may be converted to a $—C(O)N(R^{40a})R^{41a}$ group (in which $R^{40a}$ and $R^{41a}$ are as hereinbefore defined), and which reaction may (e.g. for —COOH) be performed in the presence of a suitable coupling reagent (e.g. 1,1'-carbonyldiimidazole, N,N'-dicyclohexylcarbodiimide, or the like) or, in the case of an ester (e.g. $—C(O)OCH_3$ or $—C(O)OCH_2CH_3$), be performed in the presence of e.g. trimethylaluminium, or, alternatively the $—C(O)OH$ group may first be activated to the corresponding acyl halide (e.g $—C(O)Cl$, by treatment with oxalyl chloride, thionyl chloride, phosphorous pentachloride, phosphorous oxychloride, or the like), and, in all cases, the relevant compound is reacted with a compound of formula $HN(R^{10a})R^{11a}$ (in which $R^{10a}$ and $R^{11a}$ are as hereinbefore defined), under standard conditions known to those skilled in the art (e.g. optionally in the presence of a suitable solvent, suitable base and/or in an inert atmosphere);

(v) for compounds of formula I in which $R^4$ represents —OH, hydrolysis of a corresponding compound of formula I in which $R^4$ represents $—OR^{42}$, wherein $R^{42}$ is as hereinbefore defined provided that $R^{42}$ does not represent hydrogen, under basic or acidic hydrolysis conditions widely known in the art;

(vi) for compounds of formula I in which $R^5$ represents a $C_{1-12}$ alkyl group (optionally substituted as hereinbefore defined), reaction of a corresponding compound of formula I in which $R^5$ represents hydrogen, with a compound of formula VI, $$L^3-R^5 \qquad VI$$

wherein $R^5$ is as hereinbefore defined, and L wherein $R^5$ represents a $C_{1-12}$ alkyl group (optionally substituted as hereinbefore defined), and $L^3$ represents a suitable leaving group, such as one hereinbefore described in respect of $L^1$, under reaction conditions such as in the presence of an appropriate metal catalyst (or a salt or complex thereof) such as Cu, $Cu(OAc)_2$, CuI (or CuI/diamine complex), copper tris(triphenylphosphine)bromide, $Pd(OAc)_2$, tris(dibenzylideneacetone)-dipalladium(0) ($Pd_2(dba)_3$) or $NiCl_2$ and an optional additive such as $Ph_3P$, 2,2'-bis(diphenylphosphino)-1,1'-binaphthyl, xantphos, NaI or an appropriate crown ether such as 18-crown-6-benzene, in the presence of an appropriate base such as NaH, $Et_3N$, pyridine, N,N'-dimethylethylenediamine, $Na_2CO_3$, $K_2CO_3$, $K_3PO_4$, $Cs_2CO_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof). This reaction may be performed at elevated temperature or under microwave irradiation reaction conditions, for example as described in process step (i);

(vii) for compounds of formula I in which $R^3$ represents halo, reaction of a corresponding compound of formula I in which $R^3$ represents hydrogen with a source of halide ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride;

(viii) for compounds of formula I in which R³ represents an alkyl group or an aryl group, reaction of a compound of formula VII,

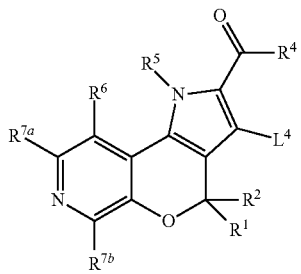

VII wherein R¹, R², R⁴, R⁵, R⁶, R⁷ᵃ and R⁷ᵇ, are as hereinbefore defined, and L⁴ represents a suitable leaving group, such as one hereinbefore described in respect of L¹, with a compound of formula VIII,

L⁵-R³   VIII wherein L⁵ represents a suitable group such as —B(OH)₂, —B(OR^{wx})₂ or —Sn(R^{wx})₃, as hereinbefore defined, and R³ is as hereinbefore defined, under reaction conditions such as those described in respect of process step (i) above; or (ix) for compounds of formula I in which R⁵ represents hydrogen, oxidation of a compound of formula IX,

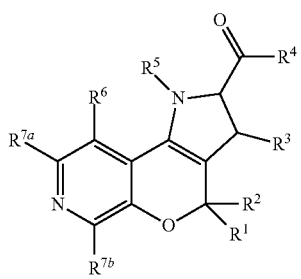

IX wherein R¹, R², R³, R⁴, R⁶, R⁷ᵃ and R⁷ᵇ, are as hereinbefore defined and R⁵ represents hydrogen, under conditions known to those skilled in the art, for example in the presence of a suitable oxidising agent, e.g. DDQ (2,3-dichloro-5,6-dicyano-1,4-benzoquinone), MnO₂ or m-cpba or the like.

Compounds of formulae II, IV, VII and IX (as well as certain other intermediate compounds) are either commercially available, are known in the literature, or may be obtained either by analogy with the processes described herein, or by conventional synthetic procedures, in accordance with standard techniques, from available starting materials using appropriate reagents and reaction conditions. The compounds of the invention may also be isolated in the form of their pharmaceutically acceptable salts, such as those described previously herein.

Compounds of the present invention can be prepared according to the procedures of the following schemes and examples, using appropriate materials, and are further exemplified by the specific examples provided herein below. Moreover, by utilizing the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

Compounds formula (I), and their respective intermediates can be prepared using conventional synthetic methods for example, but not limited to, the routes outlined in Schemes 1 to 6.

Scheme 1:
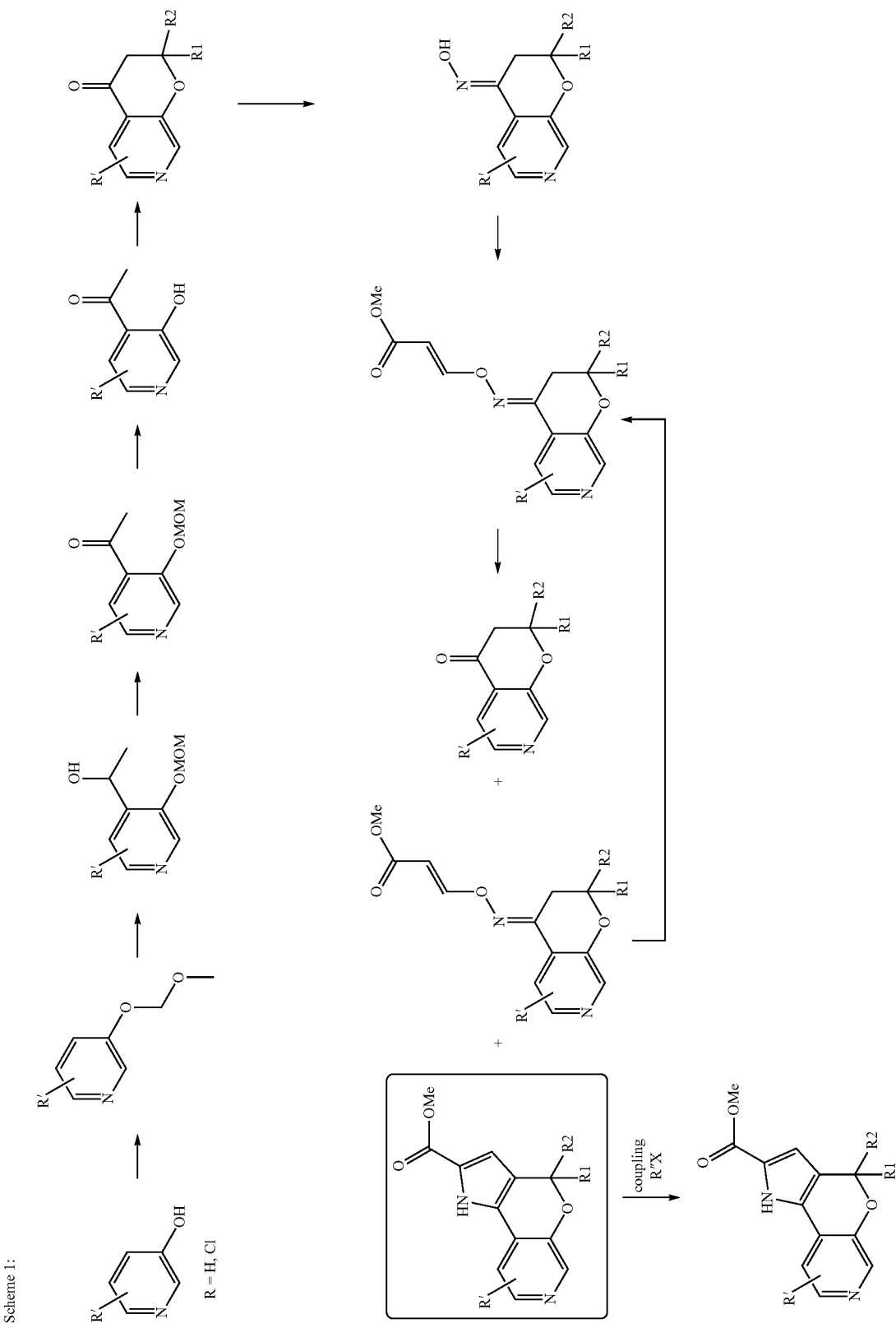

Scheme 2
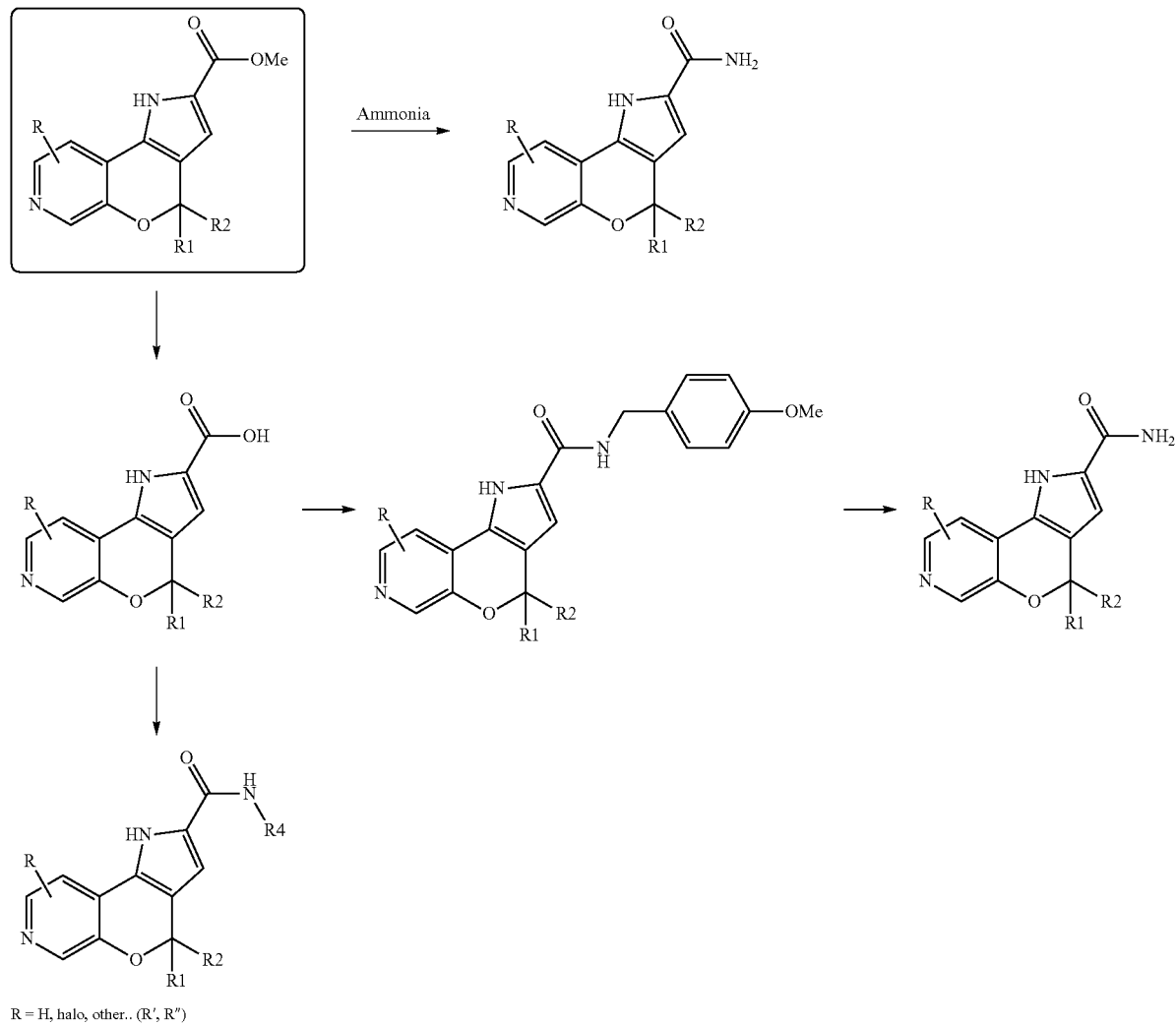
R = H, halo, other.. (R', R")
Scheme 3
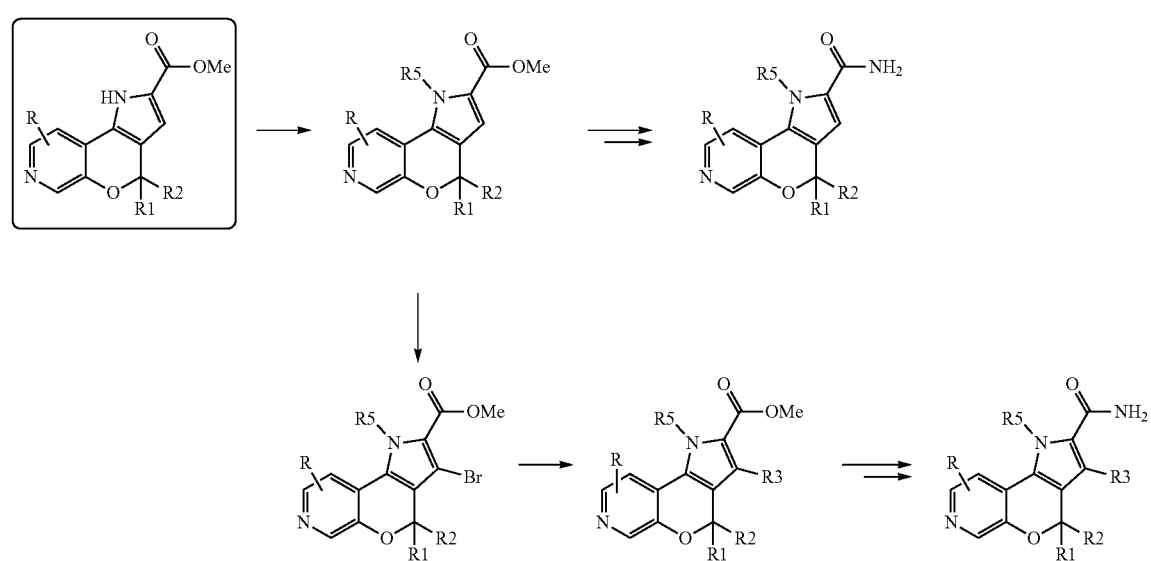

Scheme 4
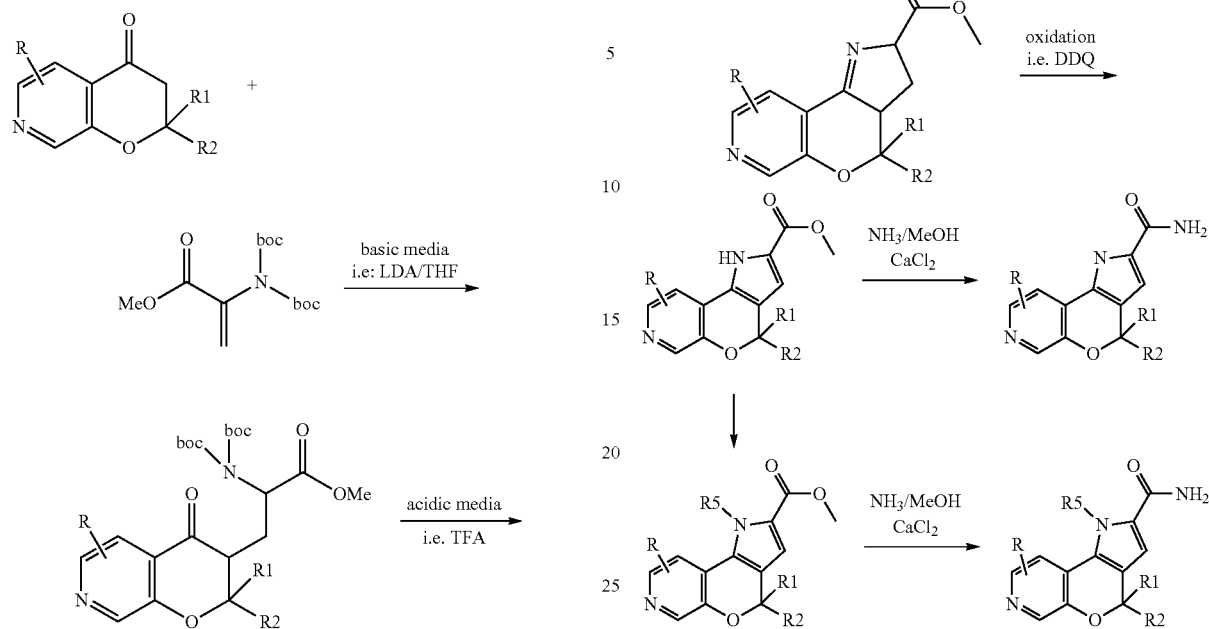
Scheme 5
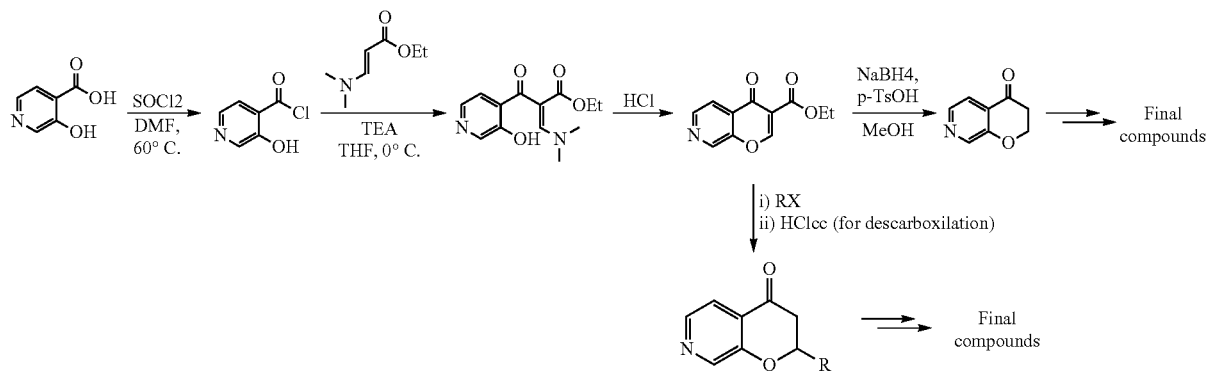
Scheme 6
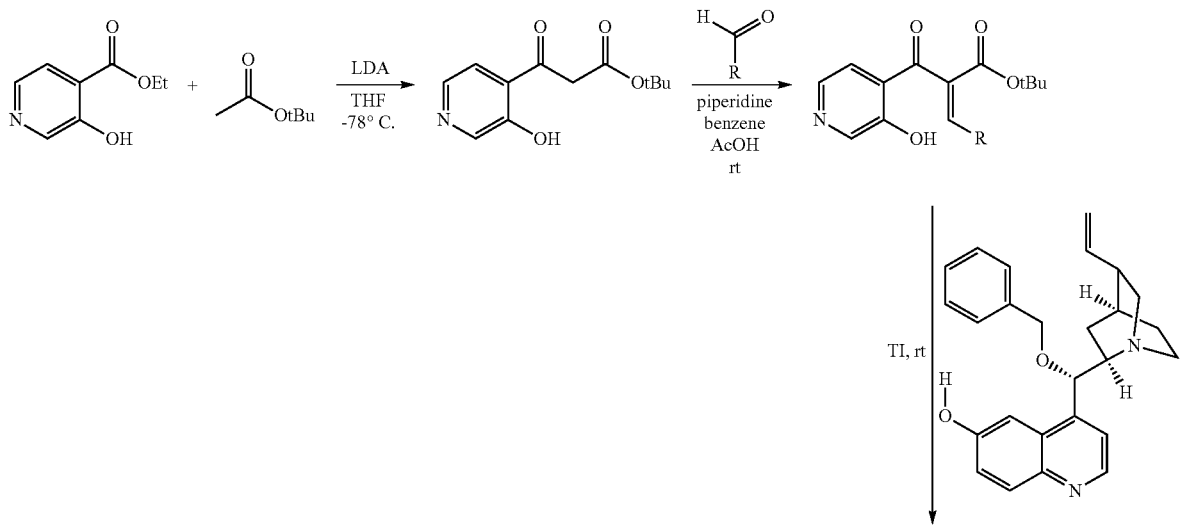

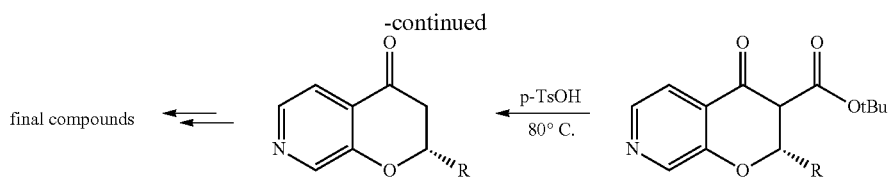

Further, processes to prepare compounds of formula I may be described in the literature, for example in:

Werber, G. et al.; *J. Heterocycl. Chem.*; EN; 14; 1977; 823-827;
Andanappa K. Gadad et al. *Bioorg. Med. Chem.* 2004, 12, 5651-5659;
Paul Heinz et al. *Monatshefte für Chemie*, 1977, 108, 665-680;
M. A. El-Sherbeny et al. *Boll. Chim. Farm.* 1997, 136, 253-256;
Nicolaou, K. C.; Bulger, P. G.; Sarlah, D. *Angew. Chem. Int. Ed.* 2005, 44, 2-49;
Bretonnet et al. *J. Med. Chem.* 2007, 50, 1872;
Asunción Marin et al. *Farmaco* 1992, 47 (1), 63-75;
Severinsen, R. et al. *Tetrahedron* 2005, 61, 5565-5575;
Nicolaou, K. C.; Bulger, P. G.; Sarlah, D. *Angew. Chem. Int. Ed.* 2005, 44, 2-49;
M. Kuwahara et al., *Chem. Pharm Bull.*, 1996, 44, 122;
Wipf, P.; Jung, J.-K. *J. Org. Chem.* 2000, 65(20), 6319-6337;
Shintani, R.; Okamoto, K. *Org. Lett.* 2005, 7 (21), 4757-4759;
Nicolaou, K. C.; Bulger, P. G.; Sarlah, D. *Angew. Chem. Int. Ed.* 2005, 44, 2-49;
J. Kobe et al., *Tetrahedron*, 1968, 24, 239;
P. F. Fabio, A. F. Lanzilotti and S. A. Lang, *Journal of Labelled Compounds and Pharmaceuticals*, 1978, 15, 407;
F. D. Bellamy and K. Ou, *Tetrahedron Lett.*, 1985, 25, 839;
M. Kuwahara et al., *Chem. Pharm Bull.*, 1996, 44, 122;
A. F. Abdel-Magid and C. A Maryanoff. *Synthesis*, 1990, 537;
M. Schlosser et al. *Organometallics in Synthesis. A Manual*, (M. Schlosser, Ed.), Wiley & Sons Ltd: Chichester, UK, 2002, and references cited therein;
L. Wengwei et al., *Tetrahedron Lett.*, 2006, 47, 1941;
M. Plotkin et al. *Tetrahedron Lett.*, 2000, 41, 2269;
Seyden-Penne, J. *Reductions by the Alumino and Borohydrides*, VCH, NY, 1991;
O. C. Dermer, *Chem. Rev.*, 1934, 14, 385;
N. Defacqz, et al., *Tetrahedron Lett.*, 2003, 44, 9111;
S. J. Gregson et al., *J. Med. Chem.*, 2004, 47, 1161;
A. M. Abdel Magib, et al., *J. Org. Chem.*, 1996, 61, 3849;
A. F. Abdel-Magid and C. A Maryanoff. *Synthesis*, 1990, 537;
T. Ikemoto and M. Wakimasu, *Heterocycles*, 2001, 55, 99;
E. Abignente et al., *Il Farmaco*, 1990, 45, 1075;
T. Ikemoto et al., *Tetrahedron*, 2000, 56, 7915;
T. W. Greene and P. G. M. Wuts, *Protective Groups in Organic Synthesis*, Wiley, NY, 1999;
S. Y. Han and Y.-A. Kim. *Tetrahedron*, 2004, 60, 2447;
J. A. H. Lainton et al., *J. Comb. Chem.*, 2003, 5, 400; or
Wiggins, J. M. *Synth. Commun.*, 1988, 18, 741.

Particular transformation steps that may be mentioned include those described in WO 2011/072064 which illustrates the synthesis of bicyclic precursor molecules by reaction of hydroxyacetyl pyridines with ketones, such as acetone. These processes facilitate in the incorporation of non-hydrogen groups at the $R^1$ and $R^2$ positions.

Other specific transformation steps (including those that may be employed in order to form compounds of formula I) that may be mentioned include:

(i) reductions, for example of a carboxylic acid (or ester) to either an aldehyde or an alcohol, using appropriate reducing conditions (e.g. —C(O)OH (or an ester thereof), may be converted to a —C(O)H or —CH$_2$—OH group, using DIBAL and LiAlH$_4$, respectively (or similar chemoselective reducing agents));

(ii) reductions of an aldehyde (—C(O)H) group to an alcohol group (—CH$_2$OH), using appropriate reduction conditions such as those mentioned at point (i) above;

(iii) reductive amination of an aldehyde and an amine, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or MgSO$_4$ or molecular sieves, etc.) followed by a reduction step (e.g. by reaction in the presence of a reducing agent such as a chemoselective one mentioned above or NaBH$_4$, AlH$_4$, or the like), for instance the conversion of —NH$_2$ to —N(H)-isopropyl by condensation in the presence of acetone (H$_3$C—C(O)—CH$_3$) followed by reduction in the presence of a reducing agent such as sodium cyanaoborohydride (i.e. overall a reductive amination);

(iv) formation of a sulfonamide, for example by reaction of a sulfonyl chloride with an amine, for example —S(O)$_2$OH, may be converted to —S(O)$_2$N(R$^{70}$)R$^{71}$ group (in which R$^{70}$ and R$^{71}$ are as hereinbefore defined, and may be linked together, e.g. as defined above), and which reaction may be performed in the presence of a suitable coupling reagent (e.g. 1,1'-carbonyldiimidazole, N,N'-dicyclohexyl-carbodiimide, or the like), and the relevant compound is reacted with a compound of formula HN(R$^{70}$)R$^{71}$ (in which R$^{70}$ and R$^{71}$ are as hereinbefore defined), under standard conditions known to those skilled in the art (e.g. optionally in the presence of a suitable solvent, suitable base and/or in an inert atmosphere);

(v) conversion of a primary amide to a nitrile functional group, for example under dehydration reaction conditions, e.g. in the presence of POCl$_3$, or the like;

(vi) nucleophilic substitution (e.g. aromatic nucleophilic substitution) reactions, where any nucleophile replaces a leaving group, e.g. an amine may replace a —S(O)CH$_3$ leaving group;

(vii) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);

(viii) alkylation, acylation or sulfonylation reactions, which may be performed in the presence of base and solvent (such as those described hereinbefore);

(ix) specific deprotection steps, such as deprotection of an N-Boc protecting group by reaction in the presence of an acid, or, a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF).

The substituents $R^1$, $R^2$, $R^3$, $R^4$, $R^5$, $R^6$, $R^{7a}$ and $R^{7b}$, (or substituents thereon, e.g. defined by each $R^{20}$, $R^{40}$, $R^{41}$, $R^{42}$, $R^{60}$, $R^{61}$, $R^{70}$, $R^{71}$, $R^{72}$ and $R^{73}$ or, $Q^1$, $Q^2$, $Q^3$, $Q^4$, $Q^5$, $Q^6$ and/or $Q^7$) in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. The precursor groups can be changed to a different such group, or to the groups defined in formula I, at any time during the reaction sequence. For example, in cases in which there is a —$CO_2H$ present, the skilled person will appreciate that at any stage during the synthesis (e.g. the final step), the relevant ester group may be hydrolysed to form a carboxylic acid functional group.

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide as described in respect of process (iii)(a) above. Analogous operative conditions apply in the preparation of N-substituted or N,N-disubstituted carboxamides wherein a suitable primary or secondary amine is used in place of ammonia or ammonium hydroxide. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in *"Protective Groups in Organic Synthesis"*, 3$^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined, for use as a pharmaceutical.

Compounds of the invention may inhibit protein kinases, such as CDK8 and/or Haspin, for example as may be shown in the tests described below and/or in tests known to the skilled person. As CDK8 kinase activity may be implicated in the regulation of nuclear β-catenin activity, the compounds of the invention may therefore be useful in the treatment of disorders in an individual in which the inhibition of CDK8 is desired and/or required (which includes disorders in which the regulation, or reduction of, nuclear β-catenin activity and/or inhibition, or modulation of, the expression of CDK8 (i.e. the oncogene) is desired/required).

Haspin kinase activity may be implicated in phosphorylation of histone H3 during mitosis. The compounds of the invention may therefore be useful in the treatment of disorders in an individual in which the inhibition of Haspin is desired and/or required (which includes disorders in which the regulation, or reduction of, phosphorylation of histone H3 during mitosis is desired/required).

The term "inhibit" may refer to any measurable reduction and/or prevention of catalytic kinase (e.g. CDK8) activity. The reduction and/or prevention of kinase activity may be measured by comparing the kinase activity in a sample containing a compound of the invention and an equivalent sample of kinase (e.g. CDK8) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein kinase activity (e.g. CDK8) at a concentration of 10 µM or below (for example at a concentration of below 5 µM, or even below 1 µM, such as below 0.1 µM), when tested in an assay (or other test), for example as described hereinafter, or otherwise another suitable assay or test known to the skilled person.

Compounds of the invention are thus expected to be useful in the treatment of a disorder in which a protein kinase (e.g. CDK8 and/or haspin) is known to play a role and which is characterised by or associated with an overall elevated activity of that kinase (due to, for example, increased amount of the kinase or increased catalytic activity of the kinase). The compounds of the invention may also be useful in the treatment of conditions/disorders associated with elevated nuclear β-catenin activity and/or elevated expression (or over-expression) of CDK8 (i.e. the known oncogene).

Hence, compounds of the invention are expected to be useful in the treatment of a disease/disorder arising from abnormal cell growth, function or behaviour associated with the protein kinase (e.g. CDK8 and/or haspin). Such conditions/disorders include cancer, immune disorders, cardiovascular diseases, viral infections, inflammation, metabolism/endocrine function disorders, neurological disorders and autoimmune disorders. In particular, such conditions/disorders include cancers, especially specific cancers such as non-small cell lung cancer, prostate cancer, and particularly colon/colorectal cancer(s), gastric adenoma, gastric adenocarcinoma, breast cancer, ovarian cancer, pancreatic cancer, cervical cancer and malignant melanoma and it is therefore particularly preferred that compounds of the invention may be of use in treating such specific cancers.

The disorders/conditions that the compounds of the invention may be useful in treating hence includes cancer (such as lymphomas, solid tumours or a cancer as described hereinafter), obstructive airways diseases, allergic diseases, inflammatory diseases (such as asthma, allergy and Crohn's disease), immunosuppression (such as transplantation rejection and autoimmune diseases), disorders commonly connected with organ transplantation, AIDS-related diseases and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, bone disorders, atherosclerosis, vascular smooth cell proliferation associated with atherosclerosis, pulmonary fibrosis, arthritis glomerulonephritis and post-surgical stenosis and restenosis. Other disease states that may be mentioned include cardiovascular disease, stroke, diabetes, hepatomegaly, Alzheimer's disease, cystic fibrosis, hormone-related diseases, immunodeficiency disorders, destructive bone disorders, infectious diseases, conditions associated with cell death, thrombin-induced platelet aggregation, chronic myelogenous leukaemia, liver disease, pathologic immune conditions involving T cell activation and CNS disorders.

As stated above, the compounds of the invention may be useful in the treatment of cancer. More, specifically, the compounds of the invention may therefore be useful in the treatment of a variety of cancer including, but not limited to: carcinoma such as cancer of the bladder, breast, colon, kidney, liver, lung (including non-small cell cancer and small cell lung cancer), esophagus, gall-bladder, ovary, pancreas, stomach, cervix, thyroid, prostate, skin, squamous cell carcinoma, testis, genitourinary tract, larynx, glioblastoma, neuroblastoma, keratoacanthoma, epidermoid carcinoma, large cell carcinoma, non-small cell lung carcinoma, small cell lung carcinoma, lung adenocarcinoma, bone, adenoma, adenocarcinoma, follicular carcinoma, undifferentiated carcinoma, papilliary carcinoma, seminona, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukaemia; hematopoietic tumours of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumours of myeloid lineage, including acute and chronic myelogenous leukemias, myelodysplastic syndrome and promyelocytic leukemia; tumours of mesenchymal origin, including fibrosarcoma and rhabdomyosarcoma; tumours of the central and peripheral nervous system, including astrocytoma, neuroblastoma, glioma and schwannomas; and other tumours, including melanoma, seminoma, teratocarcinoma, osteosarcoma, xeroderma pigmentosum, keratoxanthoma, thyroid follicular cancer and Kaposi's sarcoma. Particular forms of cancer that may be mentioned in this respect include non-small cell lung cancer and prostate cancer and, particularly, colon/colorectal cancer, gastric adenoma, gastric adenocarcinoma, breast cancer, ovarian cancer, pancreatic cancer, cervical cancer and malignant melanoma.

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein, especially colon/colorectal cancer) which is associated with the inhibition of a protein kinase (e.g. CDK8 and/or haspin) i.e. where such inhibition is desired and/or required (the disease may also be associated with increased nuclear β-catenin activity and/or elevated expression of CDK8), for example, a method of treatment of a disease/disorder arising from abnormal cell growth, function or behaviour associated with protein kinases, e.g. CDK8 and/or haspin, which method comprises administration of a therapeutically effective amount of a compound of the invention, as hereinbefore defined, to a patient suffering from, or susceptible to, such a condition.

According to a yet further aspect of the invention, there is provided a compound of the invention, as hereinbefore defined, for use in the treatment of a disease in which inhibition of CDK8 and/or haspin is desired and/or required. For example, there is provided a compound of the invention, as hereinbefore defined, for use in the treatment of cancer or another disease as mentioned herein, such as non-small cell lung cancer, prostate cancer or especially colon/colorectal cancer, gastric adenoma, gastric adenocarcinoma, breast cancer, ovarian cancer, pancreatic cancer, cervical cancer or malignant melanoma.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that are inhibitors of kinases (e.g. protein or lipid kinases, such as CDK8 and/or haspin) and/or useful in the treatment of a cancer and/or a proliferative disease. Compounds of the invention may also be combined with other therapies (e.g. radiation).

According to a further aspect of the invention, there is provided a combination product comprising:
(A) a compound of the invention, as hereinbefore defined; and
(B) another therapeutic agent that is useful in the treatment of cancer and/or a proliferative disease,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of cancer and/or a proliferative disease, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

Examples of other therapeutic agents that are useful in the treatment of cancer and/or a proliferative disease and that may be used in combination with the compounds of the invention include small molecule inhibitors anti-cancer agents such as tyrosine kinase inhibitors, Serine/Threonine kinase inhibitors, lipid kinase inhibitors, protein-protein inhibitors, etc., cytotoxic agents, antibodies and cancer vaccines for the treatment of cancer, DNA-damaging chemotherapeutics drugs (such as doxorubicin and radiotherapy). Other anti-cancer agents that may be mentioned in this respect include Aurora B inhibitors and Aurora A, Plk1, and kinesin-5 inhibitors (Lens, S. M, et al. Nat. Rev. Cancer 10: 825-841, 2010).

Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immnunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

Therapeutic agents that are useful in the treatment of cancer and/or a proliferative disease may be referred to as "chematherapeutics agents". Examples of chemotherapeutic agents include ABT-751 (microtubule inhibitor), alisertib (Aurora A kinase inhibitor), elesclomol (oxidative stress inducer) and crizotinib (tyrosine kinase inhibitor). Other examples of chemotherapeutic agents include bortezomib (VELCADE®, Millennium Pharm.), erlotinib (TARCEVA®, Genentech/OSI Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®), GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, meturedopa, carboquone, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5a-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), actinomycin, aclacinomysins, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, 111.), and TAXOTERE® (docetaxel, doxetaxel; Sanofi-Aventis); chloranmbucil; GEMZAR® (gemcitabine); mercaptopurine; 6-thioguanine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylorni thine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX; tamoxifen citrate), raloxifene, droloxifene, iodoxyfene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), fadrozole, formestanie, RIVISOR® (vorozole), FEMARA® (letrozole; Novartis), and AREVIIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idee), pertuzumab (OMNITARG®, 2C4, Genentech), tositumomab (Bexxar, Corixia), trastuzumab (HERCEPTIN®, Genentech), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgGi λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 455 (ATCC CRL HB8507), MAb 579 (ATCC CRL HB 8506), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as EI.I, E2.4, E2.5, E6.2, E6.4, E2.II, E6.3 and E7.6.3 and described in U.S. Pat. No. 6,235,883; MDX-447 (Medarex Inc); and mAb 806 or humanized mAb 806 (Johns et al, J. Biol. Chem. 279(29):

30375-30384 (2004)). The anti-EGFR antibody may be conjugated with a cytotoxic agent, thus generating an immunoconjugate (see, e.g., EP 659 439 A2, Merck Patent GmbH). EGFR antagonists include small molecules such as compounds described in U.S. Pat. Nos. 5,616,582, 5,457, 105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/50038, WO 98/14451, WO 99/09016, and WO 99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(I-methyl-piperidin-4-yl)-pyrimido[5,4-d]pyrimidine-2,8-diamine, Boehringer Ingelheim); PKI-166 ((R)-4-[4-[(I-phenylethyl)amino]-IH-pyrrolo[2,3-d]pyrimidin-6-yl]-phenol); (R)-6-(4-hydroxyphenyl)-4-[(I-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3-fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); VEGF receptor tyrosine kinase inhibitors such as vatalanib (PTK787/ZK222584, available from Novartis/Schering AG); multi-targeted tyrosine kinase inhibitors such as sunitinib (SUTENT®, available from Pfizer); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC); P I 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-ICI I (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

The invention further provides a process for the preparation of a combination product as hereinbefore defined, which process comprises bringing into association a compound of the invention, as hereinbefore defined, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein kinases (e.g. CDK8 and/or haspin). Advantageously, compounds of the invention may inhibit certain protein kinases selectively (e.g. CDK8 and/or haspin), without exhibiting inhibition (or significant inhibition) of other protein or lipid kinases. For instance, the compounds of the invention may be selective inhibitors of certain protein or lipid kinases. Selective inhibitors may be useful in that the number of side-effects associated with such compounds is reduced compared to less selective inhibitors. Compounds that are selective inhibitors may be identified by screening in a 453-468 kinases panel (KINOMEscan™ from DiscoveRx). For example, selective inhibitors may show a selectivity score of S(20)<0.05.

Selectivity Score (or S-score) is a quantitative measure of a compound's selectivity. It is calculated by dividing the number of kinases to which a compound binds by the total number of distinct kinases tested (i.e. S=Number of hits/Number of assays). S(20)=(number of kinases meeting the potency threshold: [<20% of a control test])/(total number of kinases tested). The compound of Example 43 is an example of a highly selective compound. In a panel of 468 kinases (using the KINOMEscan™ process from DiscoveRx), the S(20) result for this compound was found to be 0.038.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. This is particularly the case where compounds of the invention are selective inhibitors of certain kinases (e.g. selective inhibitors of CDK8).

Compounds of the invention may be beneficial as they are medicaments with targeted therapy, i.e. which target a particular molecular entity by interfering with or inhibiting it (e.g. in this case by inhibiting a protein kinase as hereinbefore described). Compounds of the invention may therefore also have the benefit that they have a new effect (for instance as compared to known compounds in the prior art), for instance, the new effect may be a particular mode of action or another effect resultant of the targeted therapy. Targeted therapies may be beneficial as they may have the desired effect (e.g. reduce cancer, such as colon/colorectal cancer, by reducing tumour growth or carcinogenesis) but may also have the advantage of reducing side effects (e.g. by preventing the killing of normal cells, as may occur using e.g. chemotherapy).

Furthermore, compounds of the invention may selectively target a particular protein kinase (e.g. CDK8 and/or haspin) compared to other known protein or lipid kinases. Accordingly, a compound of the invention may have the advantage that certain, specific cancers (e.g. colon/colorectal cancer) may be treated selectively by using that compound as a single agent or in combination with current therapies, which selective treatment may also have the effect of reducing side effects.

EXAMPLES/BIOLOGICAL TESTS

CDK8/Cyclin C Binding Assay

The binding assay relies on the LanthaScreen™ Eu-Kinase Binding Assay (Invitrogen. This is a kinase assay platform based on measuring the binding and displacement of an Alexa Fluor® 647 conjugate of an ATP-competitive kinase inhibitor (Kinase Tracer 236, PV5592) at a kinase active site. Binding of the tracer to the kinase is detected by addition of a europium (Eu)-labelled anti-His antibody (Invitrogen PV 5596), which specifically labels the kinase of interest. This binding results in a high degree of fluorescence resonance energy transfer (FRET), whereas displacement of the tracer with a kinase inhibitor results in a loss of FRET.

The enzyme has been purchase from Invitrogen (PV4402) as a dimer of full-length His-tagged recombinant human proteins.

Assay conditions were as indicated by the kit manufacturers with the following adaptations:
Assay buffer: 50 mM HEPES, pH 7.5, 1 mM EGTA, 0.01% Brij-35, 10 mM $MgCl_2$
Assay volume: 25 µl
Incubation time and temperature: 60 min at 25° C.
Cdk8-Cyclin C concentration: 5 nM
Tracer concentration: 10 nM
(Eu)-labeled anti-His antibody concentration: 1.5 nM
Tested compound: Serial 1:3 dilutions
Final DMSO concentration in the assay: 1%

Assays were performed in 384-well plates. The final read out was generated using an EnVision plate reader (Perkin-Elmer). The emission ratio was calculated by dividing the acceptor/tracer emission (665 nm) by the antibody/donor emission (615 nm).

CDK19/Cyclin C Binding Assay

The binding assay relies on the LanthaScreen™ Eu-Kinase Binding Assay (Invitrogen). This is a kinase assay platform based on measuring the binding and displacement of an Alexa Fluor® 647 conjugate of an ATP-competitive kinase inhibitor (Kinase Tracer 236, PV5592) at a kinase active site. Binding of the tracer to the kinase is detected by addition of a europium (Eu)-labelled anti-His antibody (Invitrogen PV 5596), which specifically labels the kinase of interest. This binding results in a high degree of fluorescence resonance energy transfer (FRET), whereas displacement of the tracer with a kinase inhibitor results in a loss of FRET.

The enzyme has been purchase from Prokinase (1384-0390-1) as a dimer of GST-His-CDK19 and His-Cyclin C recombinant human proteins.

Assay conditions were as indicated by the kit manufacturers with the following adaptations:
Assay buffer: 50 mM HEPES, pH 7.5, 1 mM EGTA, 0.01% Brij-35, 10 mM $MgCl_2$
Assay volume: 20 µl
Incubation time and temperature: 60 min at 25° C.
Cdk19-Cyclin C concentration: 2 nM
Tracer concentration: 20 nM
(Eu)-labelled anti-GST antibody concentration: 2 nM
Tested compound: Serial 1:3 dilutions
Final DMSO concentration in the assay: 1%

Assays were performed in 384-well plates. The final read out was generated using an EnVision plate reader (Perkin-Elmer). The emission ratio was calculated by dividing the acceptor/tracer emission (665 nm) by the antibody/donor emission (615 nm).

Haspin Kinase Assay

The kinase assay relies on ADP-Glo$^{KM}$ biochemical kinase assay (Promega). This is a luminescent kinase assay that measures ADP formed from a kinase reaction. Then ADP is converted into ATP, which is transformed into a light signal by Ultra-Glo™ Luciferase. The luminescent signal positively correlates with kinase activity. The assay measures the intrinsic ATPase activity (in the absence of peptidic substrate as phosphate acceptor).

The enzyme was purchase from Invitrogen (PV5708) as the kinase domain of GST tagged recombinant human proteins.

Assay conditions were as indicated by the kit manufacturers with the following adaptations:

Assay buffer: 15 mM HEPES pH 7.4, 20 mM NaCl, 1 mM EGTA, 0.02% Tween 20, 10 mM $MgCl_2$, 0.1 mg/ml BGG Assay volume: 20 μl Incubation time and temperature: 60 min at 30° C.

Haspin concentration: 20 nM

ATP concentration: 150 μM

Tested compound: Serial 1:3 dilutions

Final DMSO concentration in the assay: 1%

Assays were performed in 384-well plates. The final read out was generated using an EnVision plate reader (Perkin-Elmer). Luminescent relative units are normalized against the control activity included for each compound (i.e., 100% Haspin activity, without compound) and the percentage of inhibition is calculated.

Reporter System to Assay β-catenin Transcriptional Activity

Efficacy of compounds of the invention on the inhibition of the transcriptional activity of β-catenin driven by CDK8 is measured in a Luminescent reporter assay.

The TOPFlash luciferase reporter system has been adopted as a standard for detecting β-catenin driven transcriptional activation. The reporter used is a 6×TOPFlash reporter meaning that it contains 6 TCF/LEF-1 binding sites upstream of a minimal promoter driving expression of Firefly luciferase. A FOPFlash reporter, which contains mutated TCF sites upstream of *Renilla* luciferase open frame in the enhancer region, is used as a negative control to show that the change in luciferase activity is specifically due to β-catenin transcriptional activity (Promega). The detection is done with the Dual-Glo® Luciferase Assay System (Promega); this is a homogeneous reagent system that enables fast and simple quantitation of a stable luminescent signal from two reporter genes in a single sample. This convenient "add-and-read" system generates both firefly and *Renilla* luciferase luminescence signals from cells that have not been preconditioned or prelysed. The assay was conducted in 96-well plates making it amenable to automated high throughput screening (HTS).

Procedure

HTC116 colon cancer cells were seeded, 15000 cells per well, into 96-well plates and incubated for 16 h at 37° C., 5% $CO_2$. On day two, the cells were transfected using Effectene reactive (Quiagen) with TOPFlash and FOPFlash luciferase reporters plasmids. Cells were incubated with transfection complexes under normal growth conditions for 5 h. Eight serial 1:3 compound dilutions are made in DMSO in a 96-well plate. The compounds are added to duplicate wells in 96-well cell plates using a FX BECKMAN robot (Beckman Coulter) and are incubated at 37° C. under $CO_2$ atmosphere overnight. The third day, the inhibition of transcriptional activity of β-catenin was measured using Dual-Glo® Luciferase Assay System (Promega) and read on VICTOR (Perkin Elmer). $EC_{50}$ values are calculated using ActivityBase from IDBS.

Cellular CDK8 Inhibition Assay

Compounds can be screened for their ability to inhibit intracellular CDK8 using a western blot assay to detect phosphorylation of the CDK8 substrate STAT1 (S727) in IFN-γ treated cells. SW620 cells are plated at $1*10^6$ cells per well in 6-well plates (Solmeglas 13118) in RPMI media (Sigma-Aldrich R6504) supplemented with 10% foetal bovine serum (Sigma-Aldrich F7524), Penicillin/Streptomycin solution diluted 1:100 (Gibco 15070-063), and fungizone (Gibco, 15290-018), and allowed to adhere overnight at 37° C. in 5% $CO_2$. Compounds are then added to the cell media from a final concentration of 10 μM in 10-fold serial dilutions and the cells are incubated at 37° C. in 5% $CO_2$. After 1 hour, IFNγ (R&D systems Ref. RYD-285-IF-100) is added to a final concentration of 50 μg/ml. After 3 hours of treatment with IFNγ, the cells are washed in PBS, lysed adding 100 μl of protein lysis buffer (62.5 mM Tris pH 6.8 al 6.25%, 2% SDS y 10% glycerol) incubation 10 minutes at room temperature and heating at 95° C. 10 min. The protein content of the lysates is determined by DC protein assay (Biorad, Ref. 5000116). The proteins are resolved by SDS-PAGE and transferred to nitrocellulose membrane (VWR International eurolab, Ref. 732-4007). The membranes are incubated overnight at 4° C. with antibodies specific for total STAT1 (BD Transduction laboratory #610115), phosphoserine-727 STAT1 (Cell Signaling Ref. 9177) they are washed and then incubated with IRDye800 conjugated anti-mouse (Pierce/Cultek, 35521) and Alexa Fluor 680 goat anti-rabbit IgG secondary antibodies (Invitrogen, A21076). The bands are visualized and quantified using an Odyssey infrared imaging system (Li-Cor Biosciences). The percentage of phosphorylated STAT1 vs total STAT1 in cells treated with IFNγ is taken as hundred percent of phosphorylation. The percentage of STAT1 phosphorylation is finally plotted against concentration for each compound and $EC_{50}$s for intracellular CDK8 inhibition are calculated using ActivityBase from IDBS.

Endogenous phosphoSTAT1 inhibition can be screened in cells growing in 10% FBS. Cells are plated as described before and treated for 8 h with compounds as described before. Then cells are lysated and phospho STAT1 is evaluated as described before. The percentage of phosphorylated STAT1 vs total STAT1 in cells treated with DMSO is taken as hundred percent of phosphorylation. The percentage of STAT1 phosphorylation is finally plotted against concentration for each compound and $EC_{50}$s for intracellular CDK8 inhibition are calculated using ActivityBase from IDBS.

Cellular HASPIN Inhibition Assay

Compounds can be screened for their ability to inhibit intracellular HASPIN using a western blot assay to detect phosphorylation of the HASPIN substrate H3T3 in synchronized cells. SW620 cells are plated at 200000 cells per well in 6-well plates (Solmeglas 13118) in RPMI media (Sigma-Aldrich R6504) supplemented with 10% foetal bovine serum (Sigma-Aldrich F7524), Penicillin/Streptomycin solution diluted 1:100 (Gibco 15070-063), and fungizone (Gibco, 15290-018), and allowed to adhere overnight at 37° C. in 5% $CO_2$. Cells are then treated 16 h hours with Nocadazole (Sigma-Aldrich M1404) at 250 ng/ml to arrest them in mitosis. Proteasoma inhibitor MG132 (Sigma-Aldrich C2211) is added to a final concentration of 10 nM to keep cells arrested in mitosis. Compounds are then added to the cell media from a final concentration of 10 μM in 10-fold serial dilutions and the cells are incubated at 37° C. in 5% $CO_2$. After 1 hour and 30 minutes of treatment with the compounds, the cells are washed in PBS, lysed adding 100 μl of protein lysis buffer (62.5 mM Tris pH 6.8 al 6.25%, 2% SDS y 10% glycerol) incubation 10 minutes at room temperature and heating at 95° C. 10 min. The protein content of the lysates is determined by DC protein assay (Biorad, Ref. 5000116). The proteins are resolved by SDS-PAGE and transferred to nitrocellulose membrane (VWR International eurolab, Ref. 732-4007). The membranes are incubated overnight at 4° C. with antibodies specific for total H3 (Millipore #07424), phosphothreonine-3 H3 (Cell Signaling Ref. 14269) they are washed and then incubated with IRDye800 conjugated anti-mouse (Pierce/Cultek, 35521) and Alexa Fluor 680 goat anti-rabbit IgG secondary antibodies (Invitrogen, A21076). The bands are visualized and quantified using an Odyssey infrared imaging system (Li-Cor Biosciences). The percentage of phosphorylated H3 vs total H3 in synchronized cells is taken as hundred percent of phosphorylation. The percentage of H3 phosphorylation is finally plotted against concentration for each compound and $EC_{50}$s for intracellular HASPIN inhibition are calculated using ActivityBase from IDBS.

Endogenous phosphoH3 inhibition can be screened in cells growing in 10% FBS. Cells are plated as described before and treated for 8 h with compounds as described before. Then cells are lysated and phospho H3 evaluated as described before. The percentage of phosphorylated H3 vs total H3 in cells treated with DMSO is taken as hundred percent of phosphorylation. The percentage of H3 phosphorylation is finally plotted against concentration for each compound and $EC_{50}$s for intracellular HASPIN inhibition are calculated using ActivityBase from IDBS.

Colony Formation Assay

The in vitro potency of the compounds was measured by colony formation assays. SW620 cells in logarithmic growth phase are plated at 800 cells per well in 6-well plates (Solmeglas 13118) in RPMI media (Sigma-Aldrich R6504) supplemented with 10% foetal bovine serum (Sigma-Aldrich F7524), Penicillin/Streptomycin solution diluted 1:100 (Gibco 15070-063), and fungizone (Gibco, 15290-018), and allowed to adhere overnight at 37° C. in 5% $CO_2$. Compounds are then added to the cell media from a final concentration of 10 µM in 10-fold serial dilutions and the cells are incubated at 37° C. in 5% $CO_2$. Every three days the medium is changed by fresh medium and compounds are added again. After 11 days, colonies are washed with PBS and fixed in 0.5% crystal violet (Sigma-Aldrich Ref. V5265), 6% glutaraldehyde (Sigma-Aldrich Ref. G5882) for 30 minutes. After extensive washing, colonies are dissolved in 2 ml of 10% glacial acetic acid (Sigma-Aldrich Ref. 537020) and absorbance at 590 nm is measured in the Victor 1420 Multilabel Counter (Perkin Elmer). The absorbance in cells treated with DMSO is taken as hundred percent of proliferation. The percentage of proliferation is finally plotted against concentration for each compound and $EC_{50}$s for colony formation inhibition are calculated using ActivityBase from IDBS.

Cell Cycle Assay

Compounds can be screened for their ability to affect the cell cycle using a propidium iodine assay and analysis by flow cytometry. SW620 are plated at 500000 cells per well in 6-well plates (Solmeglas 13118) in RPMI media (Sigma-Aldrich R6504) supplemented with 10% foetal bovine serum (Sigma-Aldrich F7524), Penicillin/Streptomycin solution diluted 1:100 (Gibco 15070-063), and fungizone (Gibco, 15290-018), and allowed to adhere overnight at 37° C. in 5% $CO_2$. Cells are then treated 24 h hours with compounds at final concentration of 5, 2.5, 1 and 0.5 µM. Cells are collected by trypsinization and centrifugation at 1250 rpm and washed with PBS (Sigma Ref. D8537). Cells are fixated with 70% cold ethanol (Merck Ref 100983)) and kept at 4° C. at least for 12 hours. After centrifugation, cells are washed with PBS and DNA is stained with a solution of 0.2 mg/mL RNAase (Quiagen Ref 1007885) and 0.02 mg/mL propidium iodine (Sigma Ref P4864). After 30 minutes incubation at room temperature in the dark cells are analyzed by FACSCalibur™ (BD biosciences) and Flowjo software.

In Vitro Cell Proliferation Assay

The in vitro potency of the compounds was measured by the cell proliferation assay CellTiter-Glo® Luminescent Cell Viability Assay, commercially available from Promega Corp., Madison, Wis. This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiterGlo® Assay was conducted in 96 making it amenable to automated high throughput screening (HTS) (Cree et al (1995) AntiCancer Drugs 6:398-404).

The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 96-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

Combination Assay

The combination index (CI) of combinations of certain example compounds and various chemotherapeutic agents in the CellTitetI-Glo® in vitro cell proliferation assays may be tested. A combination index score is calculated by the Chou and Talalay method (CalcuSyn software, Biosoft). The strength of synergy is scored using the ranking system Chou and Talalay: CI less than 0.8 indicates synergy, CI between 0.8 and 1.2 indicates additivity and CI greater than 1.2 indicates antagonism.

The $EC_{50}$ values of representative combinations are also calculated. The individually measured $EC_{50}$ values of the chemotherapeutic agent and the example compounds are compared to the $EC_{50}$ value of the combination. The cell lines are characterised by tumor type. Combination assays are performed as described in: "Pim 1 kinase inhibitor ETP-45299 suppresses cellular proliferation and synergizes with PI3K inhibition". Blanco-Aparicio, Carmen; Collazo, Ana Maria Garcia; Oyarzabal, Julen; Leal, Juan F.; Albaran, Maria Isabel; Lima, Francisco Ramos; Pequeno, Belen; Ajenjo, Nuria; Becerra, Mercedes; Alfonso, Patricia; Reymundo, Maria Isabel; Palacios, Irene; Mateos, Genoveva; Quinones, Helena; Corrionero, Ana; Carnero, Amancio; Pevarello, Paolo; Lopez, Ana Rodriguez; Fominaya, Jesus; Pastor, Joaquin; Bischoff, James R. Cancer Letters (Shannon, Ireland) 2011, 300(2), 145-153

In Vivo Target Modulation Studies

The in vivo potency of the compounds was measured determining target modulation in human colon xenografts. Eight weeks old female athymic nude mice (Harlan Sprague Dawley Inc) are subcutaneously grafted with $10*10^6$ SW620 human colon cancer cells. When the tumors reach a size of 200-400 mm³ the mice are dosed orally with 5 mg/kg of Example 43 or vehicle. Tumors are excised 1, 4, 8 and 24 h after administration (n=3 mice per time point) and are processed for western blot and for HPLC/MS/MS in order to determine the concentration for Example 43 in the tumor. For western blot tumors are excised and homogenized in 500 μl of RIPA buffer (Sigma Aldrich Chemical) supplemented with 1 mM dithiothreitol (Sigma-Aldrich), 2 mM TAME (Sigma-Aldrich), 5 mM benzamide (Sigma-Aldrich), 10 μg/ml aprotinin (Sigma-Aldrich), 40 μg/ml bestatin (Sigma-Aldrich), 10 μg/ml leupeptine (Sigma-Aldrich), 0.7 μg/ml pepstatin (Sigma-Aldrich), 1 μg/ml trypsin inhibitor (Sigma-Aldrich), 1 mg/ml pefablock (Roche Diagnostics), and a tablet of protease-inhibitor cocktail (Roche Diagnostics). After homogenization, tissue samples are incubated on ice for 20 min and later centrifuged twice at 12000×g for 10 min and 4° C. The supernatants are removed and protein concentration is determined by Bradford method (Bio-Rad Protein Assay). These samples are stored at −20° C. until processing. 30-60 μg of total proteins extracts are analyzed by western blot for STAT1P/STAT1 modulation as has been described in the cellular CDK8 inhibition assay. To determine the concentration of Example 43 in tumor tissue tumor samples were homogenized in 3 volumes H₂O and sonicated for 5 min followed by centrifugation at 2000 g for 5 min. The supernatant was stored at 4° C. until processing. Specific solid phase extraction methods as well as LC-MS/MS analysis and quantification methods were developed, reaching LLOQs of 1 ng/ml. For the conversion of the tissue concentrations in ng/mL to ng/g, a tissue density of 1 was assumed.

The invention is illustrated by the following examples in which:

FIG. 4 shows the time dependent inhibition of P-STAT1 (S727).

EXAMPLES AND EXPERIMENTAL

Figure 1A:
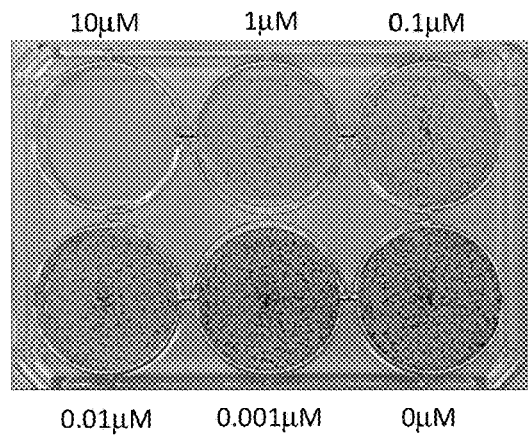
FIGS. 1A to 1C show the effect of Examples 43, 70 and 73 on colony formation assay in SW620 cells treated 11 days. The images illustrates the dose dependent effect of (1A): Example 43, (1B): Example 70, and (1C): Example 73.

The following Examples illustrate the invention.

Herein after, the term "CCTLC" means centrifugal circular thin-layer chromatography, "DAD" means diode-array detector, "DCM" means dichloromethane, "DIPEA" means diisopropylethylamine, "DME" means 1,2-dimethoxyethane, "DMF" means dimethylformamide, "eq" means equivalents, "EtOAc" means ethyl acetate, "h" means hours, "min" means minutes, "HPLC" means high performance liquid chromatography, "MeOH" means methanol, "mw" means microwave, "nBuOH" means n-butanol, "NMR" means nuclear magnetic resonance, "Pd(PPh₃)₄" means tetrakis(triphenylphosphine)-palladium, "THF" means tetrahydrofuran, "CHCl₃" means chloroform, "PdCl₂dppf" means 1,1'-bis(diphenylphosphino)ferrocene-palladium(II)dichloride dichloromethane complex, "AcCN" means acetonitrile, "Na₂SO₄" means sodium sulphate, "rt" means room temperature, "c-Hex" means cyclohexane, "CDCl₃" means deuterated chloroform, "DMSO" means dimethylsulfoxide, "NaHCO₃" means sodium bicarbonate, "H₂O" means water, "NaCl" means sodium chloride, "NH₄Cl" means ammonium chloride, "Na₂S₂O₃" means sodium thiosulfate, "EtOH" means ethanol, "AcOH" means acetic acid, "KOH" means potassium hydroxide, "Na₂CO₃" means sodium carbonate, "aq" means aqueous, "AlMe₃" means trimethylaluminium.

General Procedure

NMR spectra were recorded in a Bruker Avance II 300 spectrometer and Bruker Avance II 700 spectrometer fitted with 5 mm QXI 700 S4 inverse phase, Z-gradient unit and variable temperature controller.

The HPLC measurements were performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. Data acquisition was performed with ChemStation LC/MSD quad, software.

Method 1

Reversed phase HPLC was carried out on a Gemini-NX C18 (100×2.0 mm; 5 um). Solvent A: water with 0.1% formic acid; Solvent B: acetonitrile with 0.1% formic acid. Gradient: 5% to 100% of B within 8 min at 50° C., DAD.

Method 2

Reversed phase HPLC was carried out on a Gemini-NX C18 (100×2.0 mm; 5 um). Solvent A: water with 0.1% formic acid; Solvent B: acetonitrile with 0.1% formic acid. Gradient: 5% to 40% of B within 8 min at 50° C., DAD.

Method 3

Reversed phase HPLC was carried out on a Gemini-NX C18 (100×2.0 mm; 5 um). Solvent A: water with 0.1% formic acid; Solvent B: acetonitrile with 0.1% formic acid. Gradient: 0% to 30% of B within 8 min at 50° C., DAD.

Method 4

Reversed phase HPLC was carried out on a Gemini C18 column (50×2 mm, 3 um). Solvent A: water with 0.1% formic acid; Solvent B: acetonitrile with 0.1% formic acid. Gradient: 10% to 95% of B within 4 min at 50° C., DAD.

Method 5

Reversed phase HPLC was carried out on a Gemini C18 column (50×2 mm, 3 um). Solvent A: water with 0.1% formic acid; Solvent B: acetonitrile with 0.1% formic acid. Gradient: 0% to 30% of B within 4 min at 50° C., DAD.

"Found mass" refers to the most abundant isotope detected in the HPLC-MS.

Synthesis of Intermediate I.

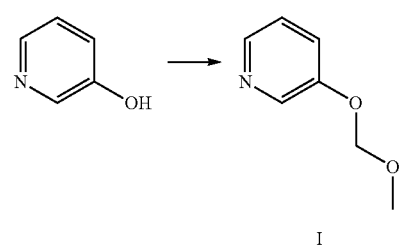

I

To a solution of 3-hydroxypyridine (30 g, 315.456 mmol, 1 eq) in DMF (158 mL) at 0° C. under argon is added portion wise NaH 60% (12.62 g, 315.456 mmol, 1 eq) over 5 min. The reaction was stirred for 1 h at 0° C., then chloromethyl methyl ether (24 mL, 315.456 mmol, 1 eq) was added and the suspension was stirred at 0° C. for 2 h, then warmed to rt and stirred for 15 h. Saturated NaHCO₃ was added slowly and the suspension was stirred for 30 min and warmed to rt. EtOAc was added and the mixture was filtered thought Celite. The organic layer was separated, and the aqueous phase was extracted with EtOAc. The combined organic layers were washed with H₂O, saturated NaCl, dried (Na₂SO₄), and concentrated in vacuo. The residue was purified by flash chromatography (Biotage, 0% to 40% EtOAc in c-Hex) to afford light yellow oil (24.6 g, yield: 56%).

HPLC-MS (method 4): Rt=0.6, [M+H]⁺ 140.

1H NMR (300 MHz, CDCl3) δ 8.37 (d, J=2.8 Hz, 1H), 8.23 (dd, J=4.8, 1.3 Hz, 1H), 7.43 (ddd, J=8.5, 2.8, 1.3 Hz, 1H), 7.32-7.23 (m, 1H), 5.19-5.13 (m, 2H), 3.46-3.39 (m, 3H).

Synthesis of Intermediate II.

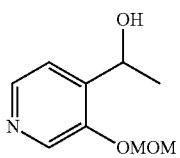

II

To a solution of intermediate I (10.830 g, 77.828 mmol, 1 eq) in THF (101.4 mL) was added a solution of tert-butyllithium (1.76M in pentane. 92 mL, 155.656 mmol, 2 eq) at −78° C. under argon atmosphere. The reaction was stirred at −78° C. for 1 h, and acetaldehyde (7.4 mL, 132.308 mmol, 1.7 eq) was added. The reaction was stirred at −78° C. for 3 hours, and then warmed up to rt and stirred at this temperature for 21 h. The reaction was quenched by addition of saturated aqueous NH₄Cl and extracted with EtOAc (×3). The combined organic layers were washed with saturated NaCl, dried (Na₂SO₄), and concentrated to give an orange oil. The residue was purified by flash chromatography (Biotage, 0% to 80% EtOAc in c-Hex) to afford a light yellow oil (8.0 g, yield: 56%).

HPLC-MS (method 4): Rt=0.4, [M+H]⁺ 184.

1H NMR (300 MHz, CDCl3) δ 8.29 (s, 1H), 8.18 (d, J=4.8 Hz, 1H), 7.36 (d, J=4.8 Hz, 1H), 5.15 (d, J=6.7 Hz, 2H), 5.13-5.03 (m, 1H), 3.44-3.37 (m, 3H), 1.41 (t, J=6.4 Hz, 3H).

Synthesis of Intermediate III.

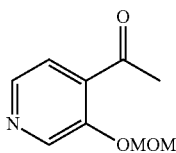

III

Dess-martin periodinane (18.521 g, 43.667 mmol, 1.6 eq) was added to a stirring mixture of intermediate II (5 g, 27.292 mmol, 1 eq) and NaHCO₃ (6.878 g, 81.875 mmol, 3 eq) in CHCl₃ (83 mL) at room temperature. After 16 h, 1.0 M aqueous Na₂S₂O₃ was added, the reaction mixture was stirred for 90 min, partitioned between EtOAc and 1.0 M aqueous Na₂S₂O₃. The layers were separated and the organic layer was washed with 1.0 M aqueous Na₂S₂O₃, water, brine, dried over Na₂SO₄, filtered, and the filtrate was concentrated. The residue was purified by flash chromatography (Biotage, c-Hex/EtOAc) affording 4.255 g of the desired compound (yield: 86.0%).

HPLC-MS (method 4): Rt=1.3, [M+H]⁺ 182.

1H NMR (300 MHz, CDCl3) δ 8.56 (s, 1H), 8.29 (d, J=4.8 Hz, 1H), 7.39 (d, J=4.8 Hz, 1H), 5.25 (s, 2H), 3.45 (s, 3H), 2.56 (s, 3H).

Synthesis of Intermediate IV.

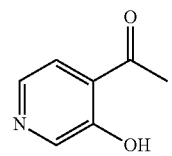

IV

To solution of intermediate III (6 g, 33.114 mmol, 1 eq) in EtOH (96 mL) was added 5M hydrochloric acid (53 mL) and the mixture was stirred at room temperature for 16 h. Solvent was evaporated, the residue was dissolved in MeOH, and silica gel was added and evaporated. It was purified by flash chromatography (Biotage, 0% to 20% MeOH in DCM) to afford an orange solid (4.5 g, 99%).

HPLC-MS (method 4): Rt=0.7, [M+H]⁺ 138.

1H NMR (300 MHz, DMSO) δ 8.58 (s, 1H), 8.33 (d, J=4.9 Hz, 1H), 7.80 (d, J=5.3 Hz, 1H), 2.64 (s, 3H).

Synthesis of Intermediate V.

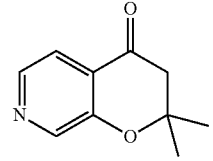

V

A mixture of intermediate IV (4.5 g, 32.814 mmol, 1 eq), DIPEA (4.6 mL, 32.814 mmol, 1 eq), pyrrolidine (4.1 mL, 49.221 mmol, 1 eq) and acetone (2.4 mL, 32.814 mmol, 1 eq) in tetrahydrofuran (328 mL) was heated at 70° C. in a pressure tube for 16 h. The reaction was concentrated and the residue was purified by flash chromatography (Biotage, 0% to 30% EtOAc in c-Hex) to afford a white solid (1.825 mg, yield: 31%).

HPLC-MS (method 4): Rt=3.0, [M+H]⁺ 178.

1H NMR (300 MHz, DMSO) δ 8.42 (s, 1H), 8.22 (d, J=5.0 Hz, 1H), 7.49 (dd, J=5.0, 0.7 Hz, 1H), 2.86 (s, 2H), 1.34 (s, 6H).

Synthesis of Intermediate VI.

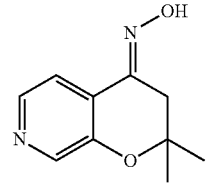

VI

To a solution of intermediate V (1 g, 5.643 mmol, 1 eq) in MeOH (56 ml) were added triethylamine (1.573 mL, 11.287 mmol, 2 eq) and hydroxylamine hydrochloride (784 mg, 11.287 mmol, 2 eq). The reaction mixture was stirred at room temperature for 16 h. Then, the reaction was concentrated to afford a white solid (912 mg, yield: 84%). The residue was used in the next step without further purification.

HPLC-MS (method 4): Rt=0.8, [M+H]+ 193.

1H NMR (300 MHz, DMSO) δ 11.73 (s, 1H), 8.14 (s, 1H), 8.04 (d, J=5.1 Hz, 1H), 7.54 (d, J=5.3 Hz, 1H), 2.76 (s, 2H), 1.26 (s, 6H).

Synthesis of Intermediate VII.

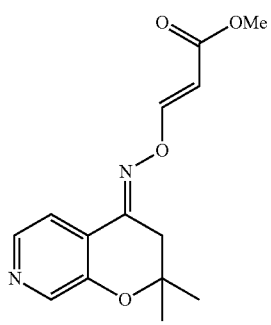

VII

To a solution of intermediate VI (900 mg, 4.682 mmol, 1 eq) in DCM (38 ml) at 0° C., were added triethylamine (131 μl, 0.936 mmol. 0.2 eq) and methyl propiolate (787 μl, 9.364 mmol, 2 eq), and the reaction became orange. The mixture was stirred at room temperature for 1 h. Water-ice was added and extracted with DCM (×3). The organic phase was dried (Na2SO4), evaporated and the residue was purified by flash chromatography (Biotage, 0% to 50% EtOAc in c-Hex) to afford the desired compound (1.250 g, 97%).

HPLC-MS (method 4): Rt=4.2, [M+H]+ 277.

1H NMR (300 MHz, DMSO) δ 8.33 (s, 1H), 8.19 (d, J=5.1 Hz, 1H), 7.76 (dd, J=5.1, 0.6 Hz, 1H), 5.80 (d, J=1.1 Hz, 1H), 5.76 (t, J=1.0 Hz, 1H), 3.66 (s, 3H), 3.33 (s, 2H), 1.39 (s, 6H).

Synthesis of Intermediate VIII.

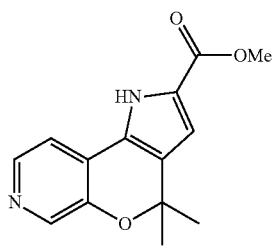

VIII

A solution of intermediate VII (2.6 g, 9.410 mmol, 1 eq) in AcOH (36 ml) was heated at 120° C. in the MW (Biotage) for 4 h. The reaction mixture was evaporated and the residue was purified by flash chromatography (Biotage, 0% to 40% EtOAc in c-Hex) to afford the desired product as a white solid (800 mg, 33%).

HPLC-MS (method 4): Rt=2.7, [M+H]+ 259.

1H NMR (300 MHz, DMSO) δ 12.61 (s, 1H), 8.08 (s, 1H), 8.06 (d, J=4.9 Hz, 1H), 7.69 (d, J=4.9 Hz, 1H), 6.76 (s, 1H), 3.75 (s, 3H), 1.50 (s, 6H).

Alternative Synthesis of Intermediate VIII.

2,3-Dichloro-5,6-dicyano-1,4-benzoquinone (560 mg, 2.466 mmol, 1 eq) was added to a mixture of intermediate CIV (642 mg, 2.466 mmol, 1 eq) in dichloromethane (49 mL) at room temperature. The reaction was stirred at room temperature for 16 hours. The solvent was evaporated under vacuum, and the residue was dissolved in MeOH and charged on a cationic exchange resin (Isolute SCX). Impurities were washed off with MeOH, and then eluted with MeOH+5% 7N NH3 in MeOH to obtain the desired intermediate. The intermediate was again purified by flash chromatography (Biotage, 1% to 5% MeOH in DCM) affording the expected intermediate as a yellow solid (360 mg, yield: 57%).

HPLC-MS (method 4): Rt=2.66, [M+H]+ 259.0.

Synthesis of Intermediate IX.

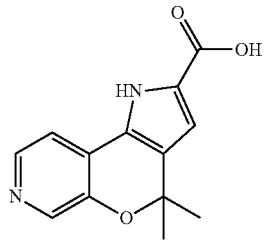

IX

To the intermediate VIII (250 mg, 0.968 mmol, 1 eq) was added 2M KOH (10 mL). The mixture was heated at 80° C. for 1 h. 1M HCl was added to neutralize, and then it was extracted with n-butanol. The organic phase was dried (Na2SO4), evaporated and the residue was purified by flash chromatography (Biotage, 0% to 20% MeOH in DCM) to afford the desired compound (220 mg, yield: 93%).

HPLC-MS (method 4): Rt=0.4 & 0.9, [M+H]+ 245.

1H NMR (300 MHz, DMSO) δ 11.99 (s, 1H), 8.00 (s, 2H), 7.69 (d, J=4.6 Hz, 1H), 6.42 (s, 1H), 1.48 (s, 6H).

Synthesis of Intermediate X.

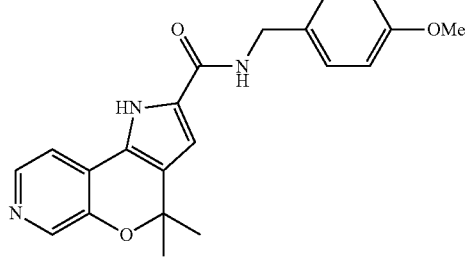

X

To a solution of intermediate IX (30 mg, 0.123 mmol, 1 eq) in dichloromethane (2.5 mL), n,n'-dicyclohexylcarbodiimide (28 mg, 0.135 mmol, 1.1 eq), 4-dimethylaminopyridine (3 mg, 0.025 mmol, 0.2 eq) and 4-methoxybenzylamine (0.015 mL, 0.135 mmol, 1.1 eq) were added. The reaction mixture was stirred at room temperature for 3 h. The reaction mixture was quenched with water (10 ml). The mixture was extracted with EtOAc (2×20 ml). The combined organic layers were dried over anhydrous Na2SO4 and evaporated. The residue was purified by flash chromatography (Biotage, 0% to 20% MeOH in DCM) to afford the desired compound (20 mg, yield: 90%).

HPLC-MS (method 4): Rt=3.1, [M+H]+ 364.

Synthesis of Intermediate XI.

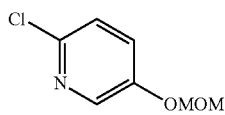

This intermediate was prepared following the same protocol which was employed to prepare the intermediate I, but using 2-chloro-5-hydroxypyridine as starting material instead of 3-hydroxypyridine. (yield: 57%).

HPLC-MS (method 4): Rt=3.5, [M+H]$^+$ 174.

1H NMR (300 MHz, DMSO) δ 8.10 (dd, J=3.1, 0.5 Hz, 1H), 7.49 (dd, J=8.8, 3.1 Hz, 1H), 7.39 (dd, J=8.8, 0.6 Hz, 1H), 5.20 (s, 2H), 3.31 (s, 3H).

Synthesis of Intermediate XII.

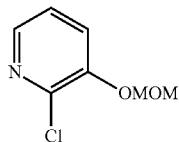

This intermediate was prepared following the same protocol which was employed to prepare the intermediate I, but using 2-chloro-3-hydroxypyridine as starting material instead of 3-hydroxypyridine. (yield: 43%).

HPLC-MS (method 4): Rt=3.2, [M+H]$^+$ 174.

1H NMR (300 MHz, DMSO) δ 7.98 (dd, J=4.6, 1.6 Hz, 1H), 7.62-7.57 (m, 1H), 7.33 (dd, J=8.2, 4.6 Hz, 1H), 5.29 (s, 2H), 3.35 (s, 3H).

Synthesis of Intermediate XIII.

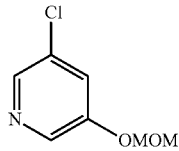

This intermediate was prepared following the same protocol which was employed to prepare the intermediate I, but using 3-hydroxy-5-chloropyridine as starting material instead of 3-hydroxypyridine. (yield: 75%).

HPLC-MS (method 4): Rt=3.7, [M+H]$^+$ 174.

1H NMR (300 MHz, CDCl$_3$) δ 8.21 (d, J=2.5 Hz, 1H), 8.16 (d, J=2.0 Hz, 1H), 7.33 (t, J=2.3 Hz, 1H), 5.12 (s, 2H), 3.41 (s, 3H).

Synthesis of Intermediate XIV.

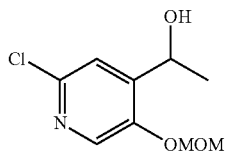

This intermediate was prepared following the same protocol which was employed to prepare the intermediate II, but using intermediate XI as starting material (yield: 14%).

HPLC-MS (method 4): Rt=3.3, [M+H]$^+$ 218.

1H NMR (300 MHz, DMSO) δ 8.05 (s, 1H), 7.37 (s, 1H), 5.29-5.22 (m, 2H), 4.87 (dt, J=12.3, 6.3 Hz, 1H), 3.34 (s, 3H), 1.24 (d, J=6.5 Hz, 3H).

Synthesis of Intermediate XV.

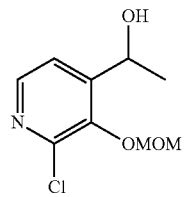

This intermediate was prepared following the same protocol which was employed to prepare the intermediate II, but using intermediate XII as starting material (yield: 36%).

HPLC-MS (method 4): Rt=3.1, [M+H]$^+$ 218.

1H NMR (300 MHz, DMSO) δ 8.12 (d, J=4.9 Hz, 1H), 7.45 (dd, J=4.9, 0.4 Hz, 1H), 5.05 (d, J=1.8 Hz, 2H), 4.98 (ddd, J=11.0, 6.3, 2.0 Hz, 1H), 3.47 (s, 3H), 1.26 (d, J=6.5 Hz, 3H).

Synthesis of Intermediate XVI.

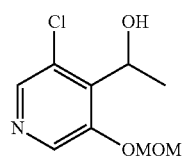

This intermediate was prepared following the same protocol which was employed to prepare the intermediate II, but using intermediate XIII as starting material (yield: 90%).

HPLC-MS (method 4): Rt=3.1, [M+H]$^+$ 218.

1H NMR (300 MHz, DMSO) δ 8.25 (s, 1H), 8.17 (s, 1H), 5.26 (s, 2H), 5.24-5.16 (m, 1H), 3.37 (s, 3H), 1.39 (d, J=6.6 Hz, 3H).

Synthesis of Intermediate XVII.

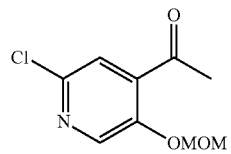

This intermediate was prepared following the same protocol which was employed to prepare the intermediate III, but using intermediate XIV as starting material (yield: 77%).

HPLC-MS (method 4): Rt=3.8, [M+H]+ 215.

1H NMR (300 MHz, DMSO) δ 8.38 (s, 1H), 7.54 (s, 1H), 5.39 (s, 2H), 3.43 (s, 3H), 2.58 (s, 3H).

Synthesis of Intermediate XVIII.

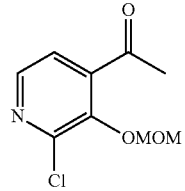

This intermediate was prepared following the same protocol which was employed to prepare the intermediate III, but using intermediate XV as starting material (yield: 65%).

HPLC-MS (method 4): Rt=3.8, [M+H]+216.

1H NMR (300 MHz, DMSO) d 8.32 (d, J=4.9 Hz, 1H), 7.57 (d, J=4.9 Hz, 1H), 5.10 (s, 2H), 3.43 (s, 3H), 2.59 (s, 3H).

Synthesis of Intermediate XIX.

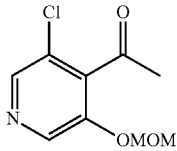

XIX

This intermediate was prepared following the same protocol which was employed to prepare the intermediate III, but using intermediate XVI as starting material (yield: 40%).

HPLC-MS (method 4): Rt=3.6, [M+H]+216.

1H NMR (300 MHz, DMSO) δ 8.51 (s, 1H), 8.41 (d, J=0.4 Hz, 1H), 5.37 (s, 2H), 3.39 (s, 3H), 2.52 (s, 3H).

Synthesis of Intermediate XX.

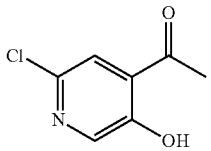

XX

This intermediate was prepared following the same protocol which was employed to prepare the intermediate IV, but using intermediate XVII as starting material (yield: 77%).

HPLC-MS (method 4): Rt=3.0, [M+H]+172.

1H NMR (300 MHz, DMSO) δ 11.22 (s, 1H), 8.19 (s, 1H), 7.57 (s, 1H), 2.61 (s, 3H).

Synthesis of Intermediate XXI.

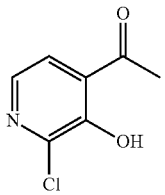

XXI

This intermediate was prepared following the same protocol which was employed to prepare the intermediate IV, but using intermediate XVIII as starting material (yield: 28%).

HPLC-MS (method 4): Rt=3.0, [M+H]+172.

1H NMR (300 MHz, DMSO) δ 11.72 (s, 1H), 8.06 (d, J=5.0 Hz, 1H), 7.77 (d, J=5.0 Hz, 1H), 2.68 (s, 3H).

Synthesis of Intermediate XXII.

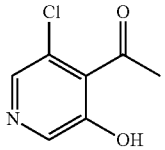

XXII

This intermediate was prepared following the same protocol which was employed to prepare the intermediate IV, but using intermediate XIX as starting material (yield: 80%).

HPLC-MS (method 4): Rt=3.3, [M+H]+172.

1H NMR (300 MHz, DMSO) δ 11.03 (s, 1H), 8.21 (s, 1H), 8.17 (s, 1H), 2.48 (d, J=3.2 Hz, 3H).

Synthesis of Intermediate XXIII.

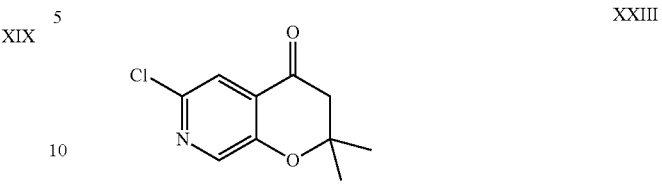

XXIII

This intermediate was prepared following the same protocol which was employed to prepare the intermediate V, but using intermediate XX as starting material (yield: 37%).

HPLC-MS (method 4): Rt=4.1, [M+H]+212.

Synthesis of Intermediate XXIV.

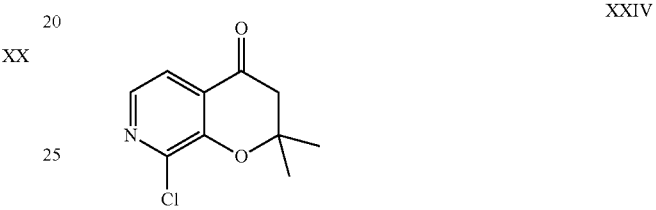

XXIV

This intermediate was prepared following the same protocol which was employed to prepare the intermediate V, but using intermediate XXI as starting material. In this case, the residue wasn't purified by flash chromatography.

HPLC-MS (method 4): Rt=4.0, [M+H]+212.

Synthesis of Intermediate XXV.

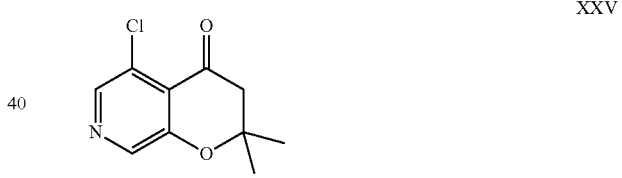

XXV

This intermediate was prepared following the same protocol which was employed to prepare the intermediate V, but using intermediate XXII as starting material (yield: 18%).

HPLC-MS (method 4): Rt=3.9, [M+H]+212.

1H NMR (300 MHz, DMSO) δ 8.35 (s, 1H), 8.20 (s, 1H), 2.88 (s, 2H), 1.36 (s, 6H).

Synthesis of Intermediate XXVI.

XXVI

This intermediate was prepared following the same protocol which was employed to prepare the intermediate VI, but using intermediate XXIII as starting material. In this case, the residue wasn't purified by flash chromatography.

HPLC-MS (method 4): Rt=4.0, [M+H]+ 227.

Synthesis of Intermediate XXVII.

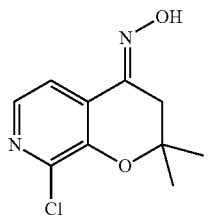
XXVII

This intermediate was prepared following the same protocol which was employed to prepare the intermediate VI, but using intermediate XXIV as starting material. In this case, the residue wasn't purified by flash chromatography.
HPLC-MS (method 4): Rt=4.0, [M+H]+ 227.

Synthesis of Intermediate XXVIII.

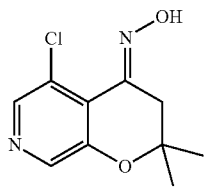
XXVIII

This intermediate was prepared following the same protocol which was employed to prepare the intermediate VI, but using intermediate XXV as starting material. In this case, the residue wasn't purified by flash chromatography.
HPLC-MS (method 4): Rt=3.7, [M+H]+ 227.

Synthesis of Intermediate XXIX.

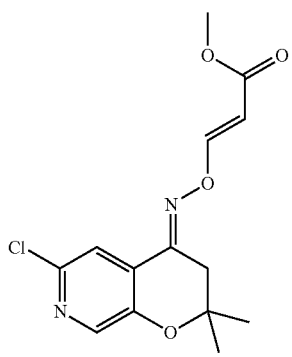
XXIX

This intermediate was prepared following the same protocol which was employed to prepare the intermediate VII, but using intermediate XXVI as starting material. In this case, the residue wasn't purified by flash chromatography.
HPLC-MS (method 4): Rt=4.6, [M+H]+ 311.

Synthesis of Intermediate XXX.

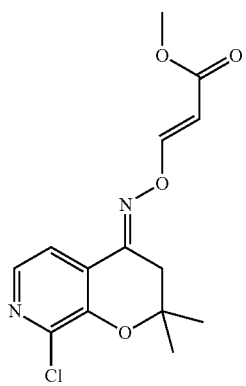
XXX

This intermediate was prepared following the same protocol which was employed to prepare the intermediate VII, but using intermediate XXVII as starting material. In this case, the residue wasn't purified by flash chromatography.
HPLC-MS (method 4): Rt=4.6, [M+H]+ 311.

Synthesis of Intermediate XXXI.

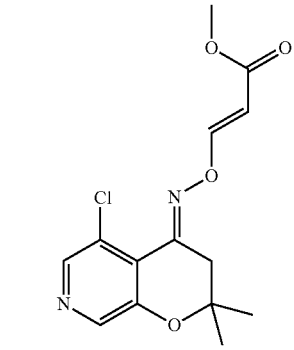
XXXI

This intermediate was prepared following the same protocol which was employed to prepare the intermediate VII, but using intermediate XXVIII as starting material. In this case, the residue wasn't purified by flash chromatography.
HPLC-MS (method 4): Rt=4.4, [M+H]+ 311.

Synthesis of Intermediate XXXII.

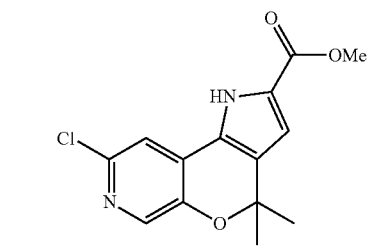
XXXII

This intermediate was prepared following the same protocol which was employed to prepare the intermediate VIII, but using intermediate XXIX as starting material. In this case the purification was carried out in DCM/MeOH 0-10% (yield: 17%).
HPLC-MS (method 4): Rt=4.4, [M+H]+ 293.

Synthesis of Intermediate XXXIII.

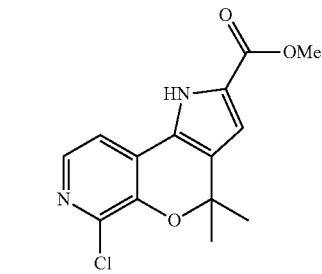
XXXIII

This intermediate was prepared following the same protocol which was employed to prepare the intermediate VIII, but using intermediate XXX as starting material. In this case the purification was carried out in DCM/MeOH 0-10% (yield: 31%).

HPLC-MS (method 4): Rt=4.3, [M+H]+ 293.

Synthesis of Intermediate XXXIV.

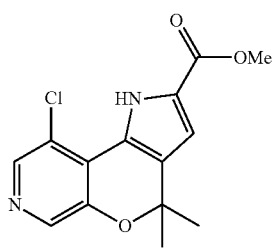

XXXIV

This intermediate was prepared following the same protocol which was employed to prepare the intermediate VIII, but using intermediate XXXI as starting material. In this case the purification was carried out in DCM/MeOH 0-10% (yield: 49%).

HPLC-MS (method 4): Rt=4.5, [M+H]+ 293.

Synthesis of Intermediate XXXV.

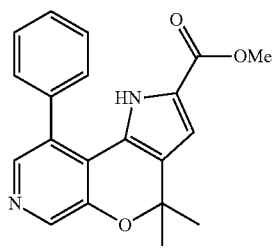

XXXV

To a mixture of intermediate XXXIV (50 mg, 0.171 mmol, 1 eq.) in 1,2-dimethoxyethane (0.8 mL), phenylboronic acid (42 mg, 0.342 mmol, 2 eq.), PdCl$_2$(dppf) (14 mg, 0.017 mmol, 0.1 eq.) and a saturated Na$_2$CO$_3$ aqueous solution (0.5 mL) were added and it was heated at 130° C. for 1 h in the MW (Biotage). The solvent was evaporated and the crude was purified by flash chromatography (Biotage, cHex/EtOAc) to afford the expected compound (45 mg, yield: 79%).

HPLC-MS (method 4): Rt=4.2, [M+H]+ 335.

Synthesis of Intermediate XXXVI.

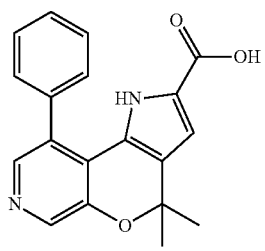

XXXVI

This intermediate was prepared following the same protocol which was employed to prepare the intermediate IX, but using intermediate XXXV as starting material. In this case, the residue wasn't purified by flash chromatography.

HPLC-MS (method 4): Rt=3.4, [M+H]+ 321.

Synthesis of Intermediate XXXVII.

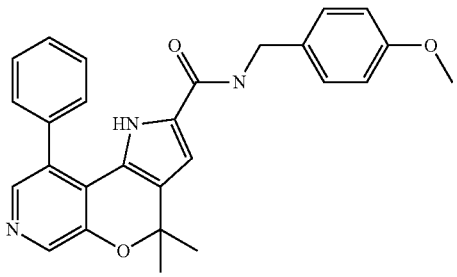

XXXVII

To a solution of intermediate XXXVI (39 mg, 0.122 mmol, 1 eq.) in DCM (2.4 mL), n,n'-dicyclohexylcarbodiimide (28 mg, 0.134 mmol, 1.1 eq.), 4-dimethylaminopyridine (3 mg, 0.024 mmol, 0.2 eq.) and 4-methoxybenzylamine (0.017 mL, 0.134 mmol, 1.1 eq.) were added. The reaction mixture was stirred at 80° C. for 16 h. The reaction mixture was concentrated under reduced pressure. The crude product was purified by flash chromatography (Biotage, 0% to 20% MeOH in DCM) to afford final compound (30 mg, yield: 56%) as an orange solid.

HPLC-MS (method 4): Rt=4.1, [M+H]+440.

Synthesis of Intermediate XXXVIII.

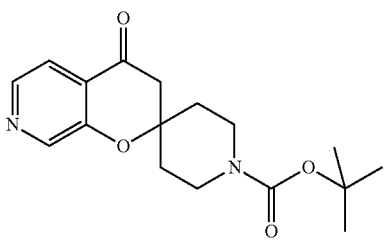

XXXVIII

A mixture of intermediate IV (0.300 mg, 2.188 mmol, 1 eq.), N,N-diisopropylethylamine (0.381 mL, 2.188 mmol, 1 eq.), pyrrolidine (0.274 mL, 3.281 mmol, 1.5 eq.) and 1-Boc-4-piperidone (1.090 g, 5.469 mmol, 2.5 eq.) in toluene (36 mL) with a Dean-Stark trap was heated at 140° C. for 2 h. The mixture was cooled down to room temperature, and diluted with EtOAc. The organic layer was washed with water, with a saturated aqueous solution of NH$_4$Cl, and with a saturated aqueous solution of NaCl. Then, it was dried over Na$_2$SO$_4$ and concentrated till dryness. The residue was purified by flash chromatography (Biotage, 0% to 40% EtOAc in c-Hex) affording the expected intermediate (319 mg, yield: 46%).

HPLC-MS (method 4): Rt=4.2, [M+H]+ 319.3.

Synthesis of Intermediate XXXIX.

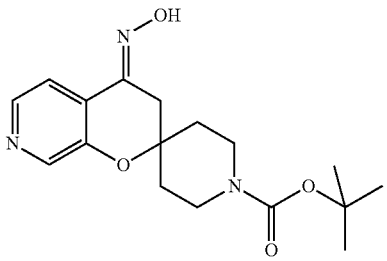

XXXIX

This intermediate was prepared following the same protocol which was employed to prepare the intermediate VI, but using intermediate XXXVIII as starting material. In this case, the residue wasn't purified by flash chromatography.

HPLC-MS (method 4): Rt=3.5, [M+H]+ 334.1.

Synthesis of Intermediate XL.

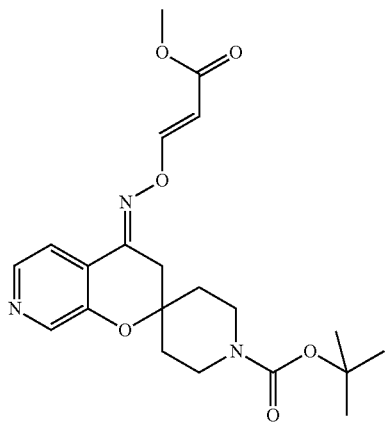

XL

This intermediate was prepared following the same protocol which was employed to prepare the intermediate VII, but using intermediate XXXIX as starting material (yield: 77%).

HPLC-MS (method 4): Rt=4.6, [M+H]+ 418.1.

$^1$H NMR (700 MHz, CDCl$_3$) δ 8.35 (d, J=28.6 Hz, 1H), 8.17 (s, 1H), 7.96 (d, J=12.6 Hz, 1H), 7.73 (s, 1H), 5.62 (dd, J=12.5, 5.1 Hz, 1H), 3.91-3.72 (m, 2H), 3.67-3.65 (m, 3H), 3.06 (brs, 2H), 2.88 (s, 2H), 1.80 (brs, 2H), 1.54 (brs, 2H), 1.37 (d, J=4.3 Hz, 9H).

Synthesis of Intermediate XLI.

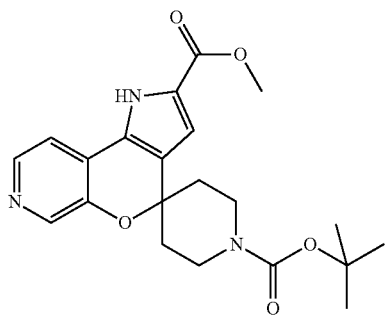

XLI

This intermediate was prepared following the same protocol which was employed to prepare the intermediate VIII, but using intermediate XL as starting material (yield: 29%).

HPLC-MS (method 4): Rt=3.5, [M+H]+ 400.1.

Synthesis of Intermediate XLII.

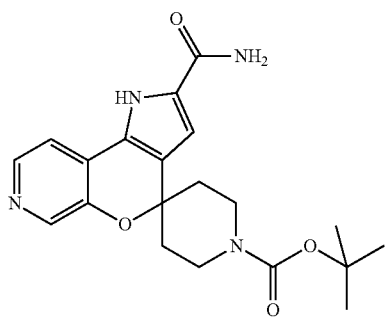

XLII

A solution of intermediate XLI (79 mg, 0.198 mmol, 1 eq.) in ammonia (7N in MeOH, 6 mL) was heated in a pressure tube at 100° C. for 48 hours. The solvent was evaporated under vacuum, and the residue was purified by flash chromatography (Biotage, 0% to 40% MeOH in DCM) affording the expected intermediate as a yellow solid (30 mg, yield: 39%).

HPLC-MS (method 4): Rt=3.1, [M+H]+ 385.1.

$^1$H NMR (300 MHz, DMSO) δ 12.79 (s, 1H), 8.42 (s, 1H), 8.29 (d, J=5.7 Hz, 1H), 8.06 (d, J=5.8 Hz, 1H), 7.79 (s, 1H), 7.37 (s, 1H), 6.80 (d, J=2.0 Hz, 1H), 3.77 (s, 2H), 1.95 (d, J=13.7 Hz, 2H), 1.73 (d, J=12.2 Hz, 2H), 1.35 (s, 9H), 1.15 (s, 1H), 0.74 (s, 1H).

Synthesis of Intermediate XLIII.

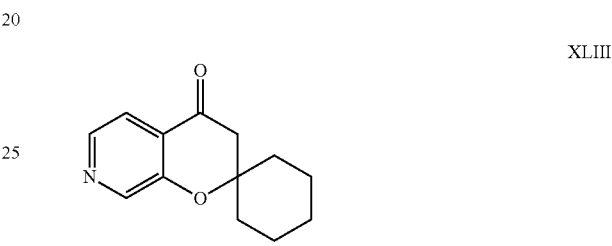

XLIII

A mixture of intermediate IV (0.300 mg, 2.188 mmol, 1 eq.), n,n-diisopropylethylamine (0.381 mL, 2.188 mmol, 1 eq.), pyrrolidine (0.274 mL, 3.281 mmol, 1.5 eq.) and cyclohexanone (0.567 mL, 5.469 mmol, 2.5 eq.) in toluene (36 mL) with a Dean-Stark trap was heated at 140° C. for 2 h. The mixture was cooled down to room temperature. The reaction was diluted with EtOAc. The organic layer was washed with water, with a saturated aqueous solution of NH$_4$Cl and with a saturated aqueous solution of NaCl. Then, it was dried over Na$_2$SO$_4$ and concentrated till dryness. The residue was purified by column chromatography (Biotage, cHex/EtOAc) affording the expected compound (245 mg, yield: 52%).

HPLC-MS (method 4): Rt=4.2, [M+H]+ 218.

Synthesis of Intermediate XLIV.

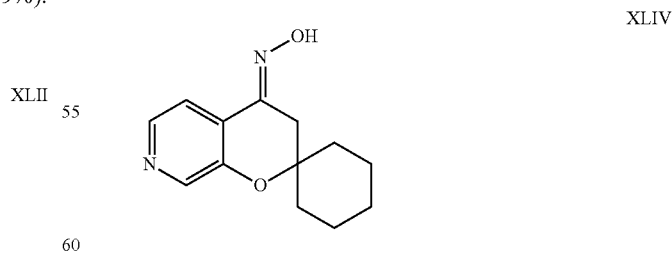

XLIV

This intermediate was prepared following the same protocol which was employed to prepare the intermediate VI, but using intermediate XLIII as starting material. In this case, the residue wasn't purified by flash chromatography.

HPLC-MS (method 4): Rt=3.0, [M+H]+ 233.

Synthesis of Intermediate XLV.

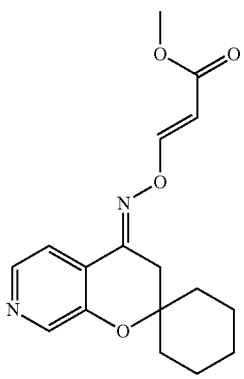

XLV

This intermediate was prepared following the same protocol which was employed to prepare the intermediate VII, but using intermediate XLIV as starting material (yield: 91%).
HPLC-MS (method 4): Rt=4.6, [M+H]+ 371.
$^1$H NMR (700 MHz, CDCl3) δ 8.35 (s, 1H), 8.12 (s, 1H), 7.97 (d, J=12.5 Hz, 1H), 7.86 (s, 1H), 5.63 (t, J=11.2 Hz, 1H), 3.67 (s, 3H), 2.88 (s, 2H), 1.81 (s, 2H), 1.60 (s, 4H), 1.46 (s, 4H).

Synthesis of Intermediate XLVI.

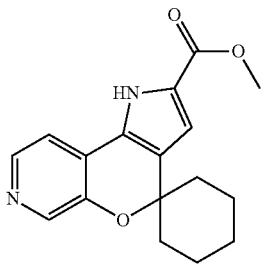

XLVI

This intermediate was prepared following the same protocol which was employed to prepare the intermediate VIII, but using intermediate XLV as starting material (yield: 17%).
HPLC-MS (method 4): Rt=3.4, [M+H]+ 299.
1H NMR (300 MHz, MeOD) δ 8.21 (s, 1H), 8.14 (d, J=5.1 Hz, 1H), 7.64 (d, J=5.1 Hz, 1H), 6.84 (s, 1H), 3.95 (s, 3H), 2.13 (d, J=13.9 Hz, 2H), 2.01-1.63 (m, 8H).

Synthesis of Intermediate XLVII.

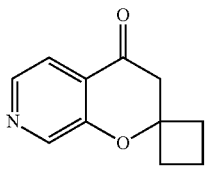

XLVII

This intermediate was prepared following the same protocol which was employed to prepare the intermediate XLIII, but using cyclobutanone instead of cyclohexanone (yield: 40%).
HPLC-MS (method 4): Rt=3.5, [M+H]+ 190.

Synthesis of Intermediate XLVIII.

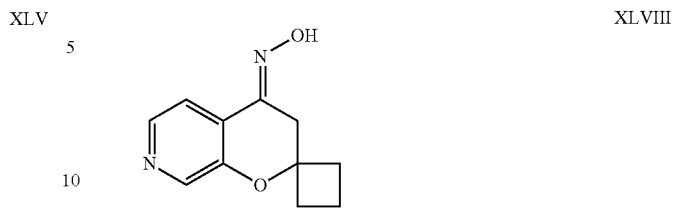

XLVIII

This intermediate was prepared following the same protocol which was employed to prepare the intermediate VI, but using intermediate XLVII as starting material. In this case, the residue wasn't purified by flash chromatography.
HPLC-MS (method 4): Rt=1.5, [M+H]+ 205.

Synthesis of Intermediate XLIX.

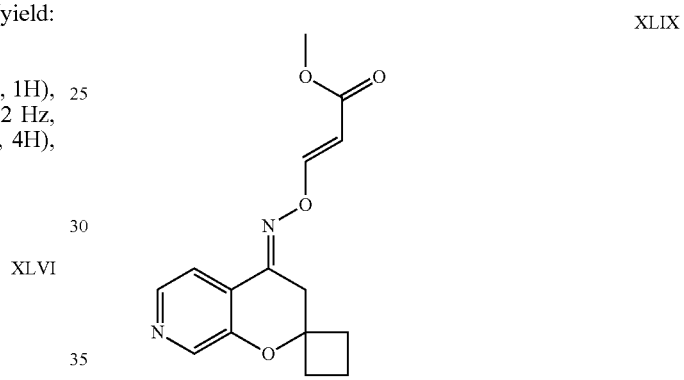

XLIX

This intermediate was prepared following the same protocol which was employed to prepare the intermediate VII, but using intermediate XLVIII as starting material (yield: 69%).
HPLC-MS (method 4): Rt=4.3, [M+H]+ 289.

Synthesis of Intermediate L.

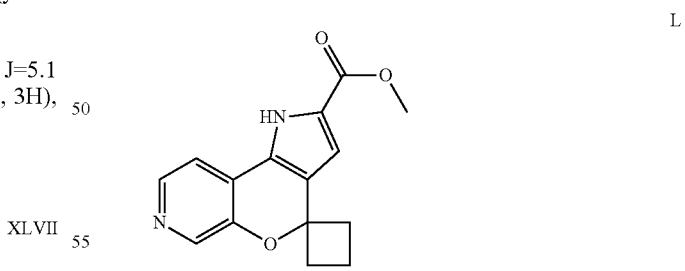

L

This intermediate was prepared following the same protocol which was employed to prepare the intermediate VIII, but using intermediate XLIX as starting material (yield: 19%).
HPLC-MS (method 4): Rt=0.4 & 2.9, [M+H]+ 271.
1H NMR (700 MHz, CDCl3) δ 10.40 (s, 1H), 8.27 (m, 1H), 8.15 (s, 1H), 7.63 (s, 1H), 6.85 (s, 1H), 3.84 (s, 3H), 2.60 (d, J=9.9 Hz, 2H), 2.38 (d, J=10.3 Hz, 2H), 1.95-1.91 (m, 7.7 Hz, 1H), 1.84-1.78 (m, 1H).

Synthesis of Intermediate LI.

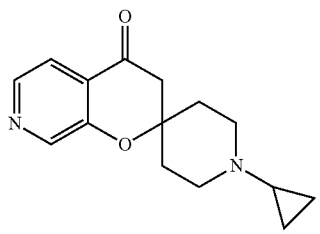

LI

This intermediate was prepared following the same protocol which was employed to prepare the intermediate V, but using 1-cyclopropyl-4-piperidone instead of acetone (yield: 71%).

HPLC-MS (method 4): Rt=0.4, [M+H]+ 259.

Synthesis of Intermediate LII.

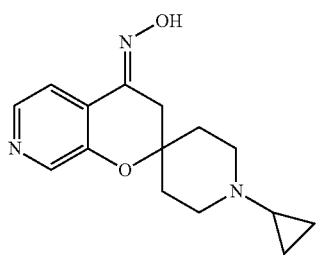

LII

This intermediate was prepared following the same protocol which was employed to prepare the intermediate VI, but using intermediate LI as starting material. In this case, the residue wasn't purified by flash chromatography.

HPLC-MS (method 4): Rt=0.4, [M+H]+ 274.

Synthesis of Intermediate LIII.

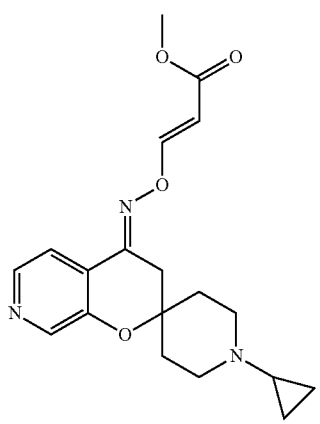

LIII

This intermediate was prepared following the same protocol which was employed to prepare the intermediate VII, but using intermediate LII as starting material. In this case, the residue wasn't purified by flash chromatography.

HPLC-MS (method 4): Rt=1.2, [M+H]+ 358.

Synthesis of Intermediate LIV.

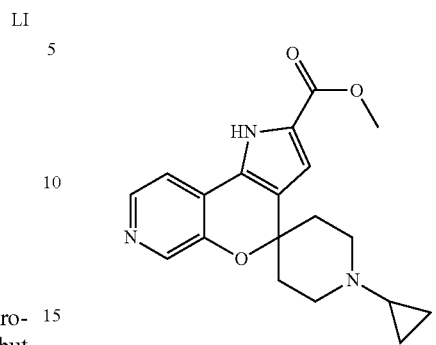

LIV

This intermediate was prepared following the same protocol which was employed to prepare the intermediate VIII, but using intermediate LIII as starting material (yield: 13%).

HPLC-MS (method 4): Rt=0.4, [M+H]+340.

Synthesis of Intermediate LV.

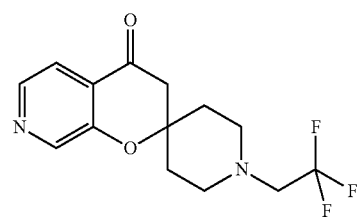

LV

This intermediate was prepared following the same protocol which was employed to prepare the intermediate V, but using 1-(2,2,2-trifluoroethyl)piperidin-4-one instead of acetone (yield: 34%).

HPLC-MS (method 4): Rt=3.6, [M+H]+ 301.

Synthesis of Intermediate LVI.

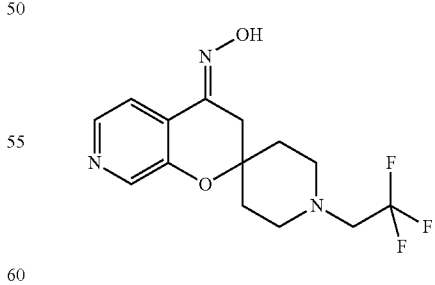

LVI

This intermediate was prepared following the same protocol which was employed to prepare the intermediate VI, but using intermediate LV as starting material. In this case, the residue wasn't purified by flash chromatography.

HPLC-MS (method 4): Rt=2.2 & 2.6, [M+H]+316.

Synthesis of Intermediate LVII.

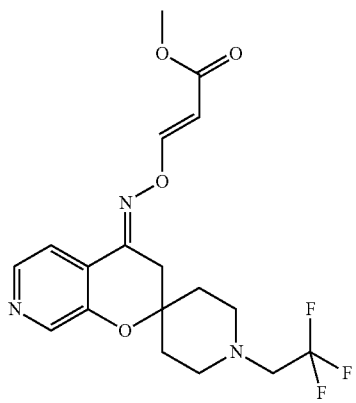
LVII

This intermediate was prepared following the same protocol which was employed to prepare the intermediate VII, but using intermediate LVI as starting material. In this case, the residue wasn't purified by flash chromatography.

HPLC-MS (method 4): Rt=4.4, [M+H]+400.

Synthesis of Intermediate LVIII.

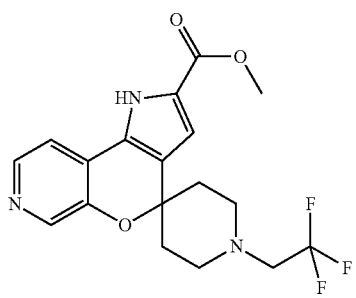
LVIII

This intermediate was prepared following the same protocol which was employed to prepare the intermediate VIII, but using intermediate LVII as starting material (yield: 35%).

HPLC-MS (method 4): Rt=3.2, [M+H]+382.

Synthesis of Intermediate LIX.

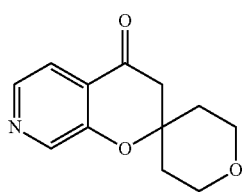
LIX

This intermediate was prepared following the same protocol which was employed to prepare the intermediate V, but using tetrahydro-4h-pyran-4-one instead of acetone (yield: 50%).

HPLC-MS (method 4): Rt=2.4, [M+H]+ 220.

1H NMR (300 MHz, DMSO) δ 8.51 (s, 1H), 8.24 (d, J=4.9 Hz, 1H), 7.50 (dd, J=4.9, 0.7 Hz, 1H), 3.64-3.61 (m, 4H), 2.92 (brs, 2H), 1.87-1.59 (m, 4H).

Synthesis of Intermediate LX.

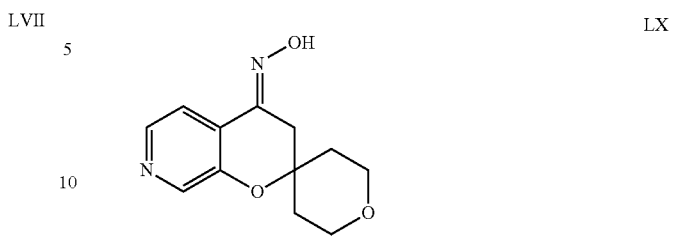
LX

This intermediate was prepared following the same protocol which was employed to prepare the intermediate VI, but using intermediate LIX as starting material. In this case, the residue wasn't purified by flash chromatography.

HPLC-MS (method 4): Rt=1.2 & 1.8, [M+H]+235.

Synthesis of Intermediate LXI.

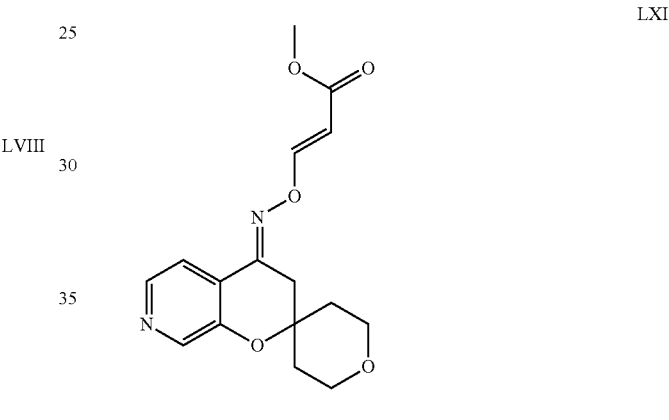
LXI

This intermediate was prepared following the same protocol which was employed to prepare the intermediate VII, but using intermediate LX as starting material. In this case, the residue wasn't purified by flash chromatography.

HPLC-MS (method 4): Rt=3.8, [M+H]+319.

Synthesis of Intermediate LXII.

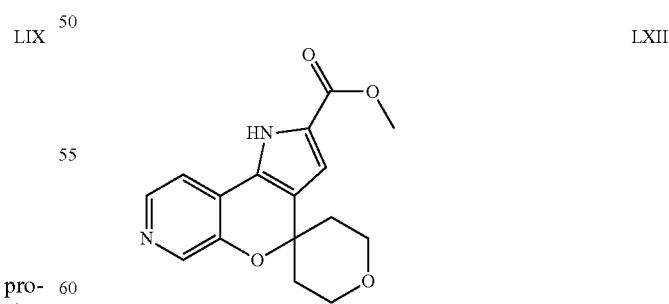
LXII

This intermediate was prepared following the same protocol which was employed to prepare the intermediate VIII, but using intermediate LXI as starting material (yield: 38%).

HPLC-MS (method 4): Rt=2.0 & 2.4 min, [M+H]+ 301.

Synthesis of Intermediate LXIII.

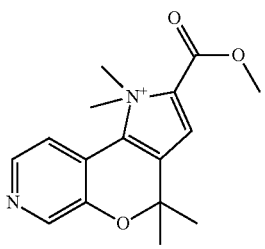

LXIII

A mixture of intermediate VIII (50 mg, 0.194 mmol, 1 eq) with potassium carbonate (59 mg, 0.426 mmol, 2.2 eq) and iodomethane (14 uL, 0.232 mmol, 1.2 eq) in acetonitrile (1.9 mL) was heated at 120° C. for 48 h. The mixture was cooled down to room temperature and concentrated in vacuo. The residue was purified by column chromatography (Biotage, 0% to 50% EtOAc in c-Hex, and 0% to 20% MeOH in DCM) to give expected product (17 mg, yield: 31%).

HPLC-MS (method 4): Rt=0.368, 0.582, 2.552 min, [M+H]+ 287.

1H NMR (300 MHz, DMSO) d 8.70 (s, 1H), 8.53 (d, J=6.5 Hz, 1H), 8.22 (d, J=6.5 Hz, 1H), 7.03 (s, 1H), 4.22 (d, J=6.5 Hz, 6H), 3.83 (s, 3H), 1.63 (s, 6H).

Synthesis of Intermediate LXIV.

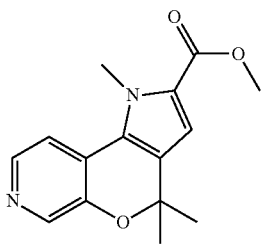

LXIV

To a stirred solution of intermediate VIII (40 mg, 0.155 mmol, 1 eq) in DMF (1.5 ml) at 0° C., a solution of sodium hydride (60% suspension in mineral oil, 24 mg, 0.155 mmol, 1 eq) in DMF (0.4 ml) was added. The mixture was stirred at 0° C. for 10 min and then, methyl iodide (0.010 ml, 0.155 mmol, 1 eq) was added. The resulting reaction mixture was stirred at 0° C. for 1 h. The reaction mixture was then quenched with water (10 ml). The mixture was extracted with EtOAc (2×50 ml). The combined organic layers were dried over anhydrous Na2SO4 and evaporated till dryness. The residue was purified by flash chromatography (Biotage, 0% to 40% EtOAc in c-Hex) to afford the expected compound (35 mg, yield: 83%).

HPLC-MS (method 4): Rt=3.2 min, [M+H]+ 273.

Synthesis of Intermediate LXV.

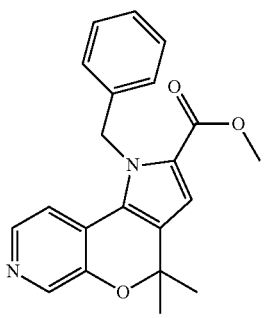

LXV

To a stirred solution of intermediate VIII (20 mg, 0.077 mmol, 1 eq) in AcCN (0.8 ml), lithium tert-butoxide (1M in THF, 0.085 mL, 0.085 mmol, 1.1 eq) was added. The mixture was stirred for 5 min and then, benzyl bromide (0.009 ml, 0.077 mmol, 1 eq) was added. The resulting reaction mixture was stirred for 1 h at room temperature. The reaction mixture was concentrated till dryness. The residue was purified by flash chromatography (Biotage, 0% to 20% MeOH in DCM) to afford the expected compound (20 mg, yield: 74%).

HPLC-MS (method 4): Rt=3.2 min, [M+H]+ 349.

Synthesis of Intermediate LXVI.

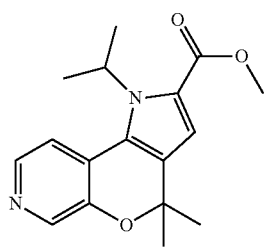

LXVI

To a stirred solution of intermediate VIII (40 mg, 0.155 mmol, 1 eq) in AcCN (1.6 ml), lithium tert-butoxide (1M in THF, 0.170 mL, 0.170 mmol, 1.1 eq) was added. The mixture was stirred for 5 min and then, 2-iodopropane (0.0015 ml, 0.077 mmol, 1 eq) was added. The reaction mixture was heated at 120° C. for 16 h. The reaction mixture was concentrated and the residue was purified by flash chromatography (Biotage, 0% to 20% MeOH in DCM) to afford the desired compound (45 mg, yield: 97%).

HPLC-MS (method 4): Rt=3.2 min, [M+H]+ 301.

Synthesis of Intermediate LXVII.

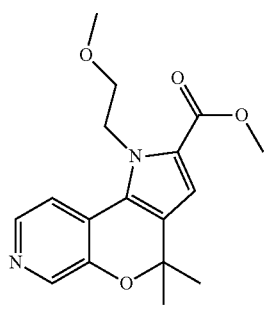

LXVII

This intermediate was prepared following the same protocol which was employed to prepare the intermediate LXVI, but using 2-chloroethyl methyl ether instead of 2-iodopropane (yield: 61%).

HPLC-MS (method 4): Rt=3.1, [M+H]+317.

Synthesis of Intermediate LXVIII.

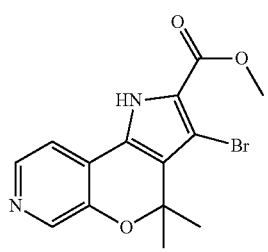

LXVIII

A solution of n-bromosuccinimide (262 mg, 1.471 mmol, 1 eq) was added to a solution of intermediate VIII (380 mg, 1.471 mmol, 1 eq) in AcCN (14.7 mL). The resulting mixture was heated at 40° C. for 2 h. After removing solvent, the residue was purified by flash chromatography (Biotage, 0% to 40% EtOAc in c-Hex) to afford the desired product as a white solid (430 mg, yield: 87%).

HPLC-MS (method 4): Rt=4.2, [M+H]+ 337

1H NMR (300 MHz, DMSO) δ 12.95 (s, 1H), 8.10 (s, 1H), 8.08 (d, J=5.0 Hz, 1H), 7.78 (d, J=5.0 Hz, 1H), 3.79 (s, 3H), 1.61 (s, 6H).

Synthesis of Intermediate LXIX.

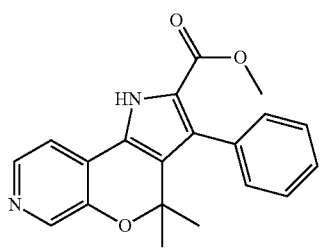

LXIX

To a mixture of intermediate LXVIII (20 mg, 0.059 mmol, 1 eq) in 1,2-dimethoxyethane (1 mL), phenylboronic acid (14 mg, 0.119 mmol, 2 eq), PdCl$_2$(dppf) (5 mg, 0.006 mmol, 0.1 eq) and a saturated Na$_2$CO$_3$ aqueous solution (0.2 mL) were added and it was heated at 100° C. for 1 h under microwave irradiation (Biotage). Then, water was added and it was extracted with dichloromethane, dried over Na$_2$SO$_4$ and evaporated till dryness. The residue was purified by flash chromatography (Biotage, 0% to 40% EtOAc in c-Hex) to afford a yellow solid (20 mg, yield: 99%).

HPLC-MS (method 4): Rt=3.8, [M+H]+ 335.

1H NMR (300 MHz, DMSO) δ 12.69 (s, 1H), 8.23-8.10 (m, 2H), 7.88 (d, J=4.9 Hz, 1H), 7.37 (s, 3H), 7.26 (s, 2H), 3.57 (s, 3H), 1.28 (s, 6H).

Synthesis of Intermediate LXX.

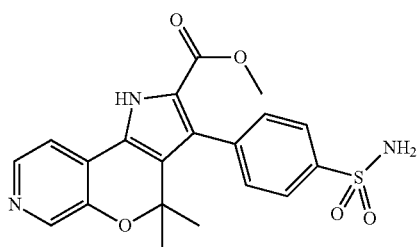

LXX

This intermediate was prepared following the same protocol which was employed to prepare the intermediate LXIX, but using 4-sulfamoylphenylboronic acid pinacol ester instead of phenylboronic acid (yield: 41%).

HPLC-MS (method 4): Rt=3.8, [M+H]+ 414.

1H NMR (300 MHz, DMSO) δ 12.77 (s, 1H), 8.11 (d, J=5.0 Hz, 1H), 8.09 (s, 1H), 7.83 (d, J=5.0 Hz, 1H), 7.77 (d, J=8.2 Hz, 2H), 7.50-7.27 (m, 4H), 3.54 (s, 3H), 1.24 (s, 6H).

Synthesis of Intermediate LXXI.

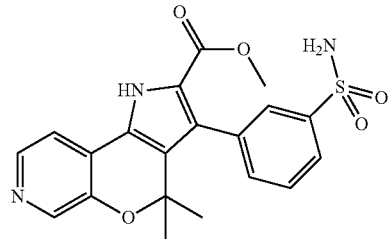

LXXI

This intermediate was prepared following the same protocol which was employed to prepare the intermediate LXIX, but using benzenesulfonamide-3-boronic acid pinacol ester instead of phenylboronic acid (yield: 41%).

HPLC-MS (method 4): Rt=2.9, [M+H]+ 414.

Synthesis of Intermediate LXXII.

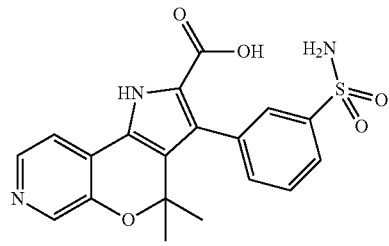

LXXII

To a solution of intermediate LXXI (20 mg, 0.048 mmol) in AcCN (0.4 mL), ammonium hydroxide (0.5 mL) was added. The reaction mixture was heated in a sealed tube at 150° C. for 48 h. The solvent was evaporated to dryness. The residue was used in the next step without further treatment (19 mg).

HPLC-MS (method 4): Rt=2.6, [M+H]+400.

Synthesis of Intermediate LXXIII.

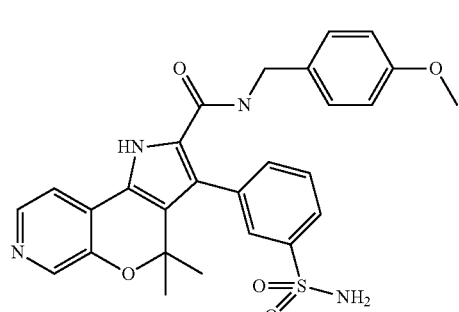

LXXIII

This intermediate was prepared following the same protocol which was employed to prepare the intermediate XXXVII, but using intermediate LXXII as starting material (yield: 40%).

HPLC-MS (method 4): Rt=3.3, [M+H]+519.

Synthesis of Intermediate LXXIV.

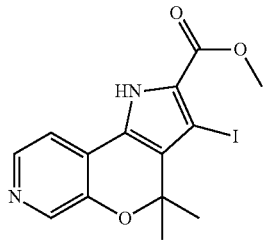

A solution of n-iodosuccinimide (61 mg, 0.271 mmol, 1 eq) was added to a solution of intermediate VIII (70 mg, 0.271 mmol, 1 eq) in AcCN (2.7 mL). The resulting mixture was heated at 40° C. for 2 h. After removing solvent, the residue was purified by flash chromatography (Biotage, 0% to 10% MeOH in DCM) to afford desired product as an orange solid (100 mg, 96%)

HPLC-MS (method 4): Rt=3.4, [M+H]+385.

Synthesis of Intermediate LXXV.

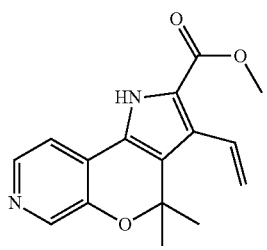

This intermediate was prepared following the same protocol which was employed to prepare the intermediate LXIX, but using vinylboronic acid pinacol ester instead of phenylboronic acid (yield: 54%).

HPLC-MS (method 4): Rt=3.2, [M+H]+285.

Synthesis of Intermediate LXXVI.

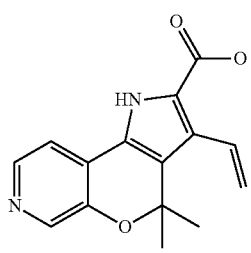

This intermediate was prepared following the same protocol which was employed to prepare the intermediate IX, but using intermediate LXXV as starting material. In this case, the residue wasn't purified by flash chromatography.

HPLC-MS (method 4): Rt=3.1, [M+H]+271.

Synthesis of Intermediate LXXVII.

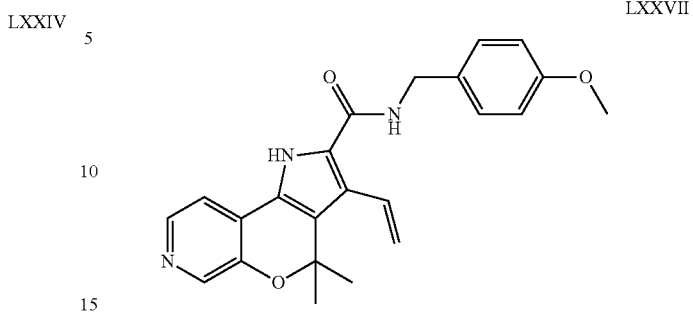

This intermediate was prepared following the same protocol which was employed to prepare the intermediate XXXVII, but using intermediate LXXVI as starting material (yield: 48%).

HPLC-MS (method 4): Rt=3.7, [M+H]+390.

Synthesis of Intermediate LXXVIII.

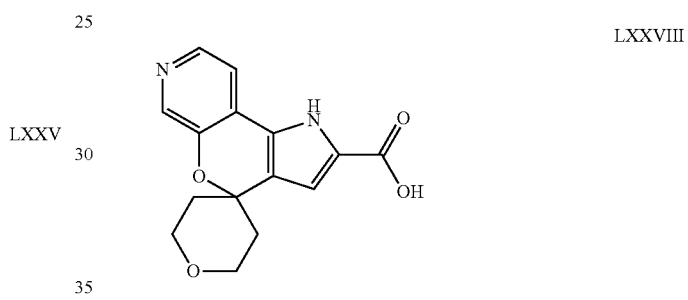

To a solution of intermediate LXII (65 mg, 0.216 mmol) in AcCN (1 mL), ammonium hydroxide (2 mL) was added. The mixture was heated in the MW at 130° C. for 1 h. The solvent was evaporated. The crude was purified by preparative HPLC and two products were detected: the acid derivative (10 mg, yield: 16%) and the amide derivative (1 mg, yield: 2%).

HPLC-MS (method 4): Rt=0.8, [M+H]+287.

Synthesis of Intermediate LXXIX.

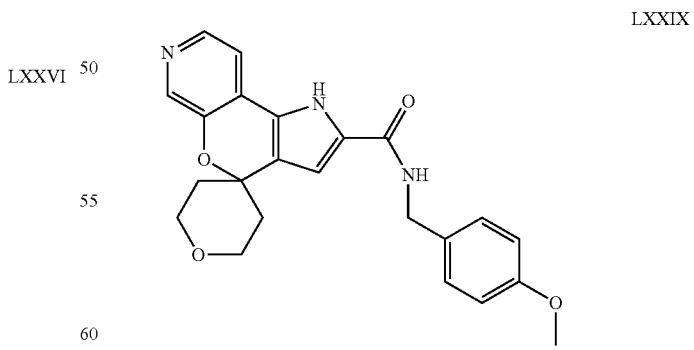

This intermediate was prepared following the same protocol which was employed to prepare the intermediate X, but using intermediate LXXVIII as starting material (yield: 28%).

HPLC-MS (method 4): Rt=3.1, [M+H]+406.

Synthesis of Intermediate LXXX.

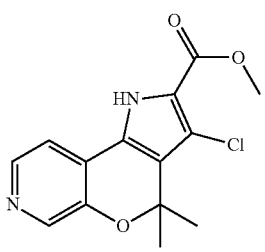

A solution of n-chlorosuccinimide (26 mg, 0.194 mmol, 1 eq) in dry AcCN (2 mL) was added dropwise to an ice-cooled solution of intermediate VIII (50 mg, 0.194 mmol, 1 eq) in AcCN (2 mL). Upon completion of addition (ca. 20 min), the resulting mixture was allowed to warm up to room temperature and stirred for an additional 16 h. Then, the reaction was heated at 50° C. for another 16 h. After removing solvent, the residue was purified by flash chromatography (Biotage, 0% to 40% EtOAc in c-Hex) to afford the desired product (20 mg, yield: 35%).

HPLC-MS (method 4): Rt=3.2, [M+H]+293.

1H NMR (300 MHz, CDCl3) δ 9.32 (s, 1H), 8.44 (s, 1H), 8.31 (s, 1H), 7.96 (d, J=4.7 Hz, 1H), 3.82-3.73 (m, 3H), 1.71 (dd, J=14.4, 6.4 Hz, 6H).

Synthesis of Intermediate LXXXI.

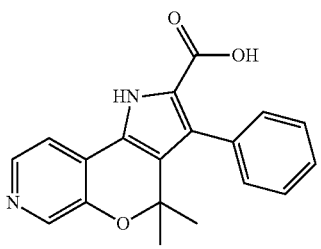

This intermediate was prepared following the same protocol which was employed to prepare the intermediate IX, but using intermediate LXIX as starting material (yield: 84%).

HPLC-MS (method 4): Rt=3.3, [M+H]+321.

Synthesis of Intermediate LXXXII.

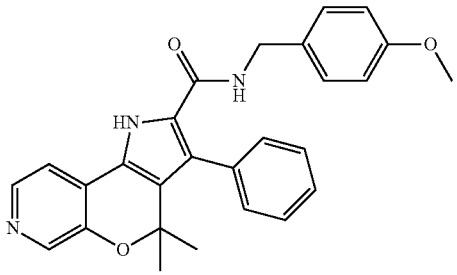

This intermediate was prepared following the same protocol which was employed to prepare the intermediate X, but using intermediate LXXXI as starting material (yield: 26%).

HPLC-MS (method 4): Rt=3.8, [M+H]+440.

1H NMR (300 MHz, DMSO) δ 8.28 (s, 2H), 7.97 (d, J=8.4 Hz, 2H), 7.82 (d, J=8.4 Hz, 2H), 7.68-7.60 (m, 4H), 7.30 (d, J=8.4 Hz, 2H), 3.42 (s, 2H), 1.35 (s, 9H).

Synthesis of Intermediate LXXXIII.

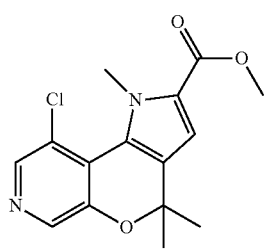

Cesium carbonate (178 mg, 0.547 mmol, 3 eq) was added to a stirred solution of the intermediate XXXIV (80 mg, 0.273 mmol, 1 eq) in acetonitrile (2.7 mL) at room temperature. The mixture was stirred at room temperature for 5 minutes, and then a solution of iodomethane (1N in acetonitrile, 0.273 mL, 0.273 mmol, 1 eq) was added. The resulting reaction mixture was stirred at room temperature for 16 hours. The reaction was quenched with water (10 mL), and the aqueous layer was extracted with EtOAc (2×50 mL). The combined organic layers were dried over anhydrous Na2SO4, filtered and evaporated under reduced pressure to obtain the crude product that was used in the next step without further purification.

HPLC-MS (method 4): Rt=4.7, [M+H]+307.2.

Synthesis of Intermediate LXXXIV.

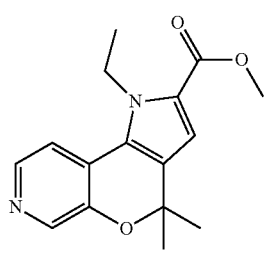

This intermediate was prepared following the same protocol which was employed to prepare the intermediate LXXXIII, but using iodoethane instead of iodomethane, and employing the intermediate VIII as starting material. The intermediate was purified by flash chromatography (Biotage, 0% to 40% EtOAc in c-Hex) to afford the desired product (yield: 72%).

HPLC-MS (method 4): Rt=3.2, [M+H]+287.3.

Synthesis of Intermediate LXXXV.

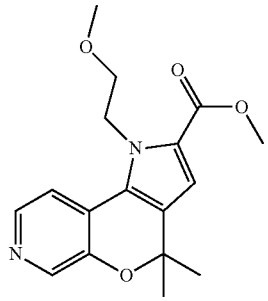

This intermediate was prepared following the same protocol which was employed to prepare the intermediate LXXXIII, but using 2-bromoethyl methyl ether instead of iodomethane, and employing the intermediate VIII as starting material. The intermediate was purified by flash chromatography (Biotage, 0% to 40% EtOAc in c-Hex) to afford the desired product (yield: 90%).

HPLC-MS (method 4): Rt=3.2, [M+H]+317.3.

Synthesis of Intermediate LXXXVI.

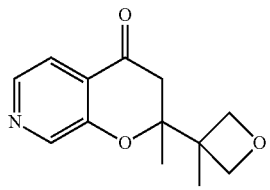

LXXXVI

This intermediate was prepared following the same protocol which was employed to prepare the intermediate XLIII, but using 1-(3-methyl-oxetan-3-yl)ethanone instead of cyclohexanone (yield: 22%).

HPLC-MS (method 4): Rt=2.7, [M+H]+234.1.

Synthesis of Intermediate LXXXVII.

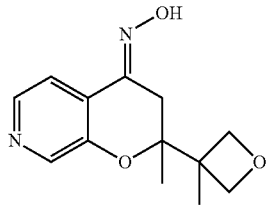

LXXXVII

This intermediate was prepared following the same protocol which was employed to prepare the intermediate VI, but using intermediate LXXXVI as starting material instead of intermediate V. The reaction was carried out by heating at 40° C. instead of at room temperature. The intermediate was used without further purification.

HPLC-MS (method 4): Rt=0.7, [M+H]+249.1.

Synthesis of Intermediate LXXXVIII.

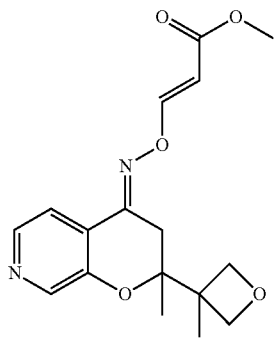

LXXXVIII

This intermediate was prepared following the same protocol which was employed to prepare the intermediate VII, but using intermediate LXXXVII as starting material instead of intermediate VI. In this case, the intermediate was not purified by column chromatography.

HPLC-MS (method 4): Rt=3.6, [M+H]+333.1.

Synthesis of Intermediate LXXXIX.

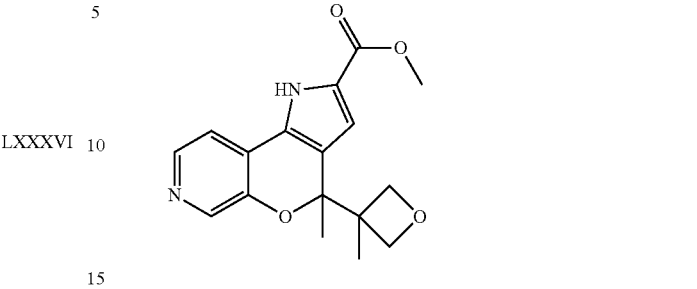

LXXXIX

This intermediate was prepared following the same protocol which was employed to prepare the intermediate VIII, but using intermediate LXXXVIII as starting material instead of intermediate VII (yield: 22%).

HPLC-MS (method 4): Rt=2.2, [M+H]+315.3.

Synthesis of Intermediate XC.

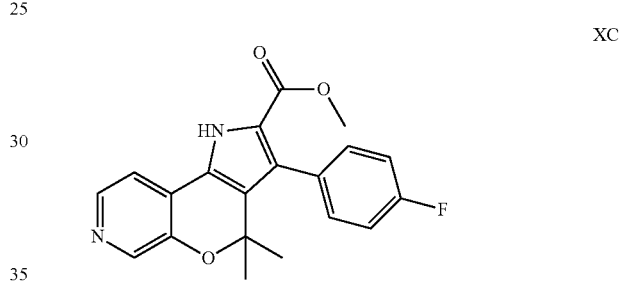

XC

This intermediate was prepared following the same protocol which was employed to prepare the intermediate LXIX, but using 4-fluorophenylboronic acid instead of phenylboronic acid. The purification was carried out by flash chromatography (Biotage) eluting with 0% to 2% MeOH in DCM (yield: 88%).

HPLC-MS (method 4): Rt=3.5, [M+H]+ 353.1.

Synthesis of Intermediate XCI.

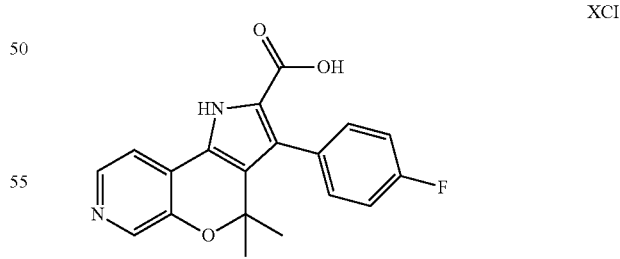

XCI

This intermediate was prepared following the same protocol which was employed to prepare the intermediate IX, but using intermediate XC as starting material. The reaction was carried out by heating at 100° C. for 16 hours instead of 80° C. for 1 hour. In this case, the intermediate was not purified by flash chromatography.

HPLC-MS (method 4): Rt=3.3, [M+H]+ 339.1.

Synthesis of Intermediate XCII.

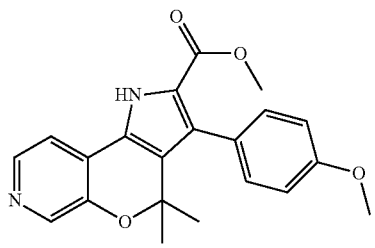

XCII

This intermediate was prepared following the same protocol which was employed to prepare the intermediate LXIX, but using 4-methoxyphenylboronic acid instead of phenylboronic acid. The purification was carried out by flash chromatography (Biotage) eluting with 0.5% to 3% MeOH in DCM (yield: 56%).

HPLC-MS (method 4): Rt=3.5, [M+H]+ 365.1.

Synthesis of Intermediate XCIII.

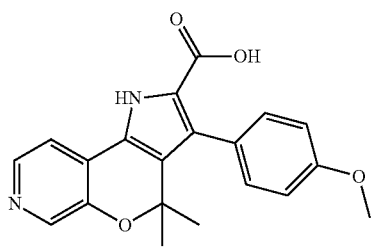

XCIII

This intermediate was prepared following the same protocol which was employed to prepare the intermediate IX, but using intermediate XCII as starting material. The reaction was carried out by heating at 100° C. for 16 hours instead of 80° C. for 1 hour. In this case, the intermediate was not purified by flash chromatography.

HPLC-MS (method 4): Rt=3.0, [M+H]+ 351.1.

Synthesis of Intermediate XCIV.

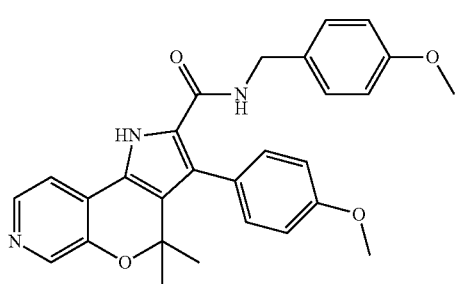

XCIV

This intermediate was prepared following the same protocol which was employed to prepare the intermediate X, but using intermediate XCIII as starting material. The reaction was carried out under reflux conditions for 16 hours instead of at room temperature for 3 hours. In this case, the intermediate was not purified by flash chromatography.

HPLC-MS (method 4): Rt=3.6, [M+H]+ 470.4.

Synthesis of Intermediate XCV.

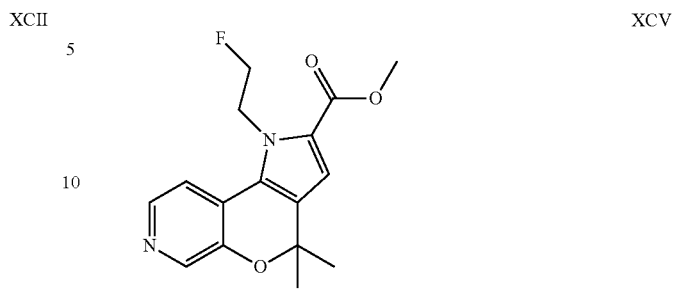

XCV

This intermediate was prepared following the same protocol which was employed to prepare the intermediate LXXXIII, but using 1-fluoro-2-iodoethane instead of iodomethane, and employing intermediate VIII as starting material. The reaction was carried out by heating at 50° C. for 16 hours instead of at room temperature for 16 hours. The intermediate was purified by flash chromatography (Biotage, 0% to 40% EtOAc in c-Hex) to afford the desired intermediate as a yellow solid (yield: 93%).

HPLC-MS (method 4): Rt=3.1, [M+H]+ 305.3.

Synthesis of Intermediate XCVI.

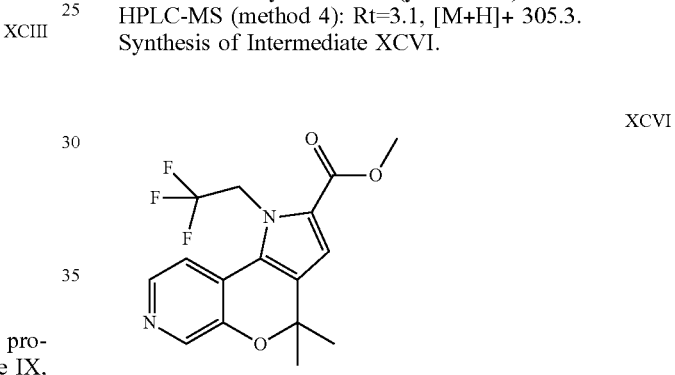

XCVI

This intermediate was prepared following the same protocol which was employed to prepare the intermediate LXXXIII, but using 2-iodo-1,1,1-trifluoroethane instead of iodomethane, and employing intermediate VIII as starting material. The reaction was carried out by heating at 80° C. for 16 hours instead of at room temperature for 16 hours. The intermediate was used in the next step without further purification.

HPLC-MS (method 4): Rt=3.7, [M+H]+ 341.3.

Synthesis of Intermediate XCVII.

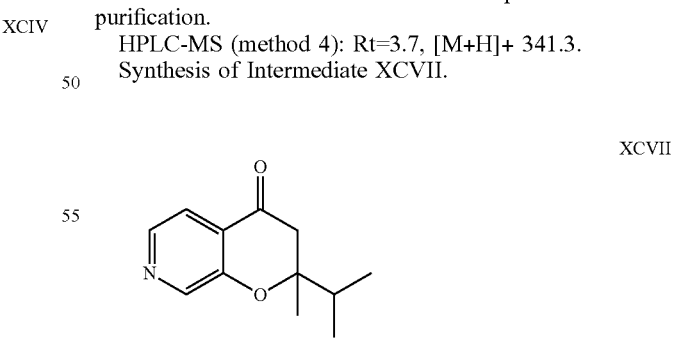

XCVII

This intermediate was prepared following the same protocol which was employed to prepare the intermediate XLIII, but using 3-methyl-2-butanone instead of cyclohexanone. The intermediate was purified by flash chromatography (Biotage, 0% to 30% MeOH in DCM) to give the desired intermediate as a white solid (yield: 22%).

HPLC-MS (method 4): Rt=3.9, [M+H]+ 206.1.

Synthesis of Intermediate XCVIII.

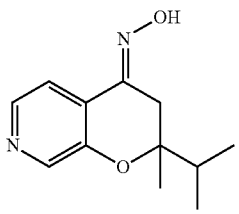
XCVIII

This intermediate was prepared following the same protocol which was employed to prepare the intermediate VI, but using intermediate XCVII as starting material. The reaction was carried out by heating at 40° C. for 16 hours instead of at room temperature for 16 hours. The intermediate was used without further purification.

HPLC-MS (method 4): Rt=2.7, [M+H]+ 221.3.

Synthesis of Intermediate XCIX.

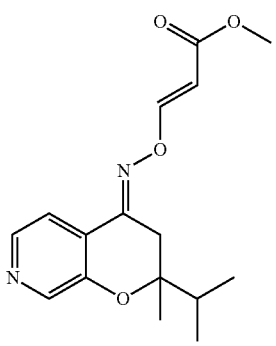
XCIX

This intermediate was prepared following the same protocol which was employed to prepare the intermediate VII, but using intermediate XCVIII as starting material. In this case, the intermediate was not purified by flash column chromatography.

HPLC-MS (method 4): Rt=4.3, [M+H]+ 305.3.

Synthesis of Intermediate C.

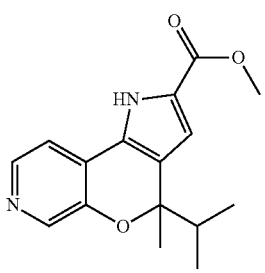
C

This intermediate was prepared following the same protocol which was employed to prepare the intermediate VIII, but using intermediate XCIX as starting material (yield: 28%).

HPLC-MS (method 4): Rt=2.9, [M+H]+ 287.1.

Synthesis of Intermediate CI.

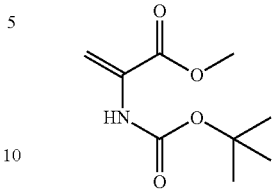
CI

Methanesulfonyl chloride (2.29 mL, 29.649 mmol, 1.3 eq) was added to a mixture of methyl 2-((tert-butoxycarbonyl)amino)-3-hydroxypropanoate (5 g, 22.807 mmol, 1 eq) in N,N-dimethylformamide (57 mL) at 0° C. under Argon, followed by the addition of triethylamine (7.95 mL, 57.016 mmol, 2.5 eq) dropwise over a period of 30 minutes. When the addition was complete, the cooling bath was removed and the yellow reaction was stirred at room temperature for 16 hours. The reaction mixture was partitioned between ice-cold water and diethyl ether. The layers were separated, and the organic phase was washed with a saturated aqueous solution of NH$_4$Cl. The organic phase was dried over Na$_2$SO$_4$, filtered and evaporated under vacuum to afford the desired intermediate as a pale yellow solid. The intermediate was used in the next step without further purification.

HPLC-MS (method 4): Rt=4.12, [M+H-Boc]+ 102.2.

Synthesis of Intermediate CII.

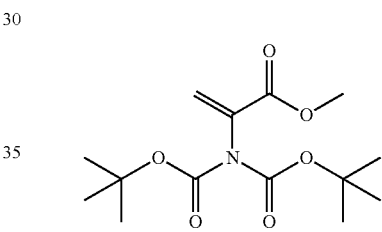
CII

Di-tert-butyl dicarbonate (4.83 g, 22.115 mmol, 1 eq) was added to a mixture of intermediate CI (4.45 g, 22.115 mmol 1 eq) in acetonitrile (44 mL) at room temperature, followed by the addition of 4-dimethylaminopyridine (540 mg, 4.423 mmol, 0.2 eq). The reaction mixture was stirred at room temperature for 16 hours. After removal of volatiles in vacuo, the residue was diluted with AcOEt. The organic layer was washed with a 10% aqueous solution of citric acid and a saturated aqueous solution of NaCl, dried over Na$_2$SO$_4$, filtered, and concentrated in vacuo to give the desired intermediate as a beige solid. The intermediate was used in the next step without further purification.

HPLC-MS (method 4): Rt=4.44, [M+H-2Boc]+ 102.2.

$^1$H NMR (300 MHz, DMSO) δ 6.28 (d, J=0.8 Hz, 1H), 5.86 (d, J=0.8 Hz, 1H), 3.74 (s, 3H), 1.40 (s, 18H).

Synthesis of Intermediate CIII.

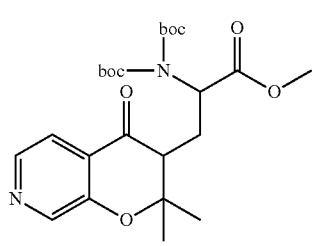
CIII

Lithium diisopropylamide (1.8M in hexanes, 3.90 mL, 7.054 mmol, 2.5 eq) was added dropwise to a mixture of intermediate V (500 mg, 2.822 mmol, 1 eq) in tetrahydrofuran (18 mL) at −50° C. under Argon. The reaction mixture was stirred at −50° C. for 90 minutes. Then, a solution of intermediate CII (1.70 g, 5.643 mmol, 2 eq) in tetrahydrofuran (10 mL) was added dropwise over a period of 10 minutes. The reaction was stirred at room temperature for 16 hours. The reaction mixture was quenched with a saturated aqueous solution of NH₄Cl, and the aqueous phase was extracted with EtOAc. The organic phase was washed with a saturated aqueous solution of NaCl, dried over Na₂SO₄, filtered and concentrated under vacuum. The residue was purified by flash chromatography (Biotage, 0% to 2% MeOH in DCM) affording the expected intermediate as a pale yellow solid and as a mixture of diastereomers (1.29 g, yield: 95%).

HPLC-MS (method 4): Rt=4.78, [M+H]+ 479.2.

Synthesis of Intermediate CIV.

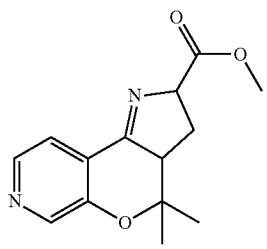

CIV

Trifluoroacetic acid (6.20 mL, 80.871 mmol, 30 eq) was added to a solution of intermediate CIII (1.29 g, 2.696 mmol, 1 eq) in dichloromethane (27 mL) at 0° C. The reaction was stirred at room temperature for 90 minutes. Then, the reaction mixture was diluted with dichloromethane, and it was washed with a saturated aqueous solution of NaHCO₃, and with a saturated aqueous solution of NaCl, dried over Na₂SO₄, filtered and concentrated under vacuum. The residue was used in the next step without further purification as a mixture of diastereomers.

HPLC-MS (method 4): Rt=3.60, [M+H]+ 261.2.

Synthesis of Intermediate CV.

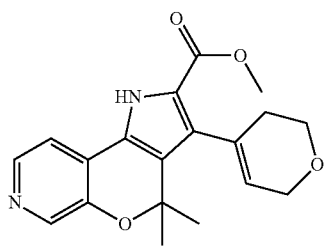

CV

A mixture of intermediate LXVIII (119 mg, 3.53 mmol, 1 eq), 3,6-dihydro-2H-pyran-4-boronic acid pinacol ester (111 mg, 0.529 mmol, 1.5 eq), dichlorobis(triphenylphosphine)palladium(II) (50 mg, 0.071 mmol, 0.2 eq) and a 2M aqueous solution of Na₂CO₃ (0.53 mL, 1.059 mmol, 3 eq) in 1,4-dioxane (3.5 mL) was heated in a pressure tube at 100° C. for 16 hours. The reaction mixture was cooled down to room temperature, and partitioned between water and dichloromethane. The phases were separated, and the organic phase was dried over Na₂SO₄, filtered and concentrated under vacuum. The residue was purified by flash chromatography (Biotage, 0.5% to 1.5% MeOH in DCM) affording the expected intermediate as a yellow solid (93 mg, yield: 74%).

HPLC-MS (method 4): Rt=2.81, [M+H]+ 341.3.

Synthesis of Intermediate CVI.

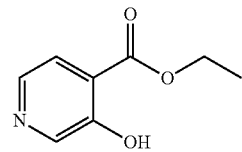

CVI

Thionyl chloride (12.58 mL, 172.527 mmol, 8 eq) was added to a mixture of 3-hydroxy-4-pyridinecarboxylic acid (3.00 g, 21.566 mmol, 1 eq) in ethanol (144 mL) at 0° C. The reaction mixture was heated under reflux conditions for 16 hours. The solvent was evaporated under vacuum, and the residue was partitioned between DCM and a 1M aqueous solution of NaHCO₃. The phases were separated, and the organic layer was dried over Na₂SO₄, filtered and concentrated to give the desired intermediate. The intermediate was used in the next step without further purification.

HPLC-MS (method 4): Rt=2.91, [M+H]+ 168.0.

$^1$H NMR (300 MHz, DMSO) δ 10.35 (s, 1H), 8.39 (s, 1H), 8.17 (d, J=5.0 Hz, 1H), 7.56 (dd, J=5.0, 0.6 Hz, 1H), 4.35 (q, J=7.1 Hz, 2H), 1.32 (t, J=7.1 Hz, 3H).

Synthesis of Intermediate CVII.

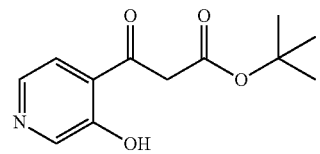

CVII n-Butyllithium (2.5M in hexanes, 18.00 mL, 44.866 mmol, 5 eq) was added to a solution of diisopropylamine (6.92 mL, 14.357 mmol, 5.5 eq) in tetrahydrofuran (36 mL) at −78° C. under Argon. The reaction was stirred at −78° C. for 45 minutes. Then, tert-butyl acetate (1.93 mL, 14.357 mmol, 1.6 eq) was added to the reaction mixture dropwise over a period of 10 minutes. After 90 minutes stirring at −78° C., a solution of intermediate CVI (1.50 g, 8.973 mmol, 1 eq) in tetrahydrofuran (18 mL) was added to the mixture, and it was allowed to warm up to room temperature. The reaction was stirred at room temperature for 16 hours. The mixture was quenched with a saturated aqueous solution of NH₄Cl, and the aqueous phase was extracted with EtOAc. The organic layer was washed with a saturated aqueous solution of NaCl, dried over Na₂SO₄, filtered and concentrated under vacuum. The residue was purified by flash chromatography (Biotage, 0% to 2% MeOH in DCM) affording the expected intermediate as a brown solid (1.66 g, yield: 78%).

HPLC-MS (method 4): Rt=3.59, [M+H]+ 238.1.

$^1$H NMR (300 MHz, DMSO) δ 11.13 (s, 1H), 8.41 (s, 1H), 8.16 (d, J=5.0 Hz, 1H), 7.51 (dd, J=5.0, 0.4 Hz, 1H), 3.96 (s, 2H), 1.36 (s, 9H).

Synthesis of Intermediate CVIII.

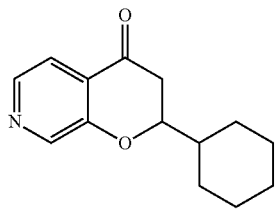

CVIII

A mixture of intermediate CVII (250 mg, 1.054 mmol, 1 eq), cyclohexanecarboxaldehyde (0.13 mL, 1.054 mmol, 1 eq), piperidine (5 µL, 0.053 mmol, 0.05 eq) and acetic acid (4 µL, 0.053 mmol, 0.05 eq) in toluene (5 mL) was heated under reflux conditions for 48 hours using a Dean-Stark trap. Then, the reaction was allowed to cool down to room temperature, and EtOAc was added. The organic layer was washed with a saturated aqueous solution of NaCl, dried over Na$_2$SO$_4$, filtered and concentrated under vacuum. The residue was purified by flash chromatography (Biotage, 0% to 1% MeOH in DCM) affording the expected intermediate as a pale yellow solid (237 mg, yield: 97%).

HPLC-MS (method 4): Rt=4.36, [M+H]+ 232.3.

$^1$H NMR (300 MHz, DMSO) δ 8.53 (s, 1H), 8.29 (d, J=5.0 Hz, 1H), 7.56 (dd, J=5.0, 0.7 Hz, 1H), 4.44 (ddd, J=13.1, 5.6, 2.7 Hz, 1H), 2.94 (dd, J=16.9, 13.1 Hz, 1H), 2.70 (dd, J=16.9, 2.8 Hz, 1H), 1.90-1.77 (m, 1H), 1.84-1.59 (m, 5H), 1.29-1.04 (m, 5H).

Synthesis of Intermediate CIX.

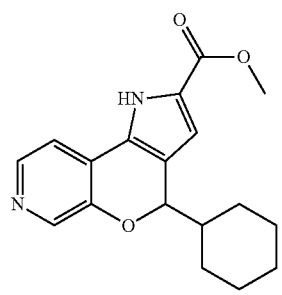

CIX

This intermediate was prepared following the same protocol which was employed to prepare the intermediate CIII, but using intermediate CVIII as starting material instead of intermediate V. The residue was also purified by flash chromatography (Biotage, 0% to 2% MeOH in DCM) affording the expected intermediate as a yellow solid and as a mixture of diastereomers (yield: 67%).

HPLC-MS (method 4): Rt=4.80, [M+H]+ 533.3.

Synthesis of Intermediate CX.

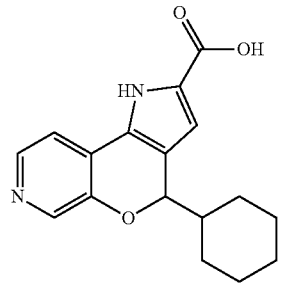

CX

This intermediate was prepared following the same protocol which was employed to prepare the intermediate CIV, but using intermediate CIX as starting material. The residue was used in the next step without further purification as a mixture of diastereomers.

HPLC-MS (method 4): Rt=4.12 & 4.33, [M+H]+ 315.2.

Synthesis of Intermediate CXI.

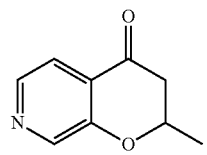

CXI

This intermediate was prepared following the same protocol which was employed to prepare the intermediate VIII employing 2,3-dichloro-5,6-dicyano-1,4-benzoquinone, but using intermediate CX as starting material (yield: 29%).

HPLC-MS (method 4): Rt=3.54, [M+H]+ 313.1.

Synthesis of Intermediate CXII.

CXII

This intermediate was prepared following the same protocol which was employed to prepare the intermediate IX, but using intermediate CXI as starting material (yield: 60%).

HPLC-MS (method 4): Rt=3.09, [M+H]+ 299.1.

Synthesis of Intermediate CXIII.

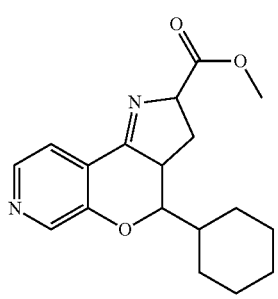

CXIII

This intermediate was prepared following the same protocol which was employed to prepare the intermediate CVIII, but using acetaldehyde instead of cyclohexanecarboxaldehyde (yield: 86%).

HPLC-MS (method 4): Rt=1.96, [M+H]+ 164.1.

Synthesis of Intermediate CXIV.

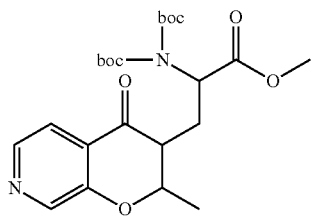
CXIV

This intermediate was prepared following the same protocol which was employed to prepare the intermediate CIII, but using intermediate CXIII as starting material. The reaction was carried out at room temperature for 4 hours instead of at room temperature for 16 hours. The residue was purified by flash chromatography (Biotage, 0% to 2% MeOH in DCM) affording the expected intermediate as a yellow solid and as a mixture of diastereomers (yield: 51%).

HPLC-MS (method 4): Rt=4.70, [M+H]+ 465.2.

Synthesis of Intermediate CXV.

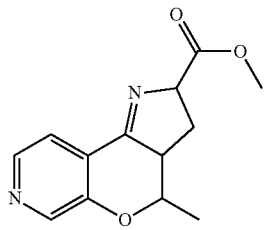
CXV

This intermediate was prepared following the same protocol which was employed to prepare the intermediate CIV, but using intermediate CXIV as starting material. The residue was purified by flash chromatography (Biotage, 0% to 3% MeOH in DCM) affording the expected intermediate as a yellow solid and as a mixture of diastereomers (yield: 51%).

HPLC-MS (method 4): Rt=2.49, [M+H]+ 247.0.

Synthesis of Intermediate CXVI.

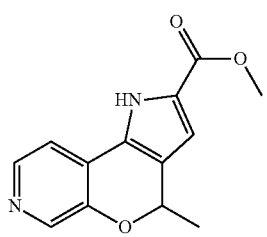
CXVI

This intermediate was prepared following the same protocol which was employed to prepare the intermediate VIII employing 2,3-dichloro-5,6-dicyano-1,4-benzoquinone, but using intermediate CXV as starting material (yield: 54%).

HPLC-MS (method 4): Rt=2.10, [M+H]+ 245.0.

Synthesis of Intermediate CXVII.

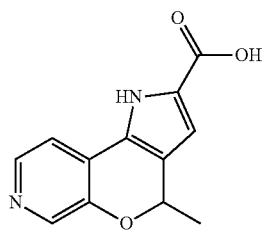
CXVII

This intermediate was prepared following the same protocol which was employed to prepare the intermediate IX, but using intermediate CXVI as starting material. In this case, the intermediate was not purify by flash chromatography.

HPLC-MS (method 4): Rt=0.45, [M+H]+ 231.0.

Synthesis of Intermediate CXVIII.

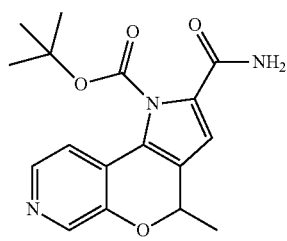
CXVIII

Di-tert-butyl dicarbonate (74 mg, 0.339 mmol, 3 eq) was added to a mixture of intermediate CXVII (26 mg, 0.113 mmol, 1 eq) in 1,4-dioxane (1.13 mL) at room temperature, followed by the addition of ammonium bicarbonate (27 mg, 0.339 mmol, 3 eq) and pyridine (18 µL, 0.226 mmol, 1 eq). The reaction mixture was stirred at room temperature for 16 hours. The solvent was evaporated under vacuum, and the residue was dissolved in EtOAc. The organic phase was washed with a 1N aqueous solution of HCl. The aqueous phase was extracted with n-butanol. The combined organic layers were dried over Na$_2$SO$_4$, filtered and concentrated under vacuum. The intermediate was used in the next step without further purification.

HPLC-MS (method 4): Rt=2.88, [M+H]+ 330.1.

Synthesis of Intermediate CXIX.

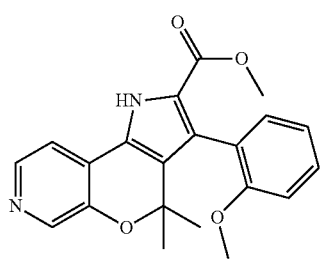
CXIX

This intermediate was prepared following the same protocol which was employed to prepare the intermediate CV, but using 2-methoxyphenylboronic acid instead of 3,6-dihydro-2H-pyran-4-boronic acid pinacol ester as starting material. The intermediate was purified by flash chromatography (Biotage, silica, 0% to 4% MeOH in DCM) to give the expected intermediate CXIX as a yellow oil (yield: 76%). HPLC-MS (method 4): Rt=3.43 min, [M+H]$^+$ 365.1.

Synthesis of Intermediate CXX.

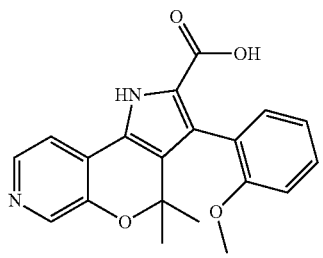

CXX

This intermediate was prepared following the same protocol which was employed to prepare the intermediate IX, but using intermediate CXIX instead of intermediate VIII as starting material. The reaction was carried out by heating at 100° C. for 16 hours instead of at 80° C. for 1 hour. The intermediate was used in the next step without further purification.

HPLC-MS (method 4): Rt=3.11 min, [M+H]$^+$ 351.2.

Synthesis of Intermediate CXXI.

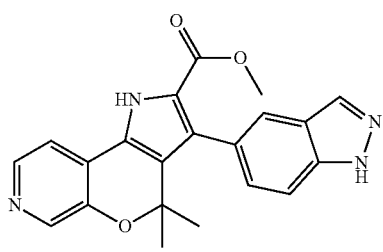

CXXI

This intermediate was prepared following the same protocol which was employed to prepare the intermediate CV, but using indazole-5-boronic acid pinacol ester instead of 3,6-dihydro-2H-pyran-4-boronic acid pinacol ester as starting material. The reaction was carried out by heating at 100° C. for 16 hours instead of at 80° C. for 1 hour. The intermediate was purified by flash chromatography (Biotage, silica, 2% to 6% MeOH in DCM) to give the expected intermediate CXXI as a yellow solid (yield: 51%). HPLC-MS (method 4): Rt=2.98 min, [M+H]$^+$ 375.1.

Synthesis of Intermediate CXXII.

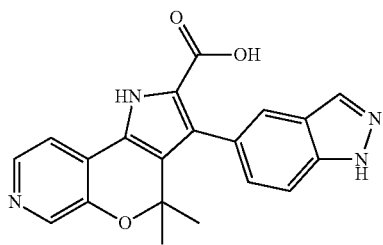

CXXII

This intermediate was prepared following the same protocol which was employed to prepare the intermediate IX, but using intermediate CXXI instead of intermediate VIII as starting material. The reaction was carried out by heating at 100° C. for 16 hours instead of at 80° C. for 1 hour. The intermediate was purified by flash chromatography (Biotage, silica, 5% to 20% MeOH in DCM with a 5% of NH$_3$ (7N in MeOH)) to give the expected intermediate CXXII as a yellow solid (yield: 33%). HPLC-MS (method 4): Rt=2.56 min, [M+H]$^+$ 361.0. $^1$H NMR (300 MHz, DMSO) δ 13.02 (s, 1H), 8.06 (dd, J=14.3, 8.2 Hz, 4H), 7.89 (d, J=5.1 Hz, 1H), 7.55 (s, 1H), 7.47 (d, J=8.2 Hz, 1H), 7.20 (d, J=8.5 Hz, 1H), 1.27 (s, 6H).

Synthesis of Intermediate CXXIII.

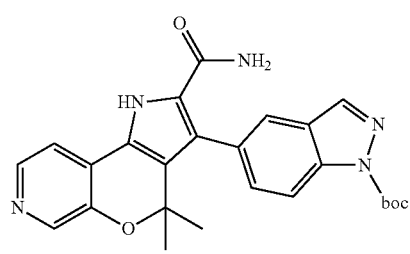

CXXIII

This intermediate was prepared by amide formation of intermediate CXXII in the presence of di-tert-butyl dicarbonate following the same protocol which was employed to prepare the intermediate CXVIII, (yield: 83%). HPLC-MS (method 4): Rt=3.12 min, [M+H]$^+$ 460.3.

Synthesis of Intermediate CXXIV.

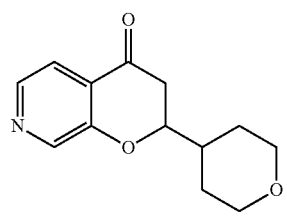

CXXIV

This intermediate was prepared following the same protocol which was employed to prepare the intermediate CVIII, but using tetrahydro-pyran-4-carbaldehyde instead of cyclohexanecarboxaldehyde as starting material (yield: 75%). HPLC-MS (method 4): Rt=3.19 min, [M+H]$^+$ 234.1.

Synthesis of Intermediate CXXV.

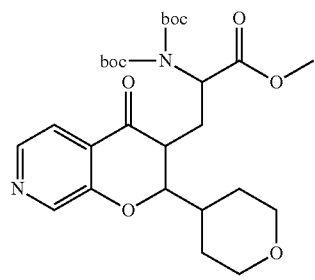

CXXV

This intermediate was prepared following the same protocol which was employed to prepare the intermediate CIII, but using intermediate CXXIV as starting material instead of intermediate V, and employing 2 eq of lithium diisopropylamide instead of 2.5 eq. The intermediate was purified by flash chromatography (Biotage, 20% to 80% EtOAc in cyclohexanes) affording the expected intermediate as a yellow oil and as a mixture of diastereomers (yield: 59%). HPLC-MS (method 4): Rt=3.45 min, [M+H]+ 535.2.

Synthesis of Intermediate CXXVI.

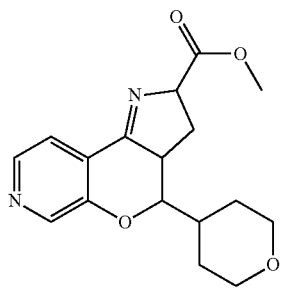

CXXVI

This intermediate was prepared following the same protocol which was employed to prepare the intermediate CIV, but using intermediate CXXV as starting material. The intermediate was purified by flash chromatography (Biotage, 0% to 3% MeOH in DCM) to give the expected intermediate as a yellow oil and as a mixture of diastereomers (yield: 69%). HPLC-MS (method 4): Rt=2.80 min, [M+H]+ 317.1.

Synthesis of Intermediate CXXVII.

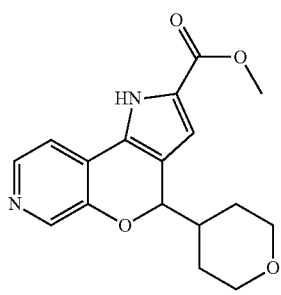

CXXVII

This intermediate CXXVII was prepared by oxidation reaction of intermediate CXXVI in dry dioxane in the presence of DDQ (1.1 eq) at room temperature.

Synthesis of Intermediate CXXVIII.

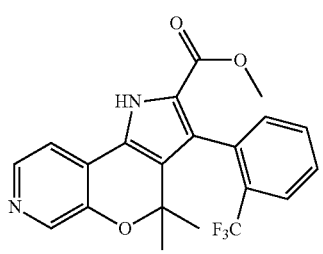

CXXVIII

This intermediate was prepared following the same protocol which was employed to prepare the intermediate LXIX, but using 2-(trifluoromethyl)phenylboronic acid instead of phenylboronic acid as starting material (yield: 42%). HPLC-MS (method 4): Rt=3.723, [M+H]+ 403.10.

Synthesis of Intermediate CXXIX.

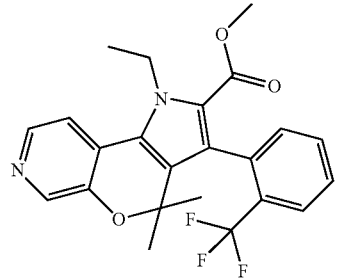

CXXIX

To a stirred solution of intermediate CXXVIII (25 mg, 0.062 mmol, 1 eq) in acetonitrile (0.6 ml), cesium carbonate (40 mg, 0.124 mmol, 2 eq) was added. The mixture was stirred 5 min and then, a solution of iodoethane 1N in acetonitrile (0.062 ml, 0.062 mmol, 1 eq) was added. The resulting reaction mixture was stirred 2 h at room temperature. The reaction mixture was then quenched with water (10 ml). The mixture was extracted with EtOAc (2×50 ml). The combined organic layer was dried over anhydrous Na$_2$SO$_4$. The solvent was evaporated, and the resulting residue, intermediate CXXIX, was used in next reaction step without further purification. HPLC-MS (method 4): Rt=4.385, [M+H]+ 431.15.

Synthesis of Intermediate CXXX

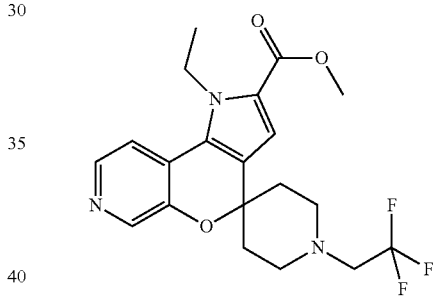

CXXX

Intermediate CXXX was prepared by alkylation reaction of intermediate LVIII (35 mg, 0.153 mmol) with iodoethane (1 eq) in the presence of cesium carbonate (2 eq) in acetonitrile (1.5 ml). The reaction mixture was stirred at 80° C. for 4 h in a seal tube and then quenched with water (10 ml). The mixture was extracted with EtOAc (2×50 ml). The combined organic layer was dried over anhydrous Na$_2$SO$_4$. The solvent was evaporated from the dried organic layer under reduced pressure to obtain a crude product, intermediate CXXX, which was used in next reaction step without further purification. HPLC-MS (method 4): Rt=3.696, [M+H]+ 410.20.

Synthesis of Intermediate CXXXI

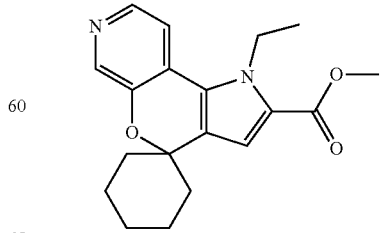

CXXXI

Intermediate CXXXI was prepared by alkylation reaction of intermediate XLVI (167 mg, 0.56 mmol) in acetonitrile (6 ml) in the presence of cesium carbonate (365 mg, 1.12 mmol) and iodoethane (1 eq), by stirring at 16 h at room temperature. Water and EtOAc were added. The organic phase was dried (Na$_2$SO$_4$), filtered and concentrated under reduced pressure to obtain a crude product, intermediate CXXXI, which was used in next reaction step without further purification. HPLC-MS (method 4): Rt=3.903, [M+H]+ 327.15.

Synthesis of Intermediate CXXXII

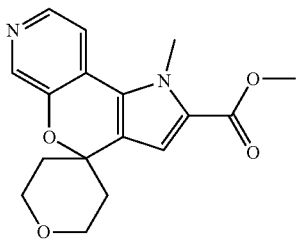

CXXXII

Intermediate CXXXII was prepared by alkylation reaction of intermediate LXII (200 mg, 0.666 mmol, 1 eq) in acetonitrile (7 ml) in the presence of cesium carbonate (434 mg, 1.332 mmol, 2 eq) and iodomethane (1 eq), by stirring at 16 h at room temperature. Water and EtOAc were added. The organic phase was dried (Na$_2$SO$_4$), filtered and concentrated under reduced pressure to obtain a crude product, intermediate CXXXII, which was used in next reaction step without further purification. HPLC-MS (method 4): Rt=2.744, [M+H]+ 315.10.

Synthesis of Intermediate CXXXIII

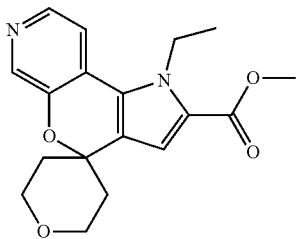

CXXXIII

Intermediate CXXXIII was prepared by alkylation reaction of intermediate LXII (200 mg, 0.666 mmol, 1 eq) in acetonitrile (7 ml) in the presence of cesium carbonate (434 mg, 1.332 mmol, 2 eq) and iodoethane (1 eq), by stirring at 16 h at room temperature. Water and EtOAc were added. The organic phase was dried (Na$_2$SO$_4$), filtered and concentrated under reduced pressure to obtain a crude product, intermediate CXXXIII, which was used in next reaction step without further purification. HPLC-MS (method 4): Rt=3.008, [M+H]+ 329.15.

Synthesis of Intermediate CXXXIV

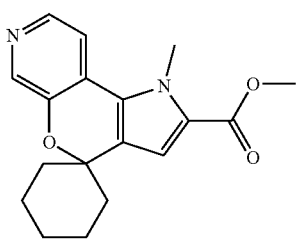

CXXXIV

Intermediate CXXXIV was prepared by alkylation reaction of intermediate XLVI (167 mg, 0.560 mmol, 1 eq) in acetonitrile (6 ml) in the presence of cesium carbonate (365 mg, 1.120 mmol, 2 eq) and iodomethane (1 eq), by stirring at 16 h at room temperature. Water and EtOAc were added. The organic phase was dried (Na$_2$SO$_4$), filtered and concentrated under reduced pressure to obtain a crude product, intermediate CXXXIV, which was used in next reaction step without further purification. HPLC-MS (method 4): Rt=3.538, [M+H]+ 313.15.

Synthesis of Intermediate CXXXV

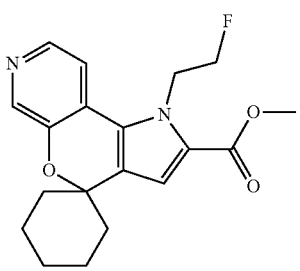

CXXXV

Intermediate CXXXV was prepared following the same synthetic protocol used for intermediate CXXXIV by alkylation reaction of intermediate XLVI (167 mg, 0.560 mmol, 1 eq) with 1-fluoro-2-iodoethane (1 eq). The resulting crude compound obtained after work-up was used in next reaction step without further purification as intermediate CXXXV.

HPLC-MS (method 4): Rt=3.783, [M+H]+ 345.20.

Synthesis of Intermediate CXXXVI

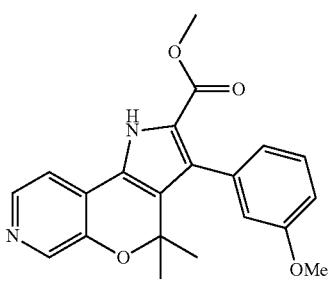

CXXXVI

A mixture of LXVIII (150 mg, 0.445 mmol; 1 equiv), 3-methoxyphenylboronic acid (101 mg, 0.667 mmol, 1.5 equiv) with 2 M aqueous solution of Na$_2$CO$_3$ (0.7 mL) and PdCl$_2$(PPh$_3$)$_2$ (62 mg, 0.089 mmol, 0.2 equiv) in dioxane (4.5 mL) was heated in a sealed tube at 100° C. for 16 h. The dark mixture was cooled down to room temperature and extracted with DCM. The organic phase was dried, filtered and concentrated in vacuo. The residue was purified by Biotage Flash Chromatography (Biotage, SiO$_2$, 20 g, c-Hexane/EtOAc 100/0 to 60/40) to afford yellow solid (150 mg, 93%) as intermediate CXXXVI. HPLC-MS (method 4): Rt=3.394, [M+H]+ 365.10.

Synthesis of Intermediate CXXXVII

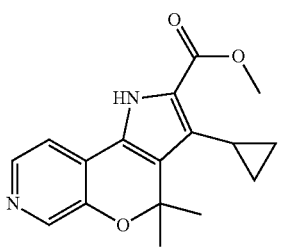

CXXXVII

Intermediate CXXXVII was prepared following the same synthetic route used for synthesis of intermediate CXXXVI by Suzuki coupling reaction of LXVIII (150 mg, 0.445 mmol; 1 equiv) with cyclopropylboronic acid (57 mg, 0.667 mmol, 1.5 equiv) in the presence of 2M aqueous solution of $Na_2CO_3$ in dioxane (4.5 mL) at 150° C. for 48 h. Biotage Flash Chromatography (SiO2, 20 g, c-Hexane/EtOAc 100/0 to 60/40) afforded intermediate CXXXVII as a yellow solid (85 mg, 64% yield). HPLC-MS (method 4): Rt=3.005, [M+H]+ 299.05) which was used in next reaction step without further purification.

Synthesis of Intermediate CXXXVIII

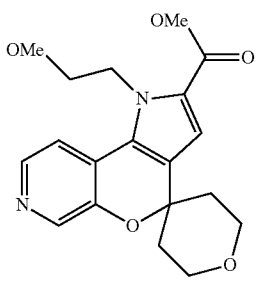

CXXXVIII

Intermediate CXXXVIII was prepared by alkylation reaction of intermediate LXII (150 mg, 0.499 mmol, 1 eq) in acetonitrile (5 ml) in the presence of cesium carbonate (325 mg, 0.999 mmol, 2 eq) and 2-bromoethyl methyl ether (1 eq), by stirring at 16 h at room temperature. Water and EtOAc were added. The organic phase was dried ($Na_2SO_4$), filtered and concentrated under reduced pressure to obtain a crude product which was purified by Biotage Flash Chromatography (silica, 20 g, DCM/MeOH 100/0 to 80/20) to afford a yellow solid (75 mg, 42% yield) as intermediate CXXXVIII. HPLC-MS (method 4): Rt=2.998, [M+H]+ 359.20.

Synthesis of Intermediate CXXXIX

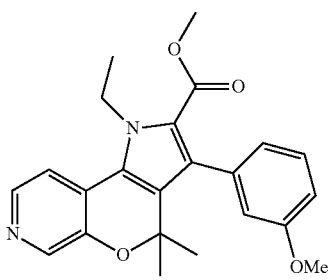

CXXXIX

Intermediate CXXXIX was prepared by alkylation reaction of intermediate CXXXVI (100 mg, 0.274 mmol, 1 eq) in acetonitrile (3 ml), in the presence of cesium carbonate (174 mg, 0.549 mmol, 2 eq) and iodoethane (1 eq), by stirring at 16 h at room temperature. Water and EtOAc were added. The organic phase was dried ($Na_2SO_4$), filtered and concentrated under reduced pressure to obtain a crude product which was purified by Biotage Flash Chromatography (silica, 20 g, DCM/MeOH 100/0 to 80/20) to afford a yellow solid (25 mg, 23% yield) as intermediate CXXXIX. HPLC-MS (method 4): Rt=3.977, [M+H]+ 393.15.

Synthesis of Intermediate CXL

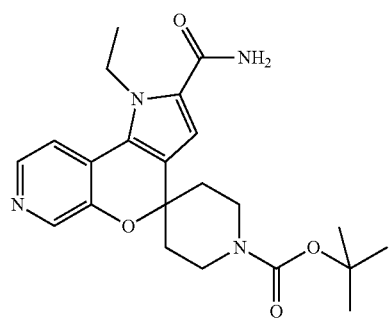

CXL

Intermediate CXL was prepared by amidation reaction of intermediate CXLI (33 mg) with $NH_3$/MeOH (7N) and 1M $CaCl_2$ in MeOH (50 ml) heating at 110° C. in a sealed tube for 72 h. The final compound was isolated by concentration of the solvent in vacuo and purification by flash chromatography in DCM/MeOH (100 to 85/15) to yield 12 mg of the desired intermediate CXL.

HPLC-MS (method 4): Rt=3.082, [M+H]+ 413.2.

Synthesis of Intermediate CXLI

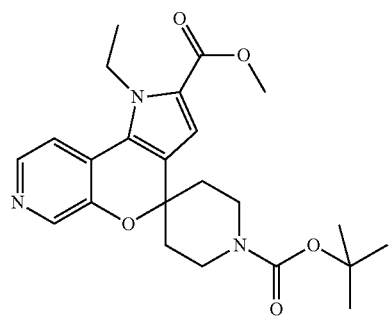

CXLI

Intermediate CXLI was prepared by alkylation of Intermediate XLI (50 mg, 0.12 mmol) with iodoethane (0.2 mmol) following similar synthetic protocol than the one used for the synthesis of intermediate CXXXIX to yield after Biotage flash column chromatography in $SiO_2$ (EtOAc/cyclohexane 25/75 to 100/0) required compound (33 mg, 64% yield).

HPLC-MS (method 4): Rt=3.946, [M+H]+ 428.2.

Synthesis of Intermediate CXLII

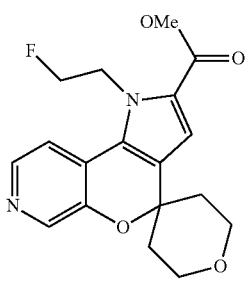

CXLII

Intermediate CXLII was prepared following the same synthetic protocol used for intermediate CXXXII by alkylation reaction of intermediate LXII (150 mg, 0.499 mmol) with 1-fluoro-2-iodoethane (1 eq). The resulting crude compound was purified by Biotage Flash Chromatography (Biotage, 20 g, 0% to 20% MeOH in DCM) to afford desired compound (40 mg).

HPLC-MS (method 4): Rt=3.004, [M+H]+ 347.15.

Synthesis of Intermediate CXLIII

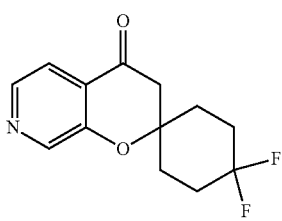

CXLIII 1-(3-hydroxypyridin-4-yl)ethanone (1 g, 7.292 mmol, 1 eq), DIPEA (1.27 mL, 7.292 mmol, 1 eq), pyrrolidine (0.609 mL, 7.292 mmol, 1 eq), 4,4-difluorocyclohexanone (0.978 g, 7.292 mmol, 1 eq) in tetrahydrofuran (73 mL) was heated at 70° C. in a presion tube 16 h. The reaction was concentrated and the residue was purified by flash chromatography (0% to 30% EtOAc in c-Hexane) to afford a white solid (1.41 g, 76% yield) as intermediate CXLIII.

HPLC-MS (method 4): Rt=3.701, [M+H]+ 254.00.

Synthesis of Intermediate CXLIV

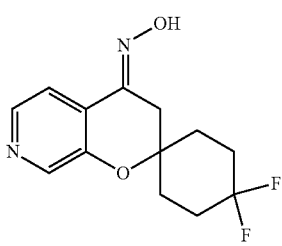

CXLIV

To a solution of CXLIII (1.41 g, 5.568 mmol, 1 eq) in MeOH (56 ml) was added TEA (1.55 mL, 11.135 mmol, 2 eq) and hydroxylamine hydrochloride (0.774 g, 11.135 mmol, 2 eq). The reaction mixture was stirred 16 h at rt. Then the reaction was concentrated and the crude was quenched with water and extracted with EtOAc (×3) to obtain a white solid (1.4 g) which was used in next reaction step without additional purification.

Synthesis of Intermediate CXLV

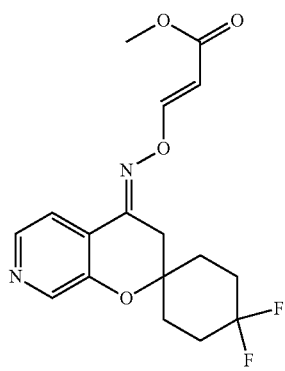

CXLV

To a solution of intermediate CXLIV (1.4 g, 5.219 mmol, 1 eq) in DCM (52 ml) was added TEA (0.873 mL, 6.263 mmol. 1.2 eq) and methyl propiolate (0.929 mL, 10.438 mmol, 2 eq), the reaction turned at orange. The mixture was stirred at rt for 3 h. Water was added and extracted with DCM (×3). The org. phase was dried ($Na_2SO_4$), evaporated and the residue was purified by biotage Flash Chromatography (Biotage, 12 g, 0% to 40% EtOAc in c-Hex. The resulting residue was used in next reaction step without further purification as intermediate CXLV.

HPLC-MS (method 4): Rt=4.283, [M+H]+ 353.1.

Synthesis of Intermediate CXLVI

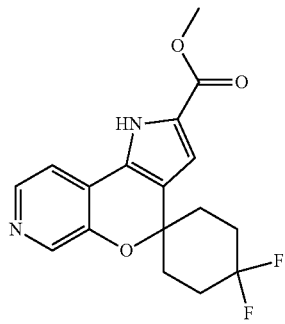

CXLVI

Intermediate CXLVI was prepared following the same protocol used for the synthesis of intermediate VIII, but using compound CXLV (5.219 mmol) as starting material to yield 300 mg (17%) of intermediate CXLVI as a yellow solid.

HPLC-MS (method 4): Rt=3.017, [M+H]+ 335.1.

Synthesis of Intermediate CXLVII

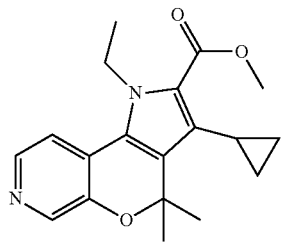

CXLVII

To a stirred solution of intermediate CXXXVII (40 mg, 0.134 mmol, 1 eq) in acetonitrile (1.3 ml), cesium carbonate (87 mg, 0.268 mmol, 2 eq) was added. The mixture was stirred 5 min and then a solution of iodoethane in AcCN 1N (0.134 ml, 0.134 mmol, 1 eq) was added. The resulting reaction mixture was stirred at rt for 24 h. The reaction mixture was then quenched with water (10 ml). The mixture was extracted with EtOAc (2×50 ml). The combined organic layer was dried over anhydrous Na$_2$SO$_4$. The solvent was evaporated under reduced pressure to obtain a crude product which was purified by Biotage Flash Chromatography (Biotage, 20 g, 0% to 20% MeOH in DCM) to afford a yellow solid as intermediate CXLVII (25 mg, 57% yield).

HPLC-MS (method 4): Rt=3.479, [M+H]+ 327.15.

Synthesis of Intermediate CXLVIII

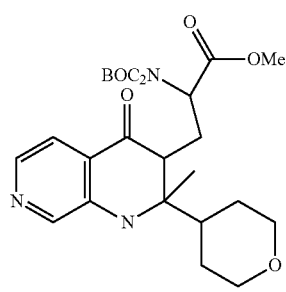

CXLVIII

CXLIX (416 mg, 1 eq.) in THF (12 mL) under Ar was cooled to −50° C., then a solution of LDA (1.53 mL, 1.5 eq. 2M in hexane) was added dropwise. The mixture was stirred at this temperature 1 h. Then 2-Propenoic acid, 2-[bis[(1,1-dimethylethoxy)carbonyl]amino]-, methyl ester (CAS 201338-62-7) (760 mg; 1.5 equiv) in THF (5 mL) was added dropwise via canula over 10 minutes. The solution was stirred at −50° C. overnight. The reaction was quenched with aq. water and extracted with CHCl$_3$:isopropanol (1:1), the combined organic phases were washed with brine, dried (MgSO$_4$) and concentrated in vacuo. The residue was purified by automated flash chromatography (CicloHx/EtOAc gradient: 0% to 70%) to give CXLVIII (320 mg).

HPLC-MS (method 4): Rt=4.582, [M+H]+ 549.3.

Synthesis of Intermediate CXLIX

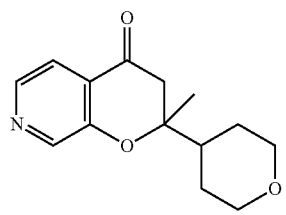

CXLIX

Intermediate IV (812 mg, 1 eq.), DIPEA (1.1 mL, 1 eq.), pyrrolidine (0.500 mL, 1 eq.) and 1-(tetrahydro-2h-pyran-4-yl)ethanone (CAS 137052-08-5; 0.741 mL, 1 eq.) in THF (60 mL) were heated at 90° C. in sealed tube during 6 hours. The reaction mixture was concentrated and the residue was purified by automated flash chromatography (CicloHx/EtOAc gradient: 0% to 100%) to give CXLIX (494 mg, 38% yield) as a yellow oil.

HPLC-MS (method 4): Rt=3.114, [M+H]+ 248.1.

Synthesis of Intermediate CL

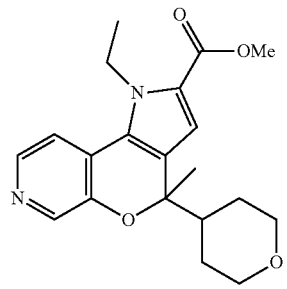

CL

Intermediate CL was prepared following a similar synthetic route to the one used for intermediate CLI but using intermediate CXLIX (217 mg) as initial starting material to build in several steps the desired tricycle compound CL which was isolated by purification chromatography with DCM/MeOH gradient: 0% to 50% (58 mg, brown oil).

HPLC-MS (method 4): Rt=3.385, [M+H]+ 357.1.

Synthesis of Intermediate CLI

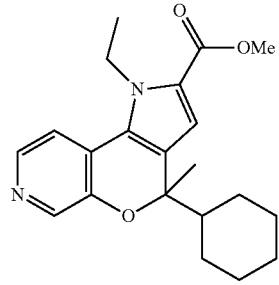

CLI

Intermediate CLI was prepared following a similar synthetic route to the one used for intermediate CLII but using intermediate CLVI as starting material. The compound was isolated by automated flash chromatography with DCM/MeOH gradient: 1% to 23% to yield CLI (86 mg, yellow solid).

HPLC-MS (method 4): Rt=4.176, [M+H]+ 355.2.

Synthesis of Intermediate CLII

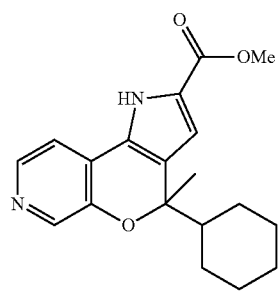

CLII

To a cooled solution of compound CLV (640 mg; 1.17 mmol, 1 equiv; mixture of diastereomers) in dry CH$_2$Cl$_2$ (12 mL) was added trifluoroacetic acid (2.7 mL) under Argon. After stirring for 90 min at rt reaction was finished. The solution was cooled and diluted with DCM and washed with aqueous solution of NaHCO₃. Organic phase was washed with brine, dried over Na₂SO₄, filtered and concentrated in vacuo. The residue was purified by automated flash chromatography (DCM/MeOH; gradient: 1% to 5%) affording the tricycle compound (partially oxidized) (280 mg; 73% yield) as a mixture of diastereoisomers. This compound was suspended in dry DCM (17 mL) and DDQ (194 mg; 1.0 equiv) was added, the mixture was stirred at rt overnight. The solvent was evaporated and a dark residue was dissolved in MeOH and charged on a cationic exchange resin (Isolute SCX). Impurities were washed off with MeOH and then elution with NH₃/MeOH (7N) to recover the desired product. After removing solvents, the residue was purified by automated flash chromatography (DCM/MeOH; gradient: 1% to 7%) to obtain intermediate CLII as a yellow solid (145 mg, 52% yield).

HPLC-MS (method 4): Rt=5.031, [M+H]+ 547.3

Synthesis of Intermediate CLIII

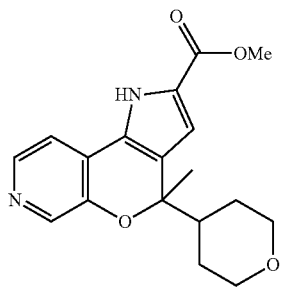

CLIII

To a cooled solution of intermediate CXLVIII (314 mg; 1 equiv; mixture of two diastereomers) in dry CH₂Cl₂ (6 mL) was added trifluoroacetic acid (1.4 mL) under Argon. The reaction was stirred for 3 h and then washed with aqueous solution of NaHCO₃. Organic phase was washed with brine, dried over Na₂SO₄, filtered and concentrated in vacuo. The residue was purified by automated flash chromatography (DCM/MeOH; gradient: 1% to 3%) affording the tricycle compound (partially oxidized) (97 mg) as a light yellow oil, mixture of diastereoisomers. This mixture (90 mg; 1 equiv) was suspended in dry DCM (5.5 mL) and DDQ was added (62 mg; 1 equiv), the reaction mixture was stirred at rt overnight. The solvent was evaporated and the resulting dark residue was dissolved in MeOH and charged on a cationic exchange resin (Isolute SCX). Impurities were washed off with MeOH, and the desired compound was then eluted with NH₃/MeOH (7N). After removing solvents the residue was purified by Biotage flash chromatography (silica; in DCM/MeOH; gradient: 1% to 10%, to afford an orange oil as intermediate CLIII.

HPLC-MS (method 4): Rt=2.607, [M+H]+ 329.1

Synthesis of Intermediate CLIV

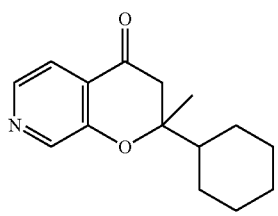

CLIV 1-(3-hydroxypyridin-4-yl)ethanone (1.3 g, 9.4 mmol, 1 eq), DIPEA (1.6 mL, 1 eq), pyrrolidine (0.8 mL, 1 eq), 1-cyclohexylethan-1-one (1.2 mL, 1 eq) in tetrahydrofuran (95 mL) was heated at 90° C. in sealed tube overnight. The reaction was concentrated and the residue was purified by automated flash chromatography (CicloHx/AcOEt: gradient: 10% to 50%) affording the desired compound CLIV (775 mg; 35% yield).

Synthesis of Intermediate CLV

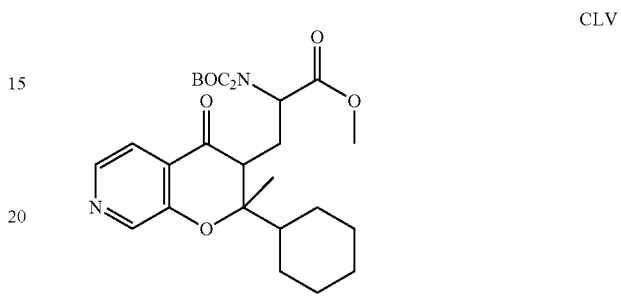

CLV

To the compound CLIV (450 mg; 1.83 mmol; 1.0 equiv) in THF (12 mL) under Ar was cooled to −50° C., a solution of LDA (1.4 mL; 1.5 equiv; 2.0M in hexane) was added dropwise. The mixture was stirred at this temperature 1 h. Then 2-Propenoic acid, 2-[bis[(1,1-dimethylethoxy)carbonyl]amino]-, methyl ester (CAS 201338-62-7) (830 mg; 1.5 equiv) in THF (6 mL) was added dropwise via canula over 10 minutes. The solution was stirred at −50° C. overnight. The reaction was quenched with aq. NH₄Cl (sat) and extracted with EtOAc, the combined organic phases were washed with brine, dried (MgSO₄) and concentrated in vacuo. The residue was purified by automated flash chromatography (CicloHx/EtOAc gradient: 10% to 50%) and with AcOEt/MeOH gradient: 5% to 20% to give CLV (640 mg; 64% yield).

Synthesis of Intermediate CLVI

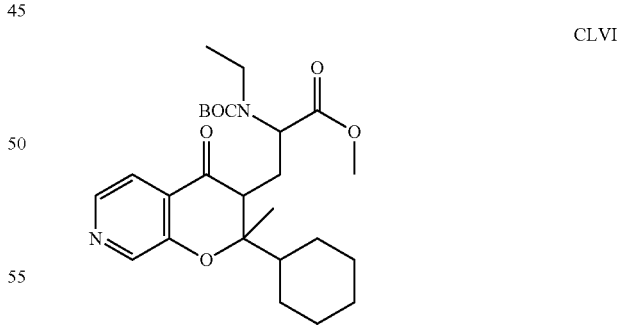

CLVI

This intermediate was synthesized following the same synthetic protocol used for the synthesis of intermediate CLV but using 2-propenoic acid, 2-(1,1-dimethylethoxy carbonyl ethylamino), methyl ether (CAS 1414376-52-5). The compound CLVI was isolated by automated flash chromatography with DCM/MeOH gradient: 0% to 3% to yield CLVI (294 g; 51% yield).

HPLC-MS (method 4): Rt=5.218, [M+H]+ 475.2

Synthesis of Intermediate CLVII

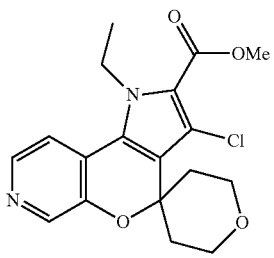
CLVII

A solution of N-chlorosuccinimide (14 mg, 1 eq) was added to a solution of compound CXXXIII (35 mg, 0.107 mmol, 1 eq) in AcCN (1 mL). The resulting mixture was stirred at rt for 10 days. After removing the solvent in vacuo, the residue was purified by Biotage Flash Chromatography (silica, 0% to 40% EtOAc in cycloHexane) to afford desired product CLVII as a solid (23 mg).

HPLC-MS (method 4): Rt=3.664, [M+H]+ 363.0/365.0

Synthesis of Intermediate CLVIII

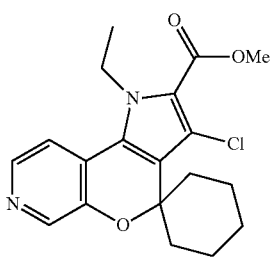
CLVIII

Chlorination reaction of compound CXXXI (30 mg, 1 eq) in the presence of N-chlorosuccinimide (1 eq) in acetonitrile after stirring at rt for 10 days. The desired compound was isolated by Biotage Flash Chromatography (silica, 0% to 40% EtOAc in cycloHexane) to afford CLVIII as a solid (21 mg).

HPLC-MS (method 4): Rt=4.411, [M+H]+ 361.1/363.0

Synthesis of Intermediate CLIX

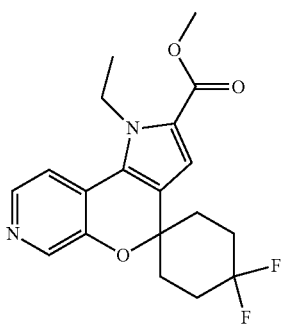
CLIX

Intermediate CLIX was prepared by alkylation reaction of CXLVI (50 mg, 0.150 mmol, 1 eq) with iodoethane in ACN 1N (0.15 ml, 0.15 mmol, 1 eq) in the presence of cesium carbonate as base to yield 25 mg (46%) of CLIX after Biotage Flash Chromatography (silica, 0% to 40% EtOAc in cycloHexane).

HPLC-MS (method 4): Rt 4.160=, [M+H]+ 363.1.

Example 1: Synthesis of Final Product 1

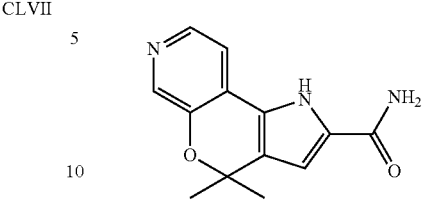

Protocol A.

Trifluoroacetic acid (1.7 mL, 22.701 mmol, 50 eq) was added to intermediate X (165 mg, 0.454 mmol, 1 eq). The reaction mixture was heated at 100° C. in the MW (Biotage) for 1 h. Trifluoroacetic acid was evaporated under reduce pressure. The resulting crude product was dissolved in DCM-MeOH and treated with NH3 7N in MeOH (~2 mL). Then, this mixture (pH=8) was concentrated and loaded into silica column. The residue was purified by flash chromatography (Biotage, 0% to 10% MeOH in DCM) to afford the final product 1 as a white solid (50 mg, yield: 45%).

Protocol B.

To a solution of intermediate X (81 mg, 0.314 mmol, 1 eq.) in DMF (3.60 mL) and MeOH (3.60 mL) was added 32% aq NH3 (7.14 mL). The reaction mixture was heated at 80° C. in a closed vessel for 24 h. Solvent was evaporated and the crude was purified by HPLC preparative to give the amide product as a white solid (38 mg, yield: 50%)

Example 2: Synthesis of Final Product 2

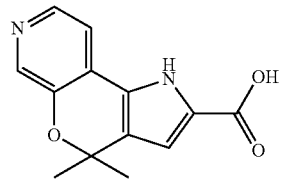 [SMILES: CC1(C)Oc2cnccc2-c2[nH]c(C(=O)O)cc21]

This product was obtained as a byproduct in the synthesis of the final product 1 following Protocol B (yield: 24%). The compounds of Examples 1 and 2 can be separated by TLC (DCM/MeOH 10:1): Rf=0.5 (Example 1) and Rf=0.2 (Example 2).

Example 3: Synthesis of Final Product 3

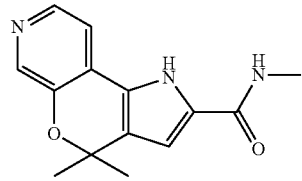 [SMILES: CNC(=O)c1cc2c([nH]1)-c1ccncc1OC2(C)C]

Intermediate VIII (50 mg, 0.194 mmol, 1 eq.) was dissolved in DCM (4.8 mL) and methylamine (0.140 mL, 3.872 mmol, 20 eq.) and AlMe$_3$ (0.041 mL, 0.387 mmol, 2 eq.) were added. The mixture was stirred at 100° C. for 16 h. The mixture was cooled down to room temperature and evaporated in vacuo. The residue was purified by flash chromatography (Biotage, 0% to 50% EtOAc in c-Hex, and 0% to 20% MeOH in DCM) to give impure expected product (15 mg). The resulted crude was purified by flash column chromatography (Isolute Si II 5 g) eluting with a solvent system of MeOH/DCM (from 0% to 10% MeOH) to afford final compound as a light yellow solid (3 mg, yield: 6%).

Example 4: Synthesis of Final Product 4

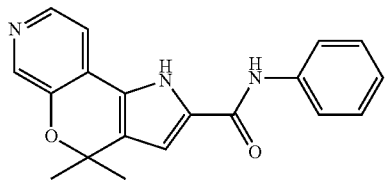 [SMILES: CC1(C)Oc2cnccc2-c2[nH]c(C(=O)Nc3ccccc3)cc21]

AlMe₃ (2M in hexanes, 0.102 ml, 0.203 mmol, 1.5 eq) was slowly added at room temperature to a solution of aniline (0.018 mL, 0.203 mmol. 1.5 eq) in DCM (0.4 mL) under Argon atmosphere. The mixture was stirred at room temperature for 15 minutes and then a solution of intermediate VIII (35 mg, 0.136 mmol, 1 eq) in DCM (0.4 mL) was added over the reaction. The mixture was heated at 100° C. for 48 h in a sealed tube. On cooling, solvent was evaporated and the residue was purified by flash chromatography (Biotage, 0% to 50% EtOAc in c-Hex, and 0% to 20% MeOH in DCM) to give impure expected product (26 mg). The product was purified by flash column chromatography (Isolute Si II 5 g) eluting with a solvent system of MeOH/DCM (from 0% to 10% MeOH) to afford impure final compound as a light yellow solid (15 mg). It was re-purified several times by flash column chromatography (Isolute Si II 2 g) eluting with a solvent system of c-Hex/EtOAc (from 0% to 50% EtOAc) to afford final compound as a white solid (5 mg, yield: 12%).

Example 5: Synthesis of Final Product 5

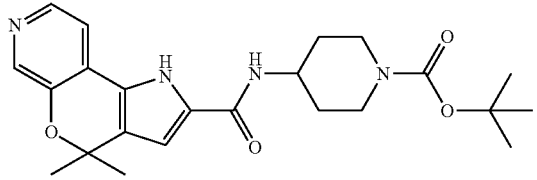 [SMILES: CC(C)(C)OC(=O)N1CCC(NC(=O)c2cc3c([nH]2)-c2ccncc2OC3(C)C)CC1]

To a solution of intermediate IX (20 mg, 0.082 mmol, 1 eq) in DCM (1.6 mL), n,n'-dicyclohexylcarbodiimide (19 mg, 0.09 mmol, 1.1 eq), 4-dimethylaminopyridine (2 mg, 0.016 mmol, 0.2 eq) and 4-amino-1-boc-piperidine (18 mg, 0.090 mmol, 1.1 eq) were added. The reaction mixture was stirred at room temperature for 16 h. The reaction mixture was then quenched with water (10 ml). The mixture was extracted with EtOAc (2×20 ml). The combined organic layer was dried over anhydrous Na₂SO₄. The solvent was evaporated from the dried organic layer under reduced pressure to obtain a crude product which was purified by flash chromatography (Biotage, 0% to 40% EtOAc in c-Hex) to afford the desired compound (17 mg, yield: 49%).

Example 6: Synthesis of Final Product 6

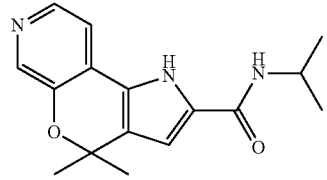 [SMILES: CC(C)NC(=O)c1cc2c([nH]1)-c1ccncc1OC2(C)C]

This product was prepared following the same protocol which was employed to prepare the example 5, but using isopropylamine instead of 4-amino-1-boc-piperidine (yield: 46%).

Example 7: Synthesis of Final Product 7

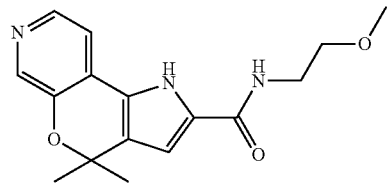 [SMILES: COCCNC(=O)c1cc2c([nH]1)-c1ccncc1OC2(C)C]

This product was prepared following the same protocol which was employed to prepare the example 5, but using 2-methoxyethylamine instead of 4-amino-1-boc-piperidine (yield: 22%).

Example 8: Synthesis of Final Product 8

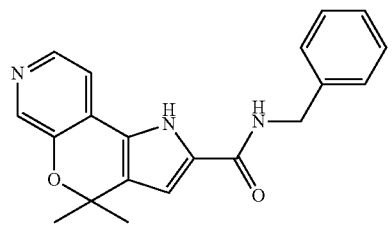 [SMILES: CC1(C)Oc2cnccc2-c2[nH]c(C(=O)NCc3ccccc3)cc21]

This product was prepared following the same protocol which was employed to prepare the example 5, but using benzylamine instead of 4-amino-1-boc-piperidine (yield: 42%).

Example 9: Synthesis of Final Product 9

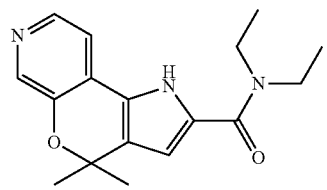 [SMILES: CCN(CC)C(=O)c1cc2c([nH]1)-c1ccncc1OC2(C)C]

This product was prepared following the same protocol which was employed to prepare the example 5, but using diethylamine instead of 4-amino-1-boc-piperidine (yield: 20%).

Example 10: Synthesis of Final Product 10

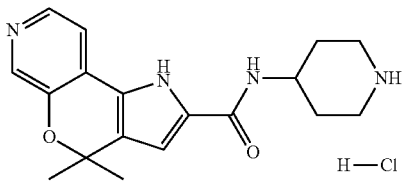

HCl (4N in 1,4-dioxane, 0.22 mL) was added to a mixture of final product 5 (13 mg, 0.030 mmol, 1 eq.) in 1,4-dioxane (1 mL) at room temperature. The reaction was stirred at room temperature for 2 hours. The solvent was evaporated under vacuum. (yield: 90%).

Example 11: Synthesis of Final Product 11

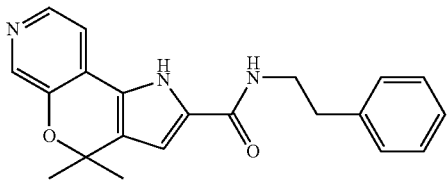 [SMILES: CC1(C)Oc2cnccc2-c2[nH]c(C(=O)NCCc3ccccc3)cc21]

This product was prepared following the same protocol which was employed to prepare the example 5, but using 2-phenylethylamine instead of 4-amino-1-boc-piperidine (yield: 28%).

Example 12: Synthesis of Final Product 12

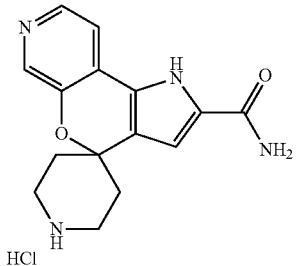 [SMILES: NC(=O)c1cc2c([nH]1)-c1ccncc1OC21CCNCC1 ; Cl]

HCl (4M in 1,4-dioxane, 3.25 mL, 1.014 mmol, 13 eq) was added to a mixture of intermediate XLII (30 mg, 0.078 mmol, 1 eq.) in 1,4-dioxane (0.4 mL) at room temperature. The reaction was stirred at room temperature for 16 hours. The resulting precipitate was filtered and washed with diethyl ether to afford the expected compound (17 mg, yield: 68%).

Example 13: Synthesis of Final Product 13

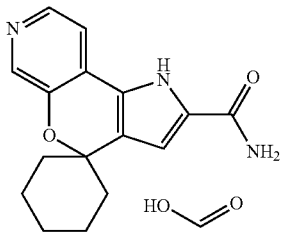

A suspension of intermediate XLVI (17 mg, 0.057 mmol, 1 eq.) in ammonium hydroxide (1 mL) was heated at 120° C. for 4 h. The solvent was evaporated to dryness. The residue was purified by preparative HPLC affording the amide derivative (1 mg, yield: 5%).

Example 14: Synthesis of Final Product 14

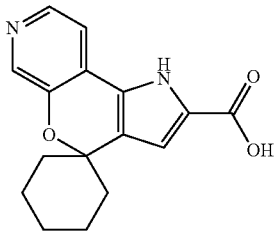 [SMILES: O=C(O)c1cc2c([nH]1)-c1ccncc1OC21CCCCC1]

This compound was obtained as a byproduct in the synthesis of the final product 13 (yield: 12%). The compounds of Examples 13 and 14 can be separated by TLC (DCM/MeOH 10:1): Rf=0.5 (Example 13) and Rf=0.2 (Example 14).

Example 15: Synthesis of Final Product 15

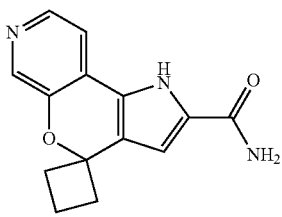 [SMILES: NC(=O)c1cc2c([nH]1)-c1ccncc1OC21CCC1]

This product was prepared following the same protocol which was employed to prepare the example 13 but using intermediate L as starting material (yield: 8%).

Example 16: Synthesis of Final Product 16

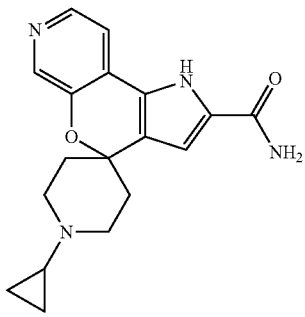 [SMILES: NC(=O)c1cc2c([nH]1)-c1ccncc1OC21CCN(C2CC2)CC1]

This product was prepared following the same protocol which was employed to prepare the example 13 but using intermediate LIV as starting material (yield: 5%).

Example 17: Synthesis of Final Product 17

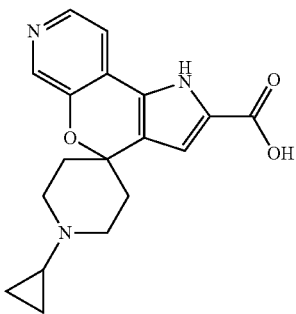 [SMILES: O=C(O)c1cc2c([nH]1)-c1ccncc1OC21CCN(C2CC2)CC1]

This compound was obtained as a byproduct in the synthesis of the final product 16 (yield: 20%). The compounds of Examples 16 and 17 can be separated by TLC (DCM/MeOH 10:1): Rf=0.5 (Example 16) and Rf=0.2 (Example 17).

Example 18: Synthesis of Final Product 18

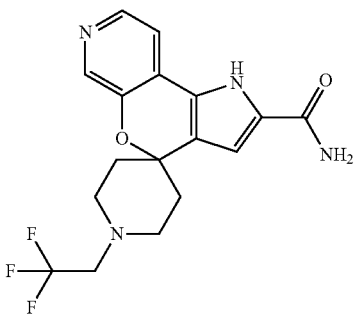 [SMILES: NC(=O)c1cc2c([nH]1)-c1ccncc1OC21CCN(CC(F)(F)F)CC1]

This product was prepared following the same protocol which was employed to prepare the example 13 but using intermediate LVIII as starting material (yield: 5%).

Example 19: Synthesis of Final Product 19

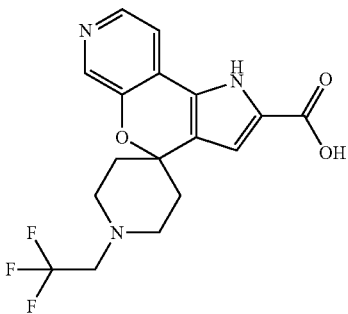 [SMILES: O=C(O)c1cc2c([nH]1)-c1ccncc1OC21CCN(CC(F)(F)F)CC1]

This compound was obtained as a byproduct in the synthesis of the final product 18 (yield: 7%). The compounds of Examples 18 and 19 can be separated by TLC (DCM/MeOH 10:1): Rf=0.5 (Example 18) and Rf=0.2 (Example 19).

Example 20: Synthesis of Final Product 20

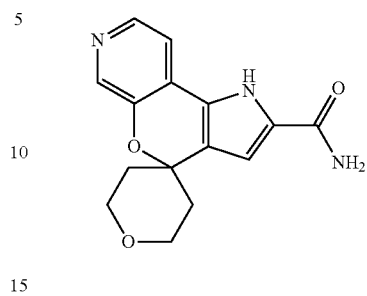

Trifluoroacetic acid (0.5 mL) was added to intermediate LXXIX (4 mg, 0.010 mmol). The reaction mixture was heated at 100° C. in MW for 30 minutes. Trifluoroacetic acid was evaporated under reduce pressure. Residue was purified several times by flash column chromatography (Isolute Si II 2 g) eluting with a solvent system of DCM/MeOH (from 0% to 10% MeOH in DCM) to afford final compound as a white solid (2 mg, yield: 81%).

Example 21: Synthesis of Final Product 21

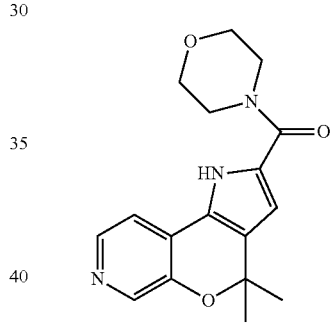

This product was prepared following the same protocol which was employed to prepare the example 5, but using morpholine instead of 4-amino-1-boc-piperidine (yield: 39%).

Example 22: Synthesis of Final Product 22

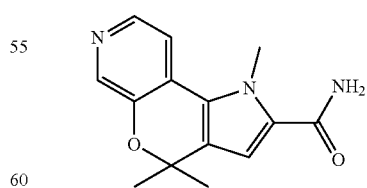

This product was prepared following the same protocol which was employed to prepare the example 13 but using intermediate LXIV as starting material. In this case, the product was purified by flash chromatography (Biotage, 0% to 40% EtOAc in c-Hex), (yield: 11%).

Example 23: Synthesis of Final Product 23

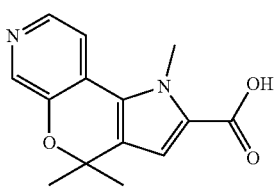 [SMILES: Cn1c(C(=O)O)cc2c1-c1ccncc1OC2(C)C]

This compound was obtained as a byproduct in the synthesis of the final product 22 (yield: 11%). The compounds of Examples 22 and 23 can be separated by TLC (DCM/MeOH 10:1): Rf=0.5 (Example 22) and Rf=0.2 (Example 23).

Example 24: Synthesis of Final Product 24

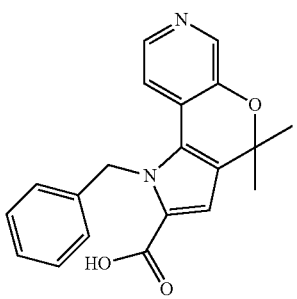 [SMILES: CC1(C)Oc2cnccc2-c2c1cc(C(=O)O)n2Cc1ccccc1]

This product was prepared following the same protocol which was employed to prepare the example 13 but using intermediate LXV as starting material. In this case the product was purified by flash chromatography (Biotage, 0% to 20% MeOH in DCM), (yield: 52%).

The corresponding amide was detected by HPLC-MS.

Example 25: Synthesis of Final Product 25

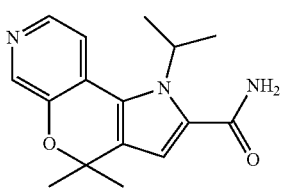 [SMILES: CC(C)n1c(C(N)=O)cc2c1-c1ccncc1OC2(C)C]

This product was prepared following the same protocol which was employed to prepare the example 13 but using intermediate LXVI as starting material. In this case the product was purified by flash chromatography (Biotage, 0% to 20% MeOH in DCM), (yield: 5%).

Example 26: Synthesis of Final Product 26

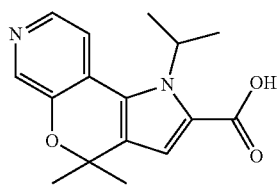 [SMILES: CC(C)n1c(C(=O)O)cc2c1-c1ccncc1OC2(C)C]

This compound was obtained as a byproduct in the synthesis of the final product 25 (yield: 7%). The compounds of Examples 25 and 26 can be separated by TLC (DCM/MeOH 10:1): Rf=0.5 (Example 25) and Rf=0.2 (Example 26).

Example 27: Synthesis of Final Product 27

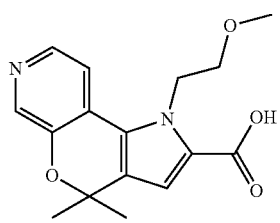 [SMILES: COCCn1c(C(=O)O)cc2c1-c1ccncc1OC2(C)C]

This product was prepared following the same protocol which was employed to prepare the example 13 but using intermediate LXVII as starting material. In this case the product was purified by flash chromatography (Biotage, 0% to 20% MeOH in DCM), (yield: 7%).

The corresponding amide compound was detected by HPLC-MS.

Example 28: Synthesis of Final Product 28

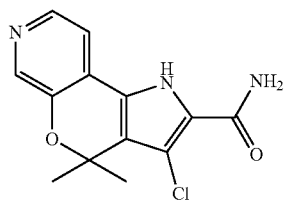 [SMILES: CC1(C)Oc2cnccc2-c2[nH]c(C(N)=O)c(Cl)c21]

This product was prepared following the same protocol which was employed to prepare the example 13 but using intermediate LXXX as starting material. In this case the product was purified by flash chromatography (Biotage, 0% to 20% MeOH in DCM), (yield: 62%).

Example 29: Synthesis of Final Product 29

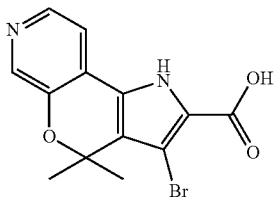 [SMILES: CC1(C)Oc2cnccc2-c2[nH]c(C(=O)O)c(Br)c21]

To intermediate LXVIII (10 mg, 0.03 mmol, 1 eq) was added 2M KOH (1 mL). The mixture was heated at 80° C. for 1 h. 1M HCl was added to neutralize the reaction mixture and then it was extracted with n-butanol. The organic phase was dried (Na$_2$SO$_4$) and evaporated till dryness. The residue was purified by flash chromatography (Biotage, 0% to 40% MeOH in DCM) to afford the final compound (5 mg, yield: 52%).

Example 30: Synthesis of Final Product 30

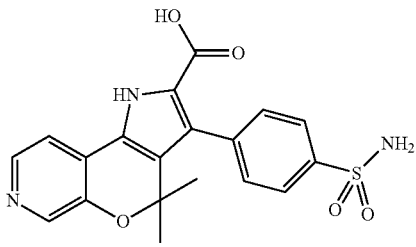 [SMILES: CC1(C)Oc2cnccc2-c2[nH]c(C(=O)O)c(-c3ccc(S(N)(=O)=O)cc3)c21]

This product was prepared following the same protocol which was employed to prepare the example 13 but using intermediate LXX as starting material and heating at 150° C. for 48 h instead of 120° C. for 4 h. In this case, the product was purified by flash chromatography (Biotage, 0% to 20% MeOH in DCM), (yield: 47%).

Example 31: Synthesis of Final Product 31

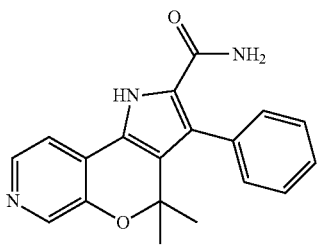 [SMILES: CC1(C)Oc2cnccc2-c2[nH]c(C(N)=O)c(-c3ccccc3)c21]

This product was prepared following the same protocol which was employed to prepare the example 20 but using intermediate LXXXII as starting material (yield: 46%).

Example 32: Synthesis of Final Product 32

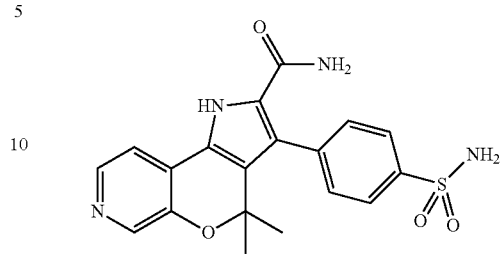

This product was prepared following the same protocol which was employed to prepare the example 13 but using intermediate LXX as starting material and heating at 150° C. for 48 h instead of 120° C. for 4 h. In this case, the product was purified by flash chromatography (Biotage, 0% to 20% MeOH in DCM), (yield: 10%). The compounds of Examples 30 and 32 can be separated by TLC (DCM/MeOH 9:1): Rf=0.3 (Example 30) and Rf=0.1 (Example 32).

Example 33: Synthesis of Final Product 33

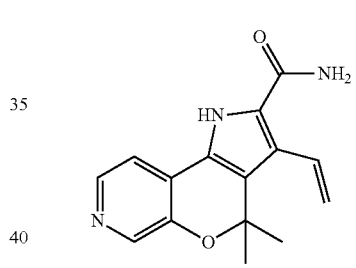

This product was prepared following the same protocol which was employed to prepare the example 20 but using intermediate LXXVII as starting material (yield: 22%).

Example 34: Synthesis of Final Product 34

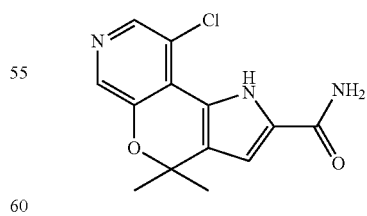

This product was prepared following the same protocol which was employed to prepare the example 13 but using intermediate XXXIV as starting material. In this case, the product was purified by flash chromatography (Biotage, 0% to 20% MeOH in DCM), (yield: 26%).

Example 35: Synthesis of Final Product 35

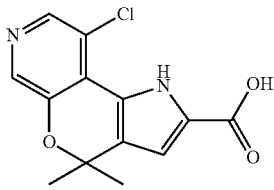 [SMILES: CC1(C)Oc2cncc(Cl)c2-c2[nH]c(C(=O)O)cc21]

This compound was obtained as a byproduct in the synthesis of the final product 34 (yield: 21%). The compounds of Examples 34 and 35 can be separated by TLC (DCM/MeOH 10:1): Rf=0.5 (Example 34) and Rf=0.2 (Example 35).

Example 36: Synthesis of Final Product 36

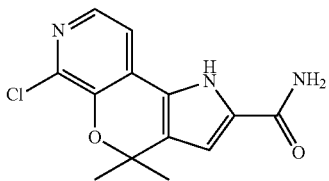 [SMILES: CC1(C)Oc2c(ccnc2Cl)-c2[nH]c(C(N)=O)cc21]

This product was prepared following the same protocol which was employed to prepare the example 13 but using intermediate XXXIII as starting material. In this case, the product was purified by flash chromatography (Biotage, 0% to 20% MeOH in DCM), (yield: 21%).

Example 37: Synthesis of Final Product 37

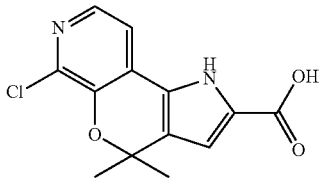 [SMILES: CC1(C)Oc2c(ccnc2Cl)-c2[nH]c(C(=O)O)cc21]

This compound was obtained as a byproduct in the synthesis of the final product 36 (yield: 21%). The compounds of Examples 36 and 37 can be separated by TLC (DCM/MeOH 10:1): Rf=0.5 (Example 36) and Rf=0.2 (Example 37).

Example 38: Synthesis of Final Product 38

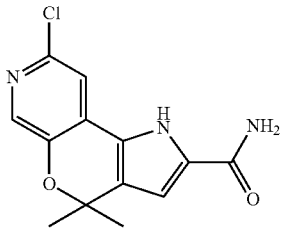 [SMILES: CC1(C)Oc2cnc(Cl)cc2-c2[nH]c(C(N)=O)cc21]

This product was prepared following the same protocol which was employed to prepare the example 13 but using intermediate XXXII as starting material. In this case, the product was purified by flash chromatography (Biotage, 0% to 20% MeOH in DCM), (yield: 18%).

Example 39: Synthesis of Final Product 39

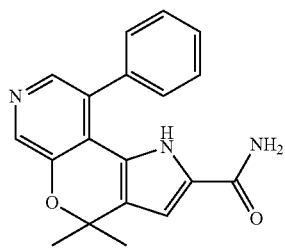 [SMILES: CC1(C)Oc2cncc(-c3ccccc3)c2-c2[nH]c(C(N)=O)cc21]

This product was prepared following the same protocol which was employed to prepare the example 20 but using intermediate XXXVII as starting material (yield: 14%).

Example 40: Synthesis of Final Product 40

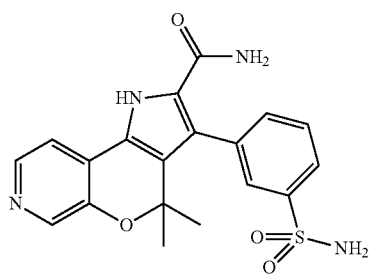 [SMILES: CC1(C)Oc2cnccc2-c2[nH]c(C(N)=O)c(-c3cccc(S(N)(=O)=O)c3)c21]

This product was prepared following the same protocol which was employed to prepare the example 20 but using intermediate LXXIII as starting material (yield: 54%).

Example 41: Synthesis of Final Product 41

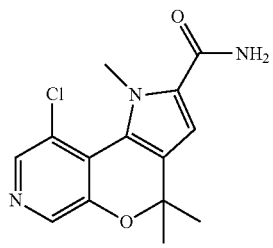 [SMILES: Cn1c(C(N)=O)cc2c1-c1c(Cl)cncc1OC2(C)C]

Ammonia (7N in MeOH, 2 mL) and calcium chloride (1M in MeOH, 0.5 mL) were added to intermediate LXXXIII (84 mg, 0.273 mmol, 1 eq) at room temperature. The reaction mixture was heated at 120° C. in a pressure tube for 16 hours. The reaction mixture was cooled down to room temperature, and the solvent was evaporated under vacuum. The residue was treated with a saturated NH4Cl aqueous solution and water. The resulting mixture was adjusted to pH 5 with hydrochloric acid, and the mixture was stirred at room temperature for 20 minutes. The aqueous layer was extracted with EtOAc. The organic layer was dried over Na2SO4, filtered and concentrated. The residue was purified by flash chromatography (Biotage, 0% to 40% MeOH in DCM) to afford the desired product as a white solid (4 mg, yield: 5%).

Example 42: Synthesis of Final Product 42

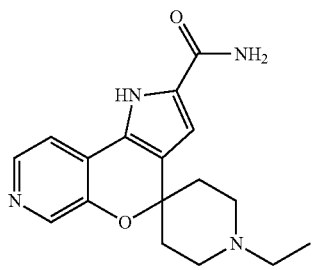 [SMILES: CCN1CCC2(CC1)Oc1cnccc1-c1[nH]c(C(N)=O)cc12]

This product was prepared following the same protocols which were employed for the synthesis of example 16, but using 1-ethyl-4-piperidone (CAS: 3612-18-8) instead of 1-cyclopropyl-4-piperidone.

Example 43: Synthesis of Final Product 43

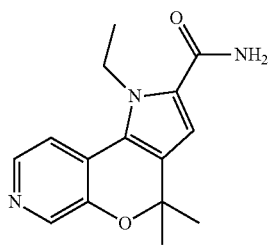 [SMILES: CCn1c(C(N)=O)cc2c1-c1ccncc1OC2(C)C]

This product was prepared following the same protocol which was employed to prepare the example 41, but using intermediate LXXXIV as starting material (yield: 8%).

Example 44: Synthesis of Final Product 44

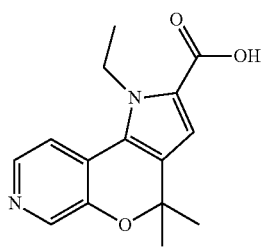 [SMILES: CCn1c(C(=O)O)cc2c1-c1ccncc1OC2(C)C]

This product was obtained as a byproduct in the synthesis of the final product 43 (yield: 89%). The compounds of Examples 43 and 44 can be separated by TLC (DCM/MeOH 10:1): Rf=0.5 (Example 43) and Rf=0.2 (Example 44).

Example 45: Synthesis of Final Product 45

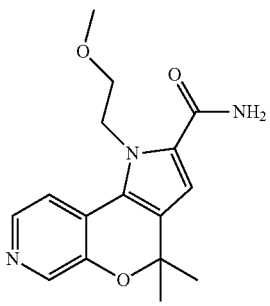 [SMILES: COCCn1c(C(N)=O)cc2c1-c1ccncc1OC2(C)C]

This product was prepared following the same protocol which was employed to prepare the example 41, but using intermediate LXXXV as starting material (yield: 10%).

Example 46: Synthesis of Final Product 46

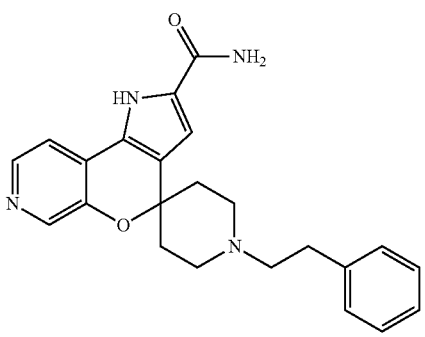 [SMILES: NC(=O)c1cc2c([nH]1)-c1ccncc1OC21CCN(CCc2ccccc2)CC1]

This product was prepared following the same protocols which were employed for the synthesis of example 16, but using 1-phenethyl-4-piperidone (CAS: 39742-60-4) instead of 1-cyclopropyl-4-piperidone.

Example 47: Synthesis of Final Product 47

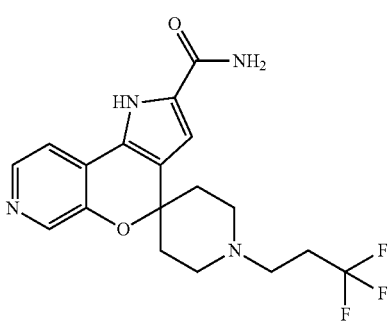 [SMILES: NC(=O)c1cc2c([nH]1)-c1ccncc1OC21CCN(CCC(F)(F)F)CC1]

This product was prepared following the same protocols which were employed for the synthesis of example 16, but using 1-(3,3,3-trifluoropropyl)piperidin-4-one (MFCD 18262851) instead of 1-cyclopropyl-4-piperidone.

Example 48: Synthesis of Final Product 48

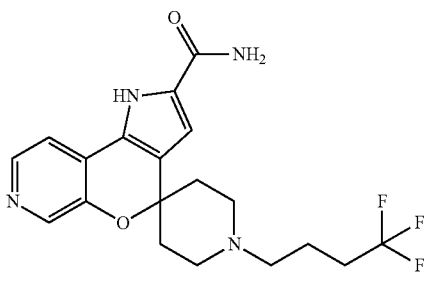 [SMILES: NC(=O)c1cc2c([nH]1)-c1ccncc1OC21CCN(CCCC(F)(F)F)CC1]

This product was prepared following the same protocols which were employed for the synthesis of example 16, but using 1-(4,4,4-trifluorobutyl)piperidin-4-one (MFCD 24222711) instead of 1-cyclopropyl-4-piperidone.

Example 49: Synthesis of Final Product 49

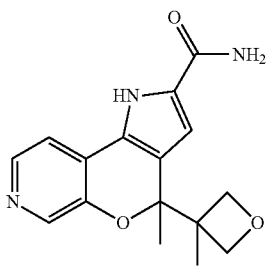 [SMILES: CC1(C2(C)Oc3cnccc3-c3[nH]c(C(N)=O)cc32)COC1]

This product was prepared following the same protocol which was employed to prepare the example 41, but using intermediate LXXXIX as starting material (yield: 18%).

Example 50: Synthesis of Final Product 50

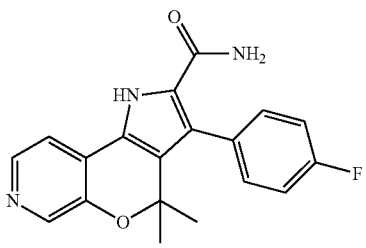 [SMILES: CC1(C)Oc2cnccc2-c2[nH]c(C(N)=O)c(-c3ccc(F)cc3)c21]

N,N'-Dicyclohexylcarbodiimide (46 mg, 0.225 mmol, 2 eq) was added to a mixture of intermediate XCI (38 mg, 0.112 mmol, 1 eq) in N,N-dimethylformamide (1.1 mL) at room temperature, followed by the addition of ammonium acetate (113 mg, 1.460 mmol, 13 eq). The reaction mixture was heated under reflux conditions for 16 hours. Then, the reaction was cooled down to room temperature, and quenched with water. The aqueous layer was extracted with EtOAc. The organic layer was dried over Na$_2$SO$_4$, filtered and concentrated under vacuum. The crude was first purified by flash chromatography (Biotage, 3% to 10% MeOH in DCM), and then by preparative HPLC to afford the desired final product as a pale yellow solid (3 mg, yield: 8%).

Example 51: Synthesis of Final Product 51

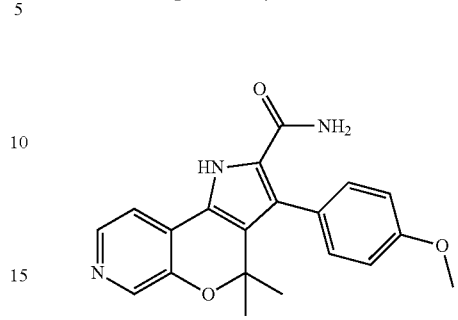

This product was prepared following the same protocol which was employed to prepare the example 1 (Protocol A), but using intermediate XCIV as starting material. The product was first purified by flash chromatography (Biotage, 5% to 20% MeOH in DCM), and then by preparative HPLC to give the desired final product as a pale yellow solid (yield: 40%).

Example 52: Synthesis of Final Product 52

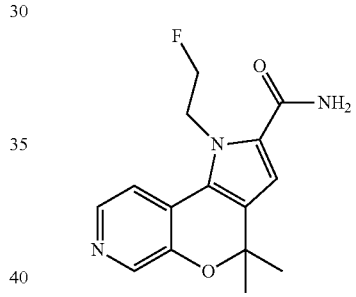

This product was prepared following the same protocol which was employed to prepare the example 41, but using intermediate XCV as starting material (yield: 34%).

Example 53: Synthesis of Final Product 53

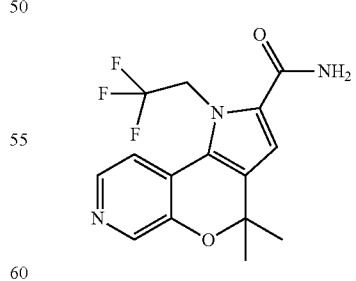

This product was prepared following the same protocol which was employed to prepare the example 41, but using intermediate XCVI as starting material. The reaction was carried out by heating at 120° C. in a pressure tube for 2 days instead of for 16 hours. The product was first purified by flash chromatography (Biotage, 0% to 40% MeOH in Example 54: Synthesis of Final Product 54

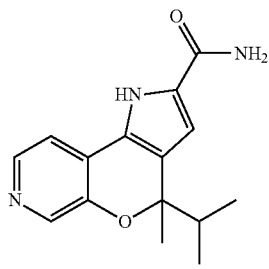 [SMILES: CC(C)C1(C)Oc2cnccc2-c2[nH]c(C(N)=O)cc21]

This product was prepared following the same protocol which was employed to prepare the example 41, but using intermediate C as starting material. The product was purified by flash chromatography (Biotage, 0% to 40% MeOH in DCM) to give the desired final product as a white solid (yield: 21%).

Example 55: Synthesis of Final Product 55

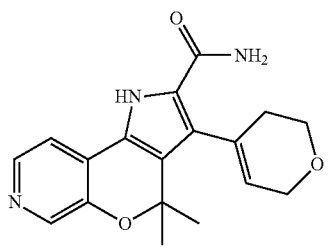 [SMILES: CC1(C)Oc2cnccc2-c2[nH]c(C(N)=O)c(C3=CCOCC3)c21]

This product was prepared following the same protocol which was employed to prepare the example 41, but using intermediate CV as starting material. The product was purified by flash chromatography (Biotage, 2% to 10% MeOH in DCM) to give the desired final product as a white solid (yield: 27%).

Example 56: Synthesis of Final Product 56

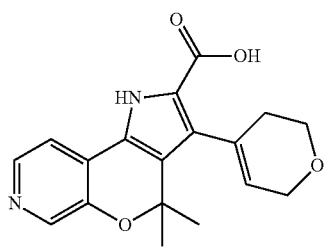 [SMILES: CC1(C)Oc2cnccc2-c2[nH]c(C(=O)O)c(C3=CCOCC3)c21]

This product was obtained as a byproduct in the synthesis of the final product 55 (yield: 12%). The compounds of Examples 55 and 56 were separated by TLC (DCM/MeOH 10:1): Rf=0.5 (Example 55) and Rf=0.2 (Example 56).

Example 57: Synthesis of Final Product 57

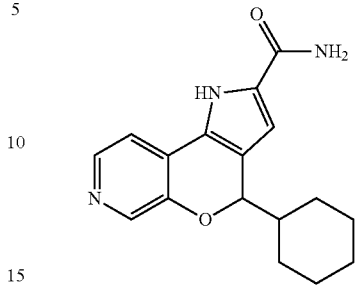

Di-tert-butyl dicarbonate (30 mg, 0.136 mmol, 1.5 eq) was added to a mixture of intermediate CXII (27 mg, 0.091 mmol, 1 eq) in 1,4-dioxane (0.4 mL) at room temperature, followed by the addition of ammonium bicarbonate (11 mg, 0.136 mmol, 1.5 eq) and pyridine (7 µL, 0.091 mmol, 1 eq). The reaction mixture was stirred at room temperature for 16 hours. The solvent was evaporated under vacuum, and the residue was dissolved in EtOAc. The organic phase was washed with 1N aqueous solution of HCl. The aqueous phase was extracted with n-butanol. The combined organic layers were dried over $Na_2SO_4$, filtered and concentrated under vacuum. The residue was purified by flash chromatography (Biotage, 2% to 8% MeOH in DCM) to give the desired final product as a white solid (5 mg, yield: 19%).

Example 58: Synthesis of Final Product 58

Trifluoroacetic acid (0.061 mL, 0.789 mmol, 20 eq) was added to a mixture of intermediate CXVIII (13 mg, 0.039 mmol, 1 eq) in dichloromethane (0.79 mL) at room temperature. The reaction was stirred at room temperature for 1 hour. Dichloromethane was added to the reaction mixture, and it was washed with a saturated aqueous solution of $NaHCO_3$. The aqueous phase was extracted with n-butanol. The combined organic layers were washed with a saturated aqueous solution of NaCl, dried over $Na_2SO_4$, filtered and concentrated under vacuum. The residue was purified by flash chromatography (Biotage, 2% to 10% MeOH in DCM) to give the desired final product as a white solid (4 mg, yield: 44%).

Example 59: Analytical Data for the Final Products

Characterisation data is provided for the compounds of Examples 1 to 58 in Table 1.

TABLE 1

LCMS and NMR data for the compounds of Examples 1 to 58

| Compound | LCMS data | NMR data |
|---|---|---|
| 1 | LCMS1, RT = 0.5 min, [M + H]+ m/z 244.1 | 1H NMR (700 MHz, DMSO) δ 12.29 (s, 1H), 8.10 (s, 1H), 8.08 (d, J = 3.6 Hz, 1H), 7.74 (d, J = 4.8 Hz, 1H), 7.69 (s, 1H), 7.19 (s, 1H), 6.75 (s, 1H), 1.55 (s, 6H). |
| 2 | LCMS1, Rt = 2.0 min, [M + H]+ m/z 245.1 | 1H NMR (700 MHz, DMSO) δ 12.46 (s, 1H), 8.12 (s, 1H), 8.10 (d, J = 4.5 Hz, 1H), 7.75 (d, J = 4.7 Hz, 1H), 6.69 (s, 1H), 1.56 (s, 6H). |
| 3 | LCMS1, Rt = 0.3 min, [M + H]+ m/z 258.1 | 1H NMR (300 MHz, DMSO) δ 12.30 (s, 1H), 8.18 (s, 1H), 8.10 (s, 1H), 8.08 (d, J = 4.9 Hz, 1H), 7.75 (d, J = 4.9 Hz, 1H), 6.69 (d, J = 2.1 Hz, 1H), 2.76 (d, J = 4.6 Hz, 3H), 1.55 (s, 6H). |
| 4 | LCMS1, Rt = 3.1 min, [M + H]+ m/z 320.1 | 1H NMR (300 MHz, DMSO) δ 12.46 (s, 1H), 9.90 (s, 1H), 8.09-7.99 (m, 2H), 7.74-7.67 (m, 3H), 7.35-7.26 (m, 2H), 7.04-6.99 (m, 2H), 1.52 (d, J = 11.2 Hz, 6H). |
| 5 | LCMS1, Rt = 3.5 min, [M + H]+ m/z 427.2 | 1H NMR (300 MHz, DMSO) δ 12.50 (s, 1H), 8.21 (s, 1H), 8.19 (d, J = 5.2 Hz, 1H), 8.12 (d, J = 8.0 Hz, 1H), 7.91 (d, J = 5.1 Hz, 1H), 6.83 (d, J = 2.0 Hz, 1H), 3.95-3.91 (m, 4H), 2.85 (s, 2H), 1.80-1.76 (m, 2H), 1.58 (s, 6H), 1.41 (s, 9H), 1.37 (s, 1H). |
| 6 | LCMS1, Rt = 0.4 & 2.6 min, [M + H]+ m/z 286.0 | 1H NMR (300 MHz, DMSO) δ 12.21 (s, 1H), 8.06 (s, 1H), 8.04 (d, J = 5.0 Hz, 1H), 7.92 (d, J = 7.8 Hz, 1H), 7.70 (d, J = 4.9 Hz, 1H), 6.75 (d, J = 1.9 Hz, 1H), 4.08-4.01 (m, 1H), 1.52 (s, 6H), 1.12 (d, J = 6.6 Hz, 6H). |
| 7 | LCMS1, Rt = 0.3 & 1.7 min, [M + H]+ m/z 302.1 | 1H NMR (300 MHz, DMSO) δ 12.23 (s, 1H), 8.18 (s, 1H), 8.05-8.00 (m, 2H), 7.67 (d, J = 4.9 Hz, 1H), 6.71 (d, J = 2.1 Hz, 1H), 3.37-3.33 (m, 4H), 3.20 (s, 3H), 1.49 (s, 6H). |
| 8 | LCMS1, Rt = 3.1 min, [M + H]+ m/z 334.2 | 1H NMR (300 MHz, DMSO) δ 12.28 (s, 1H), 8.71-8.67 (m, 1H), 8.04 (s, 1H), 8.02 (d, J = 4.9 Hz, 1H), 7.68 (d, J = 4.9 Hz, 1H), 7.33-7.23 (m, 4H), 7.23-7.14 (m, 1H), 6.75 (d, J = 2.1 Hz, 1H), 4.40 (d, J = 6.1 Hz, 2H), 1.49 (s, 6H). |
| 9 | LCMS1, Rt = 2.7 & 3.0 min, [M + H]+ m/z 300.1 | 1H NMR (300 MHz, DMSO) δ 12.15 (s, 1H), 8.04 (s, 2H), 7.69 (s, 1H), 6.37 (d, J = 2.2 Hz, 1H), 3.50-3.40 (m, 4H), 1.51 (s, 6H), 1.16 (d, J = 5.1 Hz, 3H), 1.11 (d, J = 7.0 Hz, 3H). |
| 10 | LCMS1, Rt = 0.4 min, [M + H]+ m/z 327.1 | 1H NMR (300 MHz, DMSO) δ 12.79 (s, 1H), 8.62-8.52 (m, 1H), 8.41 (s, 1H), 8.30-8.22 (m, 2H), 8.06 (s, 1H), 6.85 (s, 1H), 4.05-3.96 (m, 1H), 3.44-3.41 (m, 2H), 2.99-2.92 (m, 2H), 1.93-1.87 (m, 2H), 1.69 (s, 2H), 1.56 (s, 6H). |
| 11 | LCMS1, Rt = 3.3 min, [M + H]+ m/z 348.1 | 1H NMR (300 MHz, DMSO) δ 12.31 (s, 1H), 8.32 (s, 1H), 8.10 (s, 1H), 8.08 (d, J = 4.9 Hz, 1H), 7.73 (d, J = 4.9 Hz, 1H), 7.37-7.15 (m, 5H), 6.72 (s, 1H), 3.51-3.44 (m, 6.2 Hz, 2H), 2.86-2.81 (m, 2H), 1.55 (s, 6H). |
| 12 | LCMS1, Rt = 0.3 min, [M + H]+ m/z 285.1 | $^1$H NMR (300 MHz, DMSO) δ 13.00 (s, 1H), 9.17 (s, 1H), 8.56 (s, 1H), 8.40 (d, J = 5.7 Hz, 1H), 8.18 (d, J = 5.8 Hz, 1H), 8.07 (s, 1H), 7.48 (s, 1H), 6.87 (d, J = 1.9 Hz, 1H), 3.29 (s, 4H), 2.21 (s, 4H). |
| 13 | LCMS1, Rt = 2.5 min, [M + H]+ m/z 284.1 | 1H NMR (300 MHz, DMSO) d 12.54 (s, 1H), 8.29 (s, 1H), 8.20 (d, J = 5.3 Hz, 1H), 7.92 (d, J = 5.3 Hz, 1H), 7.79 (s, 1H), 7.30 (s, 1H), 6.83 (d, J = 2.0 Hz, 1H), 2.01-1.95 (m, 2H), 1.79-1.54 (m, 6H), 1.38-1.22 (m, 2H). |
| 14 | LCMS1, Rt = 2.9 min, [M + H]+ m/z 285.1 | 1H NMR (300 MHz, DMSO) δ 12.29-12.03 (m, 1H), 8.04 (s, 1H), 7.96 (s, 1H), 7.62 (d, J = 4.7 Hz, 1H), 6.48 (s, 1H), 1.81 (d, J = 10.2 Hz, 2H), 1.82-1.62 (m, 5H), 1.42 (s, 2H), 1.17 (s, 1H) |
| 15 | LCMS1, Rt = 0.4 & 2.0 min, [M + H]+ m/z 256.0 | 1H NMR (300 MHz, DMSO) δ 12.52 (s, 1H), 8.25 (s, 1H), 8.18 (d, J = 5.2 Hz, 1H), 7.88 (d, J = 5.2 Hz, 1H), 7.82 (s, 1H), 7.32 (s, 1H), 7.05 (d, J = 2.1 Hz, 1H), 2.64-2.56 (m, 2H), 2.41-2.33 (m, 2H), 2.04-1.80 (m, 2H). |
| 16 | LCMS1, Rt = 0.3 min, [M + H]+ m/z 325.1 | 1H NMR (300 MHz, DMSO) δ 11.90 (s, 1H), 8.53 (s, 2H), 8.13 (s, 1H), 7.66 (s, 1H), 7.21 (s, 1H), 6.67 (s, 1H), 5.33 (s, 1H), 2.01 (s, 4H), 1.71 (s, 2H), 1.44 (s, 2H), 0.85 (s, 4H). |
| 17 | LCMS1, Rt = 0.3 min, [M + H]+ m/z 326.1 | 1H NMR (300 MHz, DMSO) δ 12.31-11.90 (m, 1H), 8.09 (s, 1H), 8.02 (s, 1H), 7.68 (s, 1H), 6.44 (s, 1H), 2.75-2.65 (m, 2H), 2.58 (t, J = 9.8 Hz, 2H), 1.79 (d, J = 13.3 Hz, 4H), 1.67 (d, J = 9.3 Hz, 2H), 0.37 (d, J = 4.9 Hz, 2H), 0.26 (s, 1H). |
| 18 | LCMS1, Rt = 2.1 min, [M + H]+ m/z 367.1 | 1H NMR (300 MHz, DMSO) δ 12.35 (s, 1H), 8.13 (s, 2H), 7.75 (s, 1H), 7.67 (s, 1H), 7.21 (s, 1H), 6.79 (s, 1H), 2.80 (s, 6H), 1.98-1.82 (m, 4H). |

TABLE 1-continued

LCMS and NMR data for the compounds of Examples 1 to 58

| Compound | LCMS data | NMR data |
|---|---|---|
| 19 | LCMS1, Rt = 2.3 min, [M + H]+ m/z 368.1 | 1H NMR (300 MHz, DMSO) d 12.33 (s, 1H), 8.09 (m, 2H), 7.69 (s, 1H), 6.63 (s, 1H), 2.74 (s, 4H), 1.85 (s, 4H). |
| 20 | LCMS1, Rt = 0.3 & 0.4 min, [M + H]+ m/z 285.9 | 1H NMR (300 MHz, DMSO) δ 12.39 (s, 1H), 8.22 (s, 1H), 8.11 (s, 1H), 7.76 (s, 2H), 7.21 (s, 1H), 6.82 (s, 1H), 3.78 (s, 4H), 1.89 (s, 4H). |
| 21 | LCMS1, Rt = 0.4 & 1.7 min, [M + H]+ m/z 314.0 | 1H NMR (300 MHz, DMSO) δ 12.42 (s, 1H), 8.32-8.04 (m, 2H), 7.81 (d, J = 5.0 Hz, 1H), 6.58 (s, 1H), 3.71-3.64 (m, 8H), 1.59 (s, 6H). |
| 22 | LCMS1, Rt = 0.4 & 0.5 min, [M + H]+ m/z 258.0 | 1H NMR (300 MHz, DMSO) δ 8.12 (s, 1H), 8.10 (d, J = 5.1 Hz, 1H), 7.62 (s, 1H), 7.54 (d, J = 5.2 Hz, 1H), 7.12 (s, 1H), 6.70 (s, 1H), 4.07 (s, 3H), 1.46 (s, 6H). |
| 23 | LCMS1, Rt = 2.3 min, [M + H]+ m/z 259.1 | 1H NMR (300 MHz, DMSO) δ 12.55 (s, 1H), 8.16-8.09 (m, 2H), 7.58 (d, J = 4.8 Hz, 1H), 6.73 (s, 1H), 4.12 (s, 3H), 1.47 (s, 6H). |
| 24 | LCMS1, Rt = 3.0 min, [M + H]+ m/z 335.0 | 1H NMR (300 MHz, DMSO) δ 8.49 (s, 2H), 8.30-8.22 (m, 1H), 7.48-7.32 (m, 6H), 6.31 (s, 1H), 5.44 (s, 2H), 1.53 (s, 6H). |
| 25 | LCMS1, Rt = 0.4 min, [M + H]+ m/z 286.2 | 1H NMR (300 MHz, DMSO) δ 8.58 (s, 2H), 8.17 (s, 1H), 7.91 (s, 1H), 7.42 (s, 1H), 6.79 (d, J = 10.2 Hz, 1H), 4.67 (s, 1H), 1.58 (s, 6H), 1.47 (s, 6H). |
| 26 | LCMS1, Rt = 0.4 & 2.5 min, [M + H]+ m/z 287.1 | 1H NMR (300 MHz, DMSO) δ 8.43 (d, J = 6.8 Hz, 1H), 8.31 (s, 1H), 8.23 (d, J = 5.1 Hz, 1H), 6.30 (s, 1H), 4.65-4.54 (m, 1H), 1.57 (s, 6H), 1.46 (d, J = 6.6 Hz, 6H). |
| 27 | LCMS1, Rt = 2.4 min, [M + H]+ m/z 302.8 | 1H NMR (300 MHz, DMSO) δ 8.41 (s, 1H), 8.28 (s, 1H), 8.25 (d, J = 7.6 Hz, 1H), 8.12 (s, 1H), 6.25 (s, 1H), 4.38 (s, 2H), 3.69 (s, 2H), 3.20 (s, 3H), 1.56 (s, 6H). |
| 28 | LCMS1, Rt = 0.5 &2.6 min, [M + H]+ m/z 278.0 | 1H NMR (300 MHz, DMSO) δ 12.69 (s, 1H), 8.14 (s, 1H), 8.12 (d, J = 4.9 Hz, 1H), 7.80 (d, J = 4.9 Hz, 1H), 7.73 (s, 1H), 7.10 (s, 1H), 1.64 (d, J = 7.7 Hz, 6H). |
| 29 | LCMS1, Rt = 2.8 min, [M + H]+ m/z 325.0 | 1H NMR (300 MHz, DMSO) δ 8.07-8.02 (m, 2H), 7.79 (s, 1H), 1.61 (s, 6H). |
| 30 | LCMS1, Rt = 0.7 & 2.4 min, [M + H]+ m/z 399.9 | 1H NMR (300 MHz, DMSO) δ 8.12-8.08 (m, 2H), 7.87 (d, J = 4.9 Hz, 1H), 7.79 (d, J = 8.2 Hz, 2H), 7.47-7.37 (m, 4H), 1.29 (s, 6H). |
| 31 | LCMS1, Rt = 3.1 min, [M + H]+ m/z 320.1 | 1H NMR (300 MHz, DMSO) δ 12.48 (s, 1H), 8.13 (s, 2H), 7.86 (s, 1H), 7.44 (d, J = 35.6 Hz, 7H), 1.28 (d, J = 6.4 Hz, 6H). |
| 32 | LCMS1, Rt = 0.4 & 1.3 min, [M + H]+ m/z 398.8 | 1H NMR (300 MHz, DMSO) δ 12.56 (s, 1H), 8.13 (s, 2H), 7.93 (d, J = 7.8 Hz, 2H), 7.84 (s, 1H), 7.59 (d, J = 7.9 Hz, 2H), 7.50 (s, 2H), 7.37 (s, 1H), 5.82 (s, 1H), 1.33 (s, 6H). |
| 33 | LCMS1, Rt = 0.4 & 2.1 min, [M + H]+ m/z 269.8 | 1H NMR (300 MHz, DMSO) δ 12.28 (s, 1H), 8.16 (s, 1H), 7.78 (s, 1H), 7.52 (s, 1H), 7.28 (s, 1H), 6.93 (dd, J = 17.6, 11.0 Hz, 1H), 6.72 (s, 1H), 5.63-5.34 (m, 2H), 1.29 (s, 6H). |
| 34 | LCMS1, Rt = 3.6 min, [M + H]+ m/z 278.1 & 279.0 | 1H NMR (300 MHz, DMSO) δ 10.58 (s, 1H), 8.20 (s, 1H), 8.16 (s, 1H), 8.00 (s, 1H), 7.39 (s, 1H), 6.85 (s, 1H), 1.58 (s, 6H). |
| 35 | LCMS1, Rt = 4.27 min, [M + H]+ m/z 279.0 | 1H NMR (300 MHz, DMSO) δ 10.5 (s (broad), 1H), 8.2 (s, 1H), 8.14 (s, 1H), 6.62 (s, 1H), 1.6 (s, 6H) |
| 36 | LCMS1, Rt = 4.0 min, [M + H]+ m/z 278.2 | 1H NMR (300 MHz, DMSO) δ 12.37 (s, 1H), 7.84 (d, J = 4.9 Hz, 1H), 7.73 (d, J = 4.9 Hz, 1H), 6.79 (s, 1H), 6.71 (s, 1H), 6.60 (s, 1H), 1.52 (s, 6H). |
| 37 | LCMS1, Rt = 4.5 min, [M + H]+ m/z 279.2 | 1H NMR (300 MHz, DMSO) δ 12.26 (s, 1H), 7.82 (d, J = 4.5 Hz, 1H), 7.72 (d, J = 4.0 Hz, 1H), 6.49 (s, 1H), 1.51 (s, 6H). |
| 38 | LCMS1, Rt = 4.1 min, [M + H]+ m/z 279.1 | 1H NMR (300 MHz, DMSO) δ 12.72-11.99 (m, 1H), 7.84 (s, 1H), 7.82 (s, 1H), 7.70 (s, 1H), 7.18 (s, 1H), 6.70 (s, 1H), 1.49 (s, 6H). |
| 39 | LCMS1, Rt = 3.1 min, [M + H]+ m/z 319.8 | 1H NMR (300 MHz, DMSO) δ 8.20 (s, 1H), 8.10-7.83 (m, 2H), 7.55-7.25 (m, 6H), 7.08-6.90 (m, 1H), 6.53 (s, 1H), 1.39 (s, 6H). |
| 40 | LCMS1, Rt = 0.4 & 2.1 min, [M + H]+ m/z 399.0 | 1H NMR (300 MHz, DMSO) δ 12.58 (s, 1H), 8.24 (s, 1H), 7.93 (t, J = 7.0 Hz, 2H), 7.81 (s, 1H), 7.76-7.63 (m, 2H), 7.54 (s, 2H), 7.40 (s, 1H), 7.24 (s, 1H), 7.07 (s, 1H), 1.36 (s, 6H). |

TABLE 1-continued

LCMS and NMR data for the compounds of Examples 1 to 58

| Compound | LCMS data | NMR data |
|---|---|---|
| 41 | LCMS1, Rt = 5.3 min, [M + H]+ m/z 293.0 | 1H NMR (300 MHz, DMSO) δ 8.30 (s, 1H), 8.23 (s, 1H), 7.01 (s, 1H), 6.83 (s, 1H), 6.58 (s, 1H), 3.85 (s, 3H), 1.50 (s, 6H). |
| 42 | LCMS1, Rt = 0.37 min, [M + H]+ m/z 313.1 | 1H NMR (300 MHz, DMSO) δ 12.36 (s, 1H), 8.15 (s, 1H), 8.09 (d, J = 4.9 Hz, 1H), 7.73 (t, J = 6.8 Hz, 2H), 7.19 (s, 1H), 6.77 (s, 1H), 2.72 (dd, J = 8.4, 6.6 Hz, 2H), 2.41 (dd, J = 14.3, 7.1 Hz, 4H), 1.95 (d, J = 12.8 Hz, 2H), 1.88-1.79 (m, 2H), 1.04 (t, J = 7.2 Hz, 3H). |
| 43 | LCMS1, Rt = 0.39 min, [M + H]+ m/z 272.1 | 1H NMR (300 MHz, DMSO) δ 8.18 (d, J = 6.3 Hz, 2H), 7.68 (s, 1H), 7.48 (d, J = 5.2 Hz, 1H), 7.16 (d, J = 4.3 Hz, 1H), 6.79 (s, 1H), 4.67 (q, J = 7.0 Hz, 2H), 1.53 (s, 6H), 1.36 (t, J = 7.0 Hz, 3H). |
| 44 | LCMS1, Rt = 2.49 min, [M + H]+ m/z 273.1 | 1H NMR (300 MHz, DMSO) δ 12.58 (s, 1H), 8.20-8.07 (m, 2H), 7.45 (d, J = 5.2 Hz, 1H), 6.76 (s, 1H), 4.60 (q, J = 6.9 Hz, 2H), 1.47 (s, 6H), 1.32 (t, J = 7.0 Hz, 3H). |
| 45 | LCMS1, Rt = 0.41 min, [M + H]+ m/z 302.1 | 1H NMR (300 MHz, DMSO) δ 8.19 (s, 1H), 8.17 (d, J = 5.2 Hz, 1H), 7.71 (s, 1H), 7.65 (d, J = 5.2 Hz, 1H), 7.17 (s, 1H), 6.82 (s, 1H), 4.82 (t, J = 5.8 Hz, 2H), 3.68 (t, J = 5.7 Hz, 2H), 3.21 (s, 3H), 1.53 (s, 6H). |
| 46 | LCMS1, Rt = 0.44 min, [M + H]+ m/z 389.4 | 1H NMR (300 MHz, DMSO) δ 12.34 (s, 1H), 8.22-8.02 (m, 2H), 7.73 (t, J = 9.1 Hz, 2H), 7.33-7.17 (m, 6H), 6.79 (d, J = 2.0 Hz, 1H), 2.77 (d, J = 16.9 Hz, 4H), 2.60 (dd, J = 13.0, 11.1 Hz, 4H), 2.04-1.78 (m, 4H). |
| 47 | LCMS1, Rt = 0.38 min, [M + H]+ m/z 381.1 | 1H NMR (300 MHz, DMSO) δ 12.27 (s, 1H), 8.10 (s, 1H), 8.03 (d, J = 4.9 Hz, 1H), 7.68 (d, J = 4.9 Hz, 1H), 7.61 (s, 1H), 7.14 (s, 1H), 6.72 (s, 1H), 2.72-2.62 (m, 4H), 2.60-2.50 (m, 4H), 1.93-1.68 (m, 4H). |
| 48 | LCMS1, Rt = 0.43 min, [M + H]+ m/z 395.4 | 1H NMR (300 MHz, DMSO) δ 12.26 (s, 1H), 8.09 (s, 1H), 8.03 (d, J = 4.9 Hz, 1H), 7.67 (d, J = 4.9 Hz, 1H), 7.60 (s, 1H), 7.13 (s, 1H), 6.72 (s, 1H), 2.68-2.57 (m, 2H), 2.40-2.14 (m, 6H), 1.94-1.71 (m, 4H), 1.68-1.53 (m, 2H). |
| 49 | LCMS1, Rt = 0.41 min, [M + H]+ m/z 300.3 | 1H NMR (300 MHz, DMSO) δ 12.37 (s, 1H), 8.05 (s, 1H), 7.99 (d, J = 4.9 Hz, 1H), 7.70 (d, J = 4.9 Hz, 2H), 7.14 (s, 1H), 6.72 (s, 1H), 4.67 (d, J = 5.8 Hz, 1H), 4.48 (d, J = 6.2 Hz, 1H), 4.12 (d, J = 5.8 Hz, 1H), 4.05 (d, J = 6.2 Hz, 1H), 1.54 (s, 3H), 1.35 (s, 3H). |
| 50 | LCMS1, Rt = 2.96 min, [M + H]+ m/z 338.1 | $^{1}$H NMR (300 MHz, DMSO) δ 12.49 (s, 1H), 8.12 (s, 2H), 7.91 (s, 1H), 7.82 (d, J = 4.5 Hz, 1H), 7.48-7.35 (m, 2H), 7.36-7.22 (m, 3H), 1.28 (s, 6H). |
| 51 | LCMS1, Rt = 2.96 min, [M + H]+ m/z 350.1 | $^{1}$H NMR (300 MHz, DMSO) δ 12.44 (s, 1H), 8.45 (s, 1H), 8.10 (s, 1H), 7.85 (d, J = 4.5 Hz, 1H), 7.56 (s, 1H), 7.40 (s, 1H), 7.34-7.23 (m, 2H), 7.06 (d, J = 8.7 Hz, 2H), 3.82 (s, 3H), 1.28 (s, 6H). |
| 52 | LCMS1, Rt = 0.42 min, [M + H]+ m/z 290.1 | $^{1}$H NMR (300 MHz, DMSO) δ 8.13 (s, 1H), 8.09 (d, J = 5.2 Hz, 1H), 7.70 (s, 1H), 7.56 (t, J = 6.9 Hz, 1H), 7.16 (s, 1H), 6.82 (s, 1H), 4.97 (t, J = 4.7 Hz, 1H), 4.88 (t, J = 4.7 Hz, 1H), 4.80 (t, J = 4.7 Hz, 1H), 4.65 (t, J = 4.7 Hz, 1H), 1.47 (s, 6H). |
| 53 | LCMS1, Rt = 2.42 min, [M + H]+ m/z 326.1 | $^{1}$H NMR (300 MHz, DMSO) δ 8.15 (s, 1H), 8.11 (d, J = 5.2 Hz, 1H), 7.84 (s, 1H), 7.63 (d, J = 5.2 Hz, 1H), 7.33 (s, 1H), 6.90 (s, 1H), 1.47 (s, 6H). |
| 54 | LCMS1, Rt = 2.00 min, [M + H]+ m/z 272.1 | $^{1}$H NMR (300 MHz, DMSO) δ 12.27 (s, 1H), 8.08 (s, 1H), 8.04 (d, J = 4.9 Hz, 1H), 7.72 (d, J = 4.9 Hz, 2H), 7.18 (s, 1H), 6.75 (s, 1H), 2.02-1.87 (m, 1H), 1.52 (s, 3H), 0.94 (d, J = 6.8 Hz, 3H), 0.85 (d, J = 6.8 Hz, 3H). |
| 55 | LCMS1, Rt = 2.22 min, [M + H]+ m/z 326.1 | $^{1}$H NMR (300 MHz, DMSO) δ 12.27 (s, 1H), 8.12 (s, 1H), 8.11 (d, J = 4.7 Hz, 2H), 7.74 (d, J = 5.1 Hz, 1H), 7.45 (s, 1H), 6.46 (s, 1H), 5.84 (s, 1H), 4.20 (d, J = 2.4 Hz, 2H), 3.81 (t, J = 5.3 Hz, 2H), 2.28-2.26 (m, 2H), 1.61 (d, J = 26.9 Hz, 6H). |
| 56 | LCMS1, Rt = 2.50 min, [M + H]+ m/z 327.0 | $^{1}$H NMR (300 MHz, DMSO) δ 8.09 (s, 1H), 8.06 (s, 1H), 7.80 (d, J = 4.9 Hz, 1H), 5.52 (s, 1H), 4.13 (s, 2H), 3.78 (t, J = 5.1 Hz, 2H), 2.34 (s, 2H), 1.57 (s, 6H). |
| 57 | LCMS1, Rt = 2.83 min, [M + H]+ m/z 298.1 | $^{1}$H NMR (300 MHz, DMSO) δ 12.24 (s, 1H), 8.03 (s, 1H), 7.98 (d, J = 4.9 Hz, 1H), 7.65 (d, J = 4.9 Hz, 1H), 7.65 (s, 1H), 7.12 (s, 1H), 6.65 (d, J = 1.4 Hz, 1H), 5.19 (d, J = 5.3 Hz, 1H), 1.75-1.56 (m, 6H), 1.23-0.79 (m, 5H). |
| 58 | LCMS5, Rt = 2.82 min, [M + H]+ m/z 230.1 | $^{1}$H NMR (300 MHz, DMSO) δ 12.32 (s, 1H), 8.11 (s, 1H), 8.08 (d, J = 4.9 Hz, 1H), 7.72 (d, J = 4.9 Hz, 1H), 7.72 (s, 1H), 7.20 (s, 1H), 6.73 (s, 1H), 5.58 (q, J = 6.3 Hz, 1H), 1.55 (d, J = 6.4 Hz, 3H). |

Example 60

Compounds of the invention were found to inhibit CDK8, for example as tested in the binding assay described hereinbefore. Biological activity in CDK8 for certain examples is represented in Table 2.

TABLE 2

Inhibition of CDK8 activity expressed as $IC_{50}$ values [M] for the compounds of the examples, as well as certain other compounds that were mentioned as being useful intermediates.

| Compound number | CDK8 $IC_{50}$ (mol/L) |
| --- | --- |
| 1 | 2.59E−09 |
| 2 | 1.46E−07 |
| 3 | 9.22E−08 |
| 4 | 5.28E−06 |
| 5 | 1.87E−06 |
| 6 | 2.41E−06 |
| 7 | 1.49E−06 |
| 8 | 3.40E−07 |
| 9 | 9.79E−07 |
| 10 | 3.52E−06 |
| 11 | 1.62E−07 |
| 12 | 4.12E−07 |
| 13 | 4.18E−09 |
| 14 | 2.39E−08 |
| 15 | 1.96E−09 |
| 16 | 5.70E−06 |
| 17 | 1.53E−06 |
| 18 | 2.02E−08 |
| 19 | 6.52E−07 |
| 20 | 5.47E−08 |
| 21 | 6.71E−07 |
| 22 | 1.98E−09 |
| 23 | 6.11E−08 |
| 24 | 1.00E−05 |
| 25 | 5.87E−06 |
| 26 | 5.94E−06 |
| 27 | 1.00E−05 |
| 28 | 9.32E−09 |
| 29 | 5.25E−08 |
| 30 | 8.94E−09 |
| 31 | 2.97E−08 |
| 32 | 2.62E−08 |
| 33 | 1.23E−08 |
| 34 | 2.10E−09 |
| 35 | 1.33E−08 |
| 36 | 5.59E−07 |
| 37 | 6.29E−06 |
| 38 | 4.61E−07 |
| 39 | 2.06E−07 |
| 40 | 2.69E−07 |
| 41 | 5.55E−08 |
| 42 | 1.97E−07 |
| 43 | 1.41E−09 |
| 44 | 3.12E−07 |
| 45 | 4.64E−09 |
| 46 | 4.45E−07 |
| 47 | 1.20E−07 |
| 48 | 8.86E−07 |
| 49 | 3.15E−07 |
| 50 | 5.81E−07 |
| 51 | 3.19E−08 |
| 52 | 1.41E−09 |
| 53 | 2.16E−08 |
| 54 | 3.11E−08 |
| 55 | 3.93E−08 |
| 56 | 7.85E−08 |
| 57 | 1.41E−09 |
| 58 | 1.44E−08 |
| VIII | 6.77E−07 |
| LXIX | 2.00E−06 |
| LXVIII | 7.80E−07 |
| LXX | 2.85E−06 |

Example 61

Compounds of the invention were found to inhibit Haspin kinase, for example as tested in the ADP-Glo™ assay described hereinbefore. Biological activity in Haspin kinase for certain examples is represented in Table 3.

TABLE 3

Inhibition of Haspin kinase activity expressed as $IC_{50}$ values [M] for the compounds of certain examples.

| Compound number | HASPIN $IC_{50}$ (mol/L) |
| --- | --- |
| 1 | 3.81E−08 |
| 2 | 3.06E−07 |
| 3 | 1.80E−07 |
| 4 | 7.55E−06 |
| 5 | 1.84E−05 |
| 6 | 1.78E−06 |
| 7 | 1.02E−06 |
| 8 | 3.05E−07 |
| 9 | 2.35E−06 |
| 10 | 1.73E−06 |
| 11 | 4.18E−07 |
| 12 | 5.33E−08 |
| 13 | 5.36E−08 |
| 14 | 1.00E−06 |
| 15 | 1.59E−08 |
| 16 | 4.28E−06 |
| 17 | 5.96E−06 |
| 18 | 3.44E−07 |
| 19 | 2.95E−06 |
| 20 | 2.06E−07 |
| 21 | 8.68E−07 |
| 22 | 8.74E−08 |
| 23 | 6.48E−07 |
| 24 | 2.04E−05 |
| 25 | 2.23E−05 |
| 26 | 4.90E−05 |
| 27 | 4.99E−05 |
| 28 | 2.66E−08 |
| 29 | 8.93E−08 |
| 30 | 2.74E−06 |
| 31 | 7.32E−08 |
| 32 | 2.35E−07 |
| 33 | 9.06E−08 |
| 34 | 3.18E−08 |
| 35 | 1.51E−07 |
| 36 | 2.92E−07 |
| 37 | 1.65E−06 |
| 38 | 6.83E−06 |
| 39 | 2.33E−06 |
| 40 | 2.54E−07 |
| 41 | 1.31E−06 |
| 42 | 1.53E−07 |
| 43 | 3.68E−08 |
| 44 | 6.73E−06 |
| 45 | 1.82E−07 |
| 46 | 8.13E−08 |
| 47 | 4.66E−07 |
| 48 | 4.70E−07 |
| 49 | 5.70E−06 |
| 50 | 7.82E−07 |
| 51 | 3.21E−07 |
| 52 | 2.24E−08 |
| 53 | 1.86E−07 |
| 54 | 5.29E−08 |
| 55 | 1.46E−07 |
| 56 | 6.83E−07 |
| 57 | 2.96E−07 |
| 58 | 2.47E−07 |

Example 62

Compounds of the invention were found to inhibit CDK19-CYCC activity, for example as tested in the binding assay described hereinbefore. Biological activity in CDK19-CYCC for certain examples is represented in Table 4.

TABLE 4

Inhibition of CDK19-CYCC activity expressed as $IC_{50}$ values [M] for the compounds of certain examples.

| Compound number | CDK19-CYCC $IC_{50}$ (mol/L) |
|---|---|
| 1 | 1.19E−08 |
| 3 | 3.22E−07 |
| 12 | 5.50E−07 |
| 13 | 8.22E−09 |
| 14 | 3.01E−09 |
| 15 | 1.41E−09 |
| 18 | 4.05E−08 |
| 20 | 2.11E−07 |
| 22 | 1.41E−09 |
| 23 | 2.33E−07 |
| 28 | 1.66E−08 |
| 29 | 2.05E−07 |
| 30 | 2.07E−08 |
| 31 | 1.07E−07 |
| 32 | 8.13E−08 |
| 33 | 2.95E−08 |
| 34 | 1.41E−09 |
| 35 | 3.14E−08 |
| 41 | 1.58E−07 |
| 43 | 1.09E−09 |
| 45 | 1.15E−08 |
| 46 | 5.85E−08 |
| 51 | 1.71E−07 |
| 52 | 1.41E−09 |
| 53 | 1.94E−08 |
| 54 | 9.71E−08 |
| 55 | 7.05E−08 |
| 56 | 8.66E−08 |
| 57 | 4.73E−08 |
| 58 | 2.55E−08 |

Example 63: Synthesis of Final Product 63

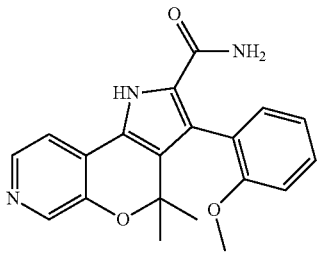 [SMILES: COc1ccccc1-c1c(C(N)=O)[nH]c2c1C(C)(C)Oc1cnccc1-2]

A mixture of intermediate CXX (20 mg, 0.057 mmol, 1 eq), 1-hydroxybenzotriazole hydrate (15 mg, 0.097 mmol, 1.7 eq) and n-(3-dimethylaminopropyl)-n'-ethylcarbodiimide hydrochloride (22 mg, 0.114 mmol, 2 eq) in N,N-dimethylformamide (0.6 mL) was heated at 50° C. for 30 minutes under argon. Then, the reaction mixture was cooled down to room temperature, and ammonium hydroxide (28% w/w aqueous solution, 0.03 mL) was added. The reaction was stirred at room temperature for 16 hours, and then heated at 80° C. for 1 hour. On cooling, the reaction mixture was evaporated under vacuum. Water was added to the residue, and it was extracted first with EtOAc and then with iPrOH/CHCl$_3$ (1:1). The combined organic layers were washed with water, and with a saturated aqueous solution of NaCl, and then dried over Na$_2$SO$_4$, filtered and evaporated under vacuum. The residue was purified by flash chromatography (Biotage, silica, 1% to 10% MeOH in DCM) to give the final product 63 as a white solid (3 mg, yield: 15%).

Example 64: Synthesis of Final Product 64

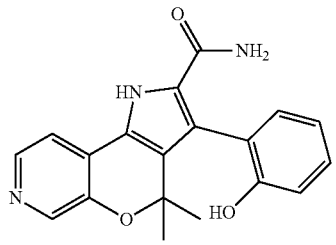 [SMILES: CC1(C)Oc2cnccc2-c2[nH]c(C(N)=O)c(-c3ccccc3O)c21]

Boron fluoride-dimethyl sulfide complex (0.027 mL, 0.258 mmol, 10 eq) was added to a solution of final product 63 (9 mg, 0.026 mmol, 1 eq) in dichloromethane (1 mL) and acetonitrile (0.172 mL) at 0° C. The reaction was stirred at room temperature for 16 hours. A saturated aqueous solution of NaHCO$_3$ was added to the reaction mixture, and it was extracted twice with iPrOH/CHCl$_3$ (1:1). The combined organic layers were dried over Na$_2$SO$_4$, filtered and concentrated under vacuum. The residue was purified by flash chromatography (Biotage, silica, 2% to 10% MeOH in DCM) to give the final product 64 as a white solid (2 mg, yield: 23%).

Example 65: Synthesis of Final Product 65

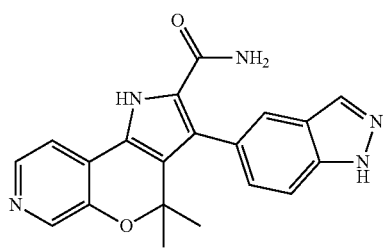 [SMILES: CC1(C)Oc2cnccc2-c2[nH]c(C(N)=O)c(-c3ccc4[nH]ncc4c3)c21]

This product was prepared following the same protocol which was employed to prepare the example 58, by BOC deprotection with trifluoroacetic acid of intermediate CXXIII in dichloromethane (yield: 14%).

Example 66: Synthesis of Final Product 66

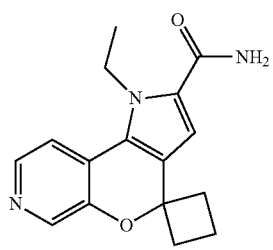 [SMILES: CCn1c(C(N)=O)cc2c1-c1ccncc1OC21CCC1]

Cesium carbonate (46 mg, 0.141 mmol, 4 eq) was added to a mixture of final product 15 (9 mg, 0.035 mmol, 1 eq) in acetonitrile (0.4 mL) and N,N-dimethylformamide (0.071 mL) at room temperature. The reaction mixture was stirred at room temperature for 30 minutes, and then iodoethane (1N in acetonitrine, 0.053 mL, 0.053 mmol, 1.5 eq) was added. The reaction was stirred at room temperature for 16 hours. The reaction mixture was quenched with water, and it was extracted 3 times with EtOAc. The combined organic layers were dried over Na₂SO₄, filtered and evaporated under vacuum. The residue was purified by flash chromatography (Biotage, silica, 2% to 7% MeOH in DCM) to give the final product 66 as a white solid (3 mg, yield: 30%).

Example 67: Synthesis of Final Product 67

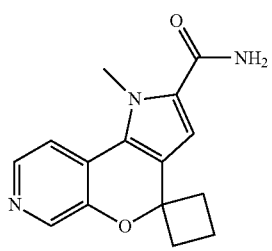 [SMILES: Cn1c(C(N)=O)cc2c1-c1ccncc1OC21CCC1]

This product was prepared following the same protocol which was employed to prepare the example 66, but using iodomethane as alkylating agent. The product was purified by flash chromatography (Biotage, silica, 1% to 5% MeOH in DCM) to give the final product 67 as a white solid (2 mg, yield: 15%).

Example 68: Synthesis of Final Product 68

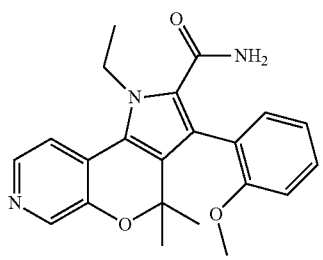 [SMILES: CCn1c(C(N)=O)c(-c2ccccc2OC)c2c1-c1ccncc1OC2(C)C]

This product was prepared following the same protocol which was employed to prepare the example 66, by alkylation reaction with iodoethane of final product 63 (yield: 15%).

Example 69: Synthesis of Final Product 69

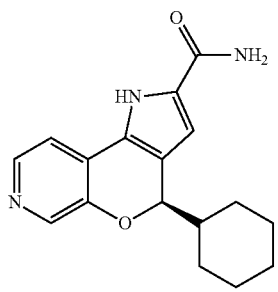 [SMILES: NC(=O)c1cc2c([nH]1)-c1ccncc1O[C@@H]2C1CCCCC1]

Ammonium hydroxide (32% aqueous solution, 3.500 mL) was added to a mixture of intermediate CXI (57 mg, 0.182 mmol, 1 eq) in methanol (1.825 mL) and N,N-dimethylformamide (1.825 mL) at room temperature under argon. The reaction was heated in a pressure tube at 120° C. for 16 hours. On cooling, the reaction mixture was evaporated under vacuum, and the residue was purified by flash chromatography (Biotage, silica, 2% to 8% MeOH in DCM) to give the final product as a white solid and as a racemic mixture (13 mg, yield: 24%). The racemic mixture was subjected to separation by preparative HPLC in a chiral column chromatography (CHIRALPAK AC column (10× 250 mm). Mobile phase: methanol/ethanol 30:70. Flow: 5 mL/min, 10 min, 225 nm) to give the final product 69 (first eluted peak, Rt=5.163 min) (ee 99%), and final product 70 (the second eluted peak, Rt=6.645 min) (ee 99%). The compound has been drawn as the R-enantiomer, however the absolute configuration of the asymmetric centre has not been determined for Compound 69.

Example 70: Synthesis of Final Product 70

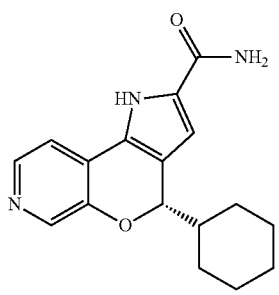 [SMILES: NC(=O)c1cc2c([nH]1)-c1ccncc1O[C@H]2C1CCCCC1]

Final product 70: Second eluted peak (Rt=6.645 min) (ee 99%). The compound has been drawn as the S-enantiomer, however the absolute configuration of the asymmetric centre has not been determined for Compound 70.

Example 71: Synthesis of Final Product 71

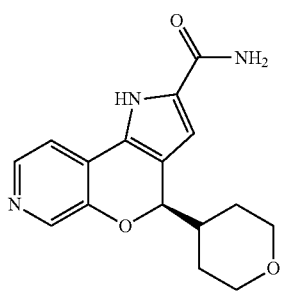 [SMILES: NC(=O)c1cc2c([nH]1)-c1ccncc1O[C@@H]2C1CCOCC1]

This product was prepared following the same protocol which was employed to prepare the example 69, but using intermediate CXXVII as starting material (yield: 18%). The racemic mixture was subjected to separation by preparative HPLC in a chiral column chromatography (CHIRALPAK AC column (10×250 mm). Mobile phase: methanol/ethanol 30:70. Flow: 5 mL/min, 10 min, 225 nm) to give the final product 71 as a white solid (first eluted peak, Rt=5.163 min) (ee 99%), and final product 72 as a white solid (second eluted peak, Rt=6.645 min) (ee 99%). The compound has been drawn as the R-enantiomer, however the absolute configuration of the asymmetric centre has not been determined for Compound 71.

Example 72: Synthesis of Final Product 72

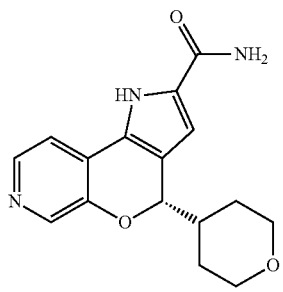 [SMILES: NC(=O)c1cc2c([nH]1)-c1ccncc1O[C@H]2C1CCOCC1]

Final product 72: Second eluted peak (Rt=6.645 min) (ee 99%). The compound has been drawn as the R-enantiomer, however the absolute configuration of the asymmetric centre has not been determined for Compound 72.

Example 73: Synthesis of Final Product 73

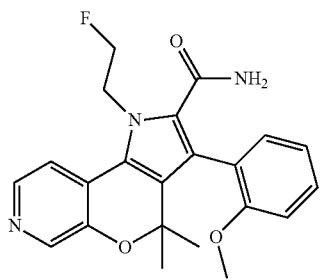 [SMILES: COc1ccccc1-c1c2c(n(CCF)c1C(N)=O)-c1ccncc1OC2(C)C]

This product was prepared following the same protocol which was employed to prepare the example 66, by alkylation reaction of final product 63 with 1-fluoro-2-iodoethane (yield: 38%).

Example 74: Synthesis of Final Product 74

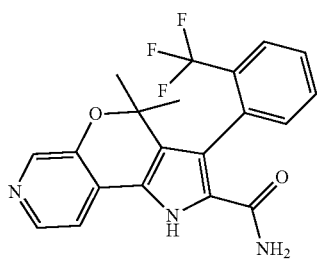 [SMILES: CC1(C)Oc2cnccc2-c2[nH]c(C(N)=O)c(-c3ccccc3C(F)(F)F)c21]

This product was prepared following the same protocol for amide formation which was employed to prepare the example 13, by reaction of intermediate CXXVIII (50 mg, 0.124 mmol) with ammnonium hydroxide to yield final product 74 (2 mg, 4% yield).

Example 75: Synthesis of Final Product 75

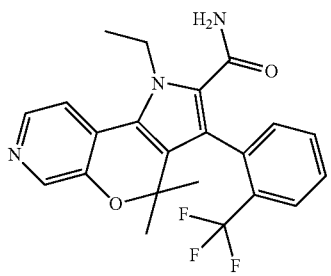 [SMILES: CCn1c(C(N)=O)c(-c2ccccc2C(F)(F)F)c2c1-c1ccncc1OC2(C)C]

To a solution of compound CXXIX (0.062 mmol, 1 eq) in 0.6 ml of DMF anh. under $N_2$ was added formamide (0.074 mL, 1.860 mmol, 30 eq) and dropwise MeONa (0.5 M in MeOH) (0.372 mL, 0.186 mmol, 3 eq). The mixture was stirred in a seal tube at 100° C. for 16 h. Then, a saturated aqueous solution of $NH_4Cl$ and diethylether were added. The organic phase was separated and dried over $Na_2SO_4$. The solvent was evaporated till dryness. The resulting residue was purified by biotage (flash automated chromatography) in a mixture of solvents of cyclohexane/EtOAc (90/10 to 60/40) to afford the desired final compound 75 as a yellow solid (5 mg, 19% yield).

Example 76: Synthesis of Final Product 76

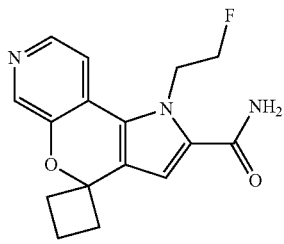 [SMILES: NC(=O)c1cc2c(n1CCF)-c1ccncc1OC21CCC1]

This product was prepared following the same protocol which was employed to prepare the example 66, by alkylation of final product 15 (8 mg, 0.031 mmol) with 1-fluoro-2-iodoethane. The product was purified by flash chromatography (Biotage, silica, 1% to 7% MeOH in DCM) to give the final product 76 as a white solid (3 mg, yield: 32%).

Example 77: Synthesis of Final Product 77

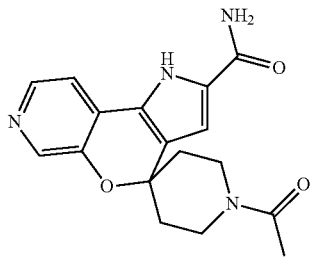 [SMILES: CC(=O)N1CCC2(CC1)Oc1cnccc1-c1[nH]c(C(N)=O)cc12]

Final product 77 was synthesized by acylation reaction of product 12 (75 mg, 0.251 mmol) with acetyl chloride (1 eq)

in DCM at 0° C. in the presence of triethylamine (1.1 eq) as base. After aqueous work up with an aqueous solution of NH₄Cl the organic phase was extracted, dried and evaporated to dryness. The resulting residue was purified by automated chromatography in DCM/MeOH 100/0 to 97/3 to yield 15 mg (18% yield) of final product 77.

Example 78: Synthesis of Final Product 78

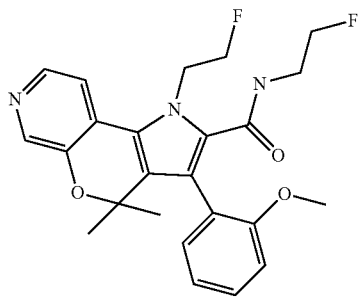 [SMILES: COc1ccccc1-c1c2c(n(CCF)c1C(=O)NCCF)-c1ccncc1OC2(C)C]

Final product 78 was synthesized by alkylation reaction of product 63 with 2 equivalents of 1-fluoro-2-iodoethane following a similar synthetic protocol than the one reported for compound 66. The final product was isolated by Biotage Flash Chromatography (Biotage, 12 g, 0% to 20% MeOH in DCM) and then HPLC purification to afford a white solid (2 mg) of desired product 78.

Example 79: Synthesis of Final Product 79

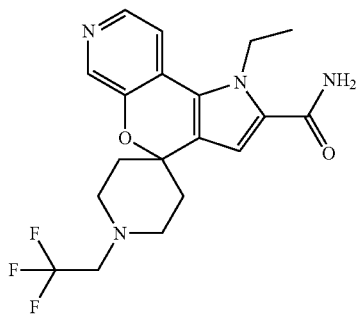 [SMILES: CCn1c(C(N)=O)cc2c1-c1ccncc1OC21CCN(CC(F)(F)F)CC1]

To a solution of intermediate CXXX (64 mg, 0.157 mmol, 1 eq) in 1.6 ml of DMF anh. under N₂ was added formamide (0.094 mL, 2.355 mmol, 15 eq) and dropwise a solution of MeONa (0.5 M in MeOH) (0.236 mL, 0.471 mmol, 3 eq). The mixture was stirred in a seal tube at 100° C. for 16 h. Then, an aqueous solution of NH₄Cl saturated and diethylether were added. The organic layer was dried over Na₂SO₄ and evaporated till dryness. The residue was purified by Biotage Flash Chromatography (DCM/MeOH 100/0 to 80/20) to afford a yellow solid (20 mg, 32% yield) as desired compound 79.

Example 80: Synthesis of Final Product 80

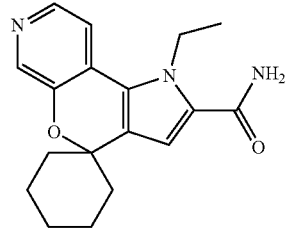 [SMILES: CCn1c(C(N)=O)cc2c1-c1ccncc1OC21CCCCC1]

To a solution of intermediate CXXXI (0.560 mmol, 1 eq) in 7 ml of DMF anh. under N₂ was added formamide (0.334 mL, 8.400 mmol, 15 eq) and MeONa (0.5 M in MeOH) (3.36 mL, 1.680 mmol, 3 eq) dropwise. The mixture was stirred in a seal tube at 100° C. for 16 h. Then, an aqueous solution of NH₄Cl saturated and diethylether were added. The organic layer was dried over Na₂SO₄ and evaporated till dryness. The residue was purified by biotage flash chromatography (silica, DCM/MeOH 100/0 to 80/20) to afford yellow solid (48 mg, 27% yield) as desired product 80.

Example 81: Synthesis of Final Product 81

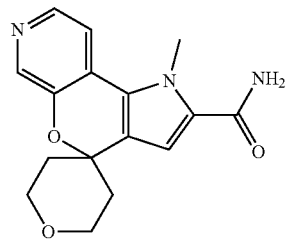 [SMILES: Cn1c(C(N)=O)cc2c1-c1ccncc1OC21CCOCC1]

To a solution of intermediate CXXXII (0.666 mmol, 1 eq) in 7 ml of DMF anh. under N₂ was added formamide (0.397 mL, 9.990 mmol, 15 eq) and dropwise a solution of MeONa (0.5 M in MeOH) (4 mL, 1.998 mmol, 3 eq). The mixture was stirred in a seal tube at 120° C. for 16 h. Then, an aqueous solution of NH₄Cl saturated and butanol were added. The organic layer was dried over Na₂SO₄ and evaporated till dryness. The residue was purified by biotage flash chromatography (silica, DCM/MeOH 100/0 to 80/20) to afford a yellow solid (45 mg, 21% yield) as final compound 81.

Example 82: Synthesis of Final Product 82

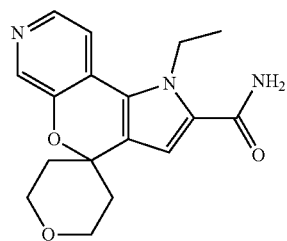 [SMILES: CCn1c(C(N)=O)cc2c1-c1ccncc1OC21CCOCC1]

Final product 82 was synthesized following the same synthetic route used for synthesis of compound 81, by amidation reaction of intermediate CXXXIII (0.666 mmol, 1 eq) with formamide to yield after biotage flash chromatography purification (silica, DCM/MeOH 100/0 to 80/20) final compound 82 (20 mg, 12% yield).

Example 83: Synthesis of Final Product 83

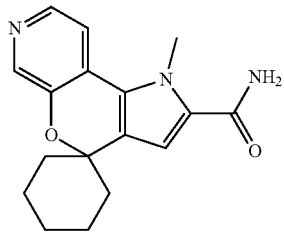 [SMILES: Cn1c(C(N)=O)cc2c1-c1ccncc1OC21CCCCC1]

Final product 83 was synthesized following the same synthetic route used for synthesis of compound 80, by amidation reaction of intermediate CXXXIV (0.560 mmol) with formamide to yield after biotage purification (silica, DCM/MeOH 100/0 to 80/20) final compound 83 (20 mg, 11% yield).

Example 84: Synthesis of Final Product 84

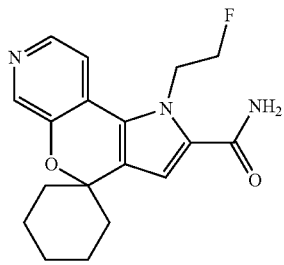 [SMILES: NC(=O)c1cc2c(n1CCF)-c1ccncc1OC21CCCCC1]

Final product 84 was synthesized following the same synthetic protocol used for synthesis of compound 80, by amidation reaction of intermediate CXXXV (0.560 mmol) with formamide to yield after Biotage Flash Chromatography purification (silica, DCM/MeOH 100/0 to 80/20) final compound 84 (5 mg, 3% yield).

Example 85: Synthesis of Final Product 85

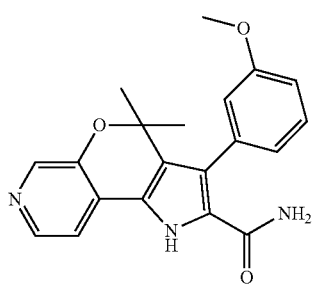 [SMILES: COc1cccc(-c2c(C(N)=O)[nH]c3c2C(C)(C)Oc2cnccc2-3)c1]

Final product 85 was synthesized following the same synthetic route used for synthesis of compound 81, by amidation reaction of intermediate CXXXVI (50 mg, 0.137 mmol, 1 eq) in 1.4 ml of DMF anh. under $N_2$ with formamide (0.082 mL, 2.058 mmol, 15 eq) and MeONa (0.5 M in MeOH) (0.824 mL, 0.412 mmol, 3 eq) at 100° C. for 48 h, to yield after aqueous work up and Biotage Flash Chromatography purification (silica, DCM/MeOH 100/0 to 80/20) final compound 85 (3 mg, 6% yield) as a yellow solid.

Example 86: Synthesis of Final Product 86

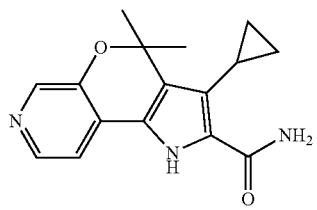 [SMILES: CC1(C)Oc2cnccc2-c2[nH]c(C(N)=O)c(C3CC3)c21]

Final product 86 was synthesized following the same synthetic route used for synthesis of compound 81, by amidation reaction of intermediate CXXXVII (40 mg, 0.134 mmol, 1 eq) in 1.5 ml of DMF anh. under $N_2$ with formamide (0.08 mL, 2.011 mmol, 15 eq) and MeONa (0.5 M in MeOH) (0.8 mL, 0.402 mmol, 3 eq) at 100° C. for 48 h, to yield after aqueous work up and Biotage Flash Chromatography purification (silica, DCM/MeOH 100/0 to 80/20) final compound 86 (5 mg, 13% yield) as a yellow solid.

Example 87: Synthesis of Final Product 87

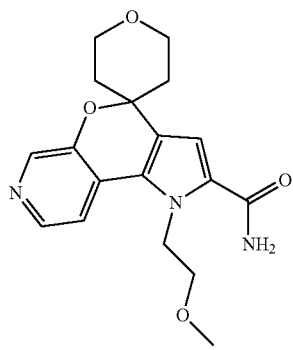 [SMILES: COCCn1c(C(N)=O)cc2c1-c1ccncc1OC21CCOCC1]

Final product 87 was synthesized following the same synthetic route used for synthesis of compound 81, by amidation reaction of intermediate CXXXVIII (65 mg, 0.181 mmol, 1 eq) in 2 ml of DMF anh. under $N_2$ with formamide (0.108 mL, 2.72 mmol, 15 eq) and MeONa (0.5 M in MeOH) (1.088 mL, 0.544 mmol, 3 eq) at 50° C. for 16 h, to yield after aqueous work up and Biotage Flash Chromatography purification (silica, DCM/MeOH 100/0 to 80/20) final compound 87 (30 mg, 48% yield) as a yellow solid.

Example 88: Synthesis of Final Product 88

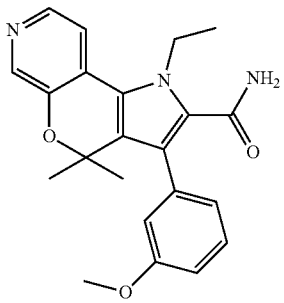 [SMILES: CCn1c(C(N)=O)c(-c2cccc(OC)c2)c2c1-c1ccncc1OC2(C)C]

Final product 88 was synthesized following the same synthetic route used for synthesis of compound 81, by amidation reaction of intermediate CXXXIX (25 mg, 0.064 mmol, 1 eq) in 2 ml of DMF anh. under $N_2$ with formamide (15 eq) and MeONa (0.5 M in MeOH) (3 eq) at 100° C. for 16 h, to yield after aqueous work up and Biotage Flash Chromatography purification (silica, DCM/MeOH 100/0 to 80/20) final compound 88 (15 mg, 62% yield) as a yellow solid.

Example 89 and Example 90

Synthesis of Final Product 89 and 90

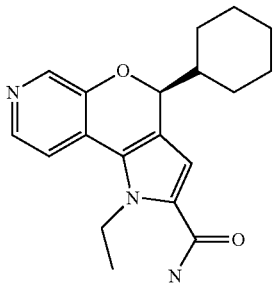
89

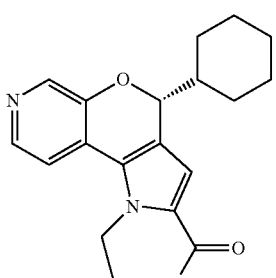
90

Final products 89 and 90 were synthesized following the same synthetic route used for synthesis of compound Example 66, by alkylation reaction of compound Example 57 with iodoethane. The final product was isolated after flash chromatography purification ($SiO_2$, DCM/MeOH 98:2 to 93:7) as a racemic mixture which was subjected to separation by preparative HPLC in a chiral column chromatography (CHIRALPAK IA column (10×250 mm). Mobile phase: cHexane/ethanol 80:20. Flow: 3 mL/min, 14 min, 300 nm) to give the final product 89 as a white solid (first eluted peak, Rt=10.519 min) (ee 99%), and final product 90 as a white solid (second eluted peak, Rt=11.568 min) (ee 99%). The compound has been drawn as particular enantiomers, however the absolute configurations of the asymmetric centres have not been determined for Compound 89 and 90.

Example 91: Synthesis of Final Product 91

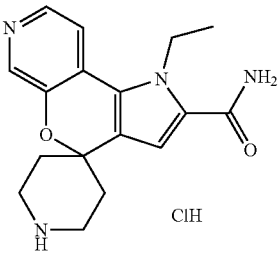 [SMILES: CCn1c(C(N)=O)cc2c1-c1ccncc1OC21CCNCC1 ; Cl]

A mixture of intermediate CXL (12 mg) in dioxane (0.5 mL) with 4 M HCl in dioxane (0.2 mL) was stirred at rt for 3 h. The white solid formed was collected, washed with diethyl ether and dried in vacuo. The required final product was obtained as a hydrochloric salt, white solid, Example 91 (4 mg).

Example 92: Synthesis of Final Product 92

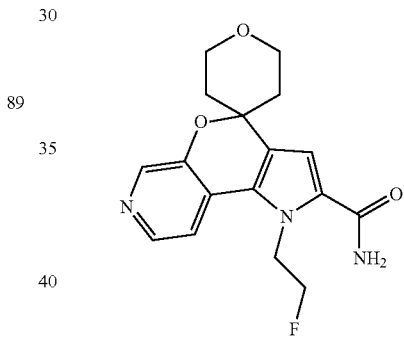

Final product 92 was synthesized by amidation reaction of intermediate CXLII (20 mg, 1 eq) in the presence of NaCN (0.03 eq) in 3 ml of Ammonia in Methanol (7N) at 45° C. in a seal tube for 2 weeks. The solvent was concentrated in vacuo and the residue purified by automated chromatography (silica, gradient 0% to 10% MeOH in DCM) to afford the final compound 92 (10 mg, white solid).

Example 93

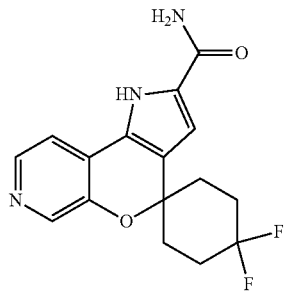
93

Final product 93 was synthesized by amidation reaction of intermediate CXLVI (50 mg, 1 eq) in the presence of formamide (30 eq) and MeONa (0.5 M in MeOH) (3 eq) at 100° C. for 16 h, to yield after aqueous work up and Biotage Flash Chromatography purification (silica, DCM/MeOH 98/2 to 90/10) final compound 93 (12 mg).

Example 94: Synthesis of Final Product 94

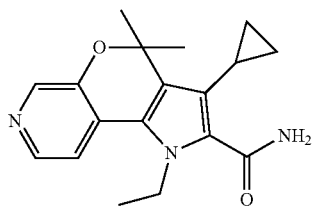 [SMILES: CCn1c(C(N)=O)c(C2CC2)c2c1-c1ccncc1OC2(C)C]

To a solution of ester intermediate CXLVII (25 mg, 0.077 mmol, 1 eq) in 0.8 ml of DMF anh under $N_2$ was added formamide (0.046 mL, 1.149 mmol, 15 eq) and dropwise MeONa (0.5 M in MeOH) (0.46 mL, 0.230 mmol, 3 eq). The mixture was stirred in a seal tube at 50° for 16 h. Then, $NH_4Cl$ sat. solution and diethylether were added. The organic layer was dried over $Na_2SO_4$ and evaporated till dryness. The resulting residue was purified by Biotage Flash Chromatography (Biotage, 20 g, 0% to 20% MeOH in DCM) to afford yellow solid which was repurified by HPLC to afford final compound 94 as a white solid (3 mg, 12% yield).

Example 95 and Example 96

Synthesis of Final Products 95 and 96

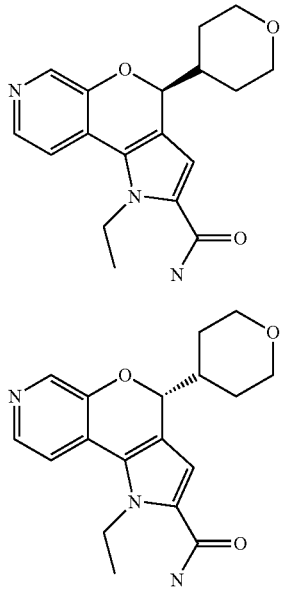

To the racemic mixture of chiral compounds Example 71 and 72 (59 mg, 0.197 mmol, 1 eq) in acetonitrile (1 mL) and DMF (1 mL), cesium carbonate (128 mg, 2 eq) was added. The mixture was stirred 30 min and then, solution of iodoethane 1N acetonitrile (0.24 mL 1.2 eq) was added. Excess of cesium carbonate (65 mg) was added till completion of the reaction after 24 h. The reaction mixture was then quenched with water and extracted with a mixture of iPrOH/$CHCl_3$ (1:1). The combined organic layers were dried over $Na_2SO_4$. The solvent was evaporated under reduced pressure to obtain a crude product which was purified together 12246302 by Biotage Flash Chromatography purification (silica, DCM/MeOH; gradient: 2% to 10%; to obtain final compound Example 96 (15 mg). The racemic mixture was subjected to separation by preparative HPLC in a chiral column chromatography (CHIRALPAK IA column (10×250 mm). Mobile phase: n-hexane/ethanol 80:20. Flow: 5 mL/min, 15 min, 300 nm) to give the final product 95 as a white solid (first eluted peak, Rt=8.296 min) (ee 96%), and final product 96 as a white solid (second eluted peak, Rt=9.137 min) (ee 90%). The compound has been drawn as particular enantiomers, however the absolute configurations of the asymmetric centres have not been determined for Compound 95 and 96.

Example 97: Synthesis of Final Product 97 and Enantiomers 106 and 107

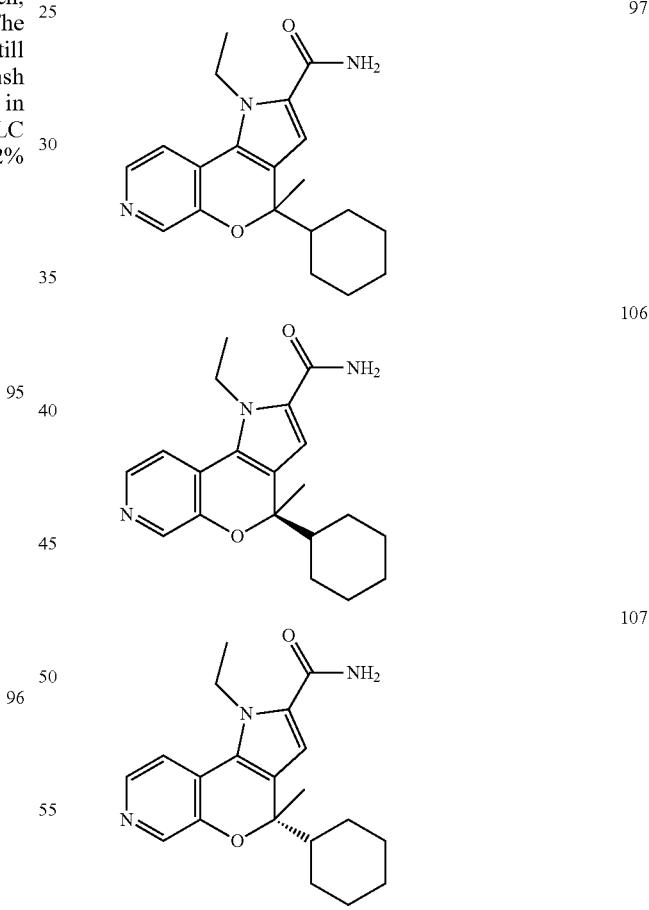

Final product 97 was synthesized following the same synthetic route used for synthesis of compound 81, by amidation reaction of intermediate CLI in DMF anh. under $N_2$ with formamide (15 eq) and MeONa (0.5 M in MeOH) (3 eq) at 100° C. for 16 h, to yield after aqueous work up and Biotage Flash Chromatography purification (silica, DCM/MeOH; gradient: 1% to 5%; final compound 97 (42 mg; 52% yield; white solid).

The racemic mixture was subjected to separation by preparative HPLC in a chiral column chromatography (CHIRALPAK IA column (10×250 mm). Mobile phase: n-hexane/ethanol 80:20. Flow: 5 mL/min, 7 min, 300 nm) to give the final product 106 as a white solid (first eluted peak, Rt=4.80 min), and final product 107 as a white solid (second eluted peak, Rt=5.15 min). Compounds 106 and 107 have been drawn as particular enantiomers, however the absolute configurations of the asymmetric centres have not been determined.

Example 98: Synthesis of Final Product 98

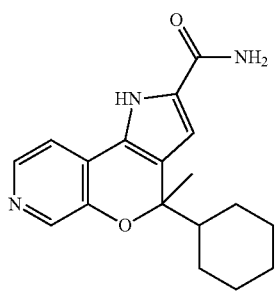

98

Final product 98 was synthesized following the same synthetic route used for synthesis of compound 81, by amidation reaction of intermediate CLII in DMF anh. under N₂ with formamide (30 eq) and MeONa (0.5 M in MeOH) (3 eq) at 100° C. for 16 h, to yield after aqueous work up and Biotage Flash Chromatography purification (silica, DCM/MeOH 98/2 to 92/8) final compound 98 (8 mg, 15% yield) as a pale yellow solid.

Example 99 and Example 100

Synthesis of Final Products 99 and 100

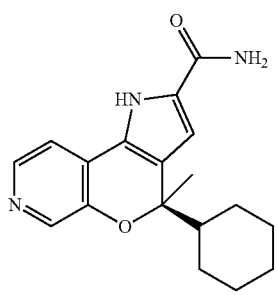

99

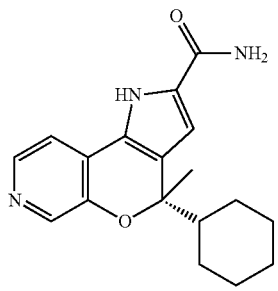

100

Chiral separation of Example 98 by preparative HPLC in a chiral column chromatography (CHIRALPAK IC column (10×250 mm). Mobile phase: nhexane/ethanol 80:20. Flow: 0.8 mL/min, 15 min, 300 nm) to give the final product 99 as a white solid (first eluted peak, Rt=9.1 min) (ee 95%), and final product 100 as a white solid (second eluted peak, Rt=10.23 min) (ee 94%).

Example 101: Synthesis of Final Product 101

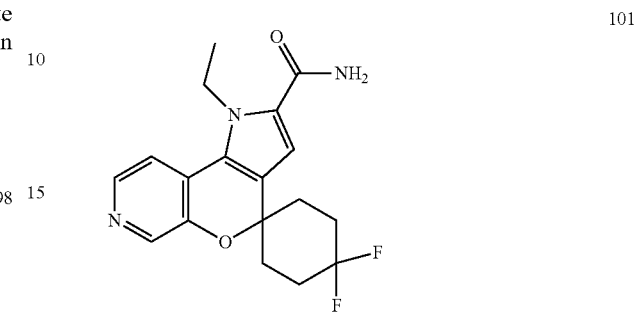

101

Final product 101 was synthesized by amidation reaction of intermediate CLIX (25 mg, 1 eq) in the presence of formamide (30 eq) and MeONa (0.5 M in MeOH) (3 eq) at 100° C. for 16 h, to yield after aqueous work up and Biotage Flash Chromatography purification (silica, DCM/MeOH 98/2 to 92/8) final compound 101 (8 mg).

Example 102: Synthesis of Final Product 102

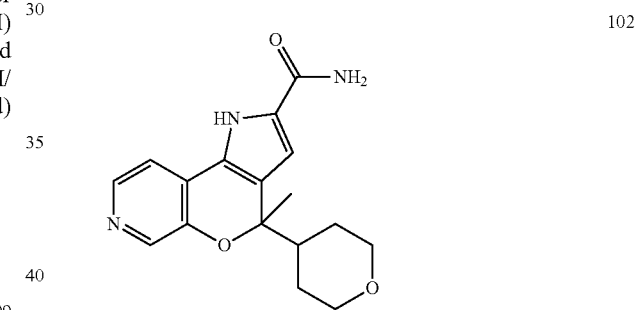

102

Final product 102 was synthesized following the same synthetic route used for synthesis of compound 81, by amidation reaction of intermediate CLIII (37 mg, 1 eq) in DMF anh. under N₂ with formamide (15 eq) and MeONa (0.5 M in MeOH) (3 eq) at 100° C. for 16 h, to yield after aqueous work up and Biotage Flash Chromatography purification (silica, DCM/MeOH gradient: 0% to 10%) final compound 102 (3 mg).

Example 103: Synthesis of Final Product 103

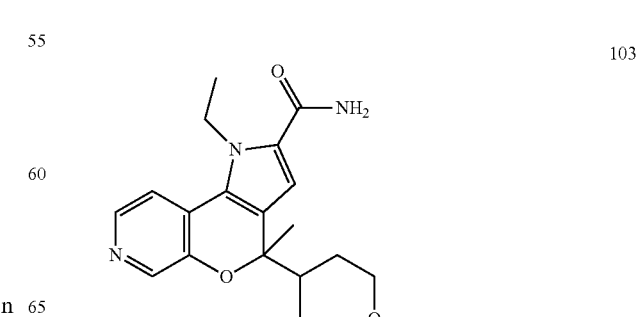

103

Final product 103 was synthesized following the same synthetic route used for synthesis of compound 81, by amidation reaction of intermediate CL (58 mg, 1 eq) in DMF anh. under $N_2$ with formamide (15 eq) and MeONa (0.5 M in MeOH) (3 eq) at 100° C. for 16 h, to yield after aqueous work up and Biotage Flash Chromatography purification (silica, DCM/MeOH gradient: 0% to 5%) final compound 103 (20 mg).

Example 104: Synthesis of Final Product 104

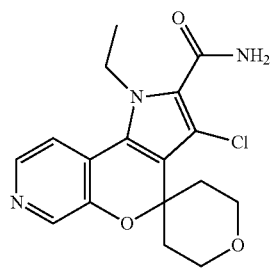

104

Final product 104 was synthesized following the same synthetic route used for synthesis of compound 81, by amidation reaction of intermediate CLVII (20 mg, 1 eq) in DMF anh. under $N_2$ with formamide (15 eq) and MeONa (0.5 M in MeOH) (3 eq) at rt for 16 h, to yield after aqueous work up and Biotage Flash Chromatography purification (silica, DCM/MeOH gradient: 0% to 10%) final compound 104 (3 mg).

Example 105: Synthesis of Final Product 105

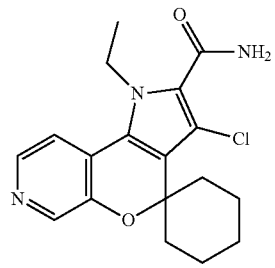

105

Final product 105 was synthesized following the same synthetic route used for synthesis of compound 104, by amidation reaction of intermediate CLVIII (22 mg, 1 eq) with formamide (15 eq) and MeONa (3 eq) by heating at 50° C. for 16 h to yield after Biotage Flash Chromatography purification (silica, DCM/MeOH gradient: 0% to 10%) final compound 105 (3 mg).

Examples 106 and 107

See Example 97.

Example 108: Analytical Data for the Final Products

Characterisation data is provided for the compounds of Examples 63 to 107 in Table 5.

TABLE 5

| LCMS and NMR data for the compounds of Examples 63 to 107 | | |
|---|---|---|
| Compound | LCMS data | NMR data |
| 63 | LCMS1, Rt = 2.86 min, [M + H]+ m/z 350.1 | $^1$H NMR (300 MHz, DMSO) δ 12.42 (s, 1H), 8.29-7.93 (m, 2H), 7.83 (d, J = 4.8 Hz, 1H), 7.63-7.37 (m, 1H), 7.25-7.15 (m, 3H), 7.09-7.01 (m, 2H), 3.73 (s, 3H), 1.25 (s, 3H), 1.22 (s, 3H). |
| 64 | LCMS1, Rt = 2.74 min, [M + H]+ m/z 336.1 | $^1$H NMR (300 MHz, DMSO) δ 12.41 (s, 1H), 9.64 (s, 1H), 8.10 (s, 2H), 7.86 (s, 1H), 7.44-7.19 (m, 2H), 7.15 (d, J = 6.3 Hz, 1H), 7.08-6.73 (m, 2H), 5.25 (s, 1H), 1.29 (s, 6H). |
| 65 | LCMS1, Rt = 2.36 min, [M + H]+ m/z 360.1 | $^1$H NMR (300 MHz, DMSO) δ 13.27 (s, 1H), 12.49 (s, 1H), 8.14-8.12 (m, 3H), 7.89 (d, J = 4.4 Hz, 1H), 7.77 (s, 1H), 7.67 (d, J = 8.5 Hz, 1H), 7.30 (dd, J = 8.5, 1.4 Hz, 1H), 7.22 (s, 1H), 1.27 (s, 6H). |
| 66 | LCMS1, Rt = 2.14 min, [M + H]+ m/z 284.2 | $^1$H NMR (300 MHz, DMSO) δ 8.24 (s, 1H), 8.18 (d, J = 5.2 Hz, 1H), 7.72 (s, 1H), 7.47 (d, J = 5.1 Hz, 1H), 7.19 (s, 1H), 7.02 (s, 1H), 4.68 (q, J = 7.3 Hz, 2H), 2.34-2.26 (m, 3H), 1.96-1.78 (m, 3H), 1.35 (t, J = 7.1 Hz, 3H). |
| 67 | LCMS1, Rt = 2.97 min, [M + H]+ m/z 270.2 | $^1$H NMR (300 MHz, DMSO) δ 8.18 (s, 1H), 8.10 (d, J = 4.2 Hz, 1H), 7.68 (s, 1H), 7.54 (d, J = 4.7 Hz, 1H), 7.15 (s, 1H), 6.94 (s, 1H), 4.09 (s, 3H), 2.50-2.52 (m, 2H), 2.31-2.16 (m, 2H), 1.90-1.72 (m, 2H). |
| 68 | LCMS1, Rt = 3.09 min, [M + H]+ m/z 378.3 | $^1$H NMR (300 MHz, DMSO) δ 8.19 (d, J = 5.1 Hz, 1H), 8.16 (s, 1H), 7.50 (d, J = 5.0 Hz, 1H), 7.40 (t, J = 7.7 Hz, 1H), 7.35 (s, 1H), 7.22 (d, J = 7.3 Hz, 1H), 7.10 (d, J = 8.3 Hz, 1H), 6.99 (t, J = 7.5 Hz, 1H), 6.19 (s, 1H), 4.49 (t, J = 6.9 Hz, 2H), 3.73 (s, 3H), 1.41 (t, J = 6.9 Hz, 3H), 1.22 (s, 3H), 1.17 (s, 3H). |
| 69 | LCMS1, Rt = 2.89 min, [M + H]+ m/z 298.2 | $^1$H NMR (300 MHz, DMSO) δ 12.32 (s, 1H), 8.10 (s, 1H), 8.05 (d, J = 4.9 Hz, 1H), 7.71 (d, J = 4.9 Hz, 2H), 7.19 (s, 1H), 6.71 (s, 1H), 5.26 (d, J = 5.4 Hz, 1H), 1.80-1.62 (m, 6H), 1.35-1.04 (m, 5H). |
| 70 | LCMS1, Rt = 2.75 min, [M + H]+ m/z 298.2 | $^1$H NMR (300 MHz, DMSO) δ 12.32 (s, 1H), 8.10 (s, 1H), 8.04 (d, J = 4.9 Hz, 1H), 7.71 (d, J = 4.9 Hz, 2H), 7.19 (s, 1H), 6.71 (s, 1H), 5.25 (d, J = 5.4 Hz, 1H), 1.79-1.62 (m, 6H), 1.26-1.08 (m, 5H). |

TABLE 5-continued

LCMS and NMR data for the compounds of Examples 63 to 107

| Compound | LCMS data | NMR data |
|---|---|---|
| 71 | LCMS1, Rt = 3.30 min, [M + H]+ m/z 300.1 | $^1$H NMR (300 MHz, DMSO) δ 12.38 (s, 1H), 8.12 (s, 1H), 8.07 (d, J = 4.9 Hz, 1H), 7.73 (d, J = 4.9 Hz, 2H), 7.20 (s, 1H), 6.73 (s, 1H), 5.29 (d, J = 6.1 Hz, 1H), 3.84 (d, J = 11.1 Hz, 2H), 3.21 (t, J = 11.0 Hz, 2H), 1.87 (brs, 1H), 1.67-1.63 (m, 1H), 1.53-1.35 (m, 3H). |
| 72 | LCMS1, Rt = 3.27 min, [M + H]+ m/z 300.0 | $^1$H NMR (300 MHz, DMSO) δ 12.37 (s, 1H), 8.12 (s, 1H), 8.06 (d, J = 4.9 Hz, 1H), 7.72 (d, J = 4.9 Hz, 2H), 7.20 (s, 1H), 6.73 (s, 1H), 5.28 (d, J = 6.1 Hz, 1H), 3.84 (d, J = 11.0 Hz, 2H), 3.20 (t, J = 10.8 Hz, 2H), 1.88-1.86 (m, 1H), 1.67-1.63 (m, 1H), 1.55-1.32 (m, 3H). |
| 73 | LCMS1, Rt = 3.15 min, [M + H]+ m/z 396.2 | $^1$H NMR (300 MHz, DMSO) δ 8.11 (d, J = 5.1 Hz, 1H), 8.11 (s, 1H), 7.55 (d, J = 5.2 Hz, 1H), 7.40-7.32 (m, 1H), 7.31 (s, 1H), 7.17 (dd, J = 7.4, 1.7 Hz, 1H), 7.06 (d, J = 7.8 Hz, 1H), 6.95 (td, J = 7.4, 0.9 Hz, 1H), 6.02 (s, 1H), 4.87-4.83 (m, 2H), 4.79 (t, J = 4.9 Hz, 1H), 4.67 (t, J = 4.6 Hz, 1H), 3.68 (s, 3H), 1.16 (s, 3H), 1.10 (s, 3H). |
| 74 | LCMS1, Rt = 3.49 min, [M + H]+ m/z 388.0 | $^1$H NMR (300 MHz, DMSO) δ 12.48 (s, 1H), 8.39 (s, 1H), 8.14 (d, J = 5.1 Hz, 1H), 8.1 (s, 1H), 7.80 (d, J = 7.8 Hz, 2H), 7.75 (d, J = 5.1 Hz, 1H), 7.29 (s, 1H), 5.9 (s, 1H), 3.73 (s, 3H), 1.27 (s, 6H). |
| 75 | LCMS1, Rt = 3.87 min, [M + H]+ m/z 416.1 | $^1$H NMR (300 MHz, DMSO) δ 8.2 (d, 1H, J = 5.1 Hz), 8.18 (s, 1H), 7.76 (d, 2H, J = 8.1 Hz), 7.55 (d, 2H, J = 8.1 Hz), 7.51 (m, 2H), 7.23 (s, 1H), 4.41 (m, 2H), 1.39 (m, 3H), 1.31 (s, 6H) |
| 76 | LCMS1, Rt = 2.24 min, [M + H]+ m/z 302.1 | $^1$H NMR (300 MHz, DMSO) δ 8.25 (s, 1H), 8.16 (d, J = 5.1 Hz, 1H), 7.80 (s, 1H), 7.60 (d, J = 5.2 Hz, 1H), 7.26 (s, 1H), 7.12 (s, 1H), 5.04 (t, J = 4.4 Hz, 1H), 4.96 (t, J = 4.5 Hz, 1H), 4.86 (t, J = 4.5 Hz, 1H), 4.70 (t, J = 4.5 Hz, 1H), 2.56 (m, 2H), 2.31 (m, 2H), 1.91 (m, 2H). |
| 77 | LCMS1, Rt = 0.379 min, [M + H]+ m/z 327.1 | $^1$H NMR (300 MHz, DMSO) δ 12.39 (s, 1H), 8.22 (s, 1H), 8.12 (d, J = 4.8 Hz, 1H), 7.75 (d, 2H, J = 5.1), 7.66 (s, 1H), 7.22 (s, 1H), 6.76 (s, 1H), 4.29 (m, 1H), 3.75 (m, 1H), 3.5 (m, 1H), 3.0 (m, 1H), 2.05 (s, 3H), 1.96 (m, 2H), 1.81 (m, 1H), 1.91 (m, 1H). |
| 78 | LCMS1, Rt = 4.362 min, [M + H]+ m/z 442.2 | $^1$H NMR (300 MHz, DMSO) δ 8.256 (s, 1H), 8.26 (d, J = 4.8 Hz, 1H), 7.33 (ddd, 1H, J = 8.4, J = 2.1 Hz), 7.20 (d, J = 4.5 Hz, 1H), 7.15 (m, 1H), 7.08 (m, 1H), 6.96 (m, 1H), 4.78 (m, 1H), 4.66 (m, 1H), 4.62 (m, 1H), 4.56 (m, 1H), 4.51 (m, 1H), 4.4 (m, 3H), 3.73 (s, 3H), 1.33 (s, 3H), 1.24 (s, 3H). |
| 79 | LCMS1, Rt = 2.625 min, [M + H]+ m/z 395.1 | $^1$H NMR (300 MHz, DMSO) δ 8.25 (s, 1H), 8.19 (d, J = 5.1 Hz, 1H), 7.65 (s, 1H), 7.48 (d, J = 5.4 Hz, 1H), 7.19 (s, 1H), 6.84 (s, 1H), 4.67 (m, 2H), 2.79 (m, 4H), 2.08 (s, 2H), 1.89 (m, 4H), 1.35 (m, 3H). |
| 80 | LCMS1, Rt = 2.46 and 2.794 min, [M + H]+ m/z 312.2 | $^1$H NMR (300 MHz, DMSO) δ 8.24 (s, 1H), 8.17 (d, J = 5.1 Hz, 1H), 7.67 (s, 1H), 7.45 (d, J = 5.1 Hz, 1H), 7.15 (s, 1H), 6.79 (s, 1H), 4.65 (q, J = 6.9 Hz, 2H), 1.9 (m, 2H), 1.7 (m, 7H), 1.89 (m, 4H), 1.35 (t, J = 7.2 Hz, 3H). |
| 81 | LCMS1, Rt = 0.375 min, [M + H]+ m/z 300.1 | $^1$H NMR (300 MHz, DMSO) δ 8.31 (s, 1H), 8.18 (d, J = 5.1 Hz, 1H), 7.71 (s, 1H), 7.62 (d, J = 5.1 Hz, 1H), 7.20 (s, 1H), 6.82 (s, 1H), 4.17 (s, 3H), 3.76 (m, 4H), 1.85 (m, 4H). |
| 82 | LCMS1, Rt = 0.375 min, [M + H]+ m/z 314.1 | $^1$H NMR (300 MHz, DMSO) δ 8.31 (s, 1H), 8.21 (d, J = 5.1 Hz, 1H), 7.71 (s, 1H), 7.48 (d, J = 5.1 Hz, 1H), 7.19 (s, 1H), 6.85 (s, 1H), 4.16 (q, J = 6.9 Hz, 3H), 3.76 (m, 4H), 1.86 (m, 4H), 1.35 (t, J = 6.9 Hz, 3H). |
| 83 | LCMS1, Rt = 2.459 min, [M + H]+ m/z 298.1 | $^1$H NMR (300 MHz, DMSO) δ 8.24 (s, 1H), 8.15 (d, J = 5.1 Hz, 1H), 7.68 (s, 1H), 7.58 (d, J = 5.1 Hz, 1H), 7.17 (s, 1H), 6.77 (s, 1H), 4.16 (s, 3H), 1.8 (m, 10H). |
| 84 | LCMS1, Rt = 2.837 min, [M + H]+ m/z 330.1 | $^1$H NMR (300 MHz, DMSO) δ 8.25 (s, 1H), 8.15 (d, J = 5.1 Hz, 1H), 7.72 (s, 1H), 7.59 (d, J = 5.1 Hz, 1H), 7.22 (s, 1H), 6.94 (s, 1H), 5.02 (m, 1H), 4.94 (m, 1H), 4.86 (m, 1H), 4.71 (m, 1H), 1.94 (m, 2H), 1.66 (m, 8H). |
| 85 | LCMS1, Rt = 2.77, 3.05 min, [M + H]+ m/z 350.1 | $^1$H NMR (300 MHz, DMSO) δ 12.46 (s, 1H), 8.13 (d, J = 4.8 Hz, 1H), 8.10 (s, 1H), 7.84 (d, J = 4.8 Hz, 1H), 7.42 (m, 1H), 7.31 (sbroad, 1H), 7.04 (m, 1H), 6.94 (m, 1H), 6.9 (s, 1H), 1.29 (s, 6H) |

TABLE 5-continued

LCMS and NMR data for the compounds of Examples 63 to 107

| Compound | LCMS data | NMR data |
|---|---|---|
| 86 | LCMS1, Rt = 0.32, 0.55 min, [M + H]+ m/z 284.1 | $^1$H NMR (300 MHz, DMSO) δ 11.99 (s, 1H), 8.09 (s, 1H), 8.07 (d, J = 5.1 Hz, 1H), 7.70 (d, J = 5.1 Hz, 1H), 7.57 (s broad, 1H), 7.08 (s broad, 1H), 1.64 (s, 6H), 0.97 (m, 2H), 0.51 (m,. 2H) |
| 87 | LCMS1, Rt = 0.4 min, [M + H]+ m/z 344.1 | $^1$H NMR (300 MHz, DMSO) δ 8.31 (s, 1H), 8.18 (d, J = 5.1 Hz, 1H), 7.72 (sbroad, 1H), 7.66 (d, J = 5.1 Hz, 1H), 7.20 (sbroad, 1H), 6.97 (s, 1H), 4.8 (m, 2H), 3.7 (m, 4H), 3.67 (m, 2H), 3.19 (s, 3H), 1.85 (m, 4H). |
| 88 | LCMS1, Rt = 2.50 min, [M + H]+ m/z 378.1 | $^1$H NMR (300 MHz, DMSO) δ 8.19 (d, J = 5.1 Hz, 1H), 8.16 (s, 1H), 7.49 (d, J = 5.1 Hz, 1H), 7.45 (sbroad, 1H), 7.31 (m, 1H), 7.04 (m, 1H), 6.99 (m, 3H), 6.83 (sbroad, 1H), 4.45 (q, J = 7.2 Hz, 2H), 1.39 (t, J = 7.2 Hz, 3H), 1.29 (s, 6H) |
| 89 | LCMS1, Rt = 3.255 min, [M + H]+ m/z 326.2 | $^1$H NMR (300 MHz, DMSO) δ 8.2 (s, 1H), 8.15 (d, J = 5.1 Hz, 1H), 7.70 (sbroad, 1H), 7.44 (d, J = 5.1 Hz, 1H), 7.14 (sbroad, 1H), 6.73 (s, 1H), 5.06 (d, J = 6.3 Hz, 1H), 4.67 (q, J = 6.9 Hz, 2H), 1.16 (m, 1H), 1.6 (m, 4H), 1.34 (t, J = 6.9 Hz, 3H), 1.12 (m, 6H) |
| 90 | LCMS1, Rt = 3.183 min, [M + H]+ m/z 326.1 | $^1$H NMR (300 MHz, DMSO) δ 8.2 (s, 1H), 8.15 (d, J = 5.1 Hz, 1H), 7.70 (sbroad, 1H), 7.44 (d, J = 5.1 Hz, 1H), 7.14 (sbroad, 1H), 6.73 (s, 1H), 5.06 (d, J = 6.3 Hz, 1H), 4.67 (q, J = 6.9 Hz, 2H), 1.16 (m, 1H), 1.6 (m, 4H), 1.34 (t, J = 6.9 Hz, 3H), 1.12 (m, 6H) |
| 91 | LCMS1, Rt = 0.354 min, [M + H]+ m/z 313.1 | $^1$H NMR (300 MHz, DMSO) δ 9.0 (m, 1H), 8.53 (s, 1H), 8.31 (d, J = 5.7 Hz, 1H), 7.88 (sbroad, 1H), 7.72 (d. J = 5.8 Hz, 1H), 7.33 (sbroad, 1H), 6.79 (s, 1H), 4.65 (q, J = 6.8 Hz, 2H), 3.1 (m, 4H), 2.1 (m, 4H), 1.31 (t, J = 7 Hz, 3H) |
| 92 | LCMS1, Rt = 0.448 min, [M + H]+ m/z 332.2 | $^1$H NMR (300 MHz, DMSO) δ 8.32 (s, 1H), 8.17 (d, J = 5.1 Hz, 1H), 7.76 (sbroad, 1H), 7.63 (d. J = 5.1 Hz, 1H), 7.25 (sbroad, 1H), 6.95 (s, 1H), 5.04 (m, 1H), 4.96 (m, 1H), 4.87 (m, 1H), 4.71 (m, 1H), 3.77 8m, 4H), 1.87 (m, 4H) |
| 93 | LCMS1, Rt = 2.7 min, [M + H]+ m/z 320.1 | $^1$H NMR (300 MHz, DMSO) δ 12.2 (s, 1H), 8.23 (s, 1H), 8.00 (d, J = 4.8 Hz, 1H), 7.57 (sbroad, 1H), 7.24 (d, J = 4.8 Hz, 1H), 7.08 (sbroad, 1H), 6.82 (s, 1H), 2.1 (m, 8H). |
| 94 | LCMS1, Rt = 0.380 min, [M + H]+ m/z 312.1 | $^1$H NMR (300 MHz, DMSO) δ 8.12 (s, 1H), 8.08 (d, J = 5.2 Hz, 1H), 7.68 (m, 2H), 7.34 (d, J = 5.1 Hz, 1H), 4.2 (q, J = 7.2 Hz, 2H), 1.68 (m, 1H), 1.59 (s, 6H), 1.22 (t, J = 7.2 Hz, 3H), 0.77 (m, 2H), 0.38 (m, 2H) |
| 95 | LCMS1, Rt = 0.473 min, [M + H]+ m/z 328.1 | 1H NMR (300 MHz, DMSO) d 8.22 (s, 1H), 8.17 (d, J = 5.1 Hz, 1H), 7.72 (s, 1H), 7.46 (d, J = 5.2 Hz, 1H), 7.15 (s, 1H), 6.75 (s, 1H), 5.11 (d, J = 6.9 Hz, 1H), 4.74 (m, 2H), 3.82 (m, 2H), 3.2 (m, 2H), 1.82 (m, 1H), 1.73 (m, 1H), 1.4 (m, 3H), 1.35 (t, J = 7.0 Hz, 3H). |
| 96 | LCMS1, Rt = 0.47 min, [M + H]+ m/z 328.1 | 1H NMR (300 MHz, DMSO) d 8.21 (s, 1H), 8.15 (d, J = 5.1 Hz, 1H), 7.72 (s, 1H), 7.46 (d, J = 5.2 Hz, 1H), 7.15 (s, 1H), 6.75 (s, 1H), 5.11 (d, J = 6.9 Hz, 1H), 4.7 (m, 2H), 3.8 (m, 2H), 3.2 (m, 2H), 1.8 (m, 1H), 1.70 (m, 1H), 1.4 (m, 3H), 1.35 (t, J = 7.0 Hz, 3H). |
| 97 | LCMS1, Rt = 3.376 min, [M + H]+ m/z 340.2 | $^1$H NMR (300 MHz, DMSO) δ 8.16 (s, 1H), 8.14 (d, J = 5.1 Hz, 1H), 7.68 (s, 1H), 7.45 (d, J = 5.2 Hz, 1H), 7.14 (s, 1H), 6.75 (s, 1H), 4.68 (m, 2H), 1.81 (m, 1H), 1.62 (m, 5H), 1.51 (s, 3H), 1.34 (t, J = 7.0 Hz, 3H), 1.08 (m, 5H). |
| 98 | LCMS3, Rt = 3.019 min, [M + H]+ m/z 312.1 | $^1$H NMR (300 MHz, DMSO) δ 12.32 (s, 1H), 8.10 (s, 1H), 8.07 (d, J = 5.0 Hz, 1H), 7.77 (d, J = 5.0 Hz, 2H), 7.70 (sbroad, 1H), 7.20 (sbroad, 1H), 6.73 (d, J = 2.1 Hz, 1H), 1.7 (m, 6H), 1.55 (s, 3H), 1.08 (m, 5H). |
| 99 | LCMS3, Rt = 3.020 min, [M + H]+ m/z 312.1 | $^1$H NMR (300 MHz, DMSO) δ 12.3 (s, 1H), 8.10 (s, 1H), 8.07 (d, J = 5.0 Hz, 1H), 7.76 (d, J = 5.0 Hz, 2H), 7.7 (sbroad, 1H), 7.19 (sbroad, 1H), 6.73 (d, J = 2.1 Hz, 1H), 1.71 (m, 6H), 1.55 (s, 3H), 1.09 (m, 5H). |
| 100 | LCMS3, Rt = 3.020 min, [M + H]+ m/z 312.1 | $^1$H NMR (300 MHz, DMSO) δ 12.31 (s, 1H), 8.10 (s, 1H), 8.07 (d, J = 5.0 Hz, 1H), 7.76 (d, J = 5.0 Hz, 2H), 7.69 (sbroad, 1H), 7.20 (sbroad, 1H), 6.73 (d, J = 2.1 Hz, 1H), 1.72 (m, 6H), 1.55 (s, 3H), 1.08 (m, 5H). |

TABLE 5-continued

LCMS and NMR data for the compounds of Examples 63 to 107

| Compound | LCMS data | NMR data |
|---|---|---|
| 101 | LCMS1, Rt = 3.160, [M + H]+ m/z 348.1 | 1H NMR (300 MHz, DMSO) δ 8.37 (s, 1H), 8.23 (d, J = 5.2 Hz, 1H), 7.65 (sbroad, 1H), 7.50 (d, J = 5.2 Hz, 1H), 7.18 (sbroad, 1H), 6.85 (s, 1H), 4.69 (q, J = 7.0 Hz, 2H), 2.01 (m, 8H), 1.37 (t, J = 6.9 Hz, 3H). |
| 102 | LCMS1, Rt = 3.68 min, [M + H]+ m/z 314.1 | $^1$H NMR (300 MHz, DMSO) δ 12.31 (s, 1H), 8.08 (s, 1H), 8.04 (d, J = 4.6 Hz, 1H), 7.73 (d, J = 4.9 Hz, 1H), 7.70 (sbroad, 1H), 7.19 (sbroad, 1H), 6.73 (d, J = 2.0 Hz, 1H), 3.8 (m, 2H), 3.17 (m, 2H), 1.86 (m, 1H), 1.55 (s, 3H), 1.4 (m, 4H). |
| 103 | LCMS3, Rt = 0.584 min, [M + H]+ m/z 342.2 | $^1$H NMR (300 MHz, DMSO) δ 8.17 (s, 1H), 8.15 (d, J = 5.2 Hz, 1H), 7.69 (sbroad, 1H), 7.46 (d, J = 5.2 Hz, 1H), 7.15 (sbroad, 1H), 6.76 (s, 1H), 4.7 (m, 2H), 3.8 (m, 2H), 3.13 (m, 2H), 1.84 (m, 1H), 1.58 (s, 1H), 1.53 (s, 3H), 1.4 (m, 3H), 1.35 (t, J = 7.0 Hz, 3H) |
| 104 | LCMS1, Rt = 0.468 & 2.46 min, [M + H]+ m/z 348.1/350.1 | $^1$H NMR (300 MHz, DMSO) δ 8.35 (s, 1H), 8.22 (d, J = 5.1 Hz, 1H), 7.91 (s broad, 2H), 7.50 (d, J = 5.4 Hz, 1H), 4.40 (q, J = 7.2 Hz, 2H), 3.79 (m, 4H), 2.31 (m, 2H), 1.82 (m, 2H), 1.33 (t, J = 7.2 Hz, 3H) |
| 105 | LCMS1, Rt = 3.596 min, [M + H]+ m/z 346.1/348.1 | $^1$H NMR (300 MHz, DMSO) δ 8.27 (s, 1H), 8.18 (d, J = 5.1 Hz, 1H), 7.89 (s broad, 2H), 7.47 (d, J = 5.4 Hz, 1H), 4.38 (q, J = 7.2 Hz, 2H), 1.98 (m, 6H), 1.7 (m, 2H), 1.6 (m, 2H), 1.32 (t, J = 7.2 Hz, 3H) |
| 106 | LCMS1, Rt = 3.37 min, [M + H]+ m/z 340.2 | $^1$H NMR (300 MHz, DMSO) δ 8.16 (s, 1H), 8.13 (d, J = 5.1 Hz, 1H), 7.67 (s, 1H), 7.44 (d, J = 5.2 Hz, 1H), 7.14 (s, 1H), 6.75 (s, 1H), 4.67 (m, 2H), 1.8 (m, 1H), 1.6 (m, 5H), 1.51 (s, 3H), 1.34 (t, J = 7.0 Hz, 3H), 1.08 (m, 5H). |
| 107 | LCMS1, Rt = 3.37 min, [M + H]+ m/z 340.2 | $^1$H NMR (300 MHz, DMSO) δ 8.16 (s, 1H), 8.14 (d, J = 5.1 Hz, 1H), 7.67 (s, 1H), 7.44 (d, J = 5.2 Hz, 1H), 7.14 (s, 1H), 6.74 (s, 1H), 4.67 (m, 2H), 1.8 (m, 1H), 1.6 (m, 5H), 1.51 (s, 3H), 1.34 (t, J = 7.0 Hz, 3H), 1.08 (m, 5H). |

Example 109

Compounds of the invention were found to inhibit CDK8, for example as tested in the binding assay described hereinbefore. Biological activity in CDK8 for certain examples is presented in Table 6.

TABLE 6

Inhibition of CDK8 activity expressed as IC$_{50}$ values [M] for the compounds of the examples, as well as certain other compounds that were mentioned as being useful intermediates.

| Compound number | CDK8 IC$_{50}$ (mol/L) |
|---|---|
| 63 | 5.54E−08 |
| 64 | 1.12E−07 |
| 65 | 1.00E−05 |
| 66 | 1.91E−10 |
| 67 | 4.66E−10 |
| 68 | 3.23E−09 |
| 69 | 1.93E−08 |
| 70 | 8.50E−09 |
| 71 | 2.81E−07 |
| 72 | 4.46E−09 |
| 73 | 1.39E−07 |
| 74 | 2.11E−07 |
| 75 | 1.44E−08 |
| 76 | 2.62E−10 |
| 77 | 7.48E−09 |
| 78 | 4.84E−07 |
| 79 | 1.11E−09 |
| 80 | 3.14E−10 |
| 81 | 3.83E−09 |
| 82 | 2.19E−09 |
| 83 | 2.78E−10 |
| 84 | 1.41E−09 |
| 85 | 1.27E−07 |
| 86 | 4.33E−09 |
| 87 | 1.42E−08 |
| 88 | 1.39E−08 |
| 89 | 4.07E−10 |
| 90 | 1.36E−09 |
| 91 | 3.01E−07 |
| 92 | <1.41E−09 |
| 94 | 2.65E−09 |
| 95 | <1.41E−09 |
| 96 | <1.41E−09 |
| 104 | 2.41E−09 |
| 105 | <1.41E−09 |

Example 110

Compounds of the invention were found to inhibit Haspin kinase, for example as tested in ADP-Glo™ described hereinbefore. Biological activity in Haspin kinase for certain examples is represented in Table 7.

TABLE 7

Inhibition of Haspin kinase activity expressed as $IC_{50}$ values [M] for the compounds of certain examples.

| Compound number | HASPIN $IC_{50}$ (mol/L) |
|---|---|
| 63 | 3.96E−06 |
| 64 | 6.56E−07 |
| 65 | 9.33E−07 |
| 66 | 2.62E−08 |
| 67 | 2.76E−08 |
| 68 | 3.54E−07 |
| 69 | 5.15E−06 |
| 70 | 2.22E−07 |
| 71 | 5.76E−06 |
| 72 | 4.06E−07 |
| 73 | 1.12E−06 |
| 74 | 7.43E−07 |
| 75 | 2.33E−07 |
| 76 | 2.42E−08 |
| 77 | 1.88E−07 |
| 78 | 3.33E−05 |
| 79 | 3.86E−08 |
| 80 | 9.56E−09 |
| 81 | 1.38E−07 |
| 82 | 1.28E−08 |
| 83 | 9.80E−09 |
| 84 | 4.21E−08 |
| 85 | 2.60E−07 |
| 86 | 3.45E−08 |
| 87 | 1.36E−07 |
| 88 | 1.06E−07 |
| 89 | 9.52E−08 |
| 90 | 5.22E−07 |
| 91 | 1.65E−08 |
| 92 | 2.56E−08 |
| 94 | 1.75E−08 |
| 96 | 3.55E−07 |
| 104 | 8.91E−09 |
| 105 | 8.82E−09 |

Example 111

Compounds of the invention were found to inhibit CDK19-CYCC activity, for example as tested in the binding assay described hereinbefore. Biological activity in CDK19-CYCC for certain examples is presented in Table 8.

TABLE 8

Inhibition of CDK19-CYCC activity expressed as $IC_{50}$ values [M] for the compounds of certain examples.

| Compound number | CDK19-CYCC $IC_{50}$ (mol/L) |
|---|---|
| 63 | 2.29E−07 |
| 65 | 1.00E−05 |
| 66 | 1.41E−09 |
| 67 | 1.41E−09 |
| 68 | 1.64E−08 |
| 69 | 8.73E−08 |
| 70 | 7.14E−09 |
| 72 | 1.42E−08 |
| 73 | 9.73E−08 |
| 75 | 1.67E−08 |
| 76 | 8.27E−10 |
| 79 | 3.14E−09 |
| 80 | 7.70E−10 |
| 81 | 6.10E−09 |
| 82 | 4.58E−09 |
| 83 | 1.41E−09 |
| 84 | 1.48E−07 |
| 86 | 4.80E−10 |
| 87 | 2.09E−08 |
| 89 | 1.41E−09 |
| 90 | 1.41E−09 |

Example 112

Various compounds were screened for their ability to inhibit intracellular CDK8 using a western blot assay to detect phosphorylation of the CDK8 substrate STAT1 (S727) in IFN-γ treated cells. Compounds were also screened for their ability to inhibit intracellular HASPIN using a western blot assay to detect phosphorylation of the HASPIN substrate H3T3 in synchronized cells. The results are shown in Tables 9 and 10.

TABLE 9

Biomarkers modulation quantitative values

| Example | SW620 P-STAT1(S727) w IFNγ (mol/l) | SW620 P-STAT1(S727) (mol/l) | SW620 PH3(T3) in synchronized cells (mol/l) | SW620 pH3(T3) (mol/l) |
|---|---|---|---|---|
| 43 | 6.40E−11 | 1.50E−09 | 1.50E−08 | 1.60E−09 |

TABLE 10

Biomarkers modulation semiquantitative values

| Example | SW620 P-STAT1(S727) w IFNγ (mol/l) | SW620 P-STAT1(S727) (mol/l) | SW620 PH3(T3) in synchronized cells (mol/l) | SW620 pH3(T3) (mol/l) |
|---|---|---|---|---|
| 15 | | *** | | |
| 44 | | | | |
| 45 | *** | | *** | |
| 52 | *** | *** | *** | *** |
| 68 | *** | *** | *** | *** |
| 69 | *** | | ** | |
| 70 | *** | *** | *** | *** |
| 71 | ** | | ** | |
| 72 | *** | | ** | |
| 73 | *** | | ** | |
| 76 | | *** | | |
| 79 | | *** | | *** |
| 80 | | *** | | |
| 82 | | *** | | *** |
| 83 | | *** | | |
| 84 | | *** | | *** |
| 86 | | *** | | |
| 90 | | *** | | *** |
| 91 | | | *** | *** |

Definition of semiquantitative values: * <500 nM; 500 nM <  < 10 μM

Example 113

The in vitro potency of test compounds was measured by the in vitro cell proliferation assay described hereinabove. The results are shown in Tables 11 and 12.

TABLE 11

Growth inhibition - quantitative values

| Example | $GI_{50}$ MV4:11 (mol/l) | $GI_{50}$ MDA-MB-231 (mol/l) | $GI_{50}$ SW620 (mol/l) | $GI_{50}$ Molm13 (mol/l) |
|---|---|---|---|---|
| 43 | 1.15E−07 | 3.50E−06 | 3.39E−06 | 3.49E−07 |

TABLE 12

Growth inhibition - semiquantitative values

| Example | $GI_{50}$ MV4:11 | $GI_{50}$ MDA-MB-231 | $GI_{50}$ SW620 | $GI_{50}$ Molm13 |
|---|---|---|---|---|
| 1 | ** | * | | |
| 15 | *** | ** | * | *** |
| 18 | ** | * | * | ** |
| 22 | *** | ** | * | ** |
| 34 | *** | | | |
| 46 | *** | ** | ** | *** |
| 52 | *** | ** | ** | *** |
| 57 | | | *** | |
| 68 | *** | * | * | *** |
| 69 | *** | ** | *** | *** |
| 70 | *** | * | ** | ** |
| 471 | *** | ** | ** | ** |
| 72 | ** | * | * | ** |
| 76 | *** | ** | ** | *** |
| 79 | *** | ** | ** | *** |
| 80 | *** | ** | ** | *** |
| 81 | *** | ** | ** | *** |
| 82 | *** | ** | ** | *** |
| 83 | *** | ** | ** | *** |
| 84 | *** | ** | ** | *** |
| 86 | *** | ** | ** | ** |
| 87 | ** | * | * | * |
| 88 | *** | * | * | ** |
| 89 | *** | * | * | *** |
| 90 | *** | * | * | ** |
| 91 | *** | ** | ** | *** |

Definition of semiquantitative values: * <1 μM; 1 μM <  < 10 μM; 10 μM < * < 100 μM Example 114

Combination index (CI) calculated for the combination of compounds of the invention and various chemotherapeutic agents in the MTT in vitro cell proliferation assays are shown in Table 13.

TABLE 13

Combination index data

| Cell line | Tumor type | Chemo-therapeutic | Example number | Chemo $GI_{50}$ (μM) | CDK8 inh $GI_{50}$ (μM) | Combination index (CI) | Synergy |
|---|---|---|---|---|---|---|---|
| SW620 | Colon cancer | Taxol | 43 | 0.005 | 4 | 0.28 | +++ |
| SW620 | Colon cancer | ABT-751 | 43 | 0.5 | 4 | 0.18 | +++ |
| SW620 | Colon cancer | Alisertib | 43 | 0.5 | 4 | 0.52 | ++ |
| SW620 | Colon cancer | Elesclomol | 43 | 0.25 | 4 | 0.05 | ++++ |
| SW620 | Colon cancer | Crizotinib | 43 | 1 | 4 | 0.65 | ++ |
| SW620 | Colon cancer | Oxaliplatin | 43 | 5 | 4 | 0.53 | ++ |
| HCT116 | Colon cancer | Taxol | 43 | 0.005 | 5 | 0.63 | ++ |
| HCT116 | Colon cancer | Alisertib | 43 | 12.5 | 5 | 0.64 | ++ |
| HCT116 | Colon cancer | Crizotinib | 43 | 5 | 5 | 0.58 | ++ |
| MDAMB231 | Breast cancer | Elesclomol | 43 | 0.25 | 5 | 0.59 | ++ |
| A549 | NSCLC | Elesclomol | 43 | 0.25 | 5 | 0.63 | ++ |
| SKMEL19 | Melanoma | Crizotinib | 43 | 5 | 1.25 | 0.55 | ++ |
| SKMEL19 | Melanoma | Elesclomol | 43 | 0.25 | 1.25 | 0.49 | ++ |
| DU145 | Prostate | Alisertib | 43 | 12.5 | 5 | 0.65 | ++ |
| DU145 | Prostate | Taxol | 43 | 0.0025 | 5 | 0.21 | +++ |
| DU145 | Prostate | Crizotinib | 43 | 20 (2x $IC_{50}$) | 5 | 0.44 | ++ |
| BXPC-3 | Pancreas | Crizotinib | 43 | 5 | 5 | 0.72 | ++ |
| BXPC-3 | Pancreas | Elesclomol | 43 | 0.062 | 5 | 0.25 | ++ |

Synergy designations are based on the CI value: CI < 0.1 (++++), 0.1 < CI < 0.3 (+++), 0.3 < CI < 0.7 (++), 0.7 < CI < 1.2 (+).

Example 115

Figure 1B:
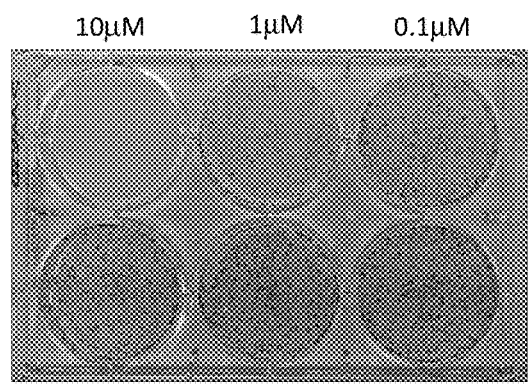
Figure 1C:
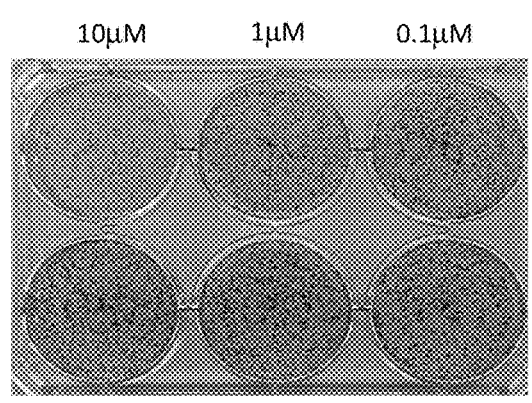

The compounds of Examples 43, 70 and 73 were tested in the colony forming assay described hereinbefore and were found to exhibit a dose-dependent effect. The activity of these compounds is represented in Table 14. Results are also shown in FIG. 1.

TABLE 14 mean $EC_{50}$ values for Examples 43, 70 and 73 as obtained from the colony forming assay:

| Compound | $EC_{50}$ (nM) |
|---|---|
| Example 43 | 51 ± 69 |
| Example 73 | 5430 ± 297 |
| Example 70 | 2110 ± 806 |

Example 116

The compound of Example 43 was screened for its ability to affect the cell cycle using a propidium iodine assay and analysis by flow cytometry.

Figure 2:
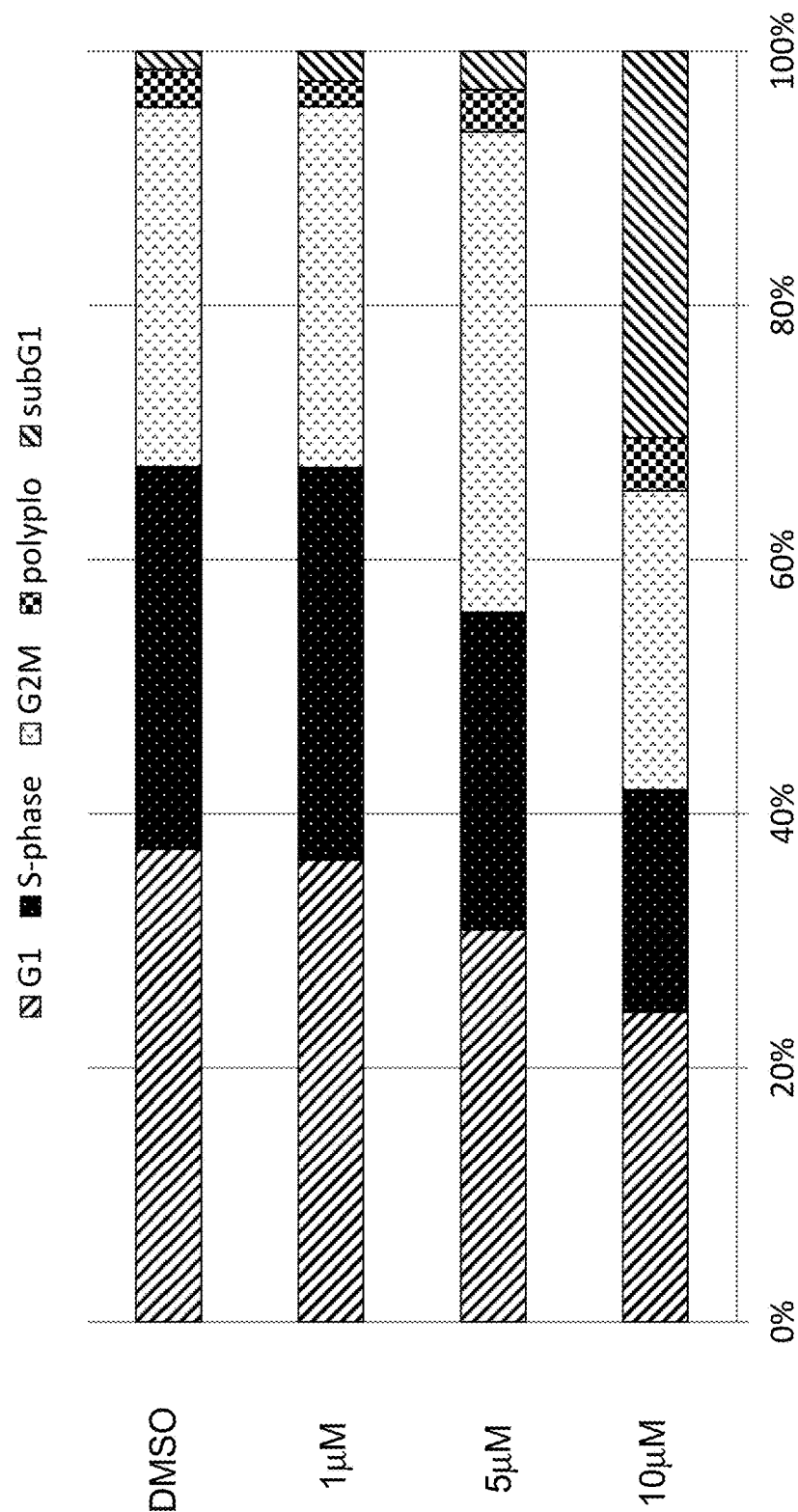
FIG. 2 shows the effect of Example 43 on cell cycle of SW620 cells.

The data shown in FIG. 2 represent the percentage of cells in each phase of the cell cycle (G1, S, G2M, polyploidy and subG1). Increasing concentrations of Example 43 induced G2M arrest and apoptosis.

Example 117

The in vivo potency of test compounds was measured to determine target modulation in human colon xenografts using the method described hereinbefore. Mice bearing SW620 human colon cancer xenografts received a single oral dose of Example 43 at 5 mg/kg or vehicle. Tumors were sampled 1, 4, 8 and 24 h after administration.

Figure 3:
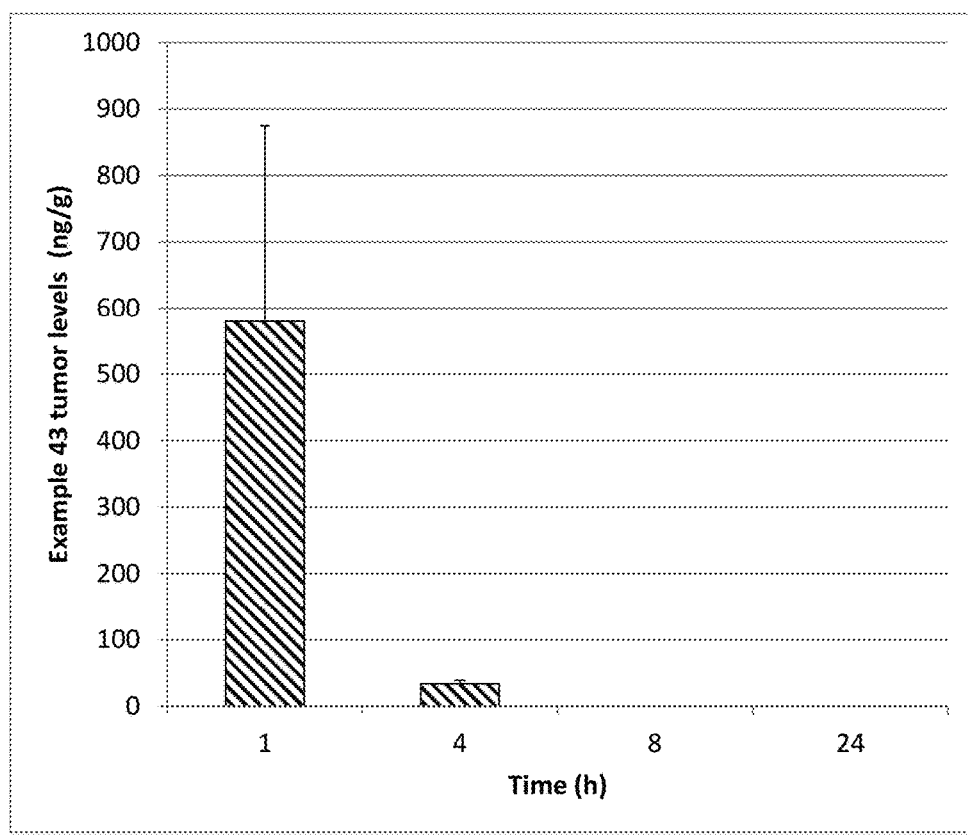
FIGS. 3 and 4 show the effect of Example 43 on CDK8 activity in vivo. The histogram in FIG. 3 represents the mean level (ng/g tissue)+standard deviation at four time points.
Figure 4:
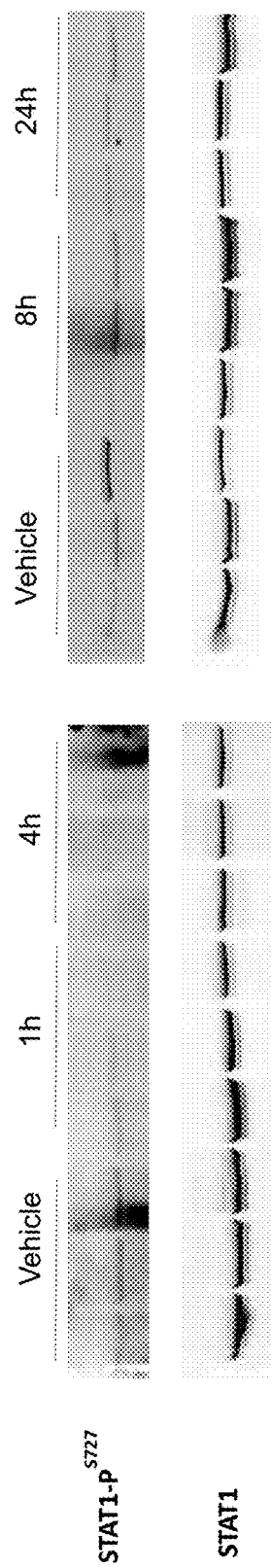

Results are summarised in FIGS. 3 and 4. Clear target modulation is observed at 1 and 4 h.

The invention claimed is:
1. A compound of formula I,

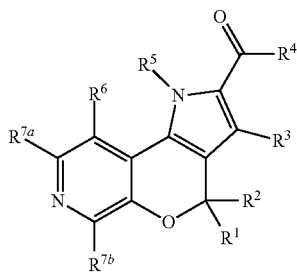

wherein:
$R^1$ and $R^2$ each independently represents hydrogen, $C_{1-12}$ alkyl, $C_{3-12}$ cycloalkyl or heterocycloalkyl (which latter three groups are optionally substituted by one or more substituents selected from =O and $Q^1$), provided that at least one of $R^1$ and $R^2$ is not hydrogen; or
$R^1$ and $R^2$ may be linked together along with the carbon atom to which they are both attached to form a 3- to 12-membered ring, optionally containing one or more heteroatoms selected from oxygen, nitrogen and sulfur, optionally containing one or more unsaturations, and which ring is optionally substituted by one or more substituents selected from =O, =S, =N($R^{20}$) and $E^1$;
$R^3$ represents hydrogen, halo, —CN, $C_{1-12}$ alkyl (optionally substituted by one or more $Q^2$ groups), $C_{3-12}$ cycloalkyl, heterocycloalkyl (which latter two groups are optionally substituted by one or more substituents selected from =O and $Q^3$), aryl or heteroaryl (which latter two groups are optionally substituted by one or more $Q^4$ groups);
$R^4$ represents —N($R^{40}$)$R^{41}$ or —O$R^{42}$;
$R^5$ represents hydrogen, $C_{1-12}$ alkyl, —C(O)—$C_{1-12}$ alkyl or —C(O)O—$C_{1-12}$ alkyl, which latter three groups are optionally substituted by one or more $Q^5$ groups;
$R^6$ represents hydrogen, halo, —CN, —N($R^{60}$)$R^{61}$, $C_{1-12}$ alkyl, $C_{3-12}$ cycloalkyl, heterocycloalkyl (which latter three groups are optionally substituted by one or more substituents selected from =O and $Q^6$), aryl or heteroaryl (which latter two groups are optionally substituted by one or more $Q^7$ groups);
$R^{7a}$ and $R^{7b}$ each independently represents hydrogen, halo, —N($R^{70}$)$R^{71}$ or —C(O)N($R^{72}$)$R^{73}$;
each $R^{20}$, $R^{40}$, $R^{41}$, $R^{42}$, $R^{60}$ and $R^{61}$ independently represents hydrogen, $C_{1-6}$ alkyl, $C_{3-6}$ cycloalkyl, heterocycloalkyl (which latter three groups are optionally substituted by one or more substituents selected from $E^2$ and =O), aryl or heteroaryl (which latter two groups are optionally substituted by one or more substituents selected from $E^3$); or
any relevant pair of $R^{40}$, $R^{41}$, $R^{60}$ and $R^{61}$, when attached to the same nitrogen atom, may be linked together along with the nitrogen atom to which they are attached to form a 4- to 12-membered ring, optionally containing one or more heteroatoms selected from oxygen, nitrogen and sulfur in addition to the requisite nitrogen atom, optionally containing one or more unsaturations, and which ring is optionally substituted by one or more substituents selected from $E^4$;
each $R^{70}$, $R^{71}$, $R^{72}$ and $R^{73}$ independently represents, hydrogen or $C_{1-3}$ alkyl optionally substituted by one or more halo atoms;
each $Q^1$, $Q^2$, $Q^3$, $Q^4$, $Q^5$, $Q^6$ and $Q^7$ independently represents halo, —CN, —N($R^{80}$)$R^{81}$, —O$R^{80}$, —C(=Y)—$R^{80}$, —C(=Y)—O$R^{80}$, —C(=Y)N($R^{80}$)$R^{81}$, —OC(=Y)—$R^{80}$, —OC(=Y)—O$R^{80}$, —OC(=Y)N($R^{80}$)$R^{81}$, —OS(O)$_2$O$R^{80}$, —P(=Y)(O$R^{80}$)(O$R^{81}$), —OP(O$R^{80}$)(O$R^{81}$), —N($R^{82}$)C(=Y)$R^{81}$, —N($R^{82}$)C(=Y)O$R^{81}$, —N($R^{82}$)C(=Y)N($R^{80}$)$R^{81}$, —N$R^{82}$S(O)$_2$$R^8$, —N$R^{82}$S(O)$_2$N($R^{80}$)$R^{81}$, —S(O)$_2$N($R^{80}$)$R^{81}$, —SC(=Y)$R^{80}$, —SC(=Y)O$R^{80}$, —SC(=Y)N($R^{80}$)$R^{81}$, —S(O)$_2$$R^{80}$, —S$R^{80}$, —S(O)$R^{80}$, —S(O)$_2$O$R^{80}$, $C_{1-12}$ alkyl, $C_{3-12}$ cycloalkyl, heterocycloalkyl (which latter three groups are optionally substituted by one or more substituents selected from =O and $E^5$), aryl or heteroaryl (which latter two groups are optionally substituted by one or more substituents selected from $E^6$);
each $E^1$, $E^2$, $E^3$, $E^4$, $E^5$ and $E^6$ independently represents:
(i) $Q^8$;
(ii) $C_{1-6}$ alkyl, $C_{3-6}$ cycloalkyl or heterocycloalkyl, each of which is optionally substituted by one or more substituents selected from =O and $Q^9$; or
(iii) aryl or heteroaryl, both of which are optionally substituted by one or more $Q^{10}$ groups;
each $Q^8$, $Q^9$ and $Q^{10}$ independently represents halo, —CN, —N($R^{83}$)$R^{84}$, —O$R^{83}$, —C(=$Y^a$)—$R^3$, —C(=$Y^a$)—O$R^{83}$, —C(=$Y^a$)N($R^{83}$)$R^{84}$, —N($R^{85}$)C(=$Y^a$)$R^{84}$, —N$R^{85}$S(O)$_2$$R^{83}$, —S(O)$_2$$R^{83}$, —S$R^{83}$, —S(O)R$^{83}$, C$_{1-6}$ alkyl or aryl, wherein the latter two groups are optionally substituted by one or more fluoro atoms;

each Y and Y$^a$ independently represents [=]O or [=]S;

each R$^{80}$, R$^{81}$, R$^{82}$, R$^{83}$, R$^{84}$ and R$^{85}$ independently represents hydrogen or C$_{1-6}$ alkyl optionally substituted by one or more substituents selected from fluoro, —OR$^{90}$ and —N(R$^{91}$)R$^{92}$;

R$^{90}$, R$^{91}$ and R$^{92}$ independently represent hydrogen or C$_{1-6}$ alkyl optionally substituted by one or more fluoro atoms;

or a pharmaceutically acceptable ester, amide, solvate or salt thereof.

2. The compound as claimed in claim 1, wherein:

R$^1$ and R$^2$ independently represent hydrogen, C$_{1-6}$ alkyl, C$_{3-6}$ cycloalkyl or a 3- to 6-membered heterocycloalkyl group (which latter three groups are optionally substituted by one or more substituents selected from =O and Q$^1$); or R$^1$ and R$^2$ may be linked together to form a 3- to 6-membered ring, optionally containing one or two heteroatoms selected from oxygen, nitrogen and sulphur, optionally containing one or two double bonds, and which ring is optionally substituted by one or more substituents selected from =O, =S, =N(R$^{20}$) and E$^1$.

3. The compound as claimed in claim 1, wherein R$^3$ represents hydrogen, halo, C$_{1-4}$ alkyl, C$_{3-6}$ cycloalkyl, heterocycloalkyl, heteroaryl or aryl (which aryl group is optionally substituted by one or more substituents selected from halo, OR$^{80}$, —S(O)$_2$N(R$^{80}$)R$^{81}$, —S(O)$_2$R$^{80}$ and C$_{1-4}$ alkyl).

4. The compound as claimed in claim 1, wherein:

R$^{40}$, R$^{41}$ and R$^{42}$ independently represent hydrogen, C$_{1-4}$ alkyl, heterocycloalkyl (which latter two groups are optionally substituted by one or more substituents selected from E$^2$) or aryl (optionally substituted by one or more substituents selected from E$^3$); or R$^{40}$ and R$^{41}$ are linked together to form a 4- to 6-membered ring, optionally containing a further heteroatom selected from oxygen, nitrogen and sulfur, and which ring is optionally substituted by one or more substituents selected from E$^4$.

5. The compound as claimed in claim 1, wherein R$^5$ represents hydrogen, C$_{1-4}$ alkyl (optionally substituted by one or more groups selected from halo, —O—C$_{1-4}$ alkyl or phenyl), carbobenzyloxy, p-methoxybenzyl carbonyl, tert-butyloxycarbonyl, acetyl, benzyl, p-methoxybenzyl or 3,4-dimethoxybenzyl.

6. The compound as claimed in claim 1, wherein R$^6$ represents hydrogen, halo, C$_{1-4}$ alkyl (optionally substituted by one or more halo atoms) or aryl (optionally substituted by one or more halo atoms).

7. The compound as claimed in claim 1, wherein R$^{7a}$ and R$^{7b}$ independently represent hydrogen, halo, —NH$_2$, —C(O)NH$_2$, —NH(R$^{70b}$), or —C(O)NHR$^{73b}$, wherein R$^{70b}$ and R$^{73b}$ independently represent C$_{1-3}$ alkyl.

8. A pharmaceutical formulation including a compound of formula I, as defined in claim 1, or a pharmaceutically acceptable ester, amide, solvate or salt thereof, in admixture with a pharmaceutically acceptable adjuvant, diluent or carrier.

9. A method of inhibiting CDK8 and/or haspin kinase in a mammalian subject, which method comprises administration of an inhibitory amount of a compound of formula I as defined in claim 1, or a pharmaceutically acceptable ester, amide, solvate or salt thereof to the mammalian subject.

10. A method for the treatment of colon/colorectal cancer comprising administering a therapeutically effective amount of a compound of formula I as defined in claim 1 to a patient suffering from such condition.

11. A combination product comprising:

(A) a compound of formula I as defined in claim 1, or a pharmaceutically acceptable ester, amide, solvate or salt thereof; and (B) another therapeutic agent that is useful in the treatment of cancer and/or a proliferative disease, wherein each of components (A) and (B) is formulated in admixture with a pharmaceutically acceptable adjuvant, diluent or carrier.

12. A process for the preparation of a pharmaceutical formulation as defined in claim 8, which process comprises bringing into association a compound of formula I, or a pharmaceutically acceptable ester, amide, solvate or salt thereof with a pharmaceutically acceptable adjuvant, diluent or carrier.

13. A process for the preparation of a combination product as defined in claim 11, which process comprises bringing into association a compound of formula I, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

\* \* \* \* \*